US012492216B2

(12) United States Patent
Kim et al.

(10) Patent No.: US 12,492,216 B2
(45) Date of Patent: Dec. 9, 2025

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

(71) Applicant: SAMSUNG SDI CO., LTD., Yongin-si (KR)

(72) Inventors: Byungku Kim, Suwon-si (KR); Yunsoo Kim, Suwon-si (KR); Hyunjung Kim, Suwon-si (KR); Min Seok Seo, Suwon-si (KR); Sunwoong Shin, Suwon-si (KR); Byoungkwan Lee, Suwon-si (KR); Kipo Jang, Suwon-si (KR); Sung-Hyun Jung, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 968 days.

(21) Appl. No.: 17/674,017

(22) Filed: Feb. 17, 2022

(65) Prior Publication Data

US 2022/0275008 A1 Sep. 1, 2022

(30) Foreign Application Priority Data

Feb. 25, 2021 (KR) ........................ 10-2021-0025840

(51) Int. Cl.

| | |
|---|---|
| ***H10K 85/40*** | (2023.01) |
| ***C07D 493/00*** | (2006.01) |
| ***C07D 495/00*** | (2006.01) |
| ***C07D 519/00*** | (2006.01) |
| ***C07F 7/08*** | (2006.01) |
| ***H10K 85/60*** | (2023.01) |
| *H10K 50/11* | (2023.01) |
| *H10K 101/00* | (2023.01) |
| *H10K 101/10* | (2023.01) |

(52) U.S. Cl.

CPC .......... *C07F 7/0812* (2013.01); *C07D 493/00* (2013.01); *C07D 495/00* (2013.01); *C07D 519/00* (2013.01); *H10K 85/40* (2023.02); *H10K 85/622* (2023.02); *H10K 85/626* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 2101/10* (2023.02); *H10K 2101/90* (2023.02)

(58) Field of Classification Search

None

See application file for complete search history.

(56) References Cited

U.S. PATENT DOCUMENTS

| | | | |
|---|---|---|---|
| 5,061,569 | A | 10/1991 | Vanslyke et al. |
| 2017/0342318 | A1 | 11/2017 | Kim et al. |
| 2019/0081253 | A1 | 3/2019 | Xia |
| 2019/0214573 | A1 | 7/2019 | Ryu et al. |
| 2020/0013957 | A1 | 1/2020 | Suh et al. |
| 2021/0091314 | A1 | 3/2021 | Shin et al. |
| 2022/0085295 | A1 | 3/2022 | Kim et al. |

FOREIGN PATENT DOCUMENTS

| | | | | | |
|---|---|---|---|---|---|
| CN | 107004776 | A | | 8/2017 | |
| CN | 109564972 | A | | 4/2019 | |
| CN | 109791981 | A | | 5/2019 | |
| CN | 110294703 | A | | 10/2019 | |
| CN | 110872313 | A | | 3/2020 | |
| CN | 111655697 | A | | 9/2020 | |
| CN | 113121584 | A | * | 7/2021 | ............ C07F 7/0816 |
| CN | 114213376 | A | | 3/2022 | |
| JP | 1993-009471 | A | | 1/1993 | |
| JP | 1995-126615 | A | | 5/1995 | |
| JP | 1998-095973 | A | | 7/1997 | |
| KR | 10-2017-0056425 | A | | 5/2017 | |
| KR | 10-2017-0082459 | A | | 7/2017 | |

(Continued)

OTHER PUBLICATIONS

Machine translation of CN-113121584-A, translation generated Mar. 2025, 20 pages. (Year: 2025).*

(Continued)

*Primary Examiner* — Robert S Loewe

(74) *Attorney, Agent, or Firm* — Lee IP Law, P.C.

(57) ABSTRACT

A compound for an organic optoelectronic device, a composition for an organic optoelectronic device including the same, an organic optoelectronic device, and a display device, the compound being represented by Chemical Formula 1:

[Chemical Formula 1]

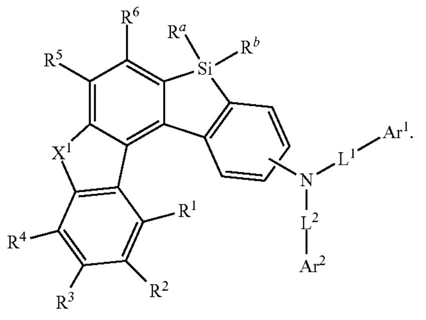

20 Claims, 2 Drawing Sheets

(56) References Cited

FOREIGN PATENT DOCUMENTS

| | | | |
|---|---|---|---|
| KR | 10-2019-0013353 | A | 2/2019 |
| KR | 10-2019-0088248 | A | 7/2019 |
| KR | 10-2019-0132261 | A | 11/2019 |
| KR | 10-2019-0132945 | A | 11/2019 |
| KR | 10-2019-0135579 | A | 12/2019 |
| KR | 10-2020-0000518 | A | 1/2020 |
| WO | WO 1995/009147 | A1 | 4/1995 |
| WO | WO 2006/108497 | A1 | 10/2006 |
| WO | WO 2010/136109 | A1 | 12/2010 |
| WO | WO 2020-175867 | A1 | 9/2020 |

OTHER PUBLICATIONS

Chinese Office Action (including a search report) dated Dec. 18, 2023, of the corresponding Chinese Patent Application No. 202210172835.X.

Korean Office action dated Jun. 11, 2024.

* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY DEVICE

CROSS-REFERENCE TO RELATED APPLICATION

This application claims priority to and the benefit of Korean Patent Application No. 10-2021-0025840 filed in the Korean Intellectual Property Office on Feb. 25, 2021, the entire contents of which are incorporated herein by reference.

BACKGROUND

1. Field

Embodiments relate to a compound for an organic optoelectronic device, a composition for an organic optoelectronic device, an organic optoelectronic device, and a display device.

2. Description of the Related Art

An organic optoelectronic device (e.g., organic optoelectronic diode) is a device capable of converting electrical energy and optical energy to each other.

Organic optoelectronic devices may be divided into two types according to a principle of operation. One is a photoelectric device that generates electrical energy by separating excitons formed by light energy into electrons and holes, and transferring the electrons and holes to different electrodes, respectively and the other is a light emitting device that generates light energy from electrical energy by supplying voltage or current to the electrodes.

Examples of the organic optoelectronic device include an organic photoelectric device, an organic light emitting diode, an organic solar cell, and an organic photoconductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

The embodiments may be realized by providing a compound for an organic optoelectronic device, the compound being represented by Chemical Formula 1:

[Chemical Formula 1]

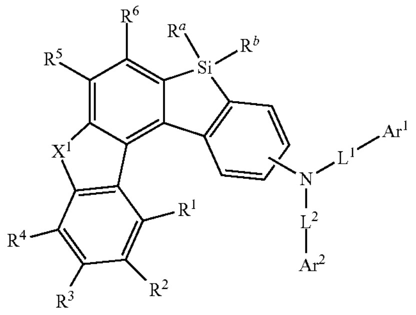

wherein, in Chemical Formula 1, $X^1$ is O or S, $Ar^1$ and $Ar^2$ are each independently a substituted or unsubstituted C6 to C30 aryl group or a substituted or unsubstituted C2 to C30 heterocyclic group, $L^1$ and $L^2$ are each independently a single bond, a substituted or unsubstituted C6 to C30 arylene group, or a substituted or unsubstituted C2 to C30 heteroarylene group, $R^1$ to $R^6$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, and $R^a$ and $R^b$ are each independently a substituted or unsubstituted C1 to C30 alkyl group or a substituted or unsubstituted C6 to C30 aryl group.

The embodiments may be realized by providing a composition for an organic optoelectronic device, the composition including a first compound and a second compound, wherein the first compound is the compound for an organic optoelectronic device according to an embodiment, the second compound is represented by Chemical Formula 2:

[Chemical Formula 2]

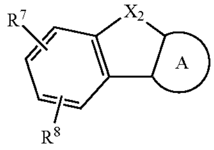

in Chemical Formula 2, $X^2$ is O, S, N-$L^a$-$R^c$, $CR^dR^e$, or $SiR^fR^g$, $L^a$ is a single bond or a substituted or unsubstituted C6 to C12 arylene group, $R^c$ is a substituted or unsubstituted C6 to C20 aryl group or a substituted or unsubstituted C2 to C30 heterocyclic group, $R^d$, $R^e$, $R^f$, and $R^g$ are each independently a substituted or unsubstituted C1 to C30 alkyl group or a substituted or unsubstituted C6 to C30 aryl group, $R^7$ and $R^8$ are each independently hydrogen, deuterium, a cyano group, a halogen, a substituted or unsubstituted C1 to C30 alkyl group, a substituted or unsubstituted C6 to C30 aryl group, or a substituted or unsubstituted C2 to C30 heterocyclic group, and A is a ring of Group II,

[Group II]

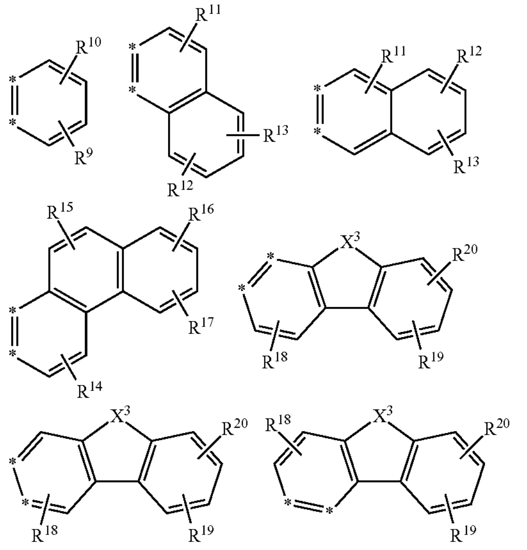

in Group II, * is a linking point, $X^3$ is O or S, $R^9$ to $R^{20}$ are each independently hydrogen, deuterium, a substituted or unsubstituted C6 to C20 aryl group, or a substituted or unsubstituted C2 to C30 heterocyclic group, and at least one of $R^c$ and $R^7$ to $R^{20}$ is a group represented by Chemical Formula a,

[Chemical Formula a]

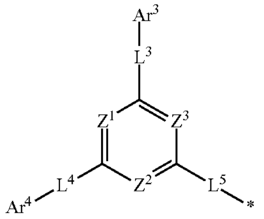

in Chemical Formula a, $Z^1$ to $Z^3$ are each independently N or $CR^h$, at least two of $Z^1$ to $Z^3$ being N, $R^h$ is hydrogen, deuterium, a substituted or unsubstituted C1 to C30 alkyl group, or a substituted or unsubstituted C6 to C30 aryl group, $L^3$ to $L^5$ are each independently a single bond or a substituted or unsubstituted C6 to C30 arylene group, $Ar^3$ and $Ar^4$ are each independently a substituted or unsubstituted C6 to C30 aryl group or a substituted or unsubstituted C2 to C30 heteroaryl group, and * is a linking point.

The embodiments may be realized by providing an organic optoelectronic device including an anode and a cathode facing each other, and at least one organic layer between the anode and the cathode, wherein the at least one organic layer includes the compound for an organic optoelectronic device according to an embodiment.

The embodiments may be realized by providing an organic optoelectronic device including an anode and a cathode facing each other, and at least one organic layer between the anode and the cathode, wherein the at least one organic layer includes the composition for an organic optoelectronic device according to an embodiment.

The embodiments may be realized by providing a display device comprising the organic optoelectronic device according to an embodiment.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
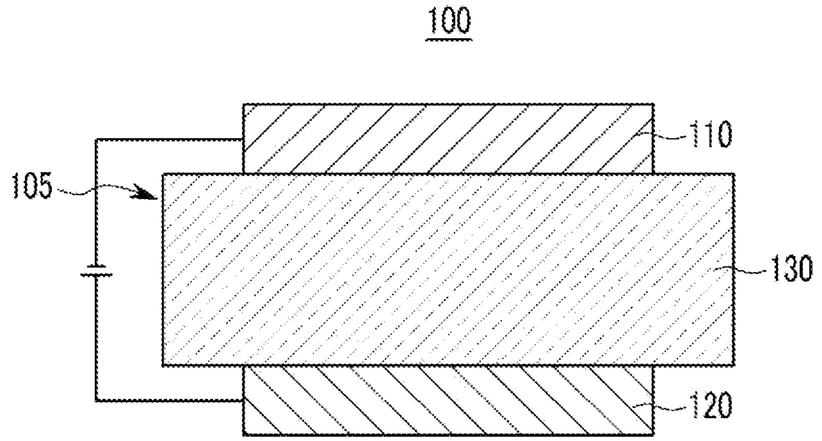
FIGS. 1 to 4 are cross-sectional views of organic light emitting diodes according to embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof. As used herein, the term "or" is not an exclusive term, e.g., "A or B" would include A, B, or A and B.

In one example, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In a specific example, the "substituted" refers to replacement of at least one hydrogen of a substituent or a compound by deuterium, a C1 to C20 alkyl group, a C6 to C30 aryl group, or a cyano group. In a specific example, the "substituted" refers to replacement of at least one hydrogen of a substituent or a compound by deuterium, a C1 to C5 alkyl group, a C6 to C18 aryl group, or a cyano group. In a specific example, the "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

In the present specification, when a definition is not otherwise provided, "hetero" refers to one including one to three heteroatoms selected from N, O, S, P, and Si, and remaining carbons in one group.

In the present specification, "an aryl group" refers to a group including at least one hydrocarbon aromatic moiety, and all elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring, for example a fluorenyl group.

The aryl group may include a monocyclic, polycyclic, or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, or a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment may be represented by, e.g., Chemical Formula 1.

[Chemical Formula 1]

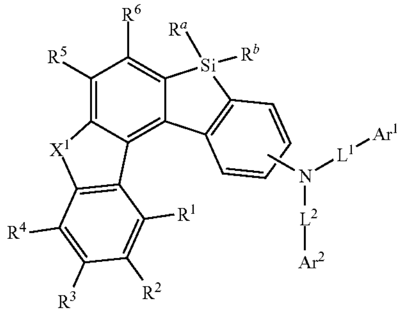

In Chemical Formula 1, $X^1$ may be, e.g., O or S.

$Ar^1$ and $Ar^2$ may each independently be or include, e.g., a substituted or unsubstituted C6 to C30 aryl group or a substituted or unsubstituted C2 to C30 heterocyclic group.

$L^1$ and $L^2$ may each independently be or include, e.g., a single bond, a substituted or unsubstituted C6 to C30 arylene group, or a substituted or unsubstituted C2 to C30 heteroarylene group.

$R^1$ to $R^6$ may each independently be or include, e.g., hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group.

$R^a$ and $R^b$ may each independently be or include, e.g., a substituted or unsubstituted C1 to C30 alkyl group or a substituted or unsubstituted C6 to C30 aryl group.

The compound for an organic optoelectronic device represented by Chemical Formula 1 may include a skeleton or core in which dibenzosilole and benzofuran (or benzothiophene) are fused, and an amine group is directly substituted in the direction of or directly bonded to (e.g., the N of the amine group is directly bonded to) the dibenzosilole moiety of the fused skeleton.

In an implementation, by including a skeleton in which dibenzosilole and benzofuran (or benzothiophene) are fused, hole injection may be made faster, which may be advantageous for a driving voltage of an organic light emitting diode including the compound. In an implementation, the amine group may be substituted or bonded directly (e.g., without a linking group), and injection into the hole may be facilitated and the driving voltage may be increased. As it is directly substituted, the molecular weight of the compound may decrease, so that heat resistance stability may be improved.

In an implementation, Chemical Formula 1 may be represented by one of Chemical Formula 1-1 to Chemical Formula 1-4, depending on the linking position of the amine group.

[Chemical Formula 1-1]

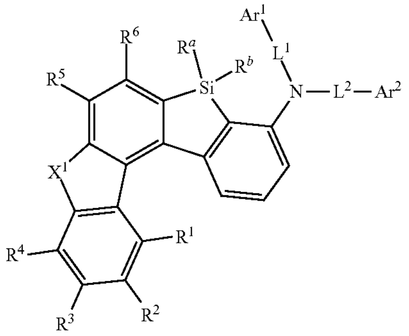

[Chemical Formula 1-2]

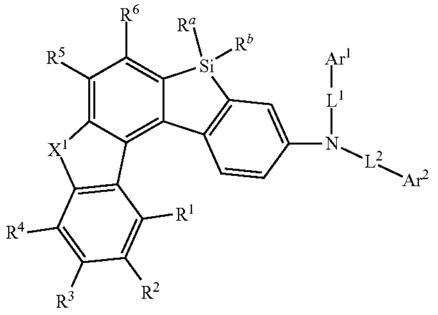

[Chemical Formula 1-3]

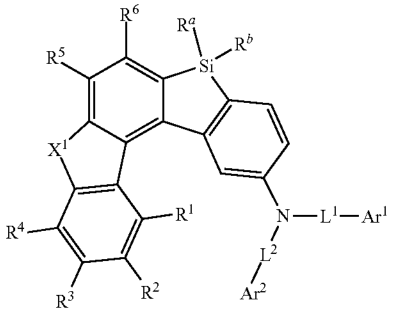

[Chemical Formula 1-4]

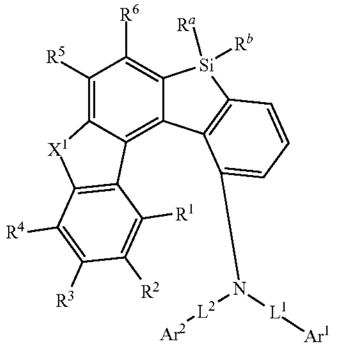

In Chemical Formula 1-1 to Chemical Formula 1-4, $X^1$, $Ar^1$, $Ar^2$, $L^1$, $L^2$, $R^1$ to $R^6$, $R^a$, and $R^b$ may be defined the same as those of Chemical Formula 1 described above.

In an implementation, $Ar^1$ and $Ar^2$ may each independently be, e.g., a substituted or unsubstituted C6 to C20 aryl group or a substituted or unsubstituted C2 to C20 heterocyclic group.

In an implementation, $Ar^1$ and $Ar^2$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted fluorenyl group, a substituted or unsubstituted chrysenyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, a substituted or unsubstituted benzonaphthothiophenyl group, or a substituted or unsubstituted benzoxazolyl group.

In an implementation, $Ar^1$ and $Ar^2$ may each independently be, e.g., a substituted or unsubstituted phenyl group, a substituted or unsubstituted biphenyl group, a substituted or unsubstituted naphthyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group. In an implementation, at least one of $Ar^1$ and $Ar^2$ may be, e.g., a substituted or unsubstituted biphenyl group, a substituted or unsubstituted naphthyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group.

In an implementation, $L^1$ and $L^2$ may each independently be, e.g., a single bond or a substituted or unsubstituted C6 to C12 arylene group.

In an implementation, $L^1$ and $L^2$ may each independently be, e.g., a single bond or a substituted or unsubstituted phenylene group.

In an implementation, moieties *-$L^1$-$Ar^1$ and *-$L^2$-$Ar^2$ may each independently be a moiety of Group I.

[Group I]

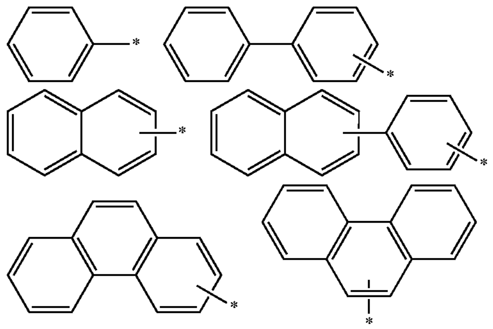

-continued
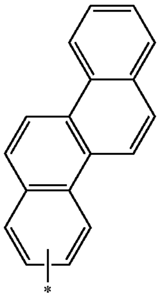
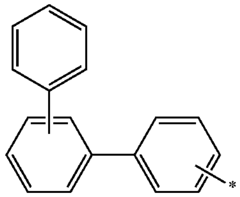
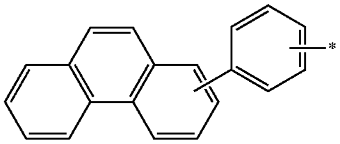
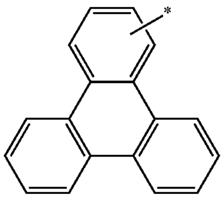
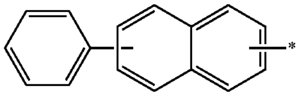
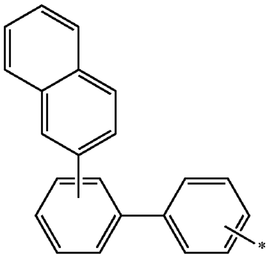
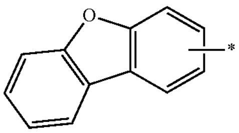
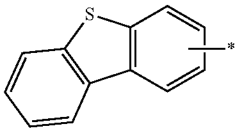
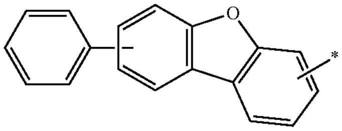
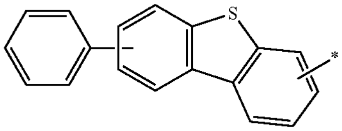
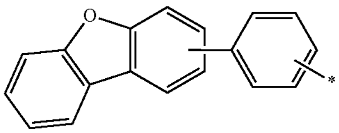
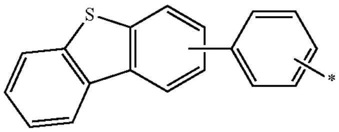
-continued
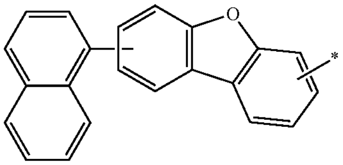
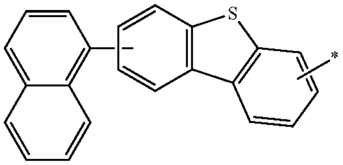
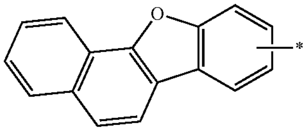
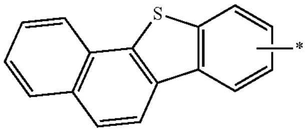
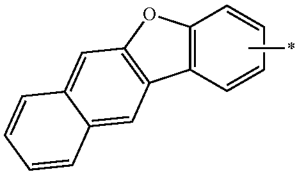
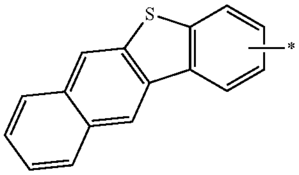
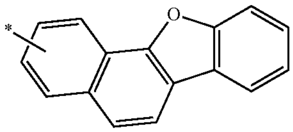
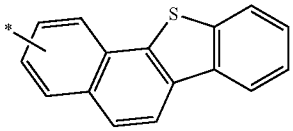
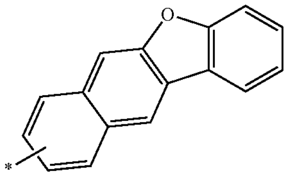
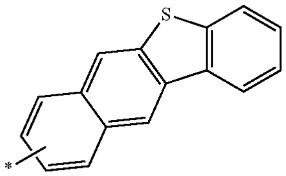
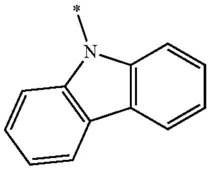

-continued

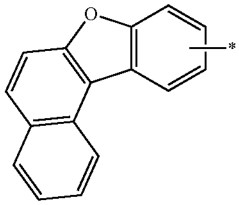

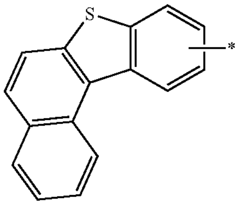

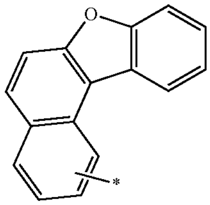

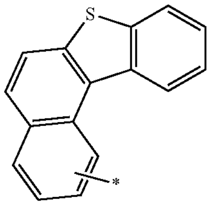

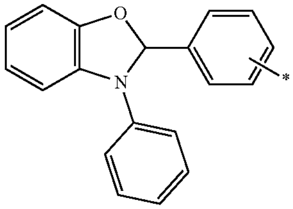

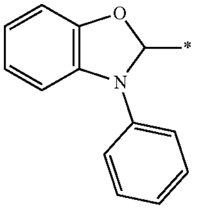

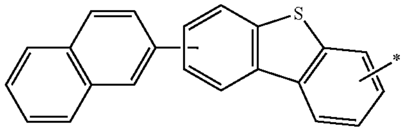

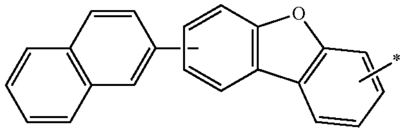

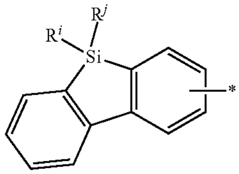

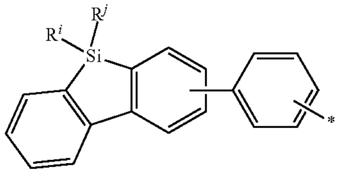

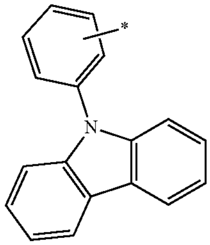

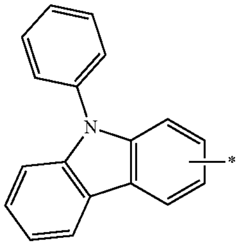

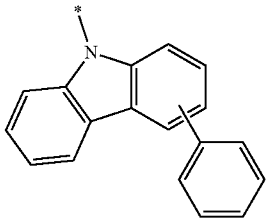

-continued

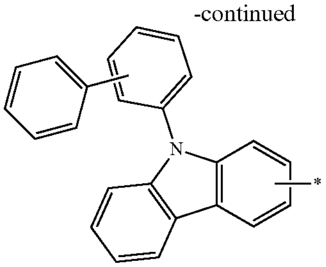

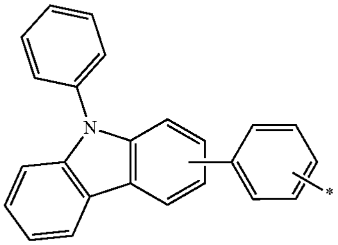

In Group I, $R^i$ and $R^j$ may each independently be, e.g., a substituted or unsubstituted C1 to C10 alkyl group or a substituted or unsubstituted C6 to C12 aryl group.

In an implementation, $R^1$ to $R^6$ may each independently be, e.g., hydrogen, deuterium, a cyano group, a halogen, a substituted or unsubstituted C1 to C10 alkyl group, or a substituted or unsubstituted C6 to C20 aryl group.

In an implementation, $R^1$ to $R^6$ may each independently be, e.g., hydrogen, deuterium, a cyano group, a halogen, a substituted or unsubstituted phenyl group, or a substituted or unsubstituted biphenyl group.

In an implementation, $R^1$ to $R^6$ may each be hydrogen.

In an implementation, $R^a$ and $R^b$ may each independently be, e.g., a substituted or unsubstituted C1 to C10 alkyl group or a substituted or unsubstituted C6 to C12 aryl group.

In an implementation, $R^a$ and $R^b$ may each independently be, e.g., an unsubstituted methyl group, an unsubstituted ethyl group, an unsubstituted propyl group (e.g., an unsubstituted iso-propyl group), a substituted or unsubstituted phenyl group, or a substituted or unsubstituted biphenyl group.

In an implementation, the compound for an organic optoelectronic device represented by Chemical Formula 1 may include, e.g., a compound of Group 1.

[Group 1]

B-1

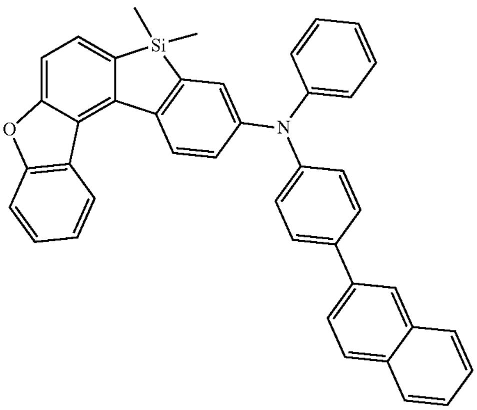

-continued
B-2
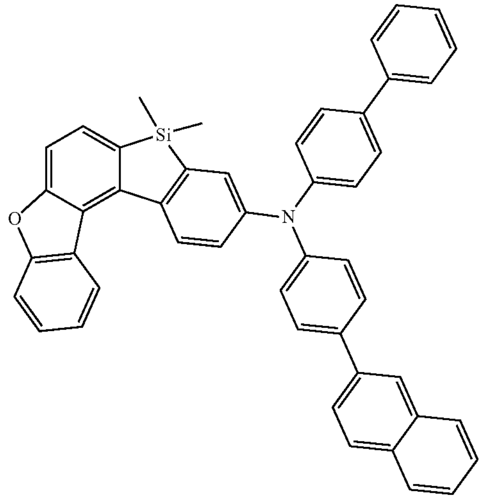
B-3
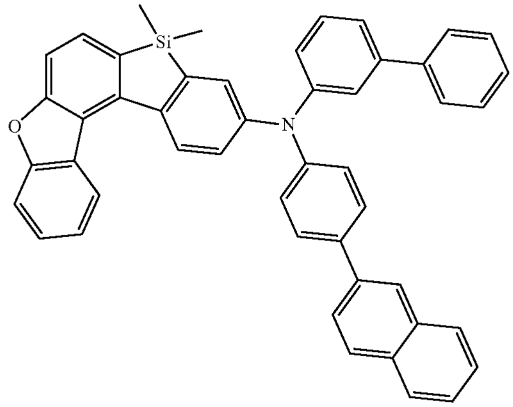
B-4
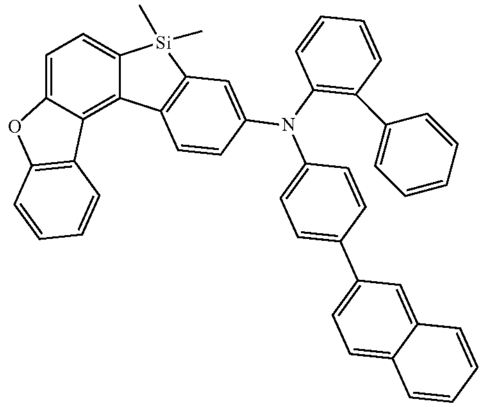
-continued
B-5
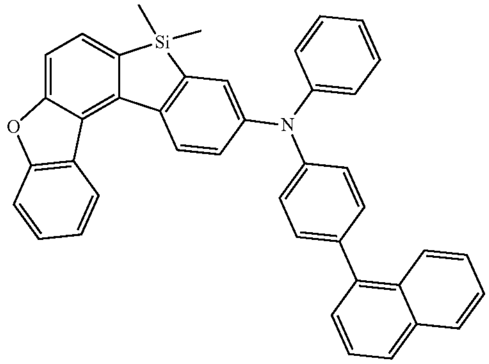
B-6
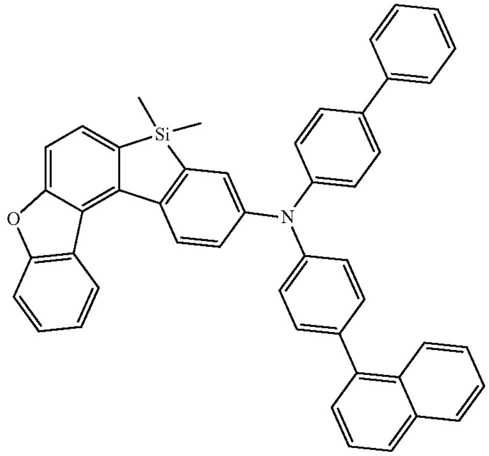
B-7
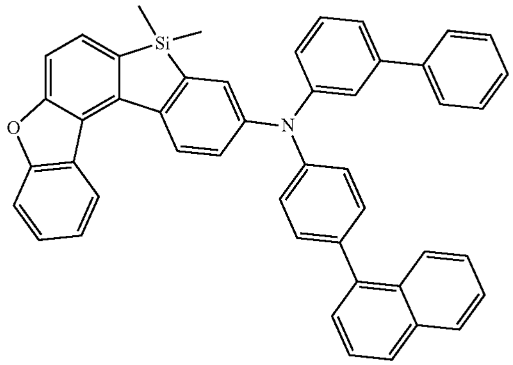
B-8
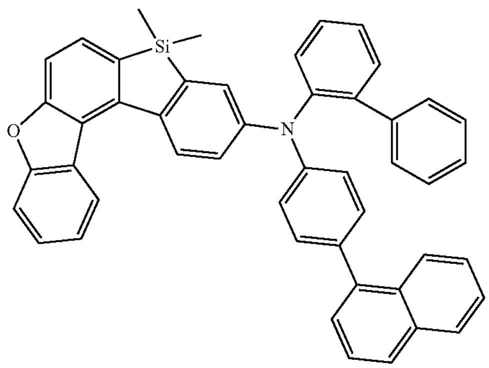

-continued
B-9
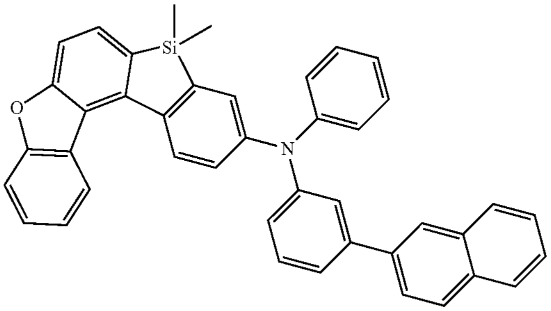
B-10
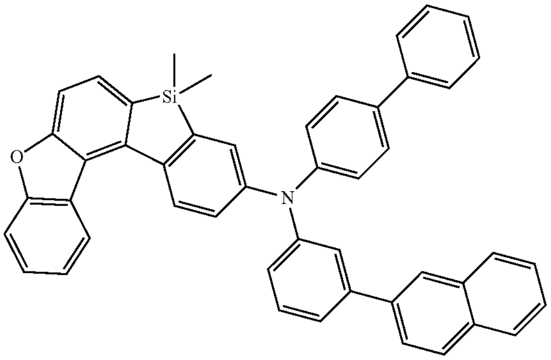
B-11
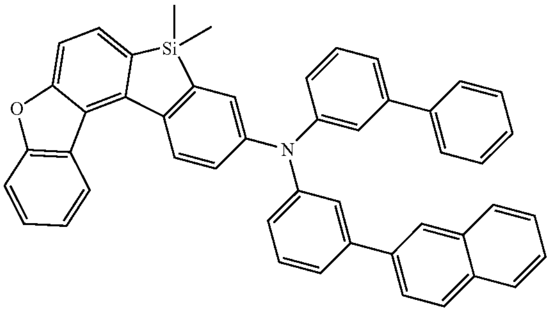
B-12
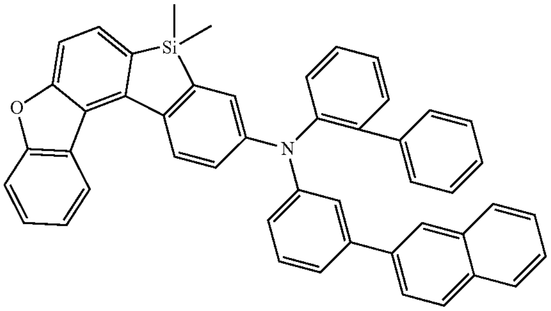
-continued
B-13
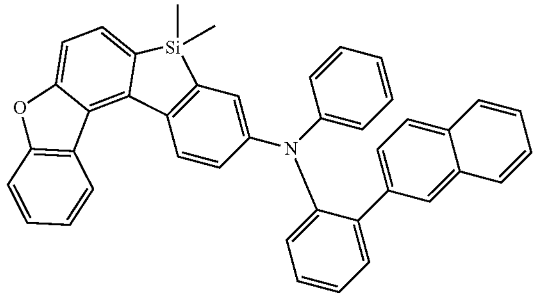
B-14
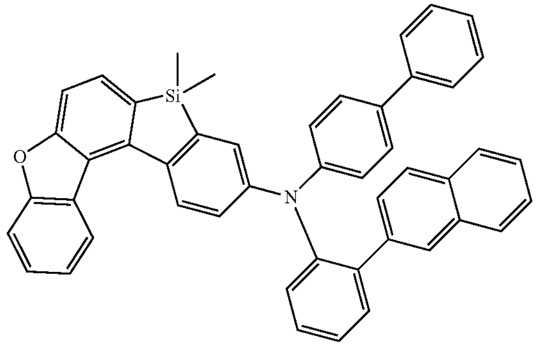
B-15
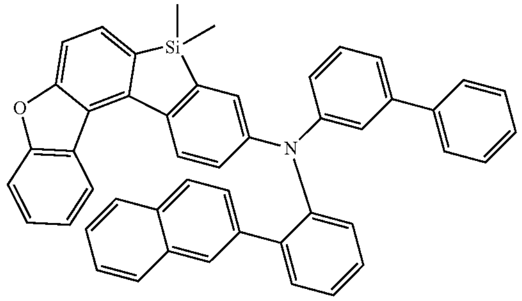
B-16
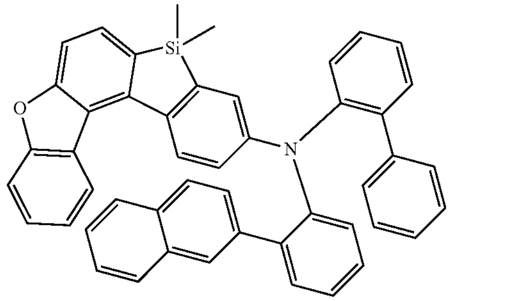

-continued
B-17
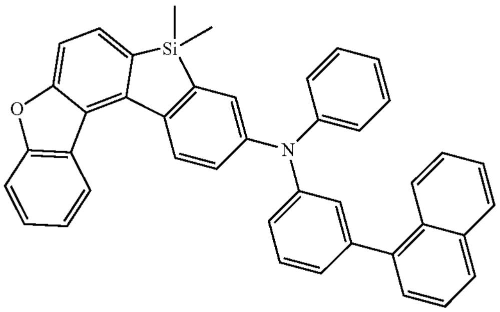
B-18
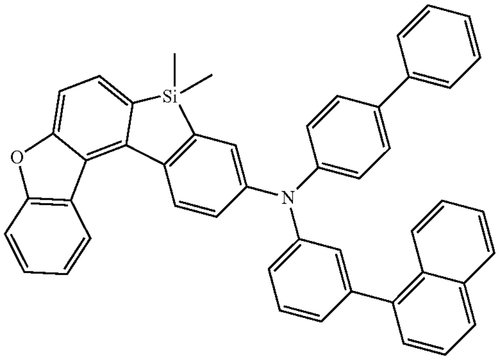
B-19
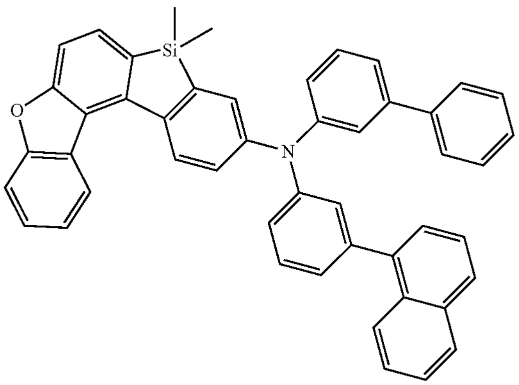
B-20
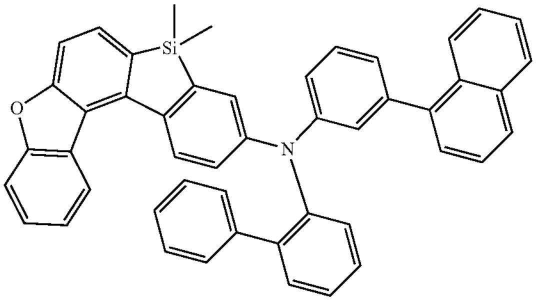
-continued
B-21
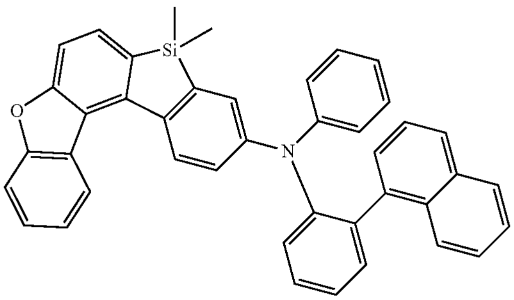
B-22
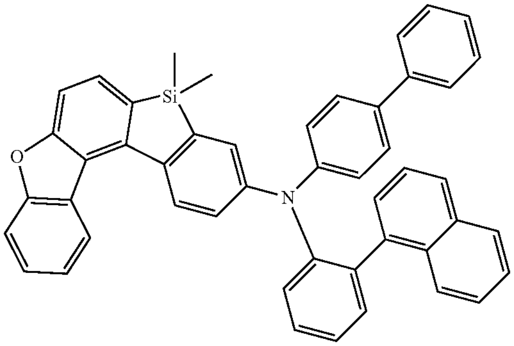
B-23
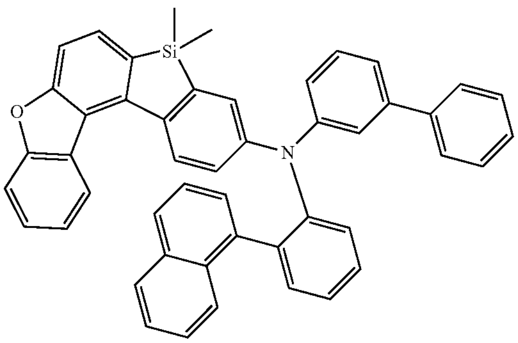
B-24
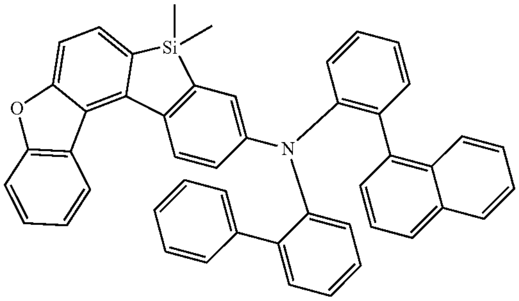

-continued
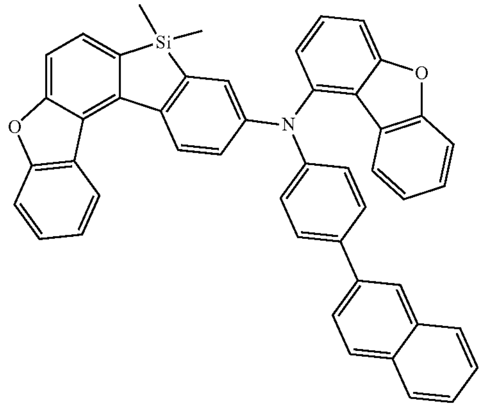
B-25
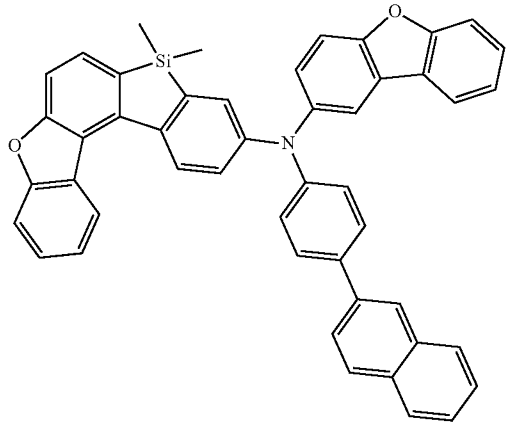
B-26
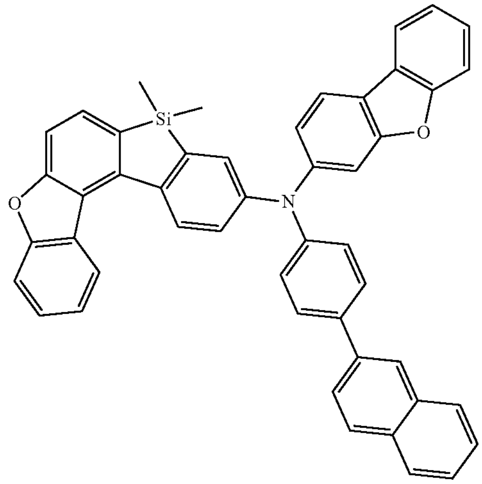
B-27
-continued
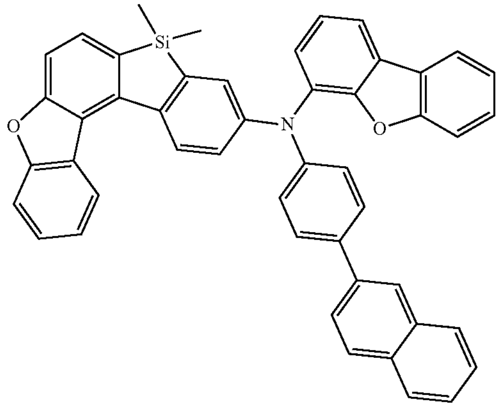
B-28
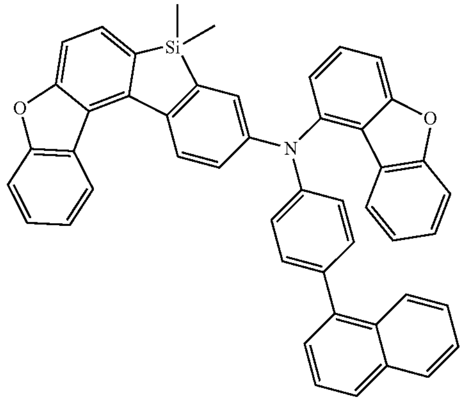
B-29
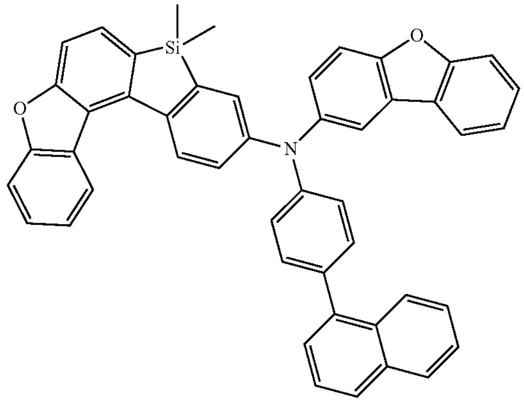
B-30

-continued
B-31
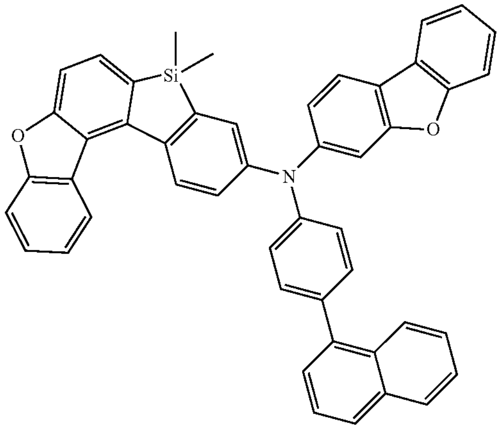
B-32
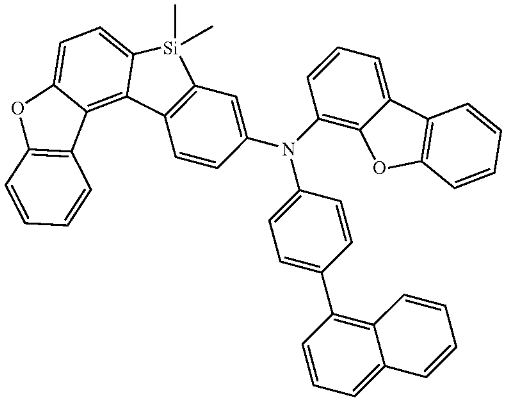
B-33
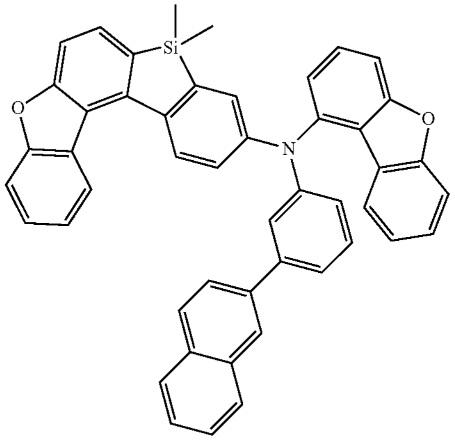
-continued
B-34
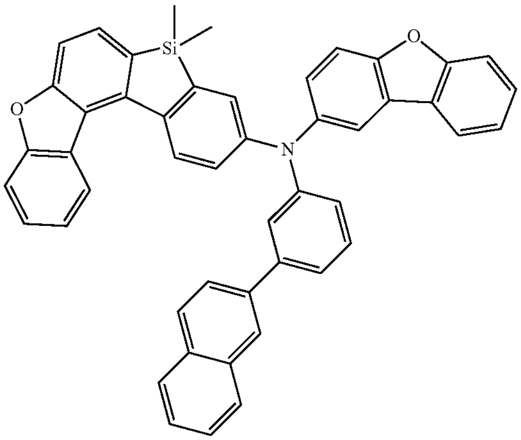
B-35
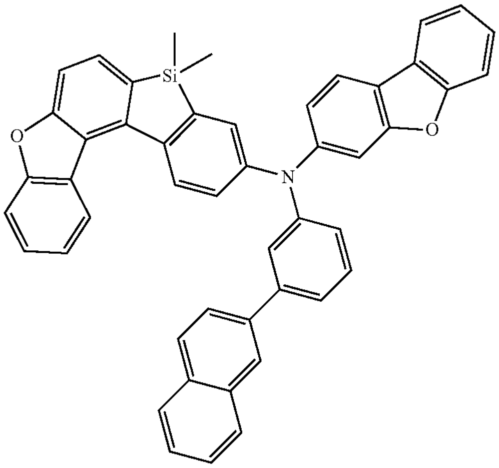
B-36
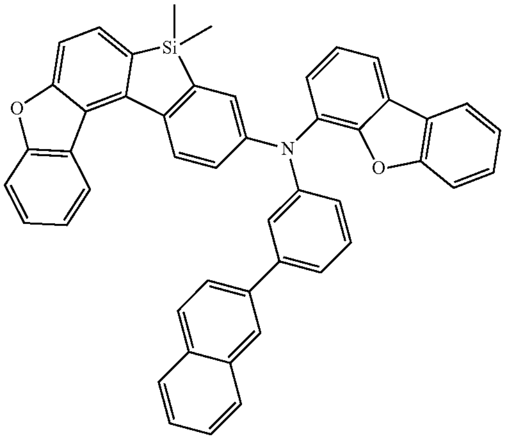

-continued
B-37
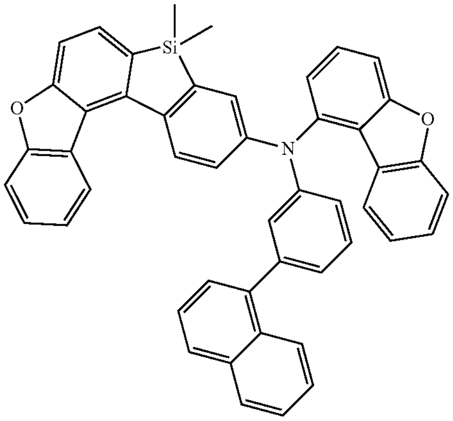
B-38
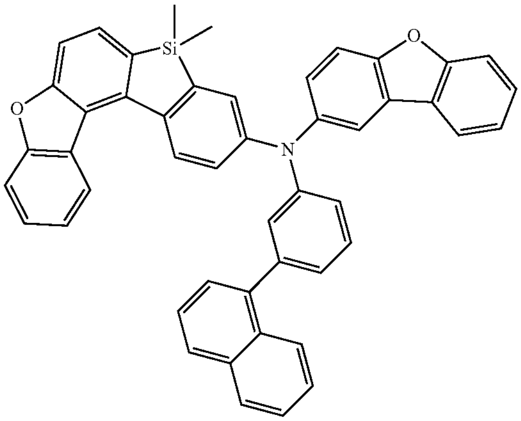
B-39
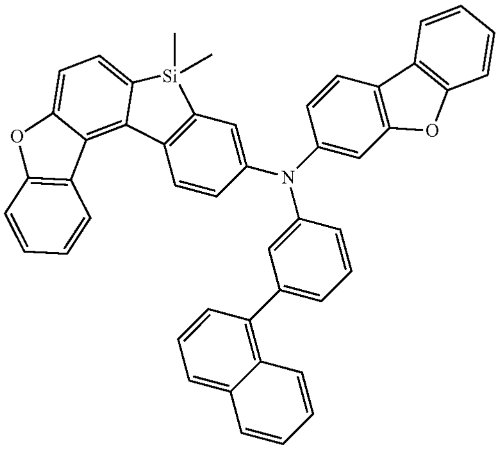
-continued
B-40
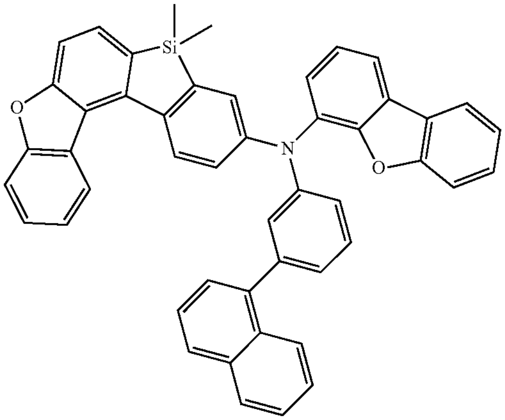
B-41
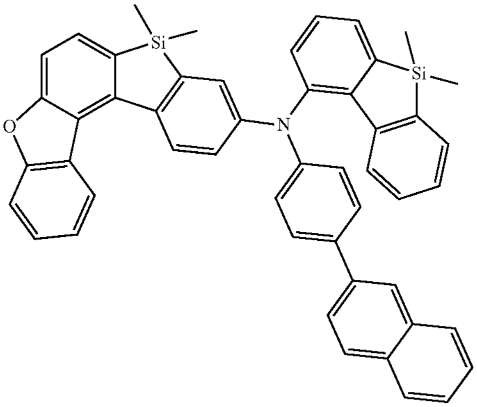
B-42
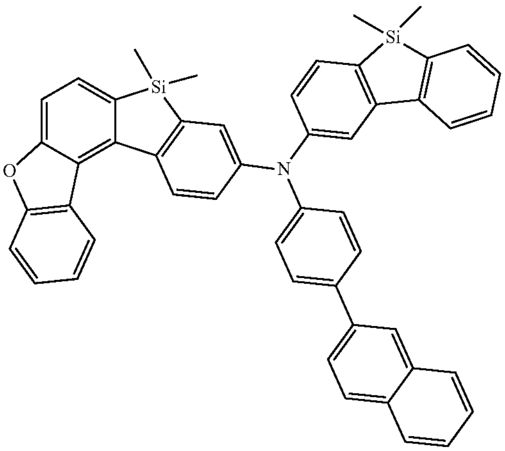

-continued
B-43
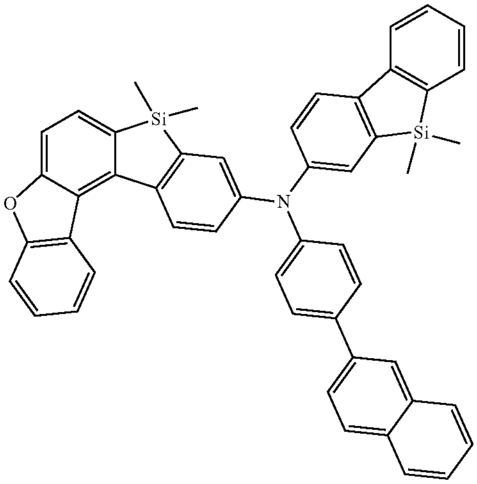
B-44
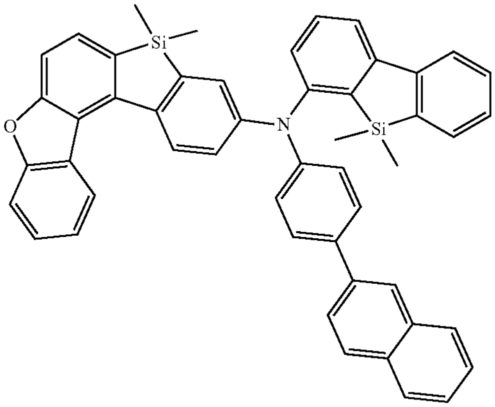
B-45
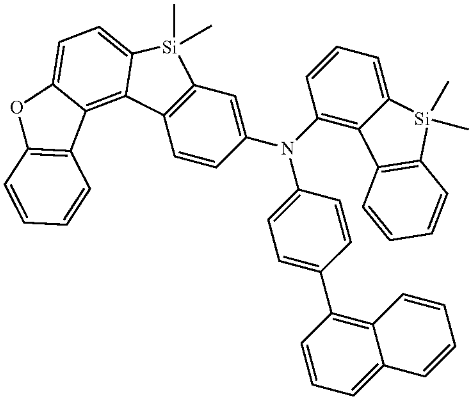
-continued
B-46
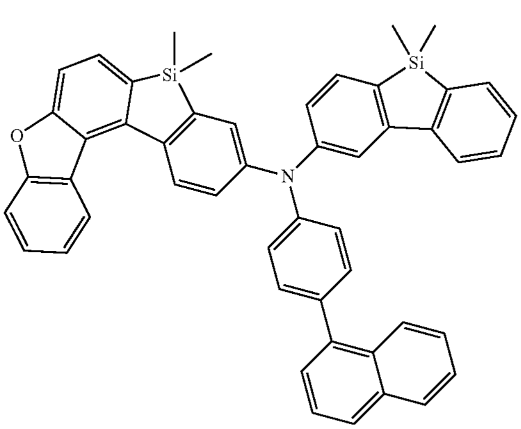
B-47
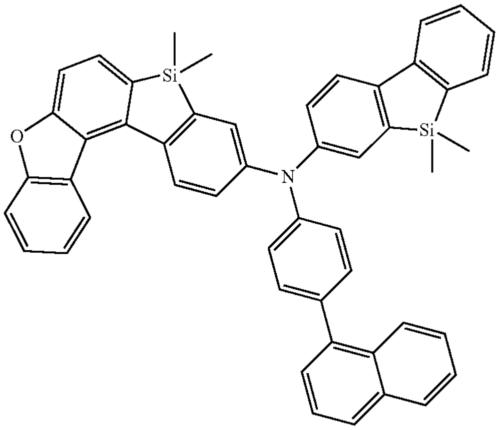
B-48
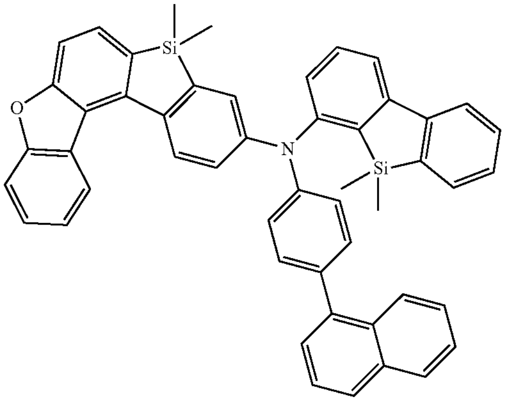

-continued
B-49
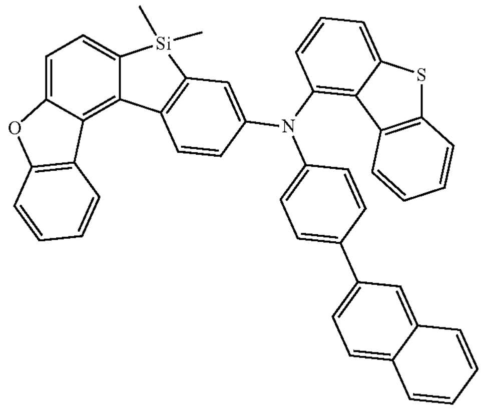
B-50
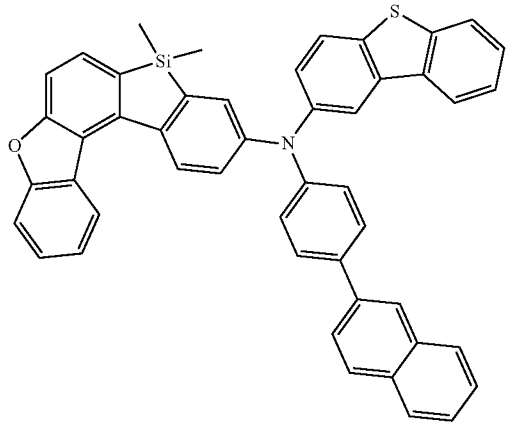
B-51
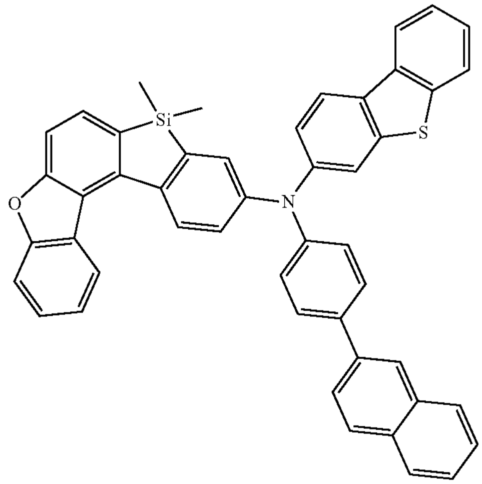
-continued
B-52
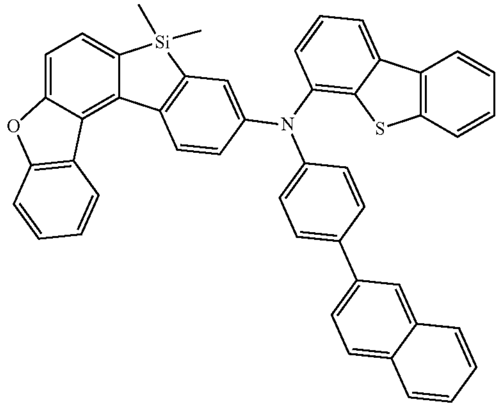
B-53
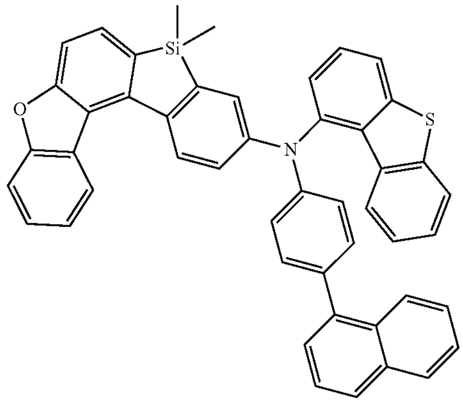
B-54
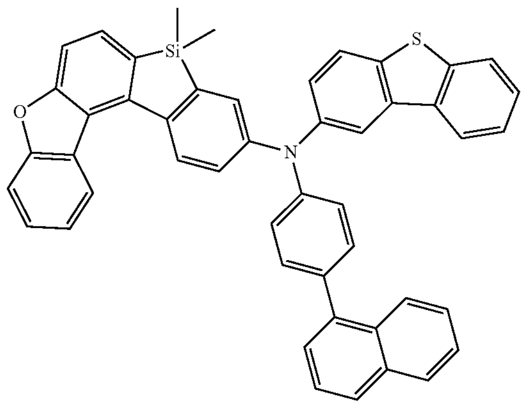

-continued
B-55
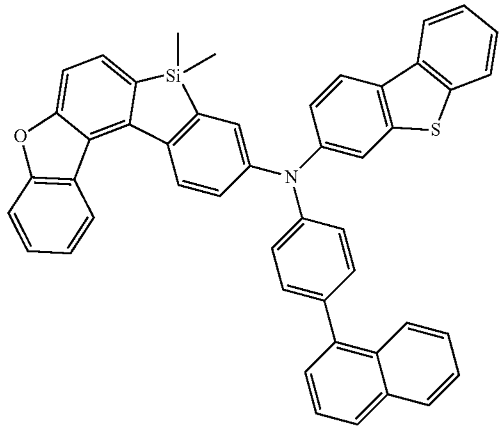
B-56
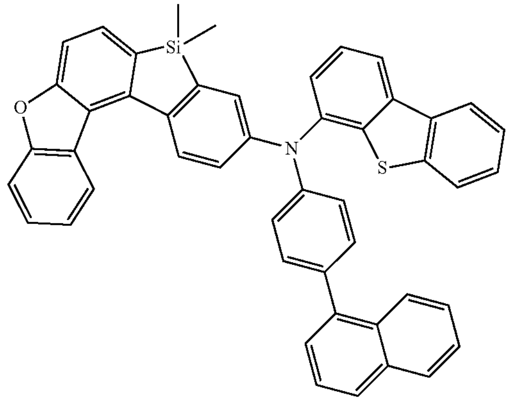
B-57
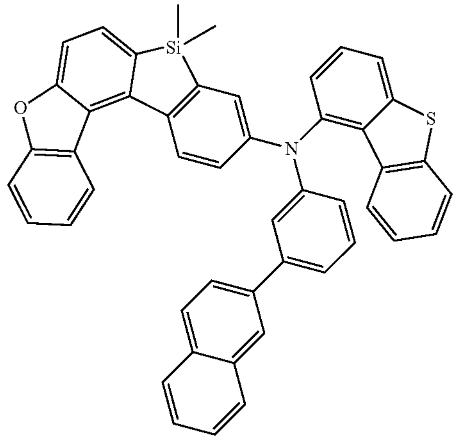
-continued
B-58
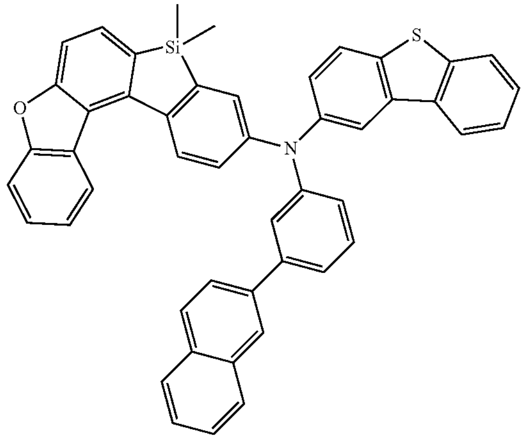
B-59
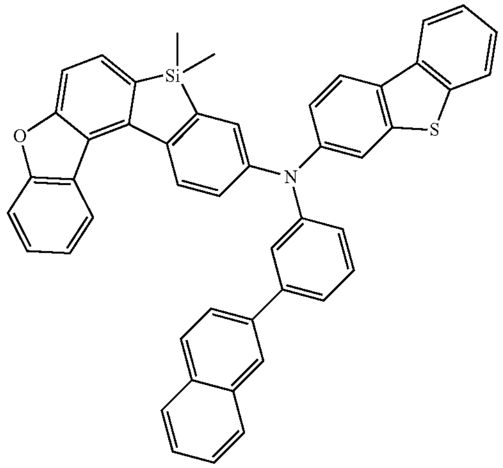
B-60
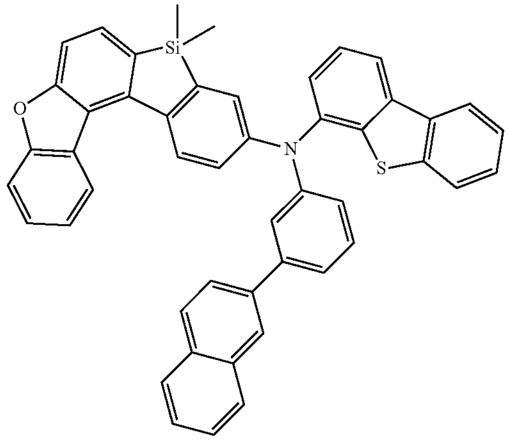

-continued
B-61
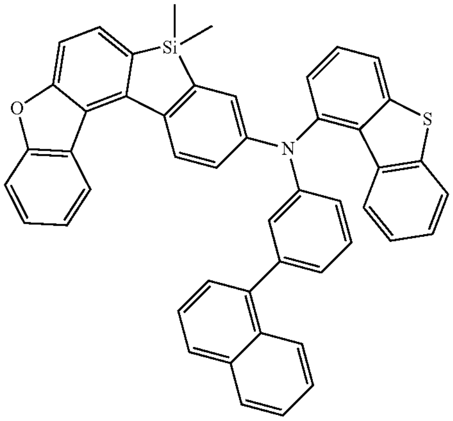
B-62
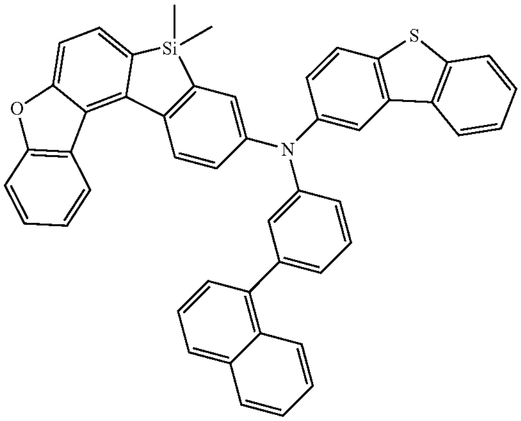
B-63
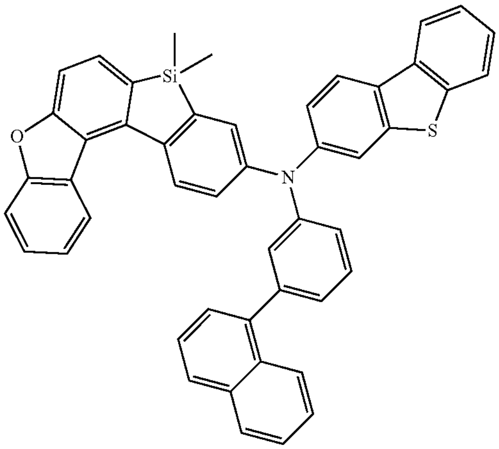
-continued
B-64
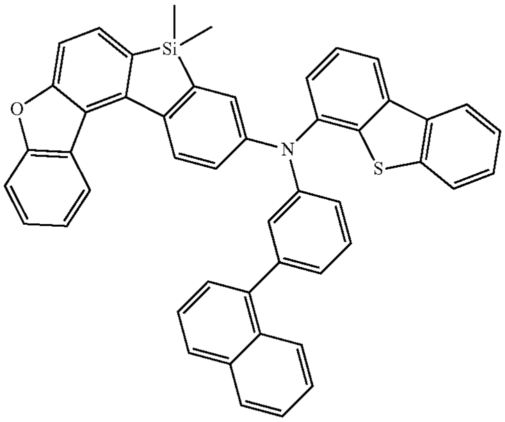
B-65
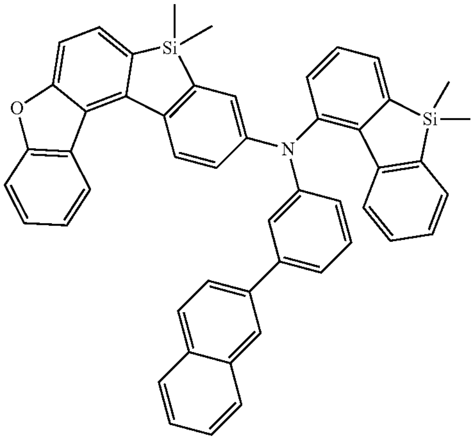
B-66
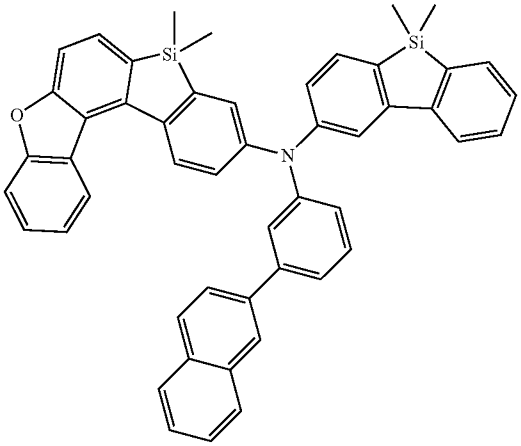

-continued
B-67
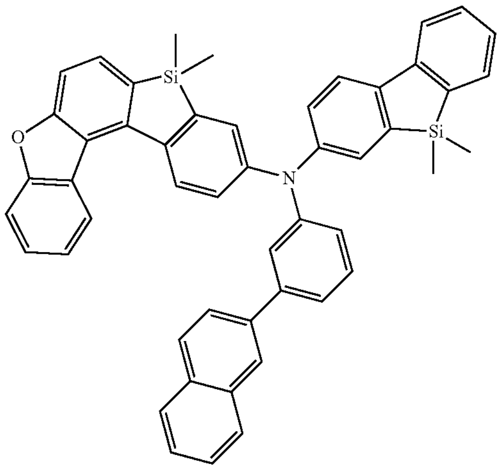
B-68
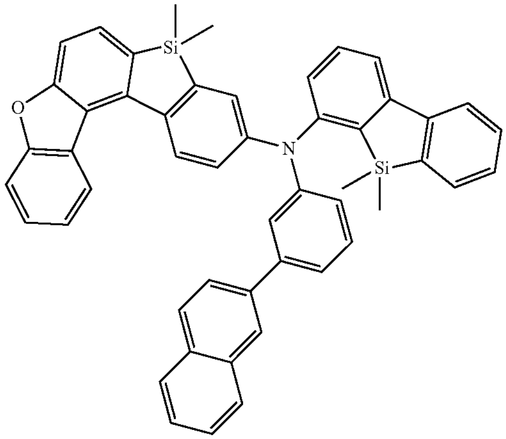
B-69
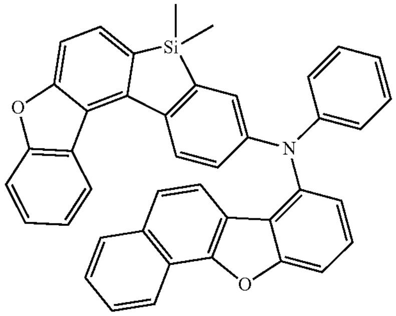
B-70
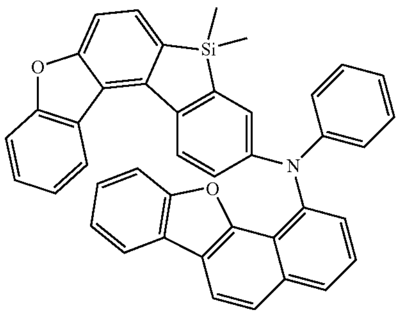
-continued
B-71
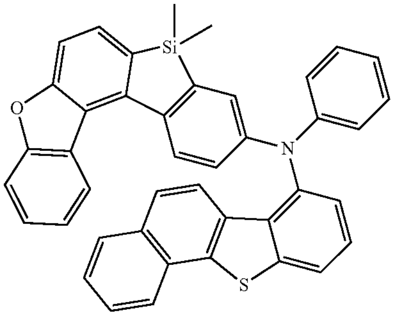
B-72
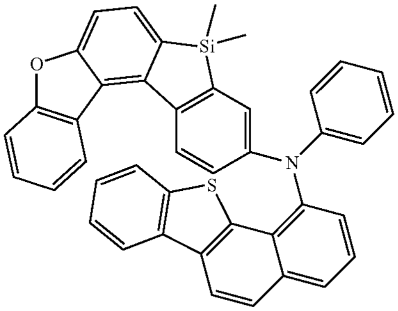
B-73
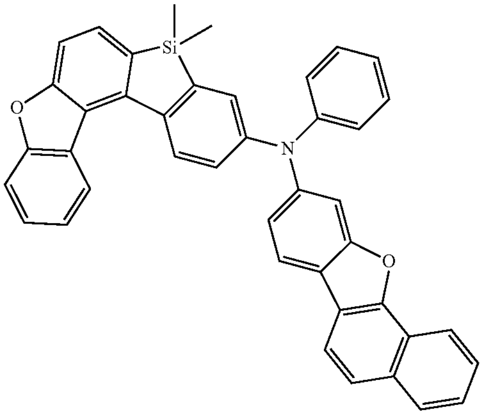
B-74
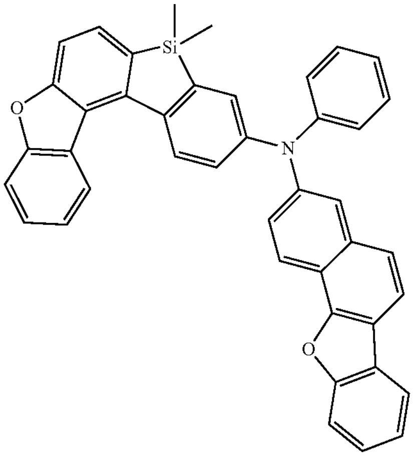

-continued
B-75
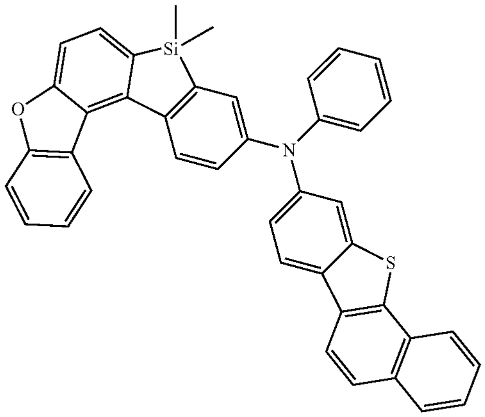
B-76
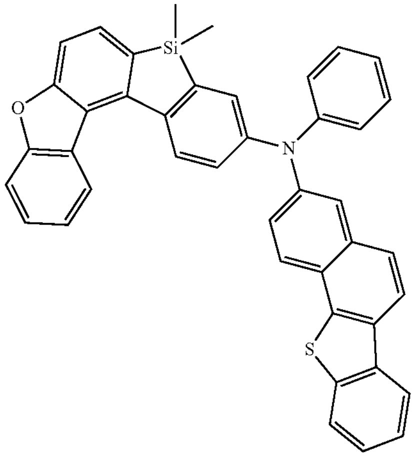
B-77
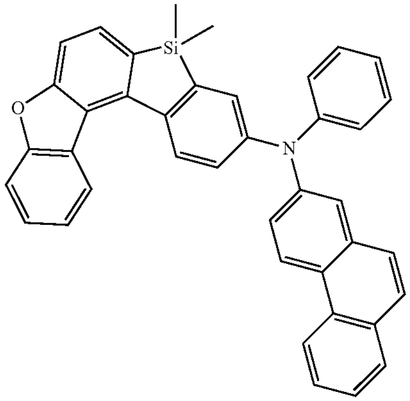
B-78
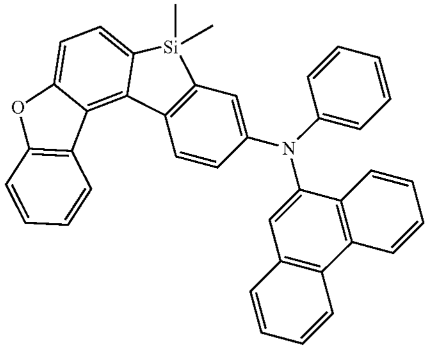
-continued
B-79
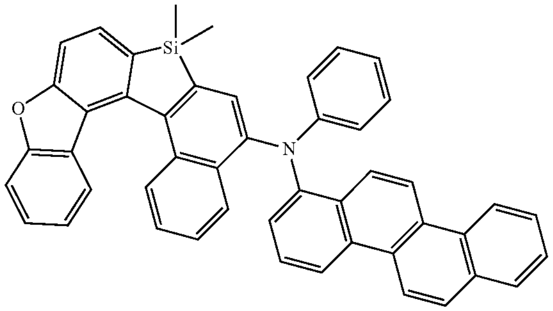
B-80
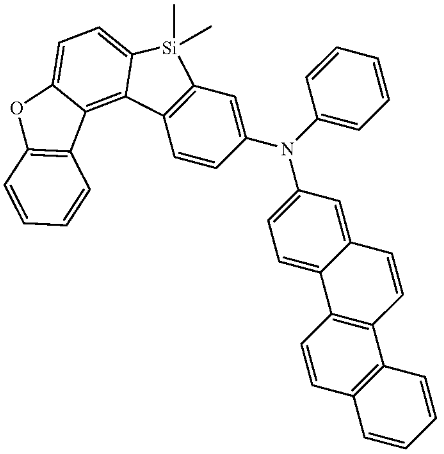
B-81
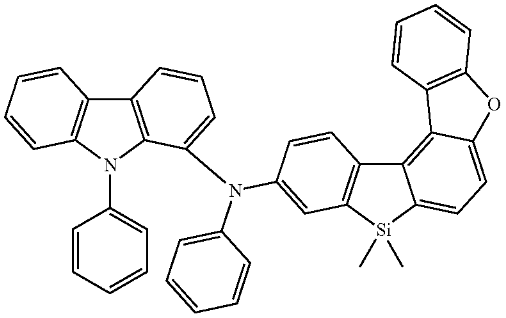
B-82
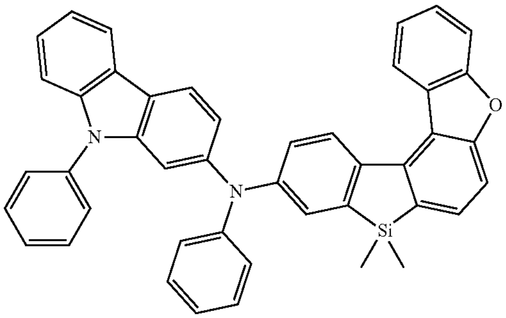

-continued
B-83
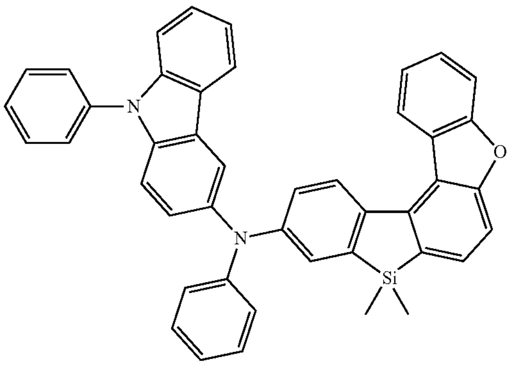
B-84
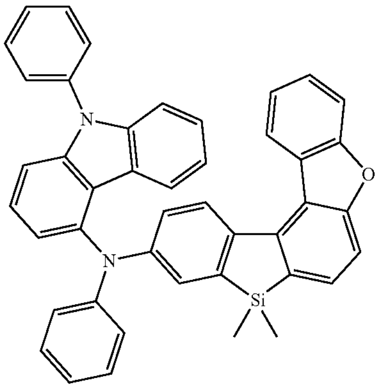
B-85
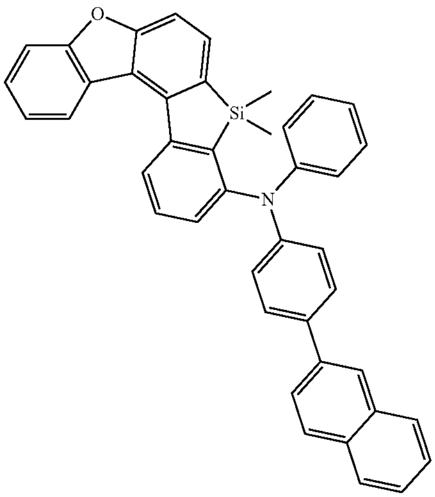
-continued
B-86
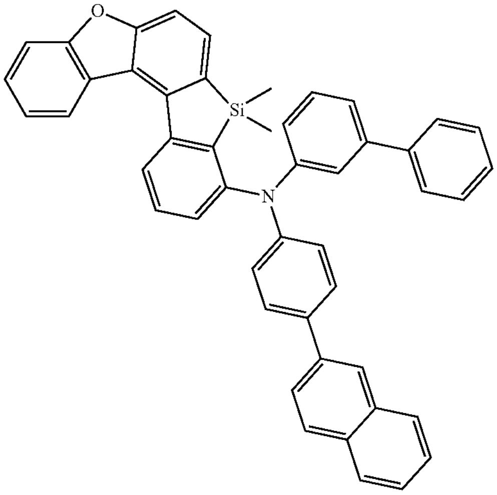
B-87
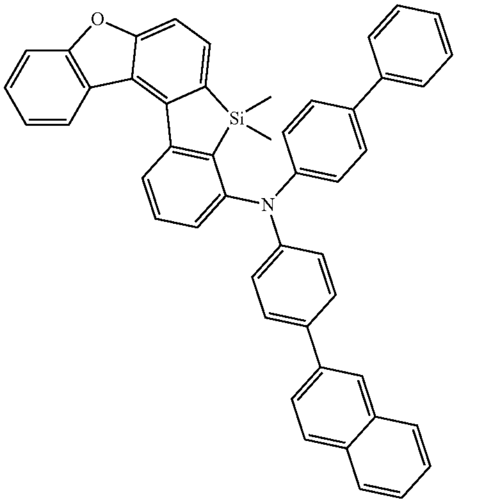
B-88
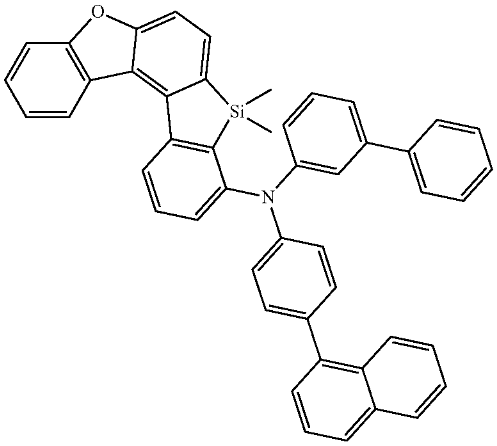

-continued
B-89
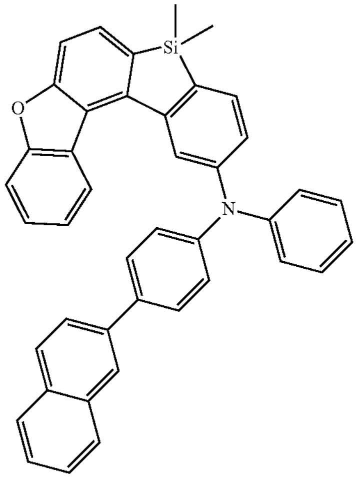
B-90
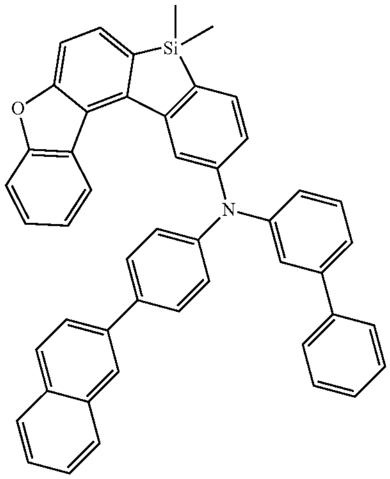
B-91
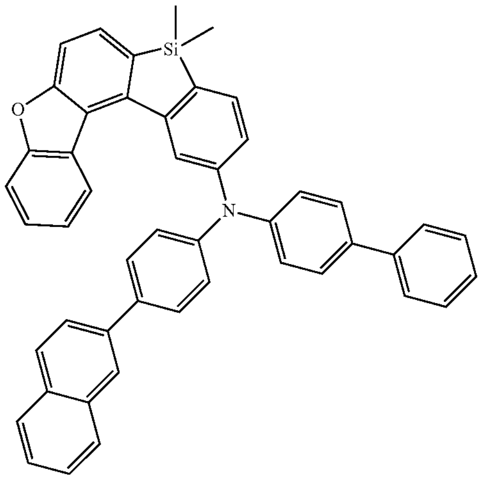
-continued
B-92
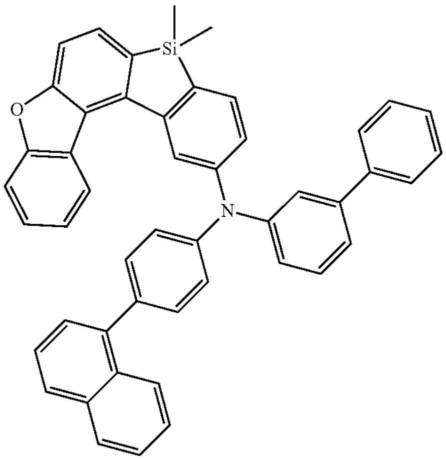
B-93
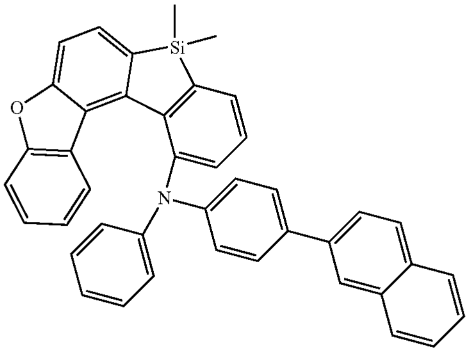
B-94
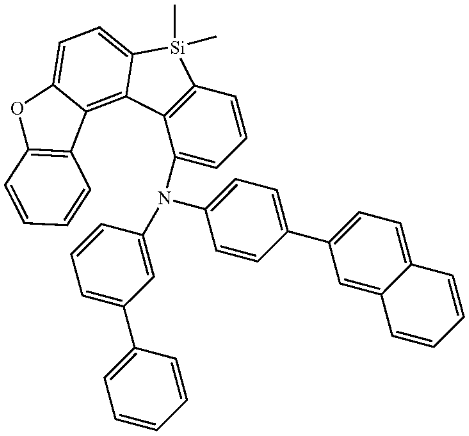

-continued
B-95
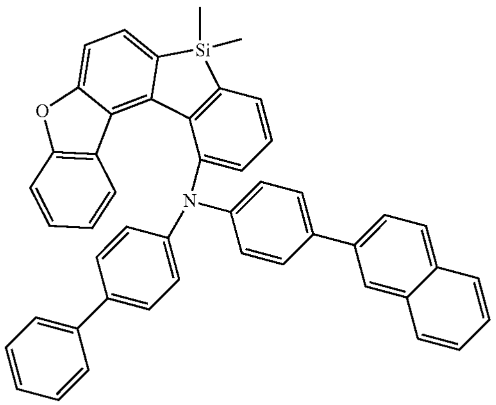
B-96
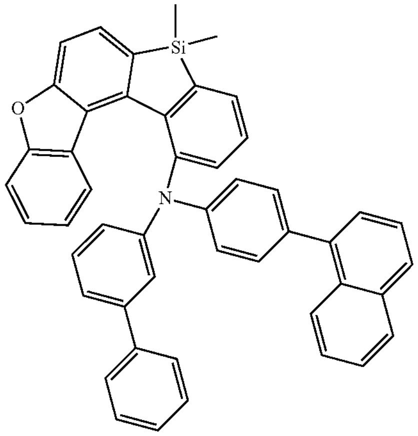
B-97
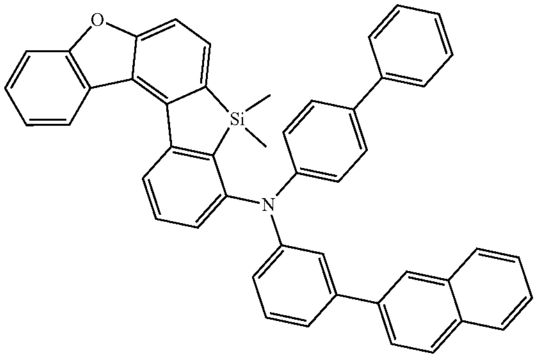
-continued
B-98
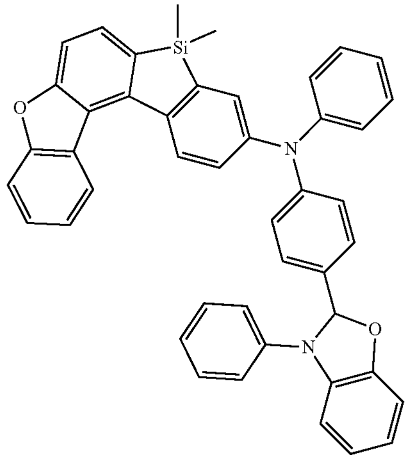
B-99
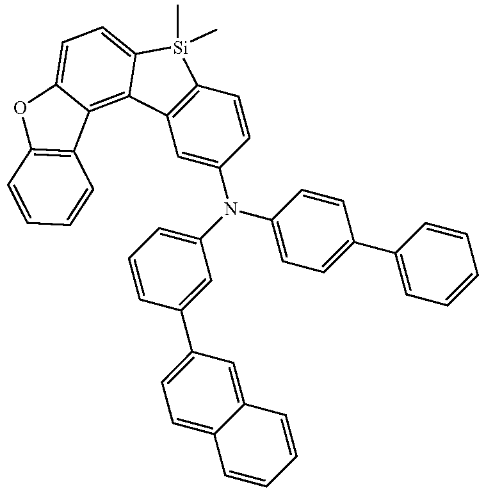
B-100
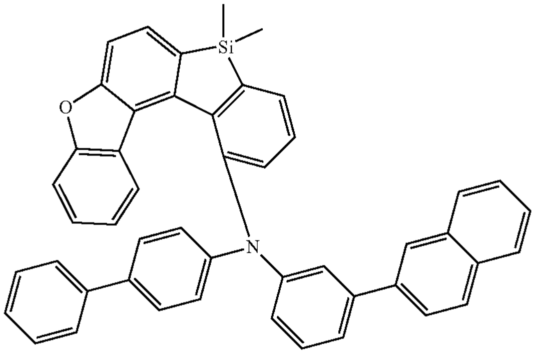

-continued
B-101
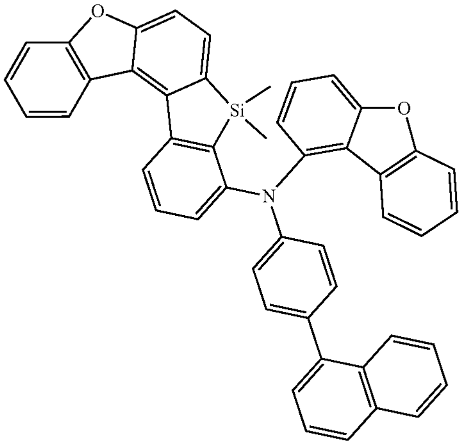
B-102
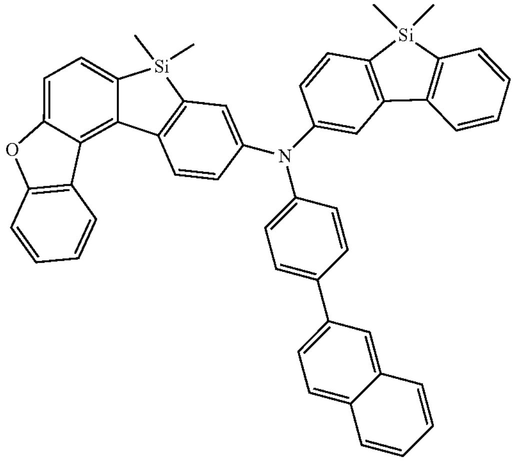
B-103
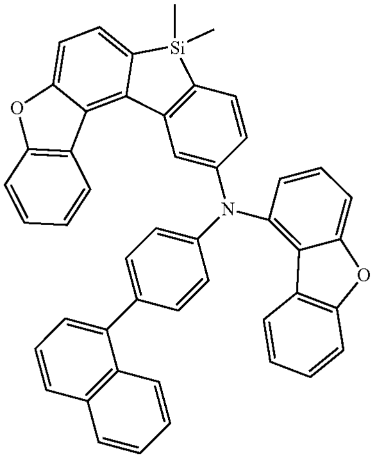
-continued
B-104
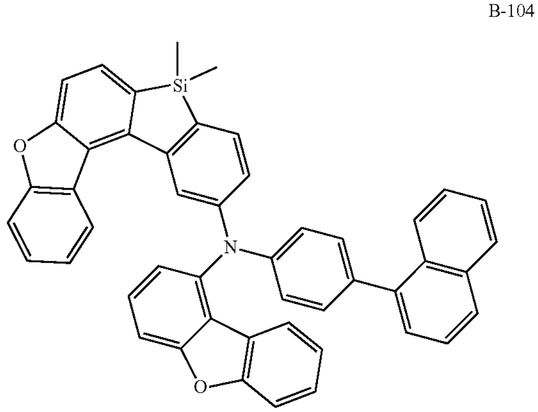
B-105
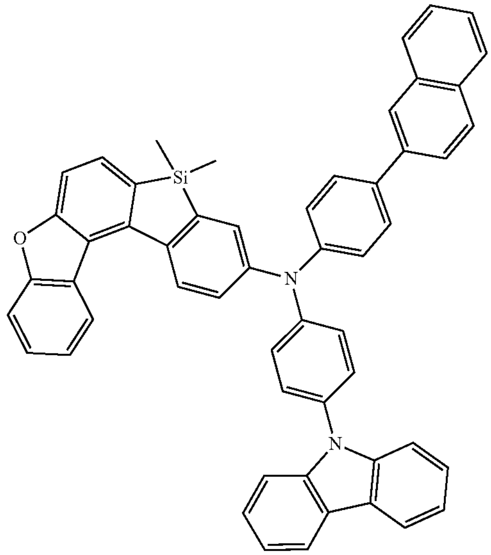
B-106
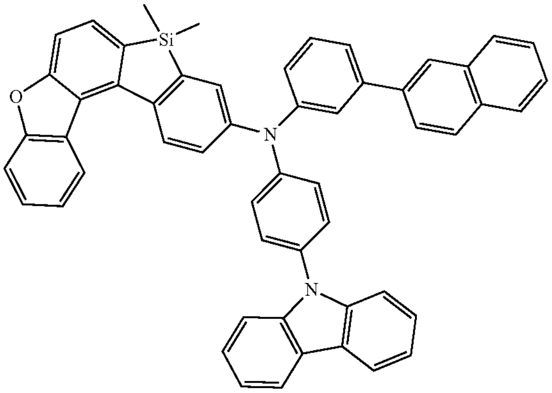

-continued
B-107
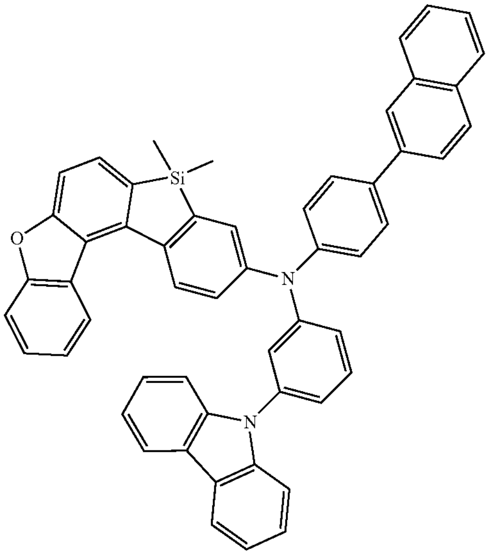
B-108
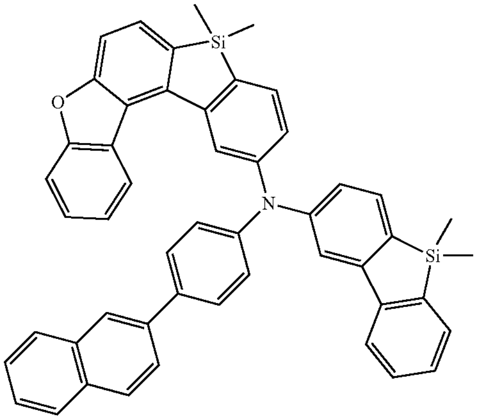
C-1
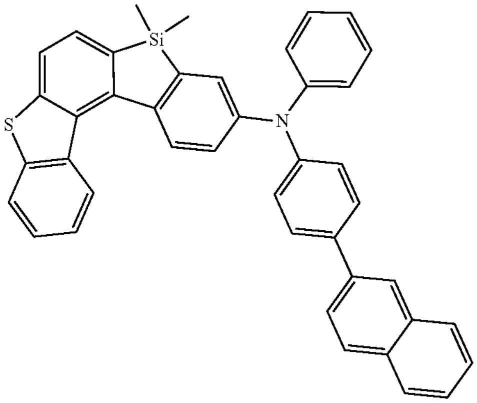
-continued
C-2
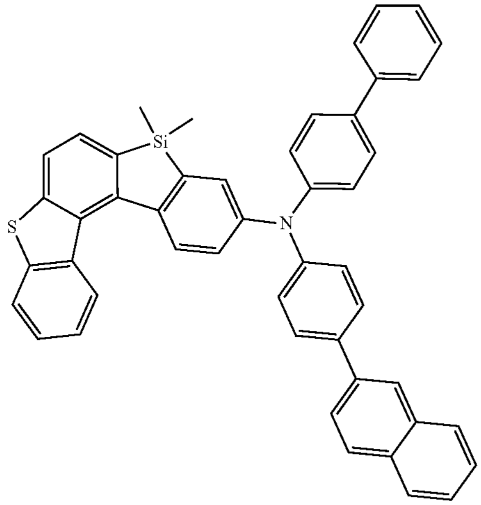
C-3
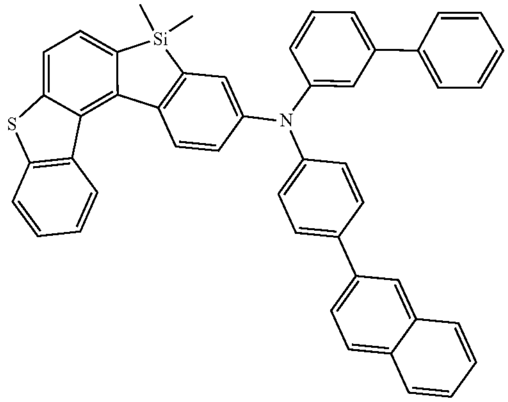
C-4
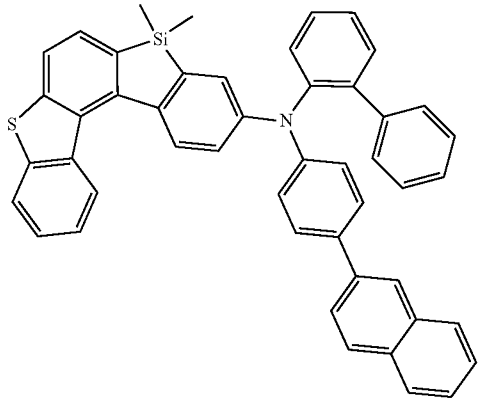

-continued
C-5
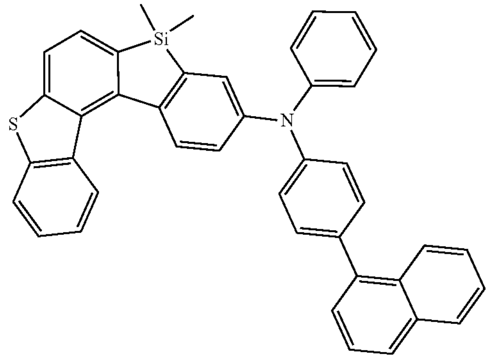
C-6
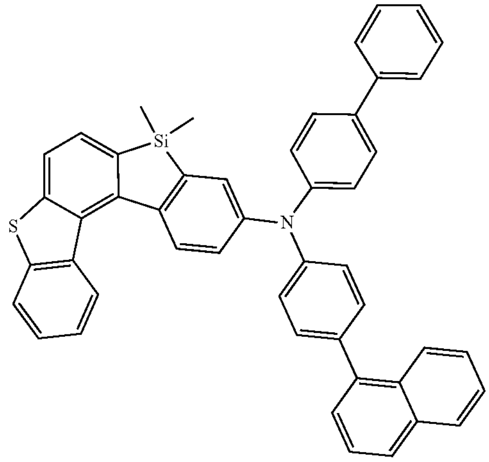
C-7
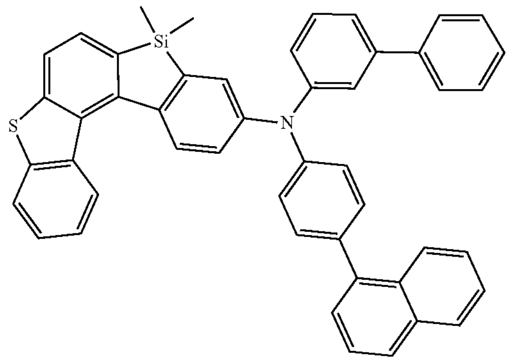
C-8
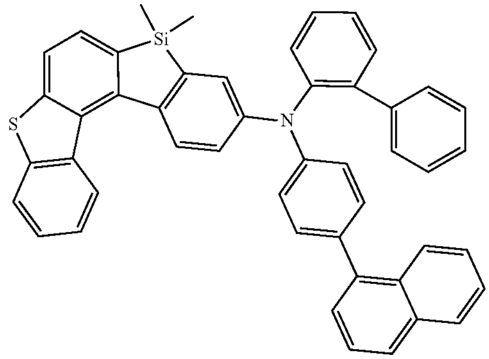
-continued
C-9
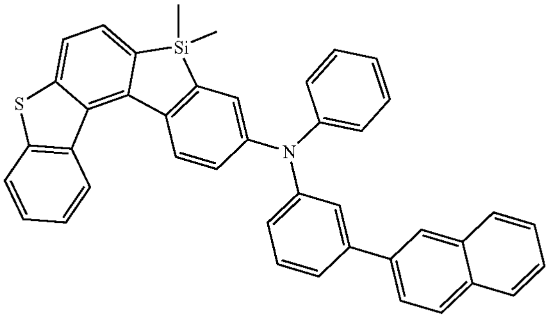
C-10
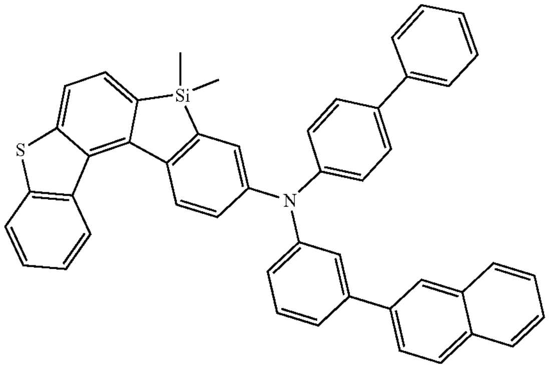
C-11
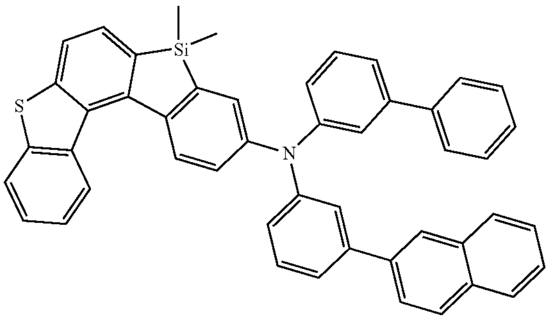
C-12
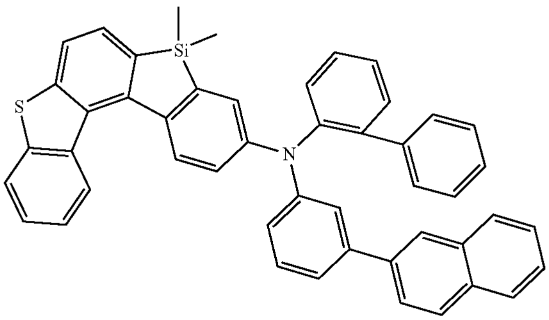

-continued
C-13
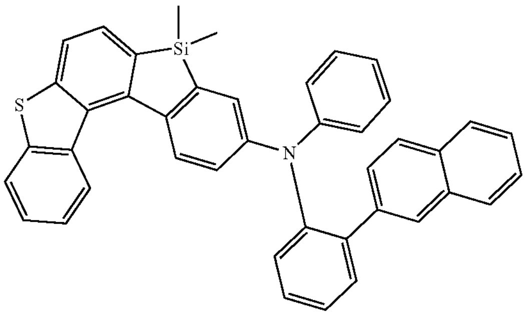
C-14
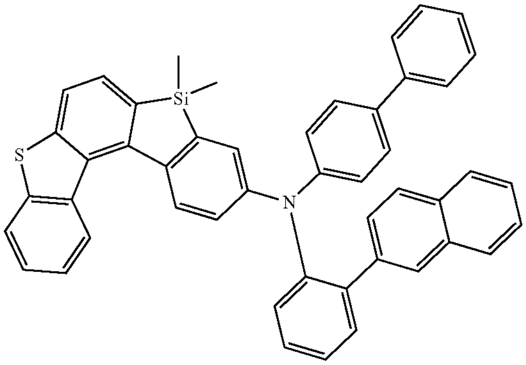
C-15
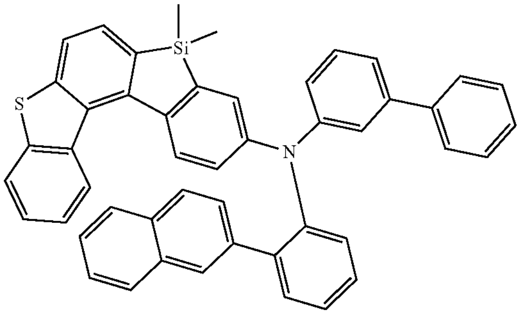
C-16
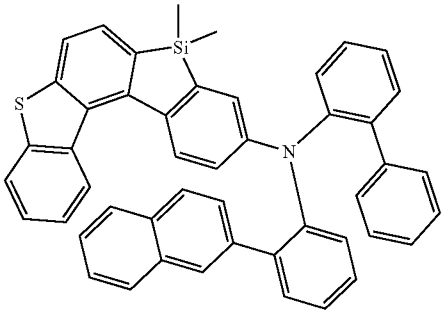
-continued
C-17
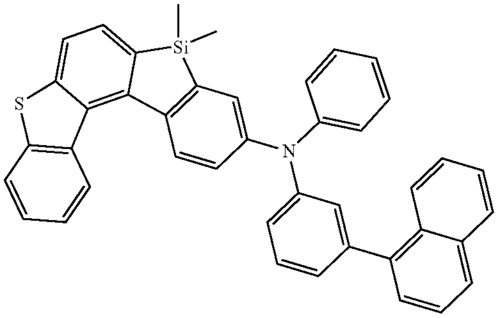
C-18
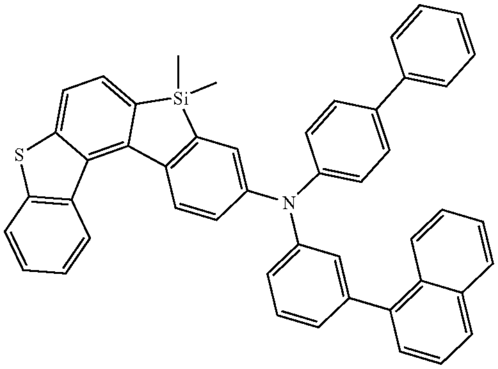
C-19
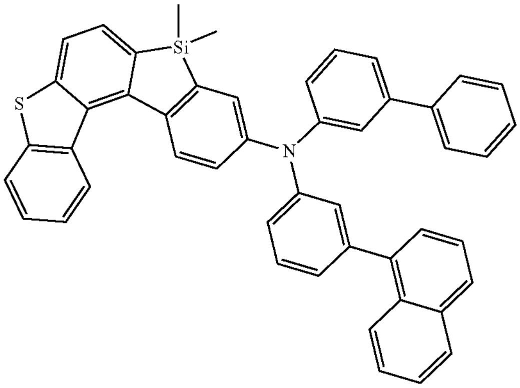
C-20
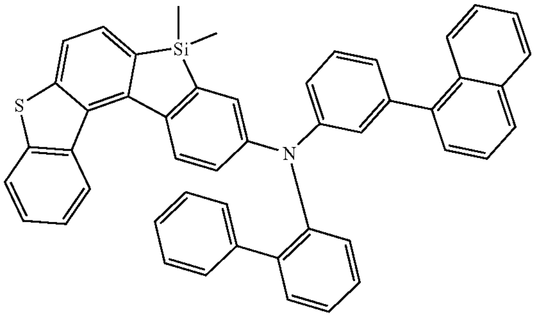

-continued
C-21
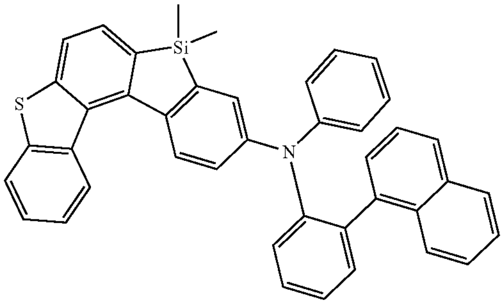
C-22
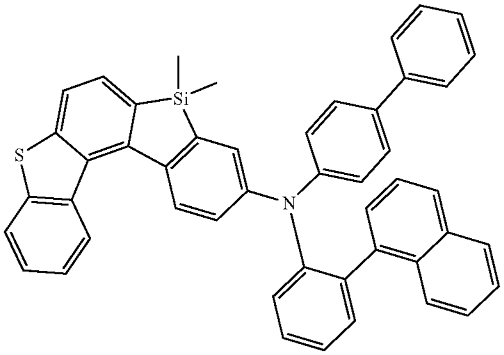
C-23
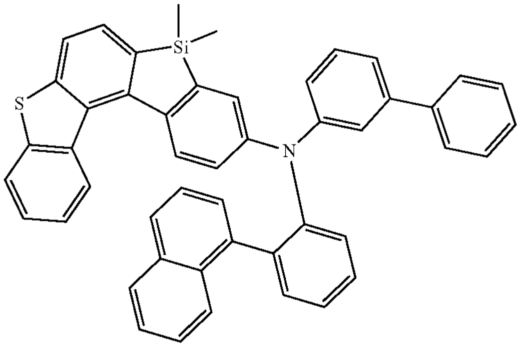
C-24
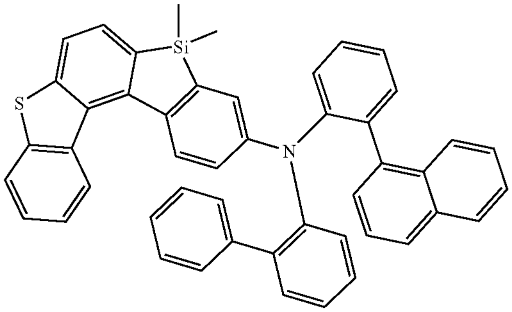
-continued
C-25
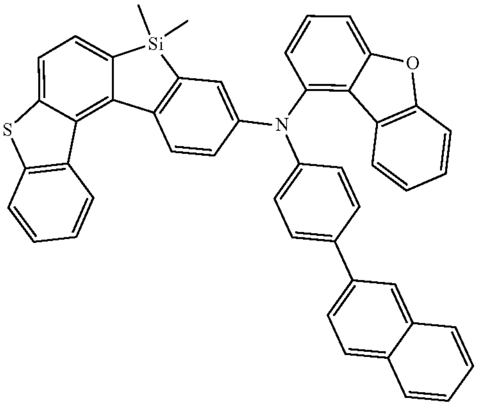
C-26
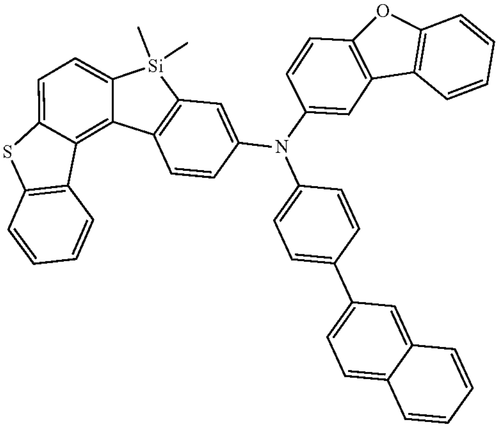
C-27
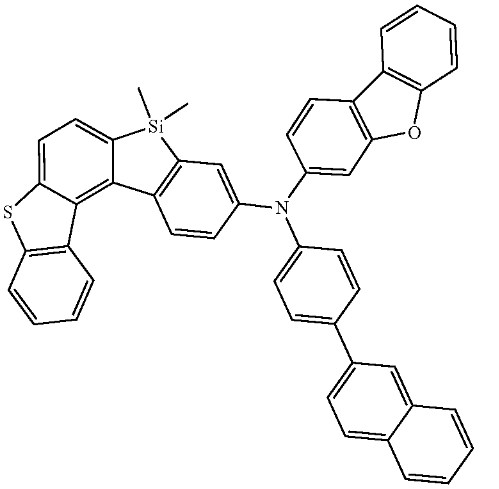

-continued
C-28
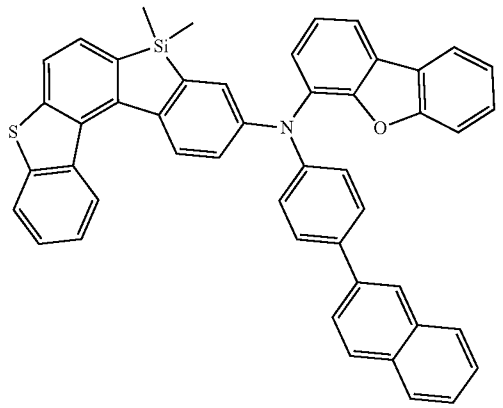
C-29
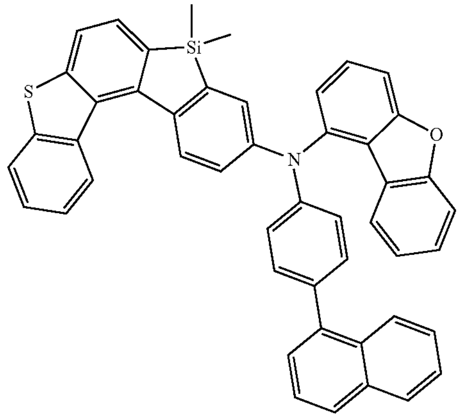
C-30
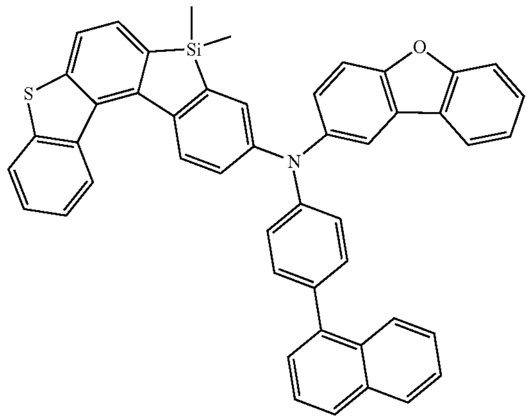
-continued
C-31
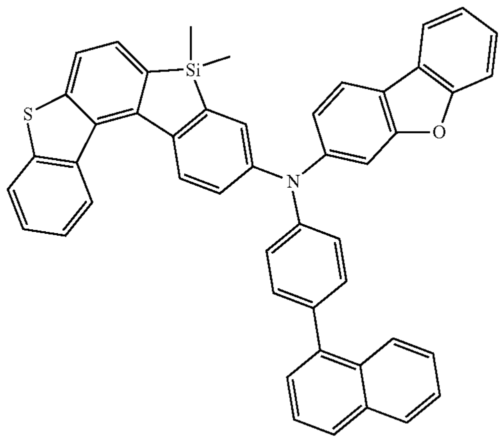
C-32
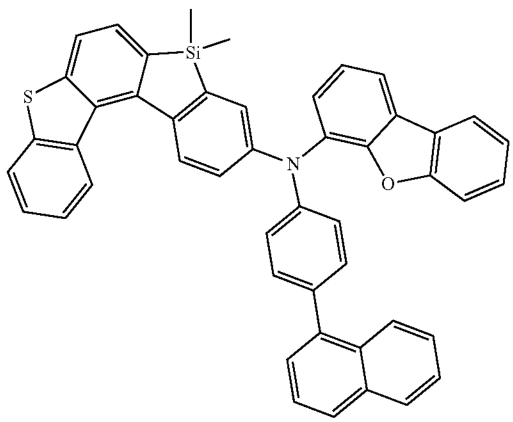
C-33
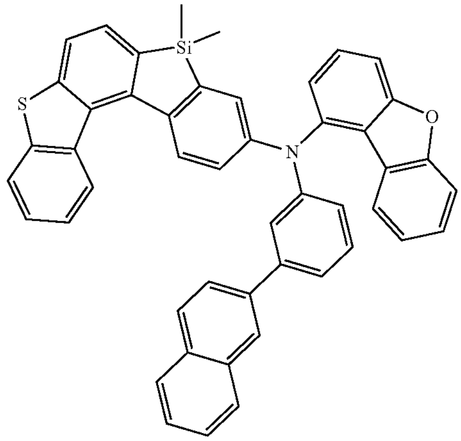

-continued
C-34
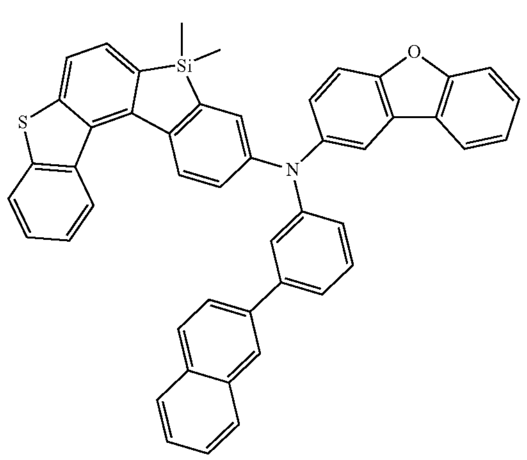
C-35
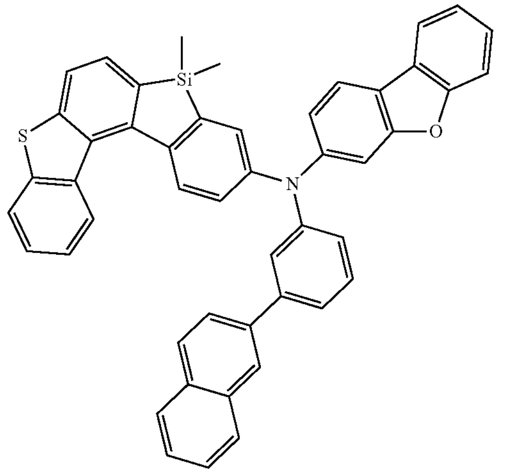
C-36
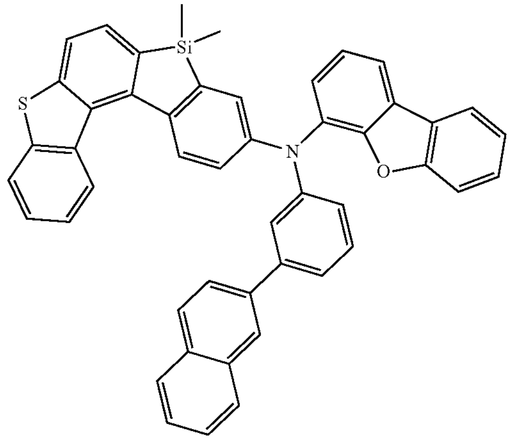
-continued
C-37
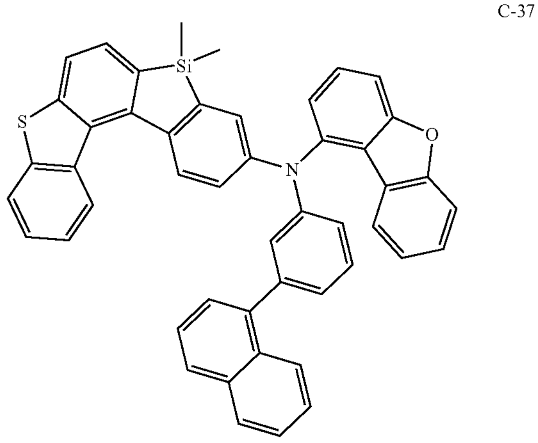
C-38
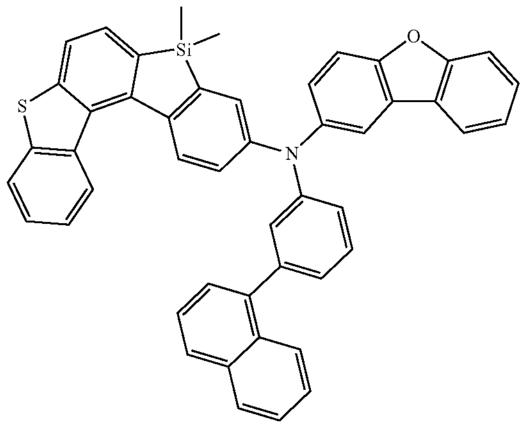
C-39
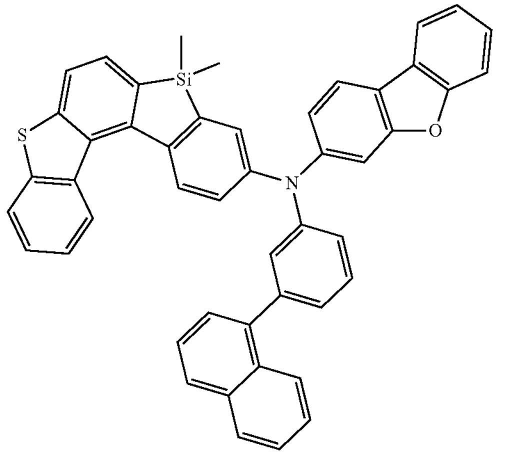

-continued
C-40
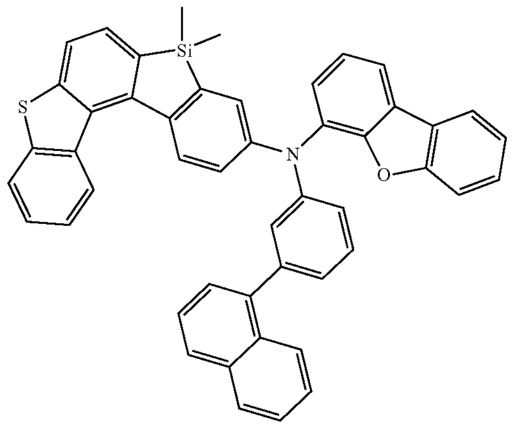
C-41
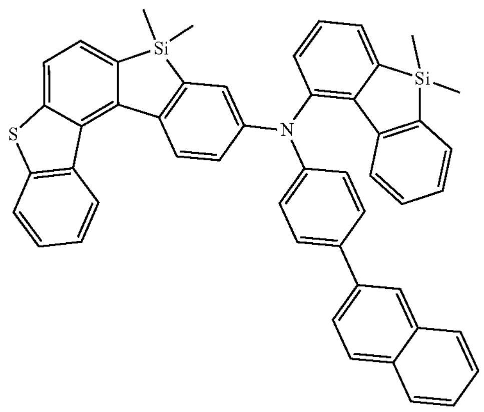
C-42
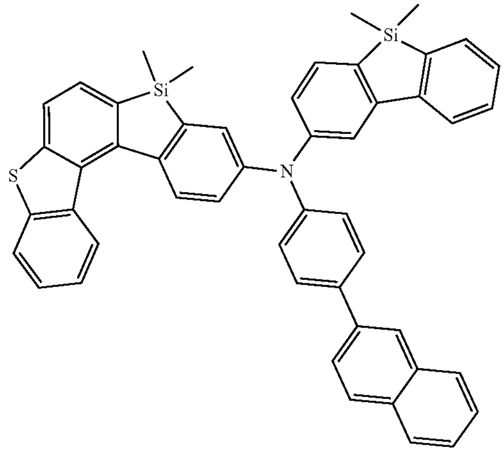
-continued
C-43
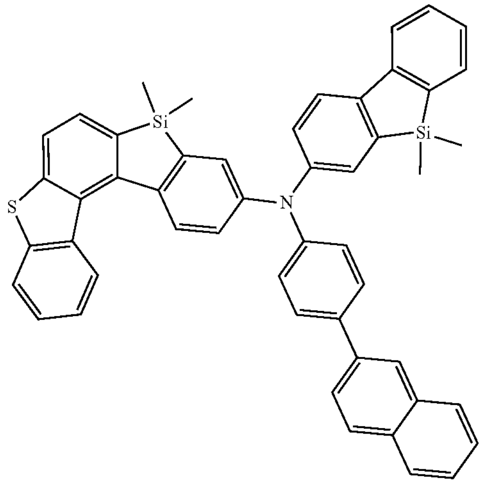
C-44
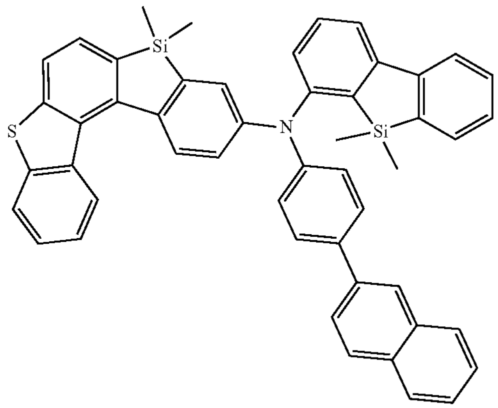
C-45
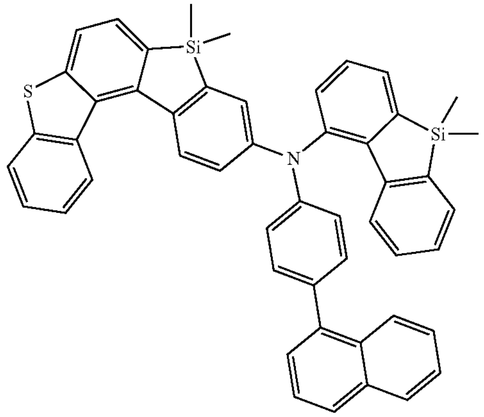

-continued
C-46
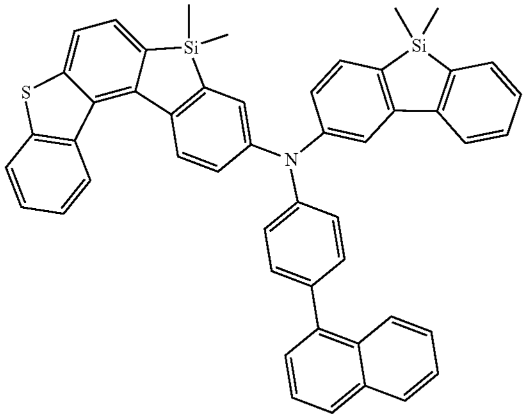
C-47
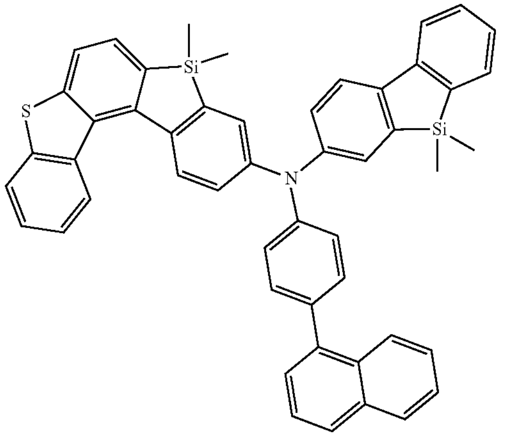
C-48
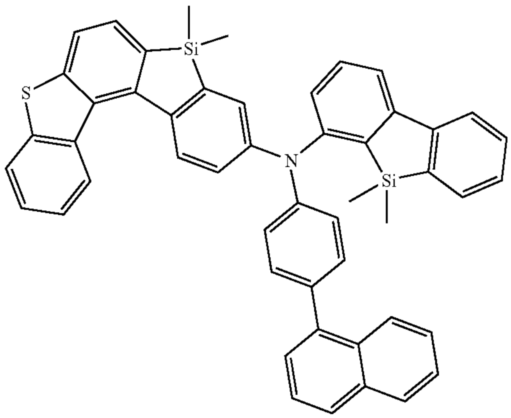
-continued
C-49
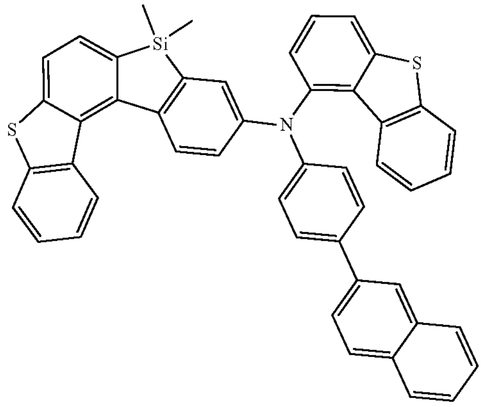
C-50
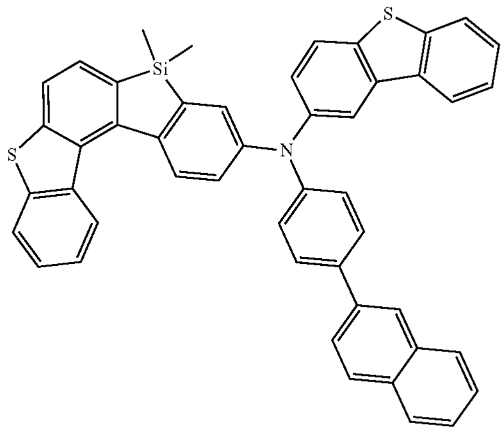
C-51
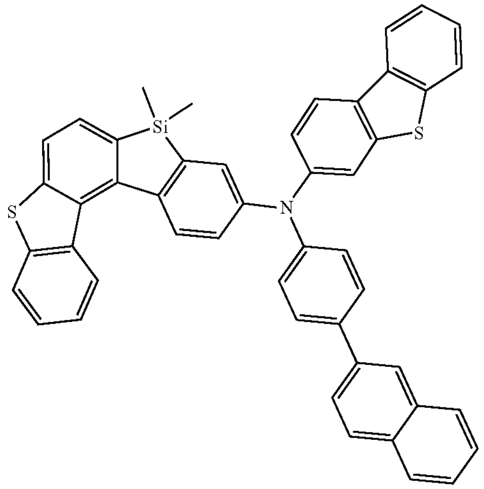

-continued
C-52
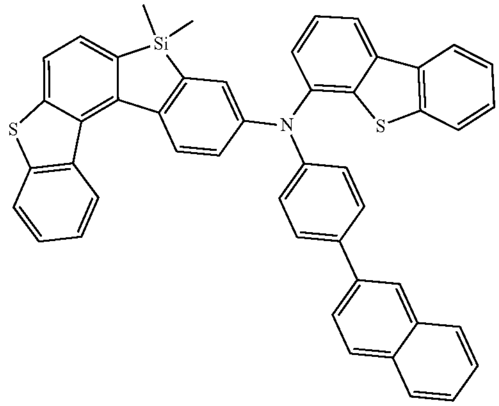
C-53
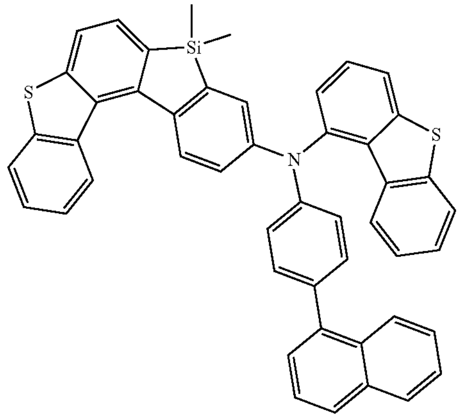
C-54
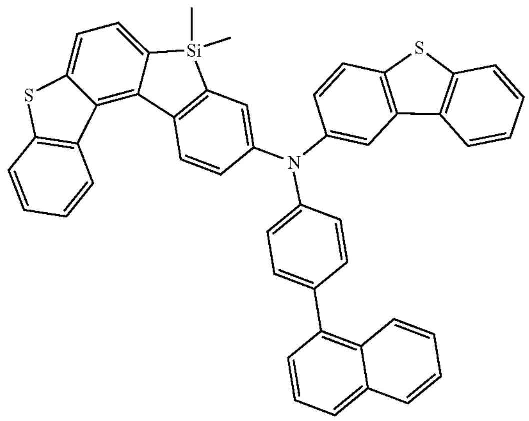
-continued
C-55
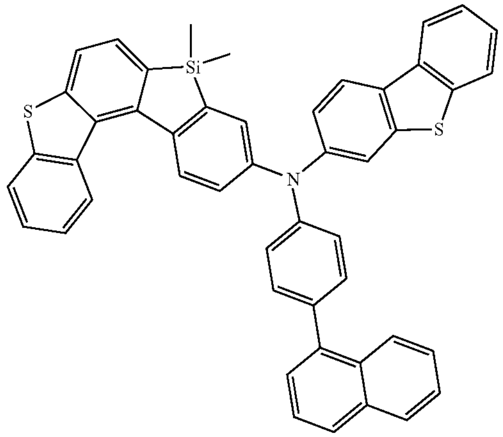
C-56
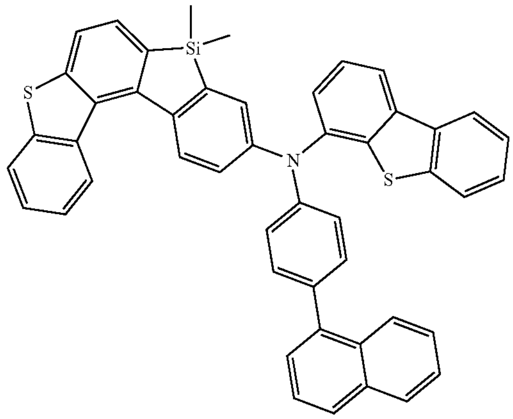
C-57
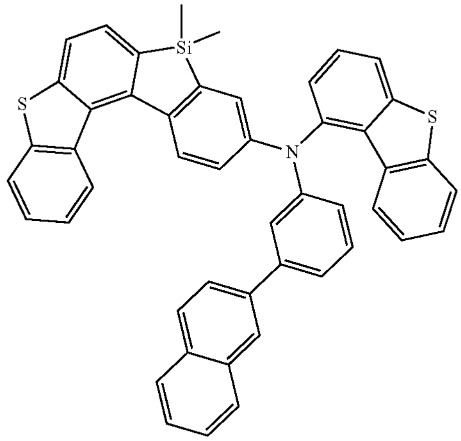

-continued
C-58
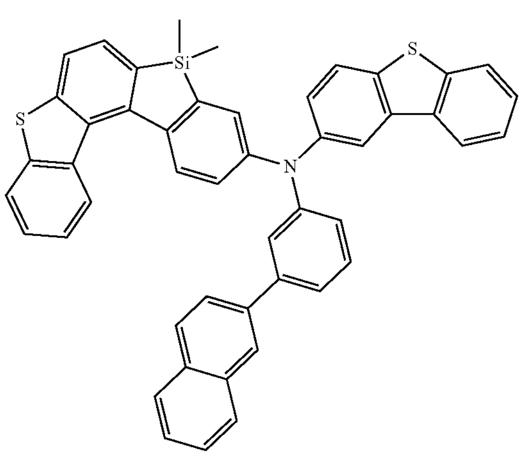
C-59
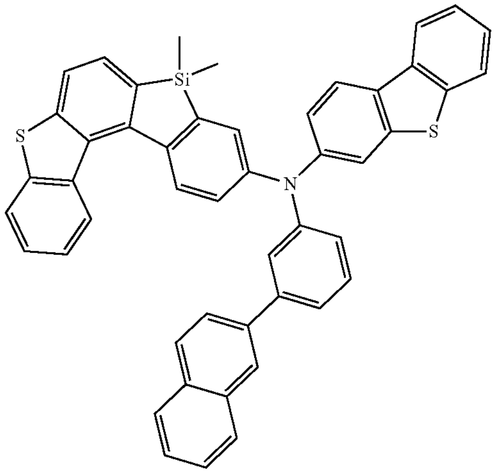
C-60
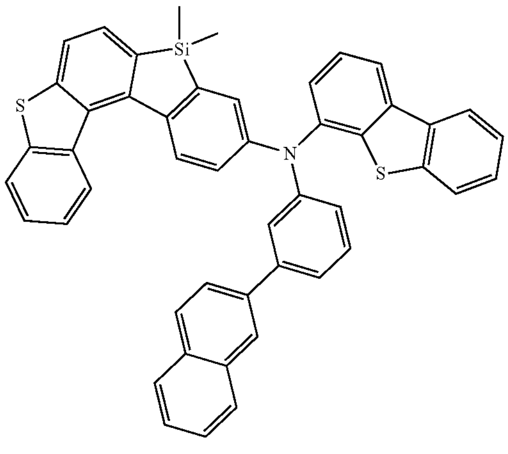
-continued
C-61
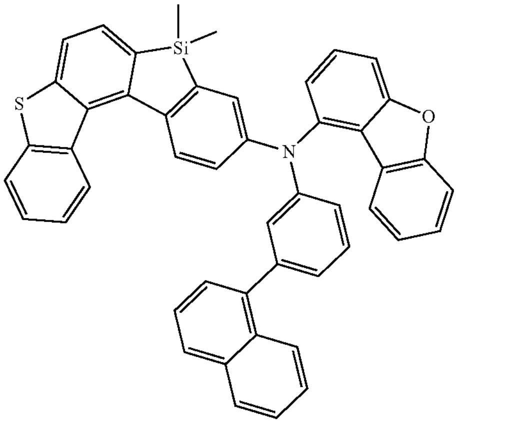
C-62
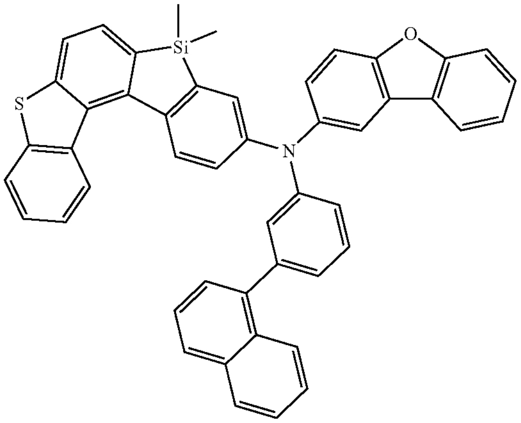
C-63
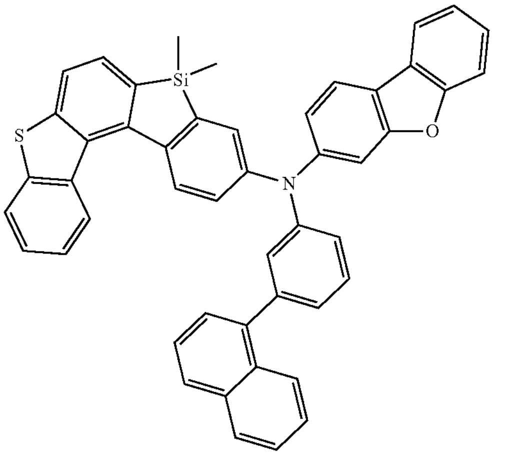

-continued
C-64
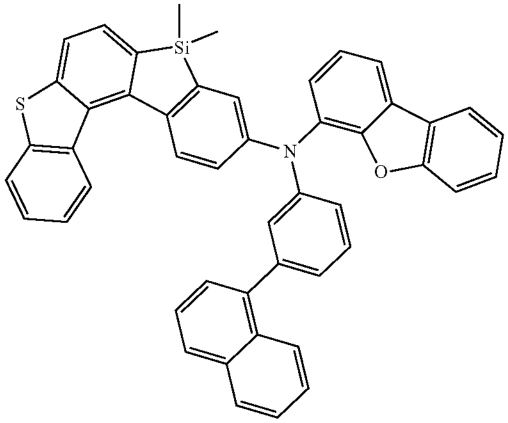
C-65
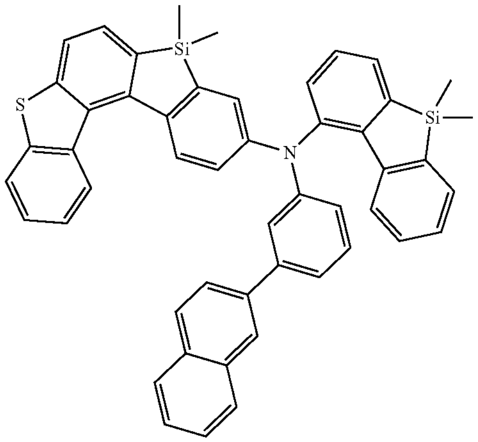
C-66
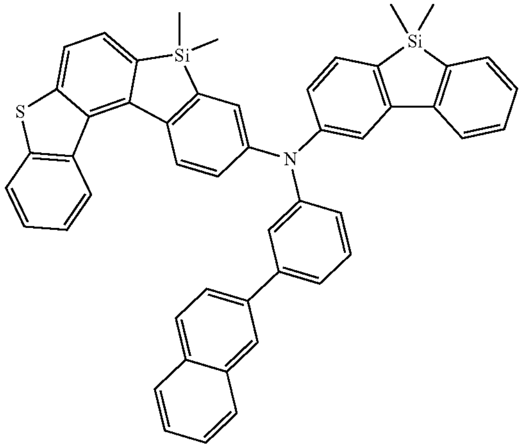
-continued
C-67
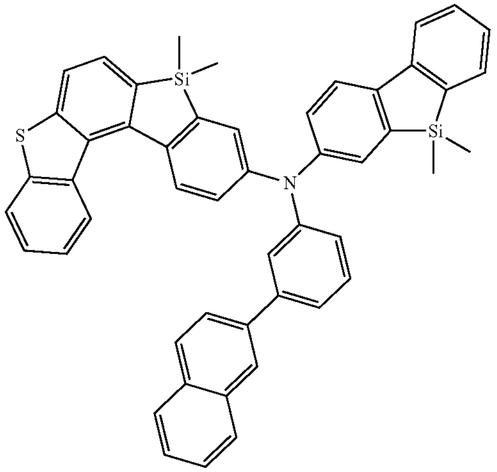
C-68
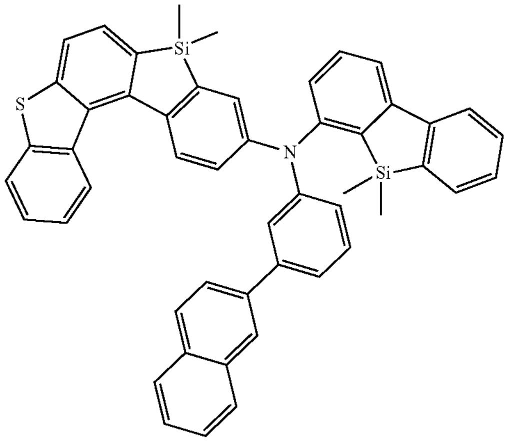
C-69
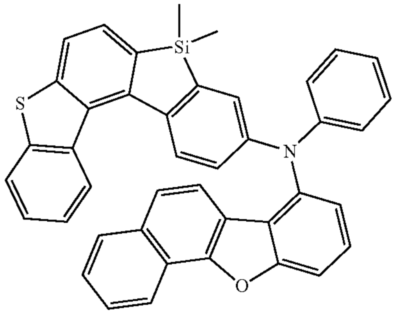
C-70
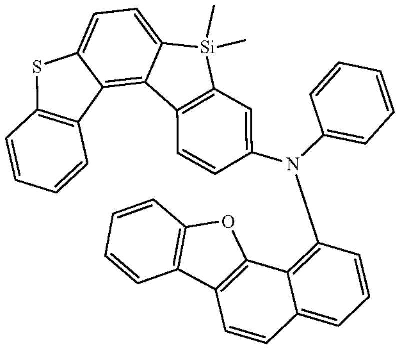

-continued
C-71
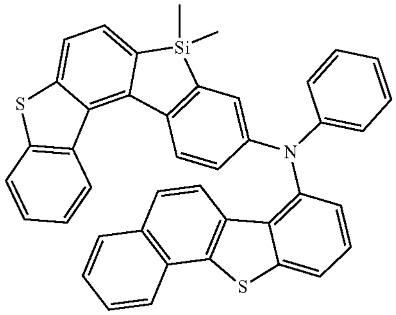
C-72
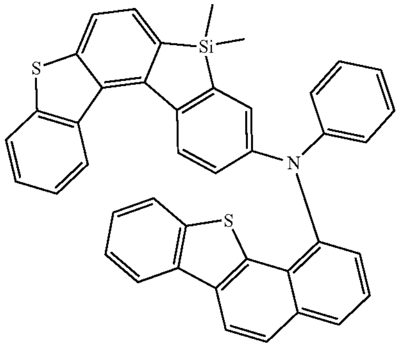
C-73
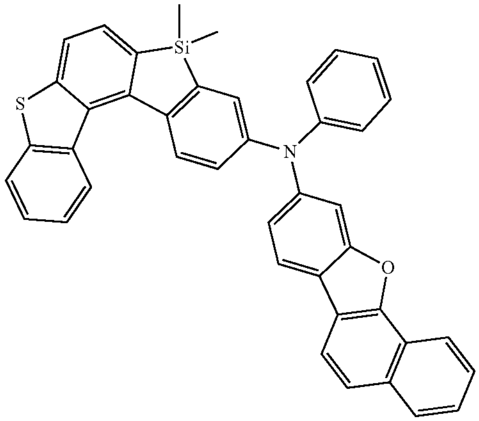
C-74
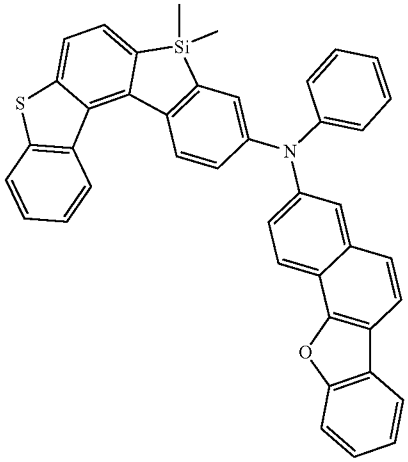
-continued
C-75
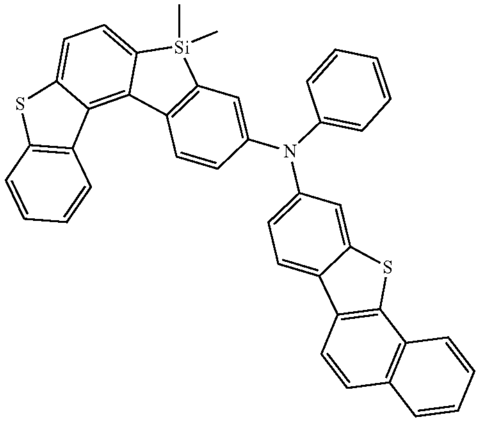
C-76
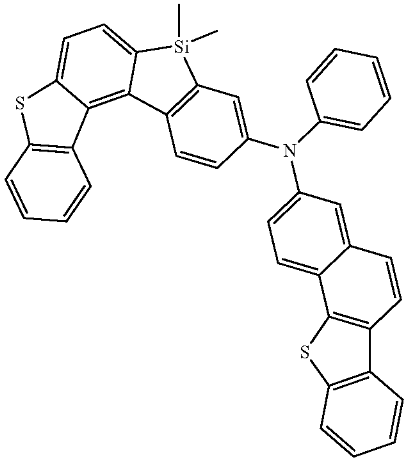
C-77
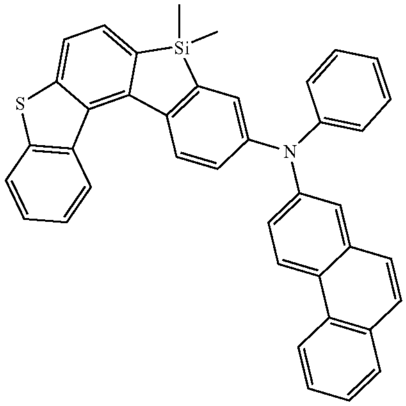
C-78
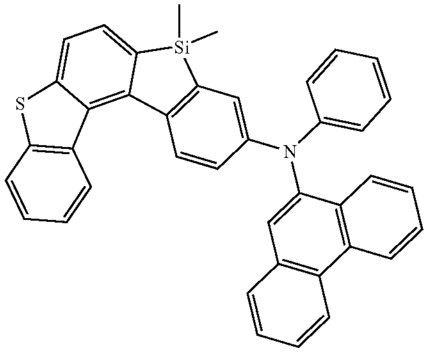

-continued
C-79
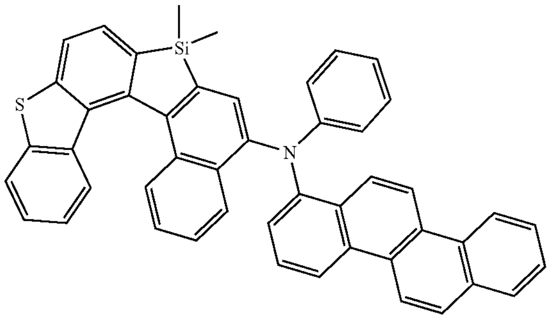
C-80
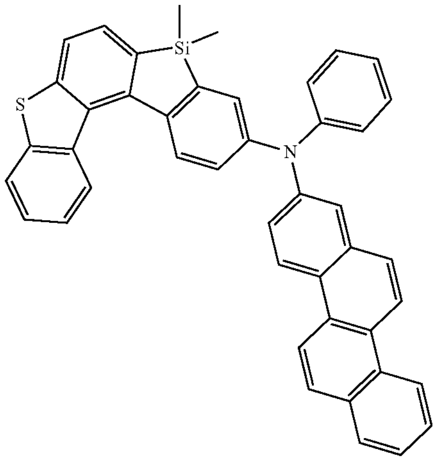
C-81
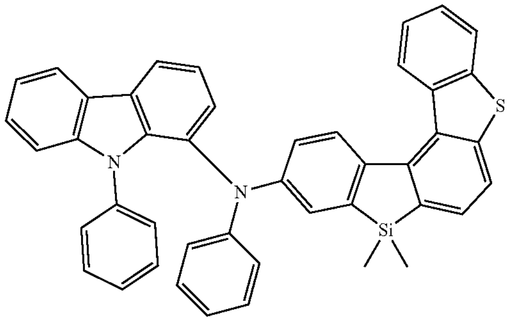
C-82
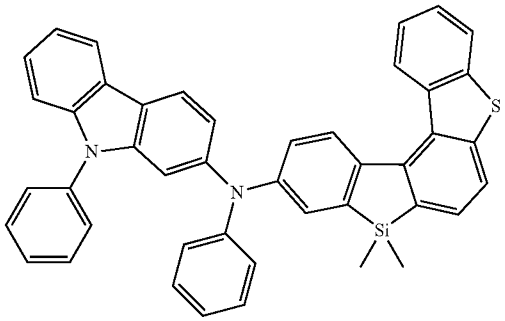
-continued
C-83
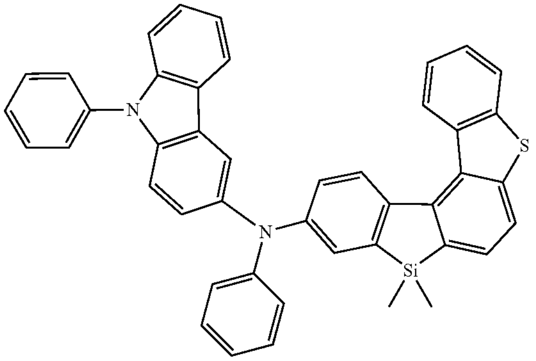
C-84
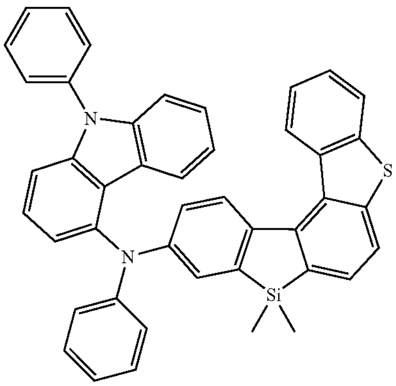
C-85
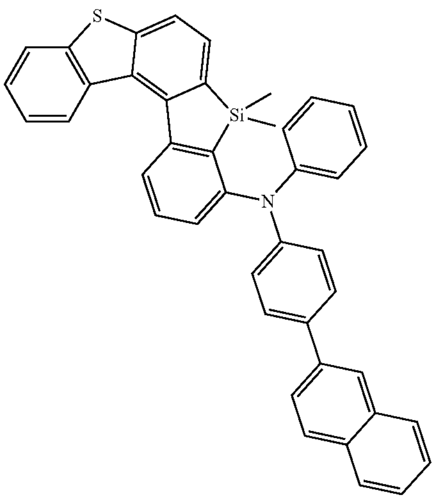

-continued
C-86
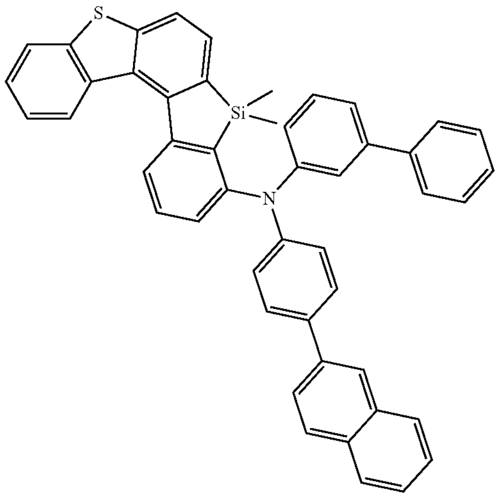
C-87
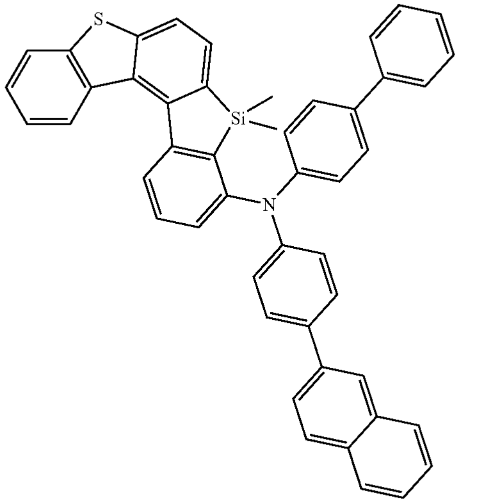
C-88
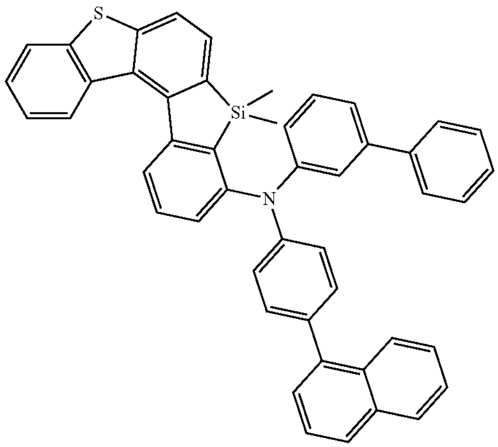
-continued
C-89
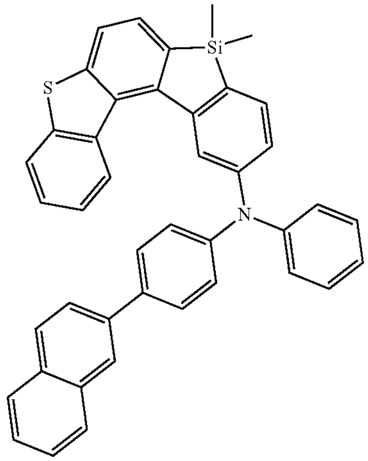
C-90
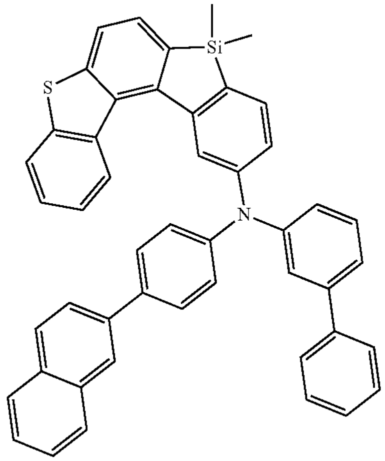
C-91
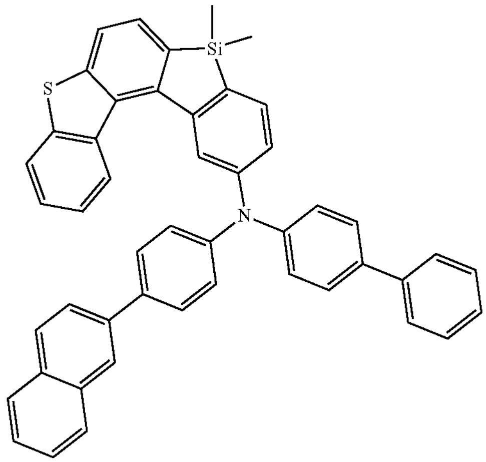

-continued
C-92
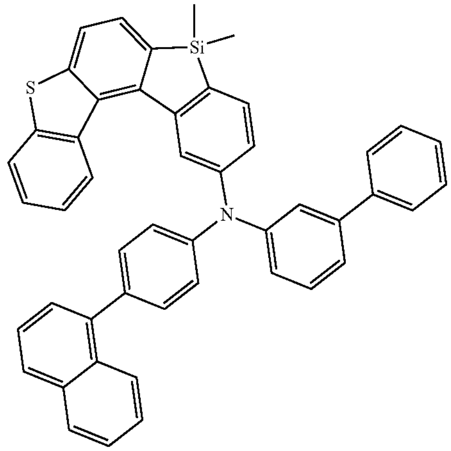
C-93
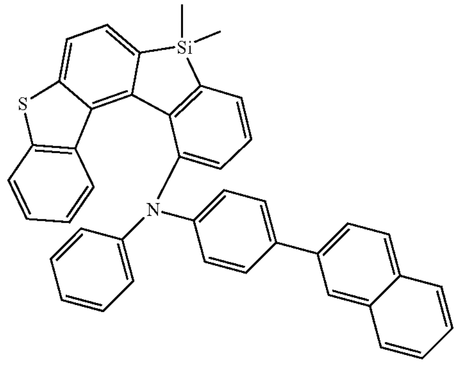
C-94
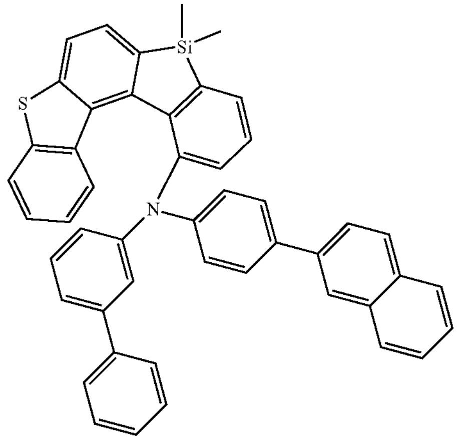
-continued
C-95
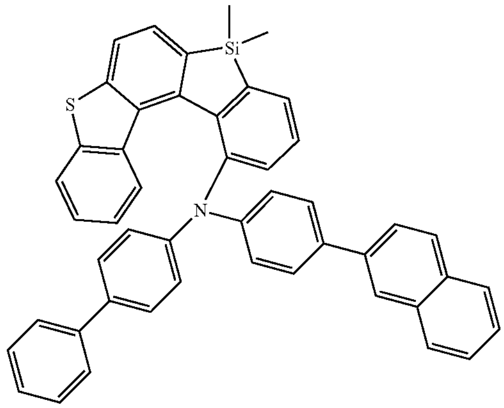
C-96
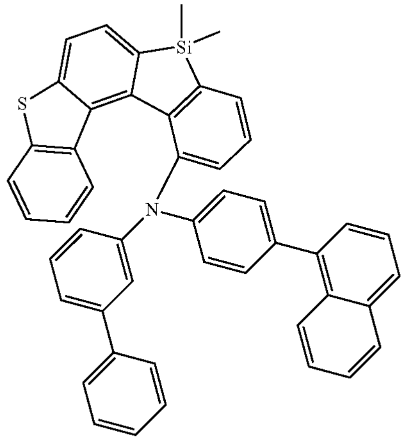
C-97
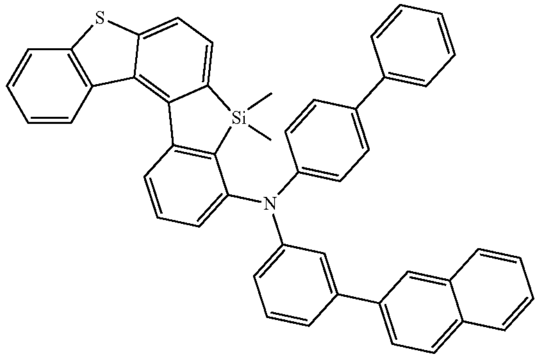

-continued
C-98
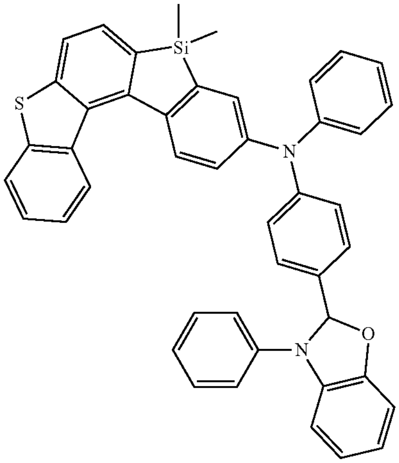
C-99
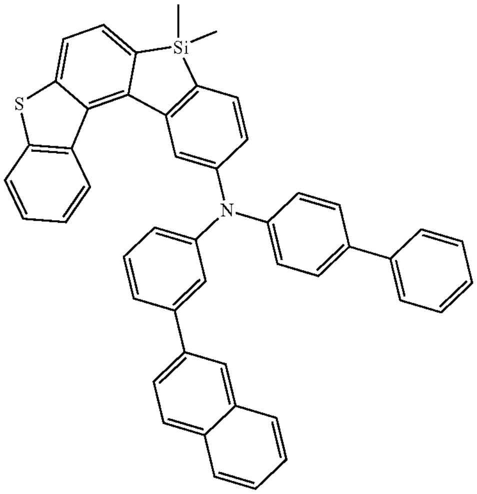
C-100
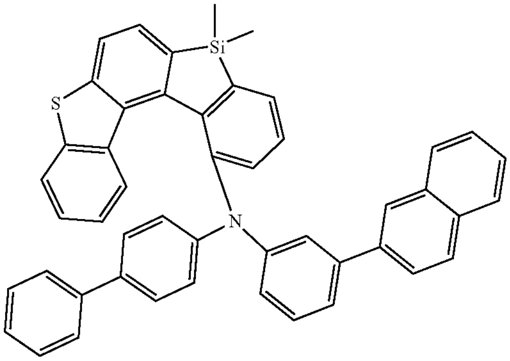
-continued
C-101
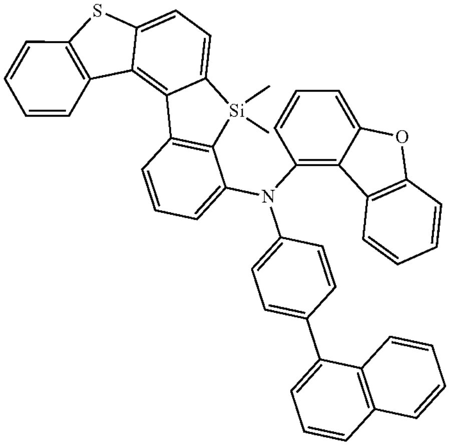
C-102
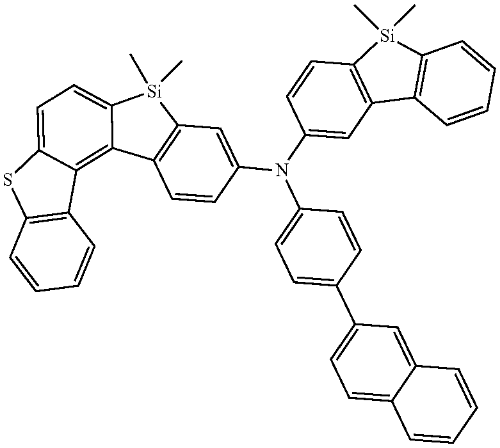
C-103
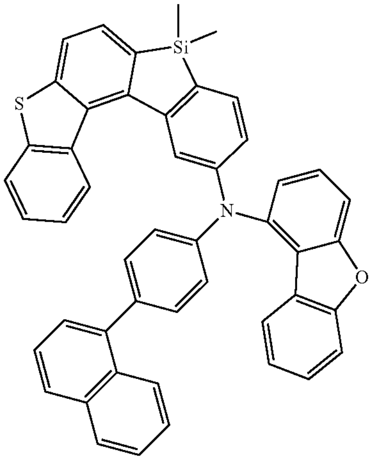

-continued

C-104

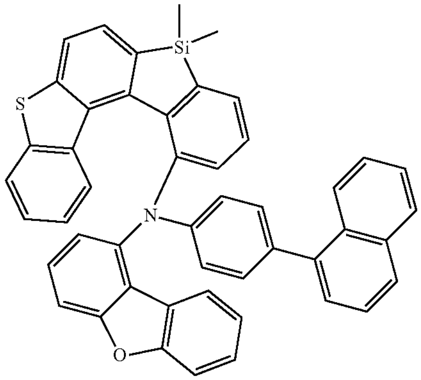

C-105

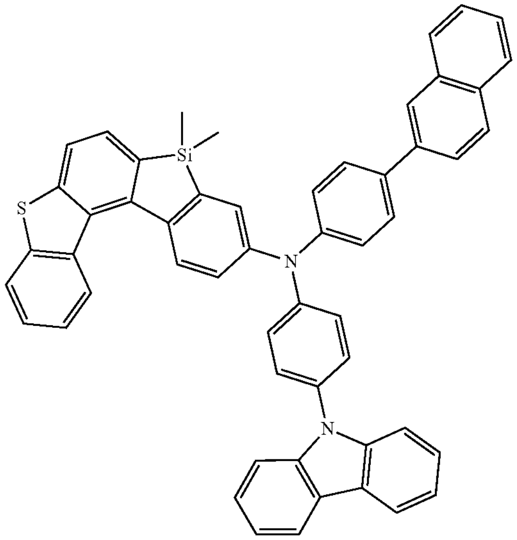

C-106

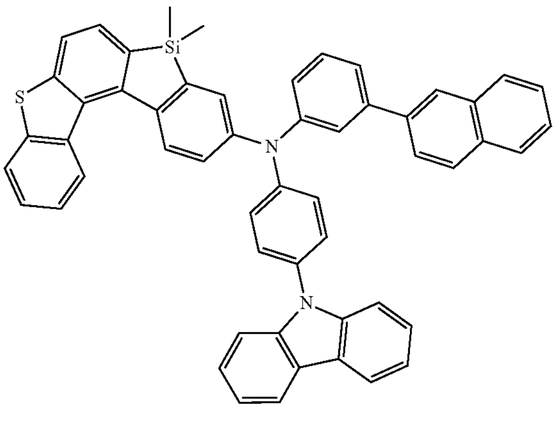

-continued

C-107

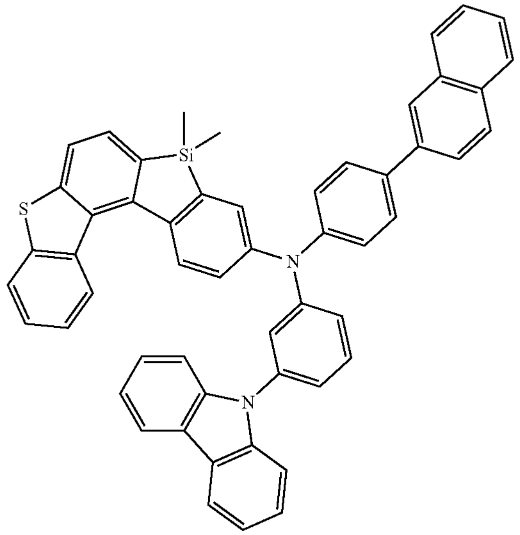

C-108

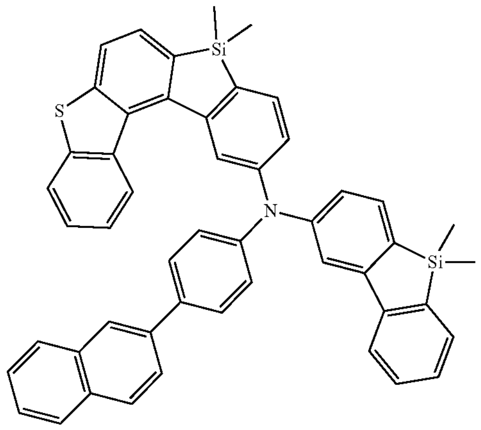

A composition for an organic optoelectronic device according to another embodiment may include, e.g., a first compound, and a second compound. In an implementation, the first compound may be the aforementioned compound for an organic optoelectronic device (e.g., represented by Chemical Formula 1) and the second compound may be, e.g., a compound represented by Chemical Formula 2.

[Chemical Formula 2]

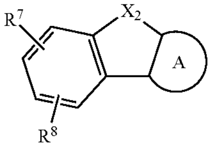

In Chemical Formula 2, $X^2$ may be, e.g., O, S, N-$L^a$-$R^c$, $CR^dR^e$, or $SiR^fR^g$.

$L^a$ may be or may include, e.g., a single bond or a substituted or unsubstituted C6 to C12 arylene group.

$R^c$ may be or may include, e.g., a substituted or unsubstituted C6 to C20 aryl group or a substituted or unsubstituted C2 to C30 heterocyclic group.

$R^d$, $R^e$, $R^f$, and $R^g$ may each independently be or include, e.g., a substituted or unsubstituted C1 to C30 alkyl group or a substituted or unsubstituted C6 to C30 aryl group.

$R^7$ and $R^8$ may each independently be or include, e.g., hydrogen, deuterium, a cyano group, a halogen, a substituted or unsubstituted C1 to C30 alkyl group, a substituted or unsubstituted C6 to C30 aryl group, or a substituted or unsubstituted C2 to C30 heterocyclic group.

A may be, e.g., a ring of Group II.

[Group II]

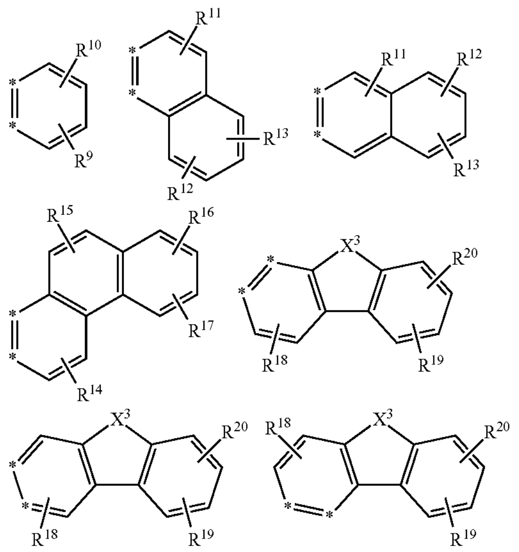

In Group II, * is a linking point.

$X^3$ may be, e.g., O or S.

$R^9$ to $R^{20}$ may each independently be or include, e.g., hydrogen, deuterium, a substituted or unsubstituted C6 to C20 aryl group, or a substituted or unsubstituted C2 to C30 heterocyclic group.

In an implementation, at least one of $R^c$ and $R^7$ to $R^{20}$ may be, e.g., a group represented by Chemical Formula a (e.g., a substituted heterocyclic group).

[Chemical Formula a]

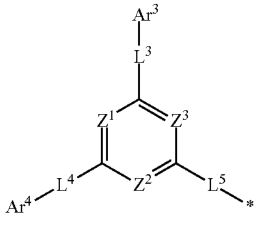

In Chemical Formula a, $Z^1$ to $Z^3$ may each independently be, e.g., N or $CR^h$. In an implementation, at least two of $Z^1$ to $Z^3$ may be N.

$R^h$ may be or may include, e.g., hydrogen, deuterium, a substituted or unsubstituted C1 to C30 alkyl group, or a substituted or unsubstituted C6 to C30 aryl group.

$L^3$ to $L^5$ may each independently be or include, e.g., a single bond or a substituted or unsubstituted C6 to C30 arylene group.

$Ar^3$ and $Ar^4$ may each independently be or include, e.g., a substituted or unsubstituted C6 to C30 aryl group, or a substituted or unsubstituted C2 to C30 heteroaryl group.

* is a linking point.

In an implementation, the second compound may effectively extend a LUMO energy band by being substituted with a nitrogen-containing 6-membered ring, and when used in the light emitting layer together with the aforementioned first compound, a balance of holes and electrons may be increased to help improve luminous efficiency and life-span characteristics of a device including the same, and to lower a driving voltage.

In an implementation, A of Chemical Formula 2 may be a ring of Group II, and the second compound may be, e.g., represented by any one of Chemical Formula 2A to Chemical Formula 2J.

[Chemical Formula 2A]

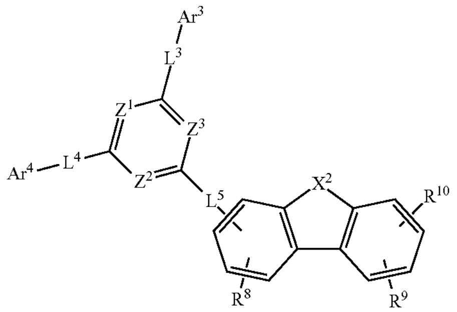

[Chemical Formula 2B]

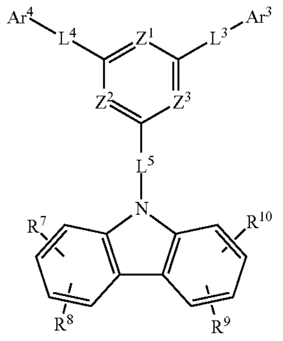

[Chemical Formula 2C]

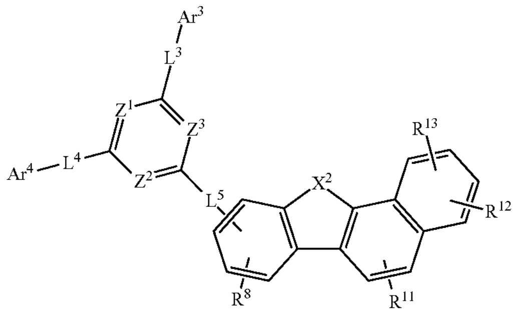

-continued

[Chemical Formula 2D]

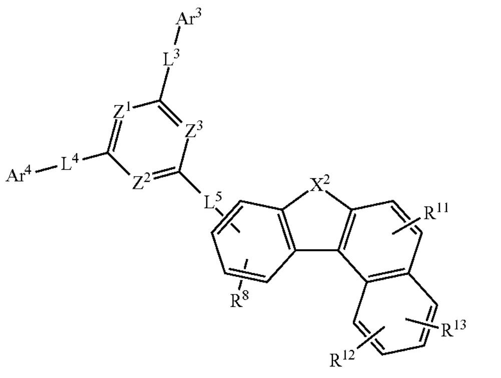

[Chemical Formula 2E]

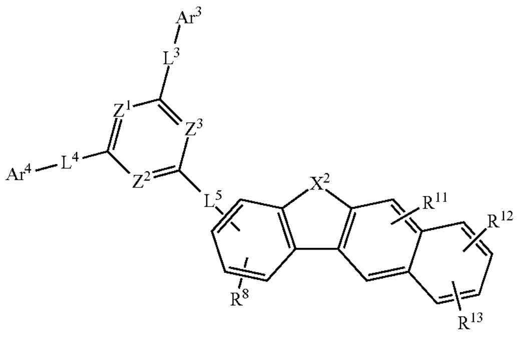

[Chemical Formula 2F]

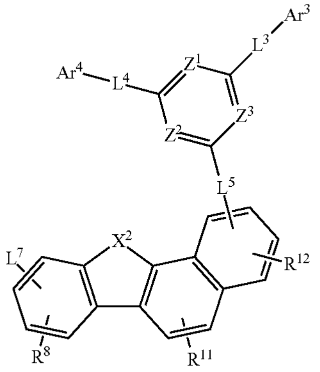

[Chemical Formula 2G]

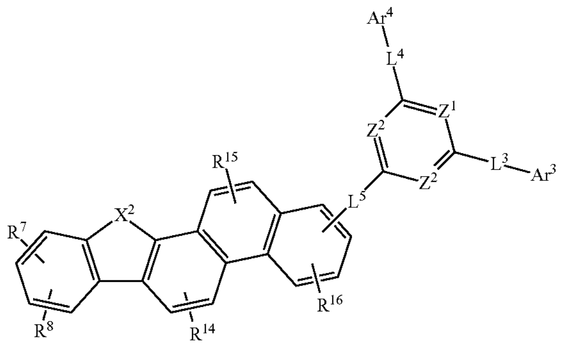

-continued

[Chemical Formula 2H]

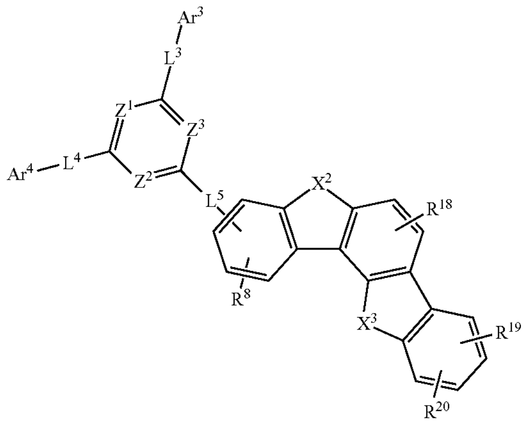

[Chemical Formula 2I]

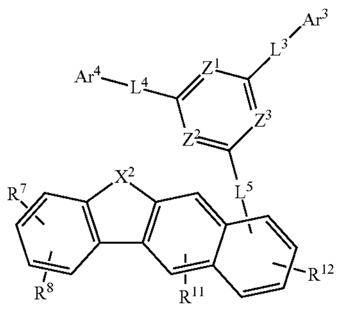

[Chemical Formula 2J]

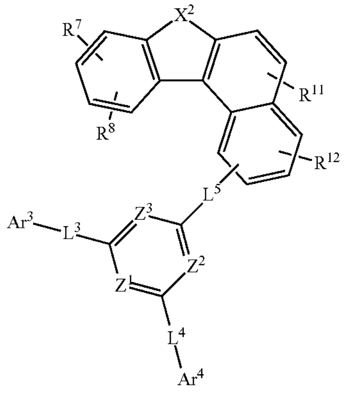

In Chemical Formula 2A to Chemical Formula 2J, $X^2$, $X^3$, $Z^1$ to $Z^3$, $R^7$ to $R^{16}$, $R^{18}$ to $R^{20}$, $L^3$ to $L^5$, $Ar^3$, and $Ar^4$ may be defined the same as those of Chemical Formula 2, described above.

In an implementation, Chemical Formula 2 may be represented by, e.g., Chemical Formula 2A-3, Chemical Formula 2C-1, Chemical Formula 2F-1, or Chemical Formula 2F-3.

[Chemical Formula 2A-3]

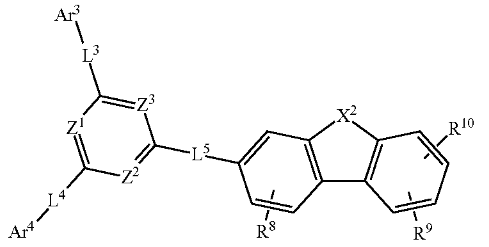

[Chemical Formula 2C-1]

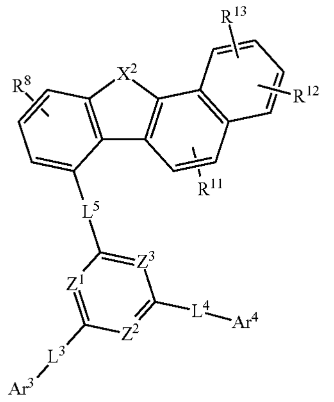

[Chemical Formula 2F-1]

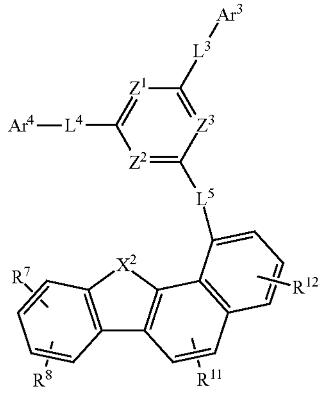

[Chemical Formula 2F-3]

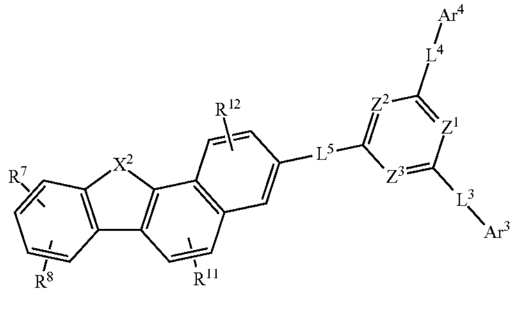

In Chemical Formula 2A-3, Chemical Formula 2C-1, Chemical Formula 2F-1, and Chemical Formula 2F-3, $X^2$, $Z^1$ to $Z^3$, $R^7$ to $R^{13}$, $L^3$ to $L^5$, $Ar^3$, and $Ar^4$ may be defined the same as those of Chemical Formula 2, described above.

In an implementation, $Ar^3$ and $Ar^4$ may each independently be, e.g., a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, or a substituted or unsubstituted dibenzosilolyl group.

In an implementation, $Ar^3$ and $Ar^4$ may each independently be, e.g., a substituted or unsubstituted phenyl group, a substituted or unsubstituted biphenyl group, or a substituted or unsubstituted naphthyl group.

In an implementation, $L^3$ to $L^5$ may each independently be, e.g., a single bond, a substituted or unsubstituted phenylene group, or a substituted or unsubstituted naphthylene group.

In an implementation, moieties $*-L^3-Ar^3$ and $*-L^4-Ar^4$ may each independently be, e.g., a moiety of Group I.

In an implementation, $R^7$ to $R^{20}$ may each independently be, e.g., hydrogen, deuterium, a cyano group, a substituted or unsubstituted C1 to C10 alkyl group, a substituted or unsubstituted C6 to C12 aryl group, or a substituted or unsubstituted C2 to C18 heterocyclic group.

In an implementation, $R^7$ to $R^{20}$ may each independently be, e.g., hydrogen, deuterium, a substituted or unsubstituted phenyl group, a substituted or unsubstituted biphenyl group, a substituted or unsubstituted naphthyl group, or a group represented by Chemical Formula a, and at least one of $R^7$ to $R^{20}$ may be a group represented by Chemical Formula a.

In an implementation, $X^2$ may be, e.g., O, S, $CR^dR^e$, or $SiR^fR^g$, and $R^d$, $R^e$, $R^f$, and $R^g$ may each independently be, e.g., a substituted or unsubstituted C1 to C10 alkyl group or a substituted or unsubstituted C6 to C20 aryl group.

In an implementation, $R^d$, $R^e$, $R^f$, and $R^g$ may each independently be, e.g., an unsubstituted methyl group, a substituted or unsubstituted phenyl group, or a substituted or unsubstituted biphenyl group.

In an implementation, the second compound may be, e.g., a compound of Group 2.

[Group 2]

A-1

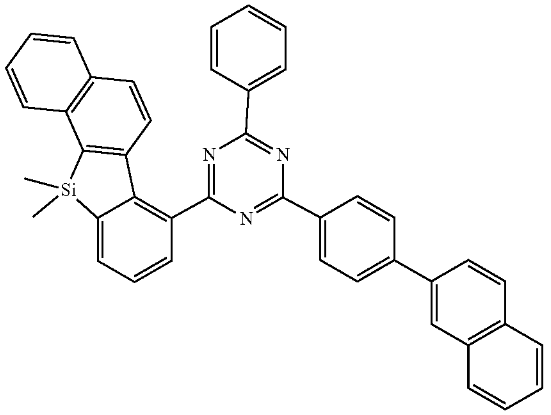

A-2
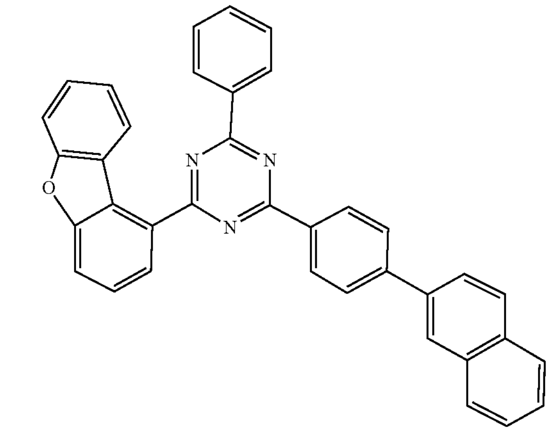
A-3
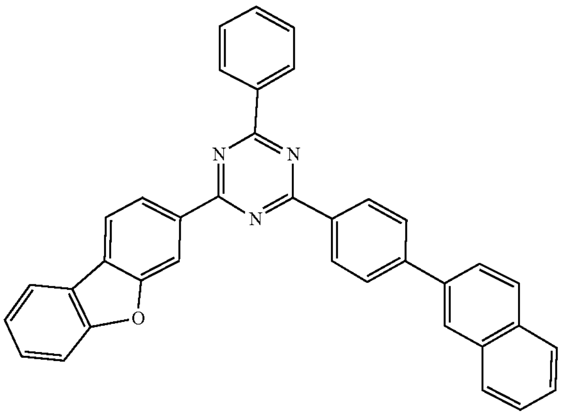
A-4
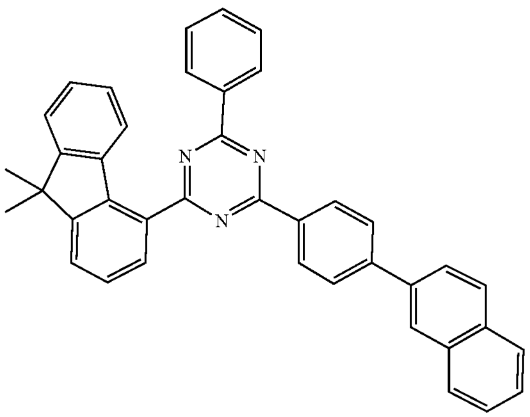
A-5
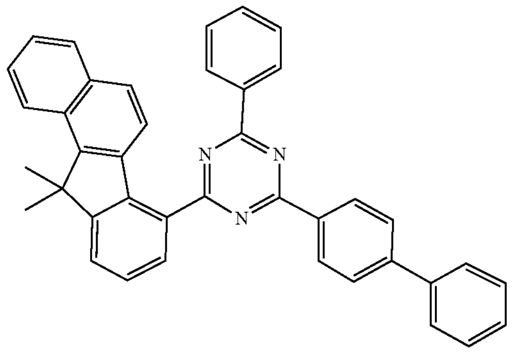
A-6
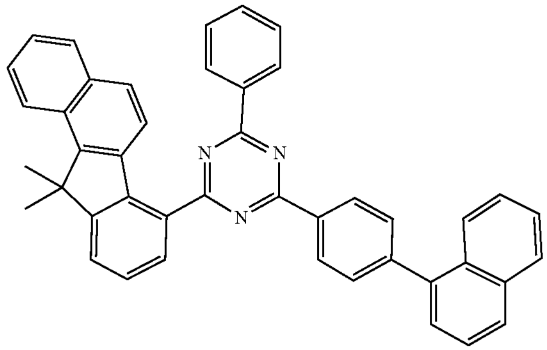
A-7
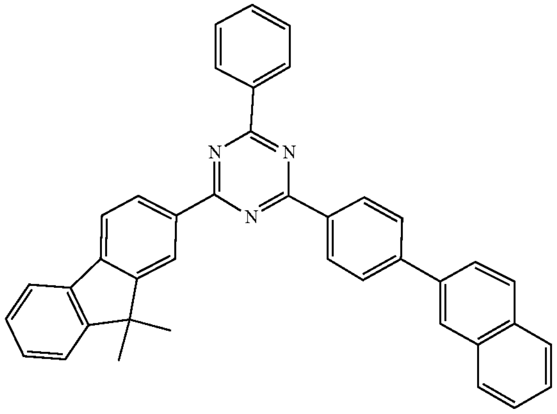
A-8
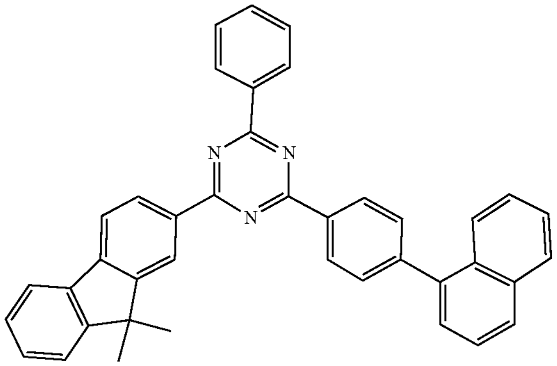

-continued
A-9
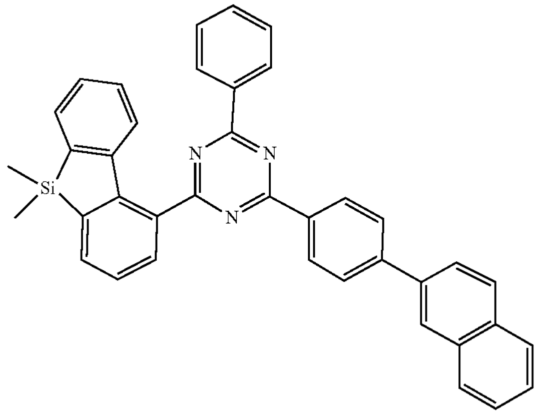
A-10
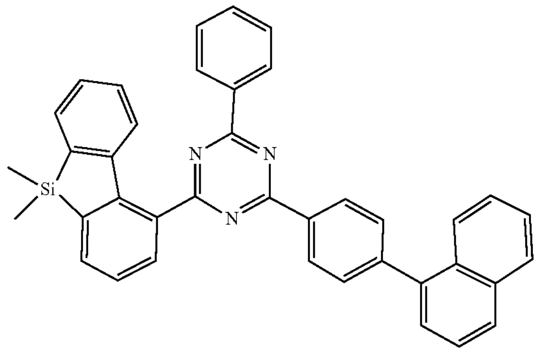
A-11
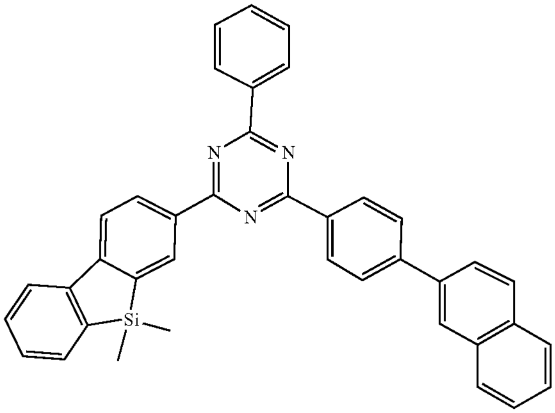
A-12
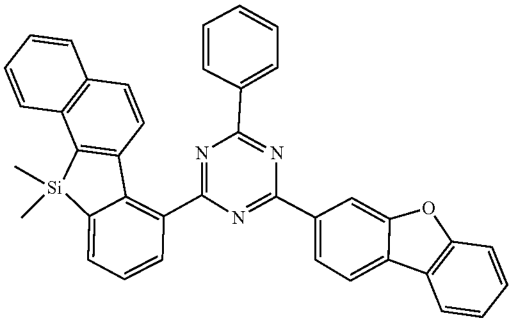
-continued
A-13
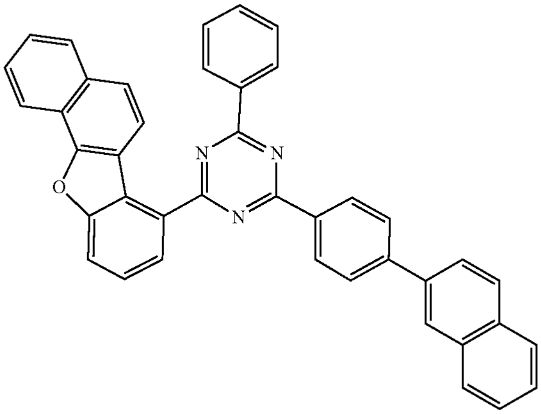
A-14
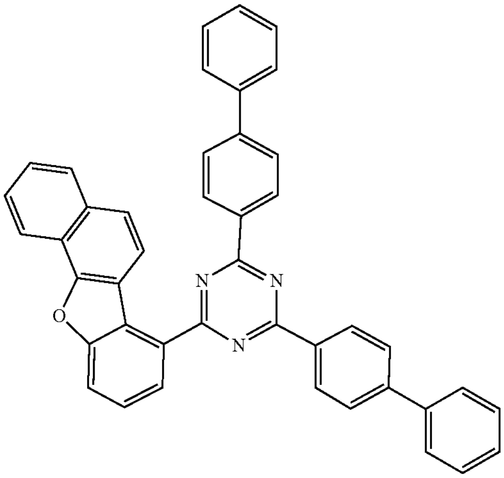
A-15
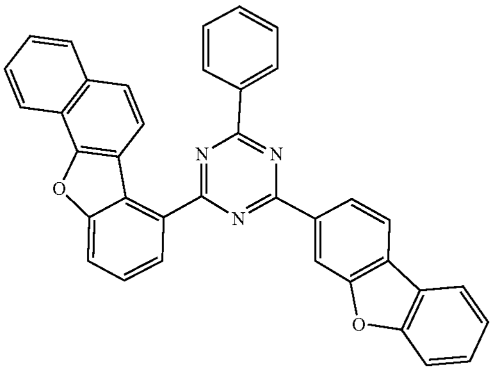

-continued
A-16
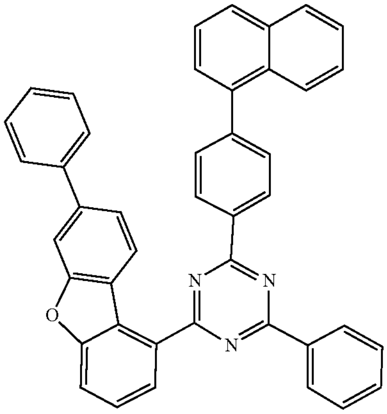
A-17
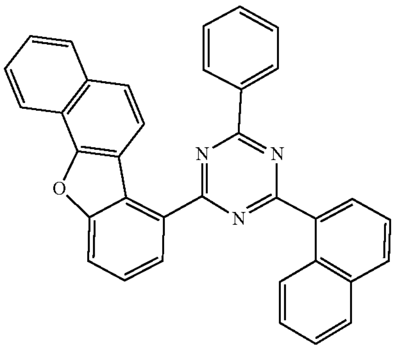
A-18
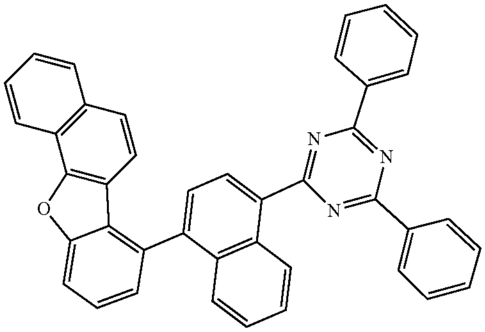
A-19
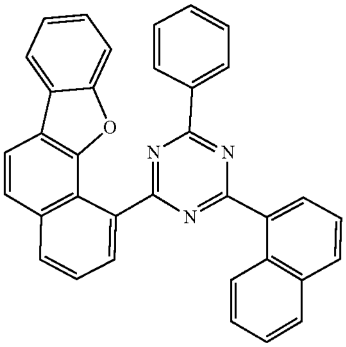
-continued
A-20
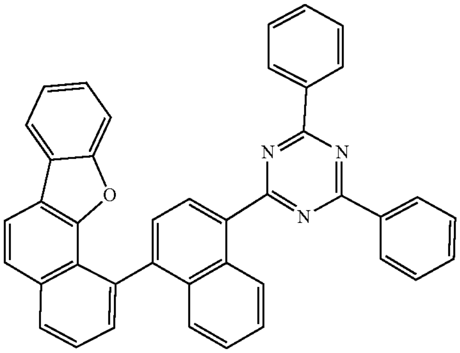
A-21
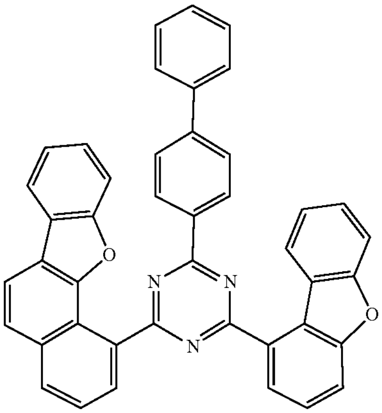
A-22
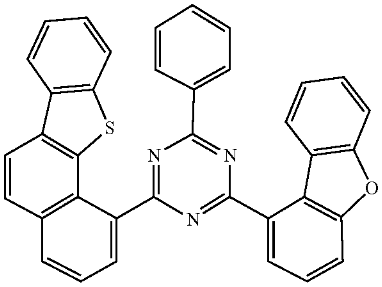
A-23
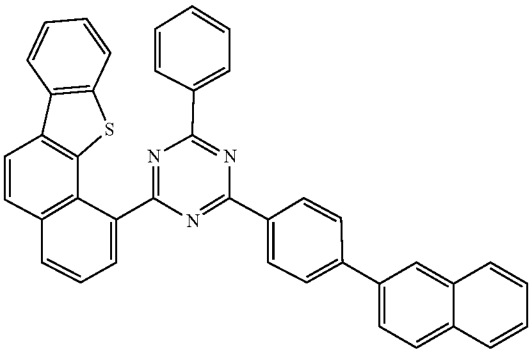

A-24
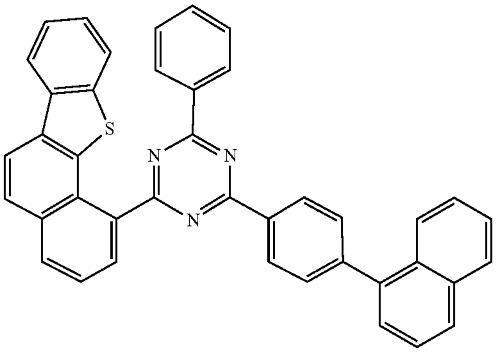
A-25
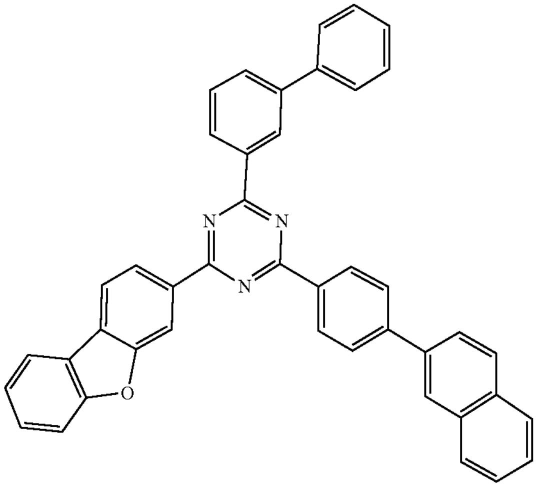
A-26
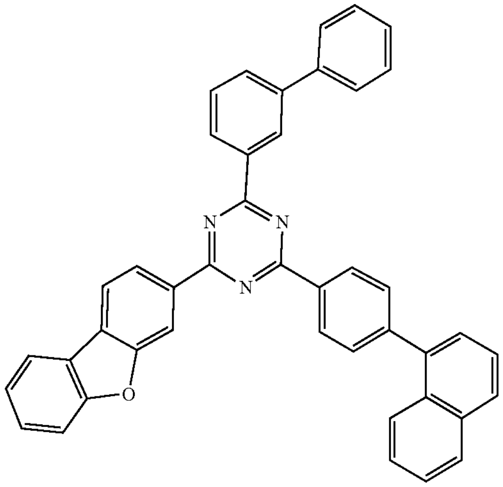
A-27
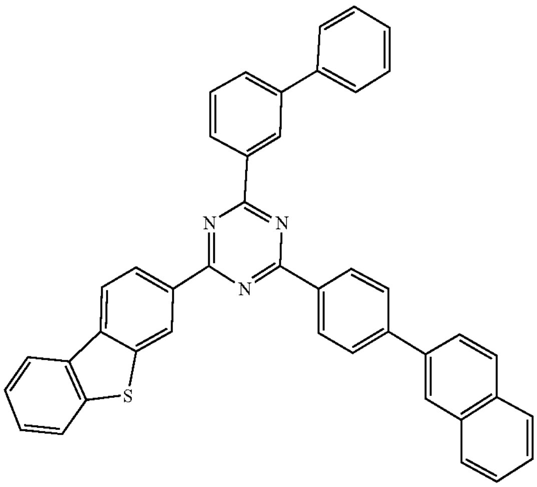
A-28
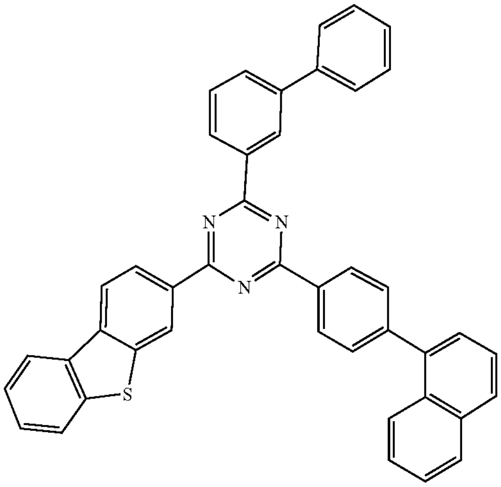
A-29
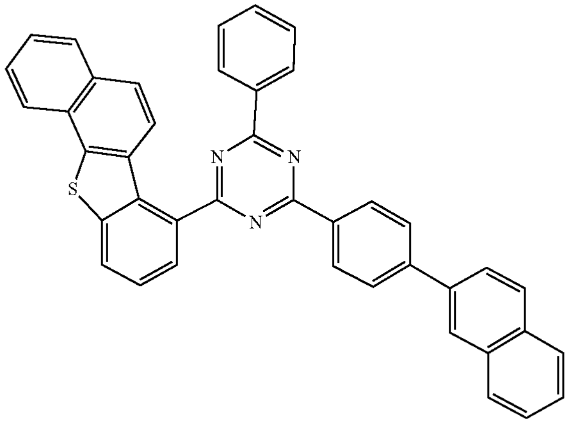

-continued
A-30
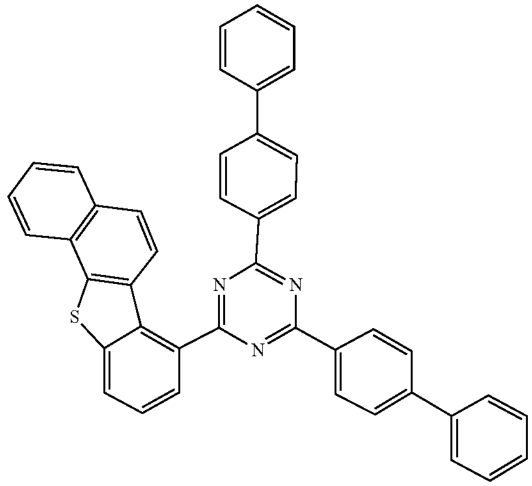
A-31
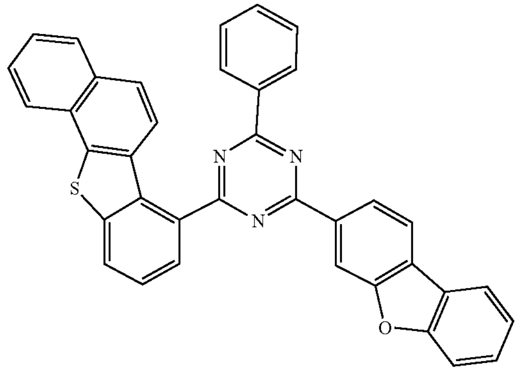
A-32
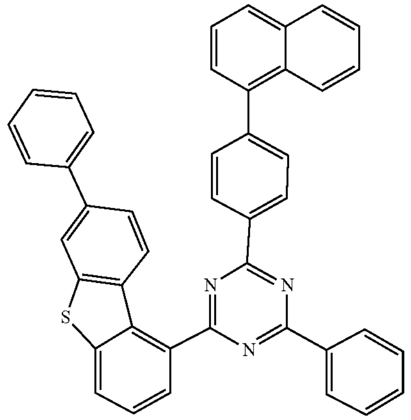
-continued
A-33
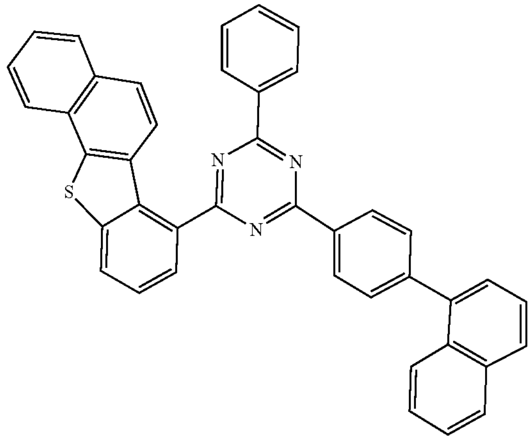
A-34
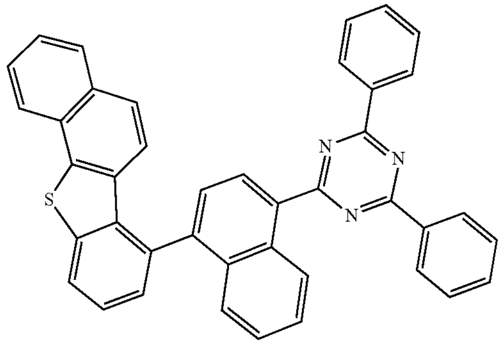
A-35
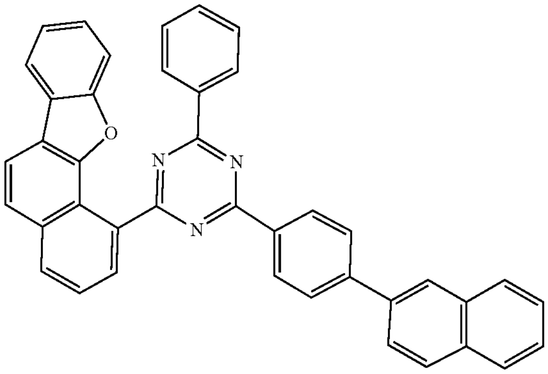
A-36
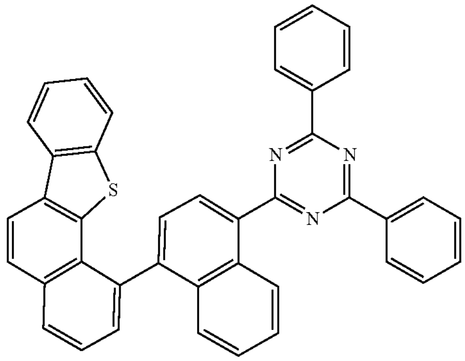

-continued
A-37
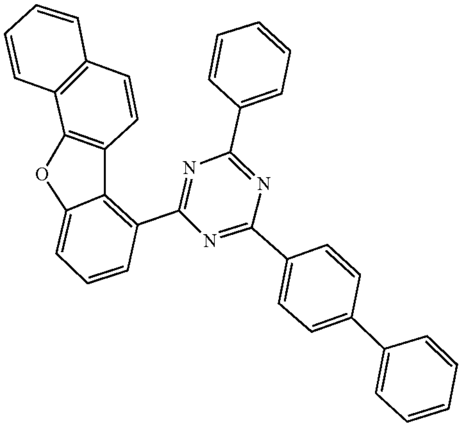
A-38
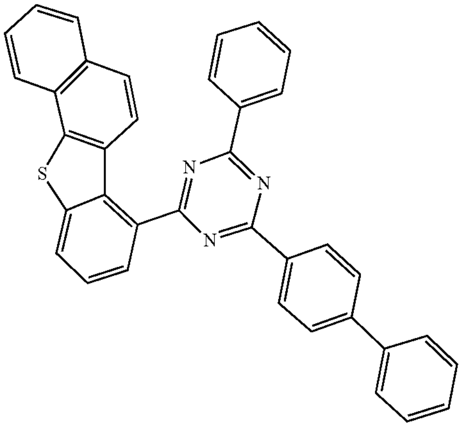
A-39
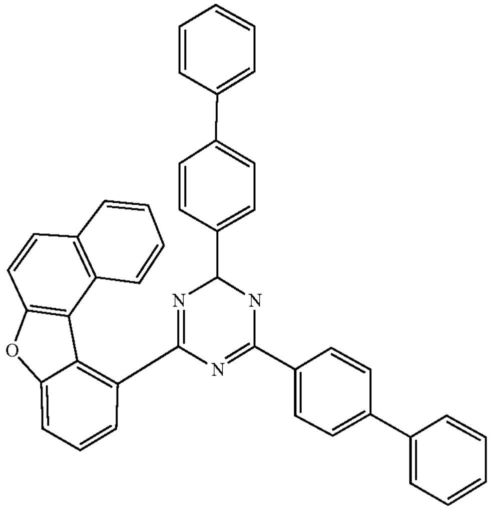
-continued
A-40
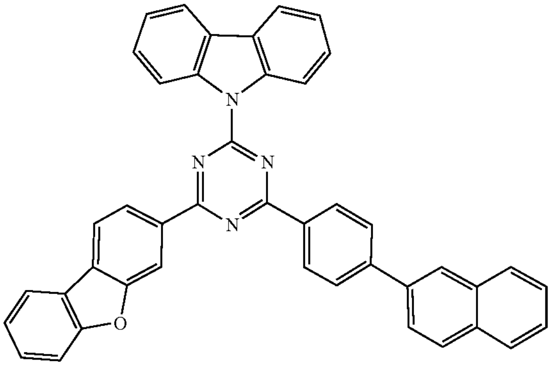
A-41
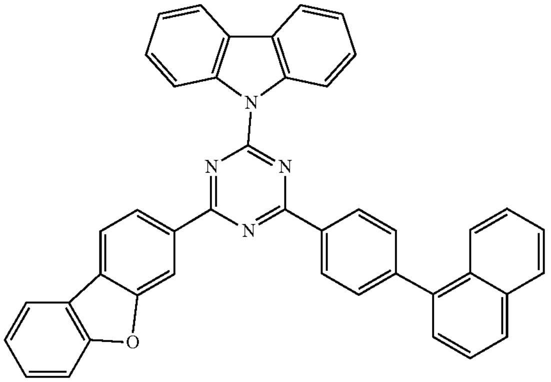
A-42
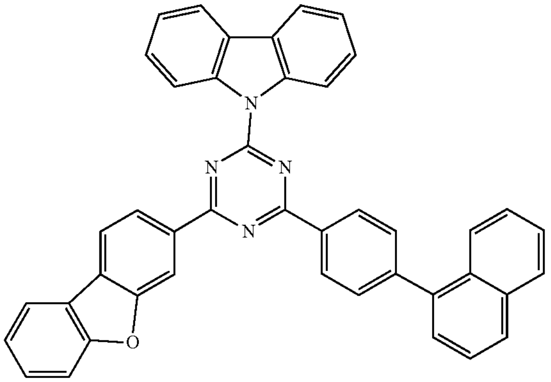

-continued
A-43
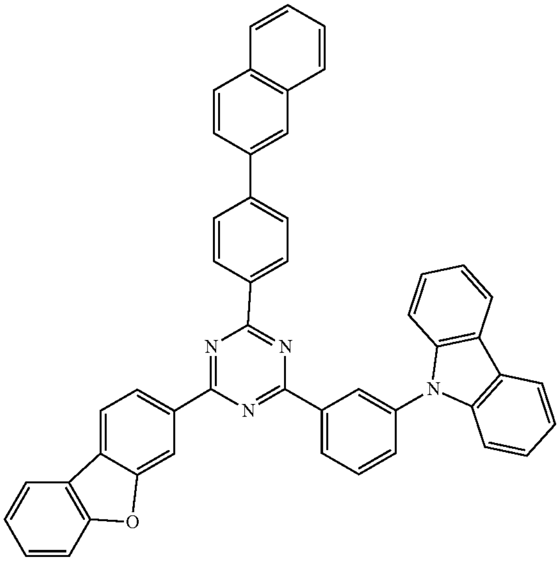
A-44
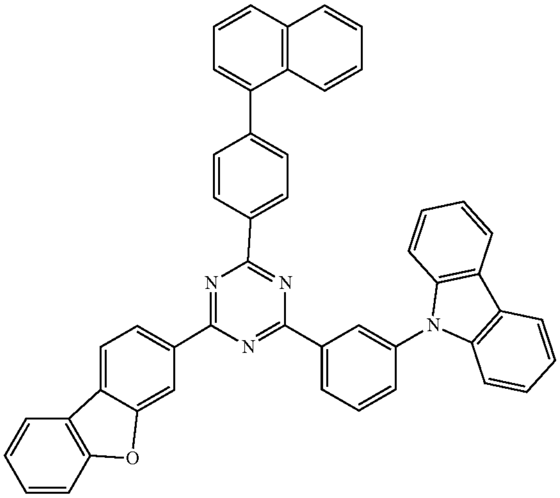
A-45
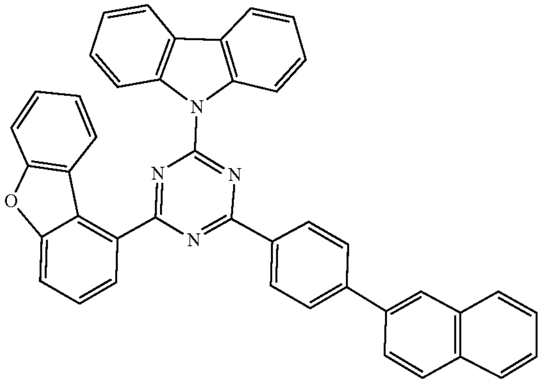
-continued
A-46
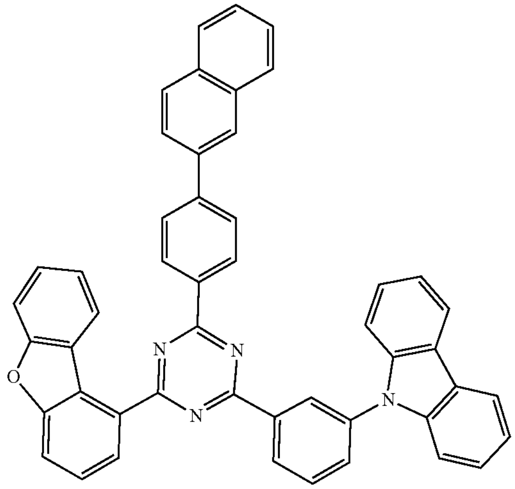
A-47
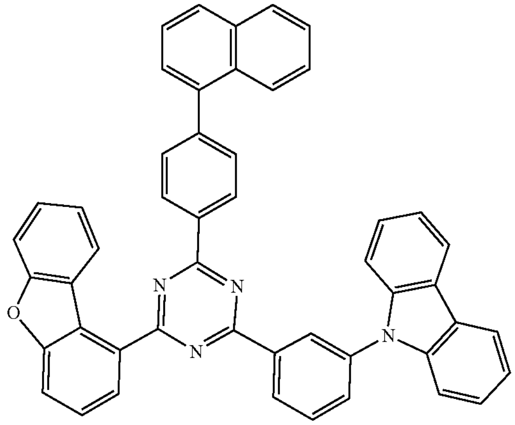
A-48
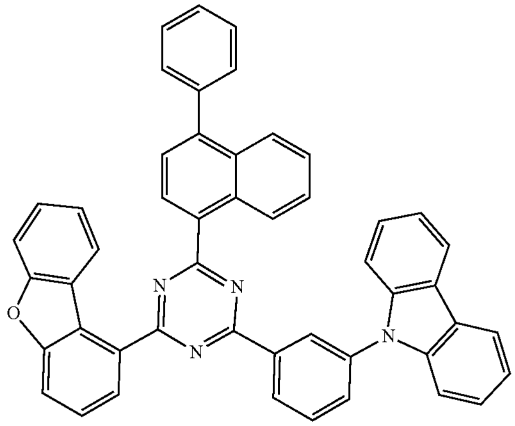

-continued
A-49
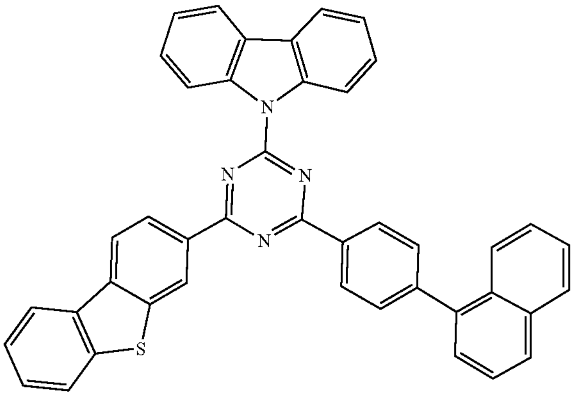
A-50
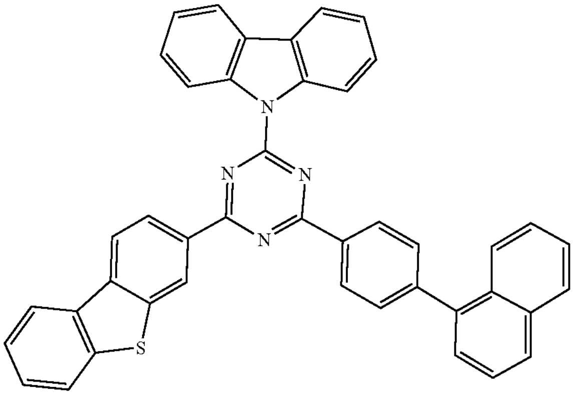
A-51
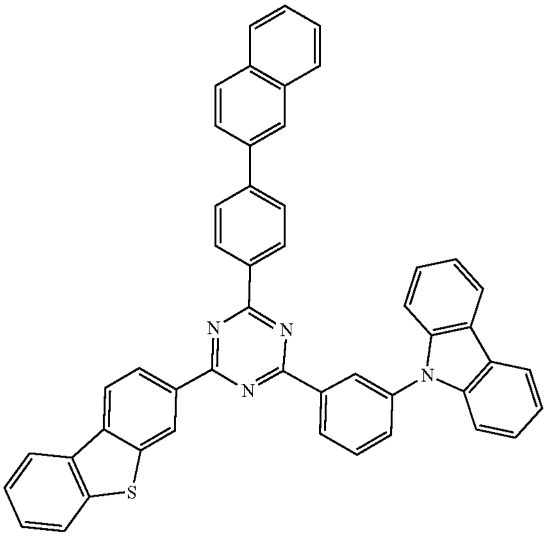
-continued
A-52
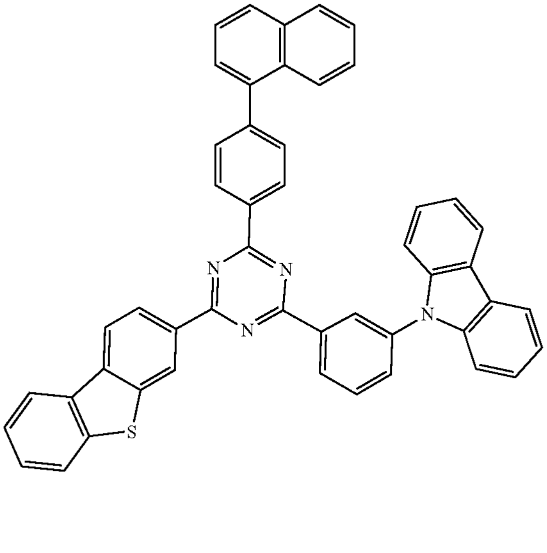
A-53
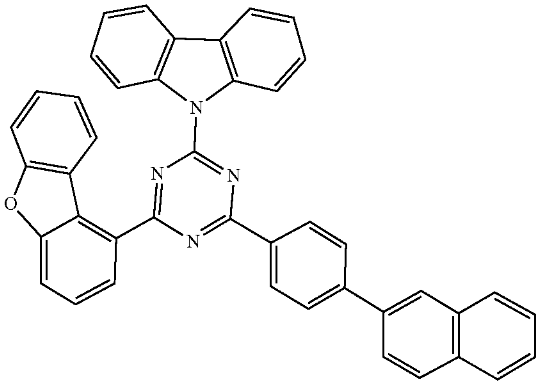
A-54
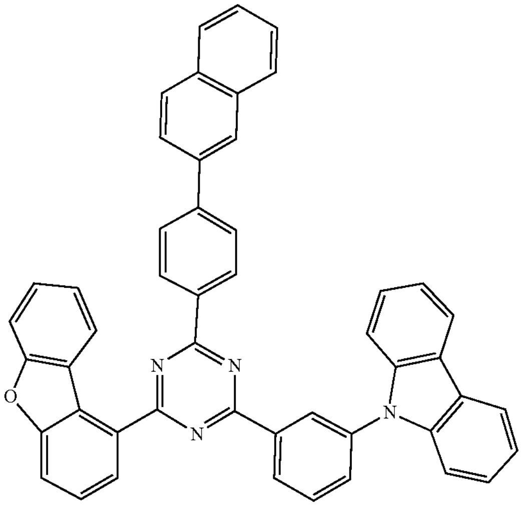

-continued
A-55
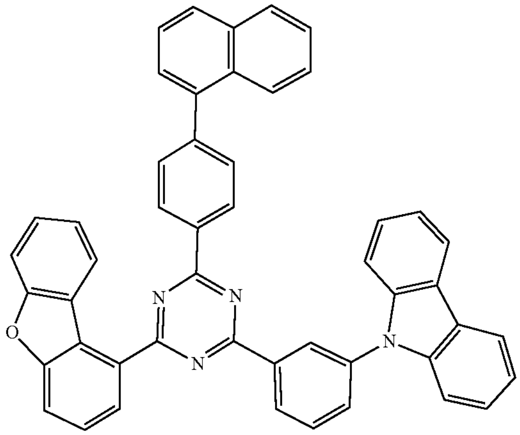
A-56
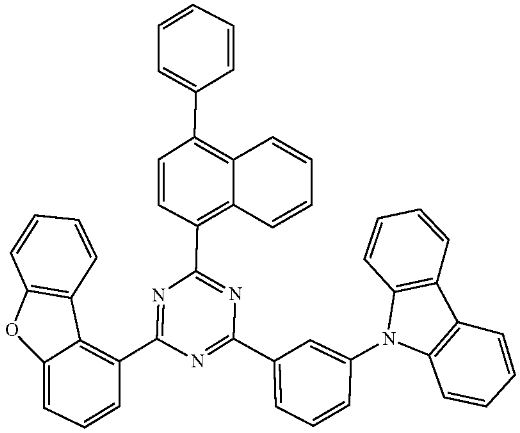
A-57
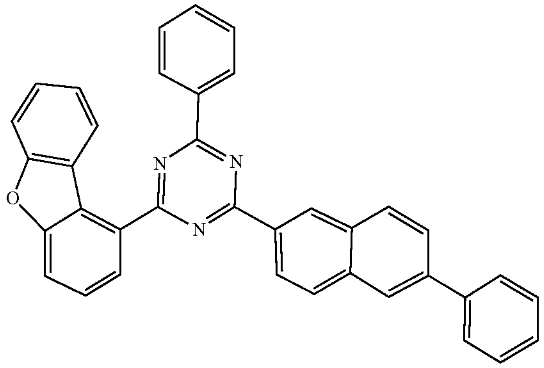
-continued
A-58
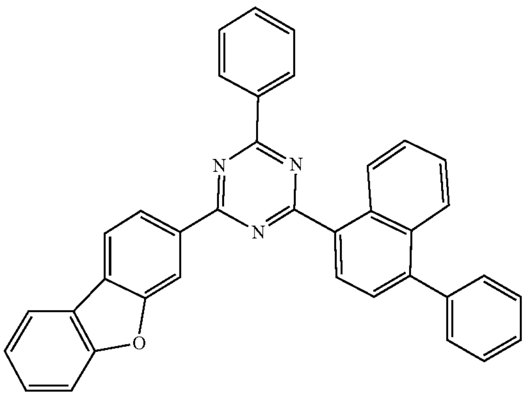
A-59
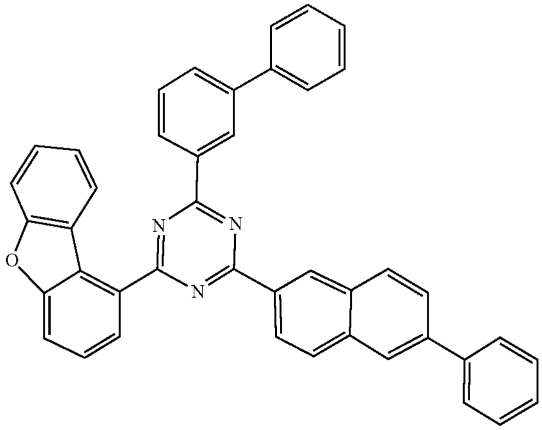
A-60
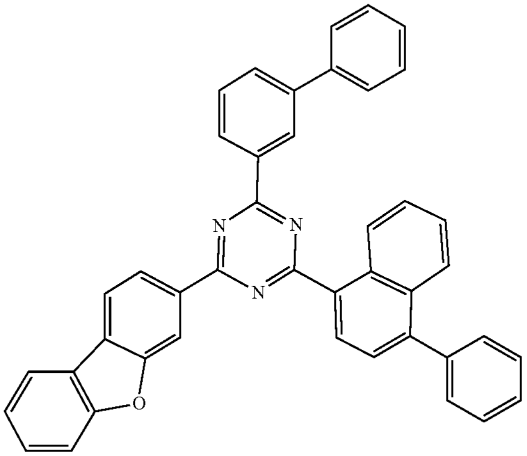

-continued
A-61
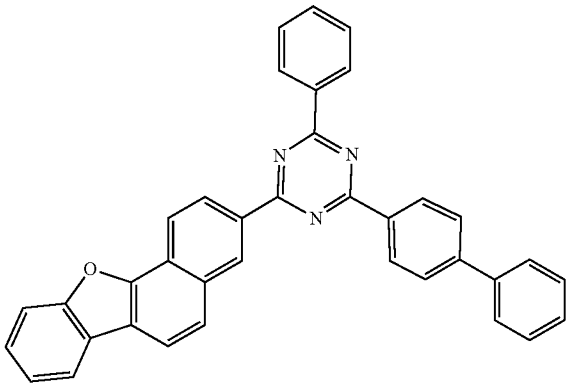
A-62
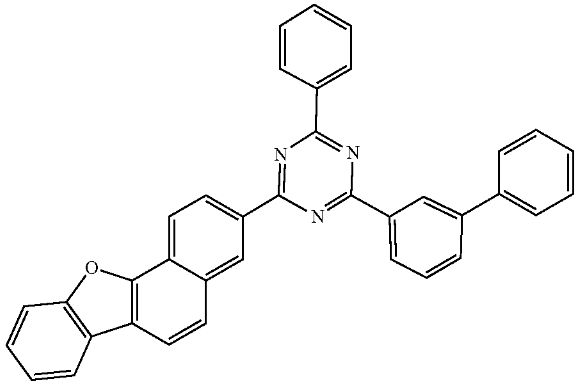
A-63
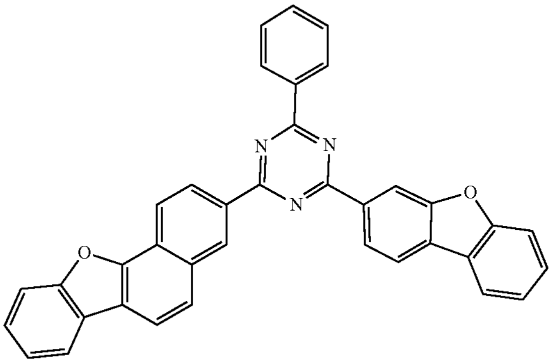
A-64
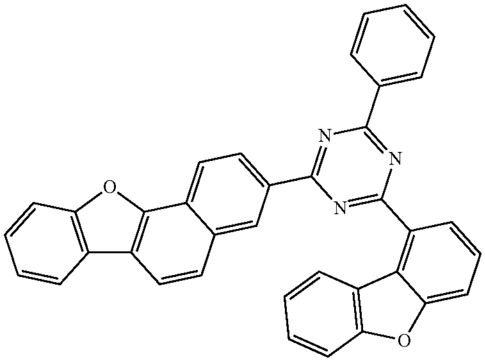
-continued
A-65
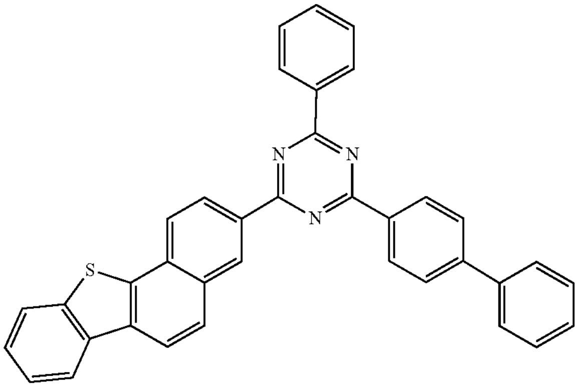
A-66
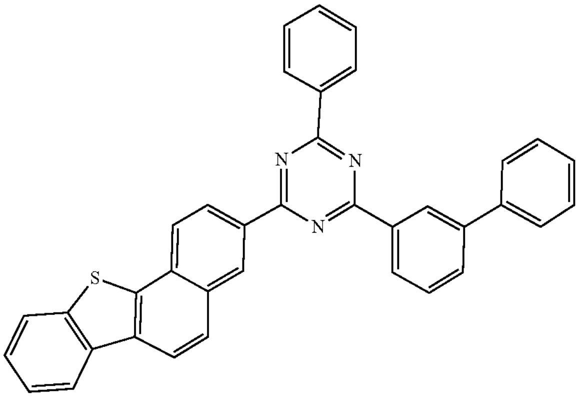
A-67
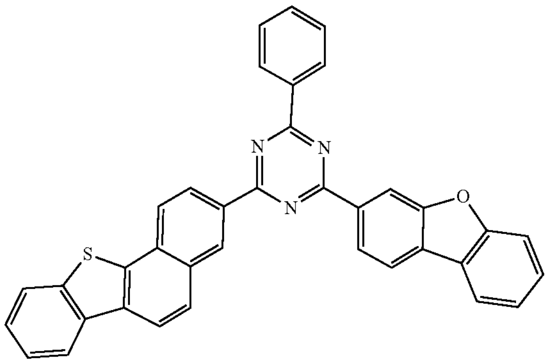
A-68
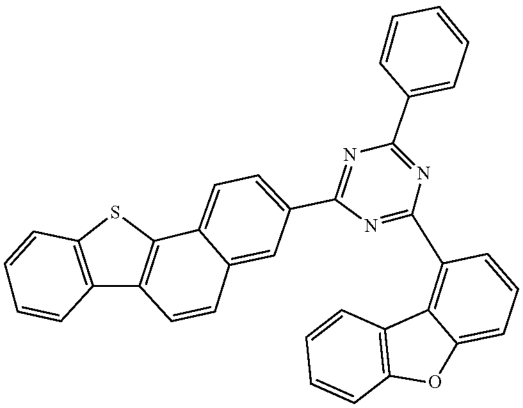

-continued
A-69
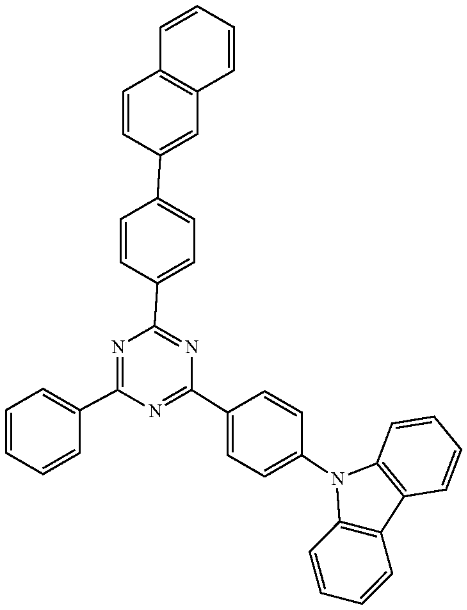
A-70
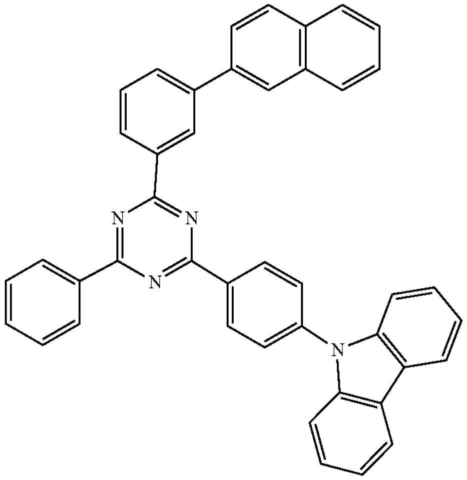
A-71
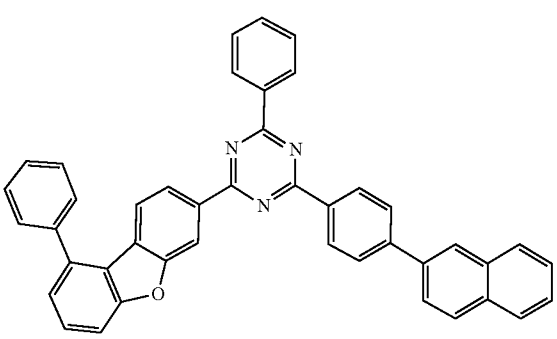
-continued
A-72
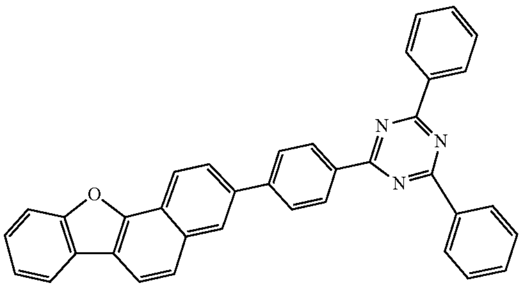
A-73
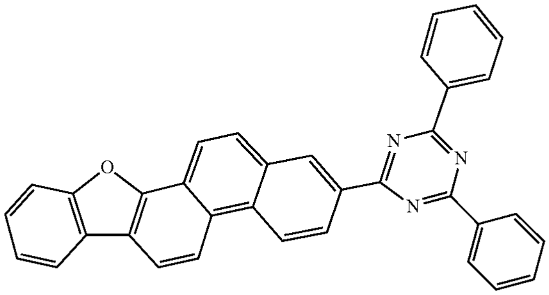
A-74
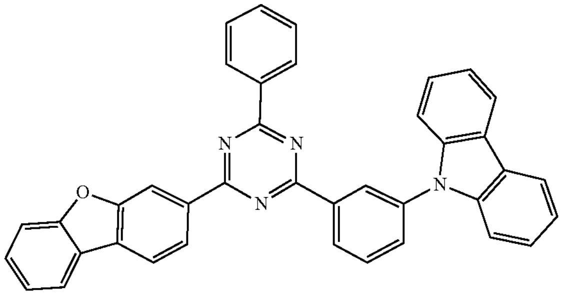
A-75
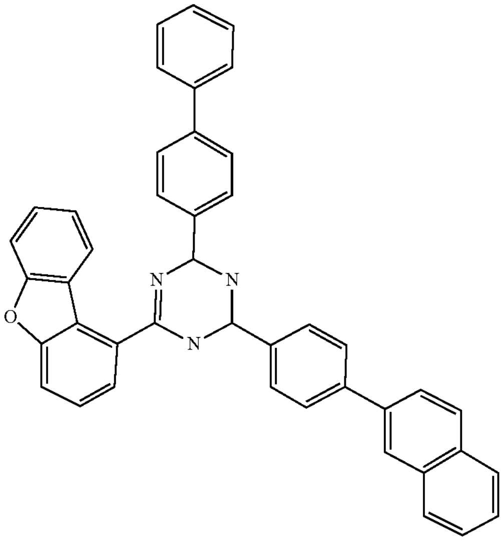

-continued
A-76
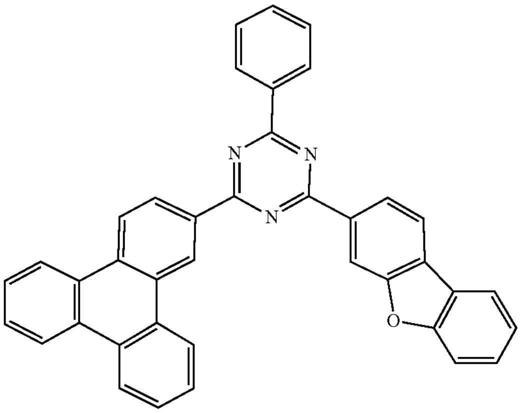
A-77
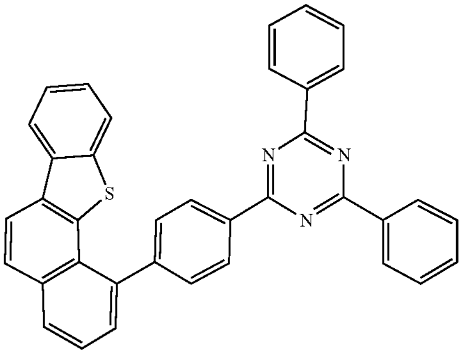
A-78
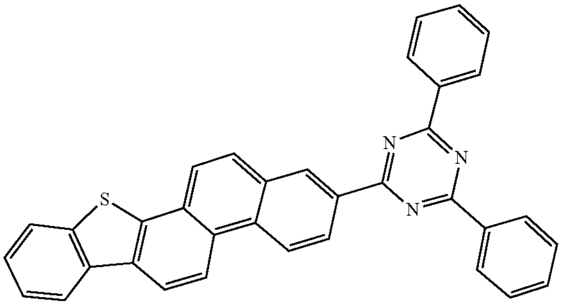
A-79
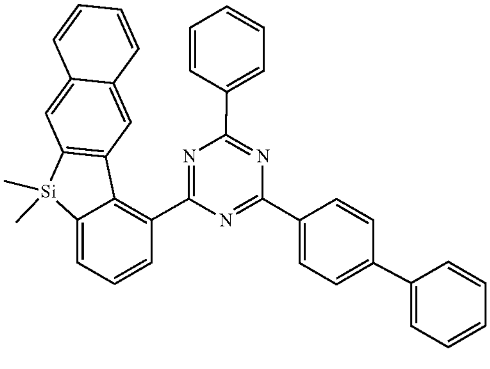
-continued
A-80
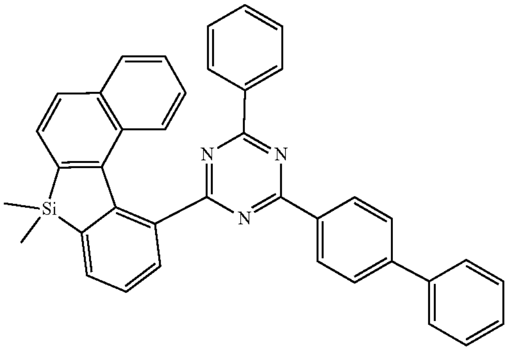
A-81
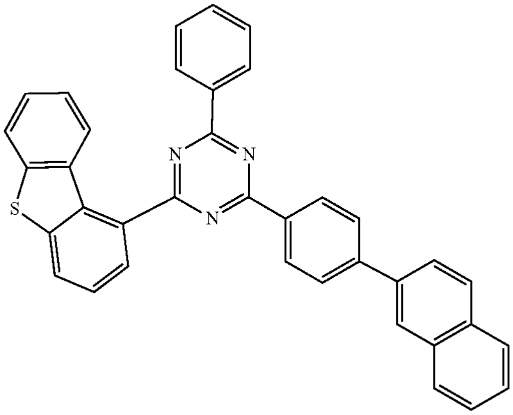
A-82
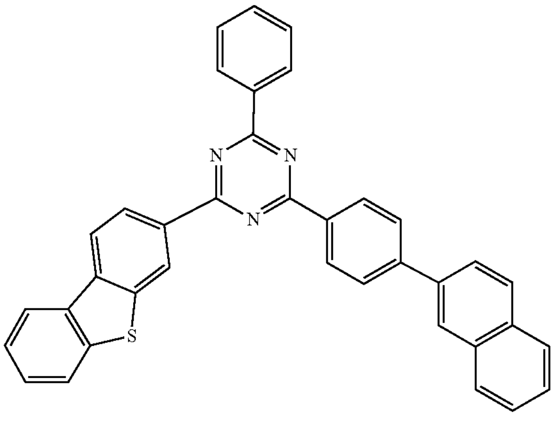

-continued
A-83
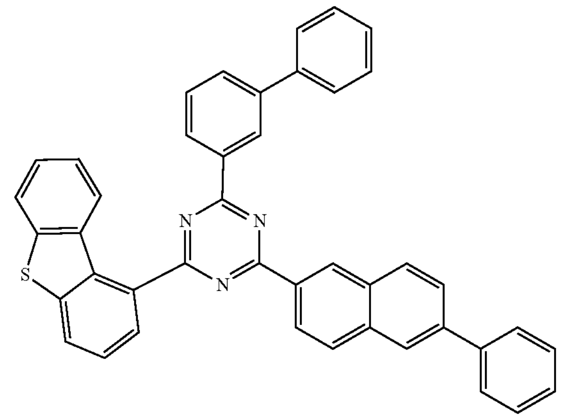
A-84
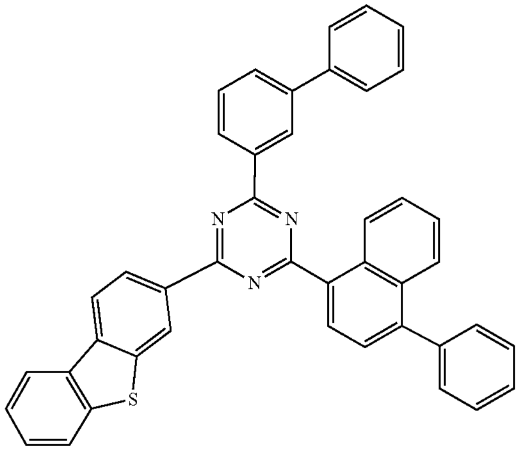
A-85
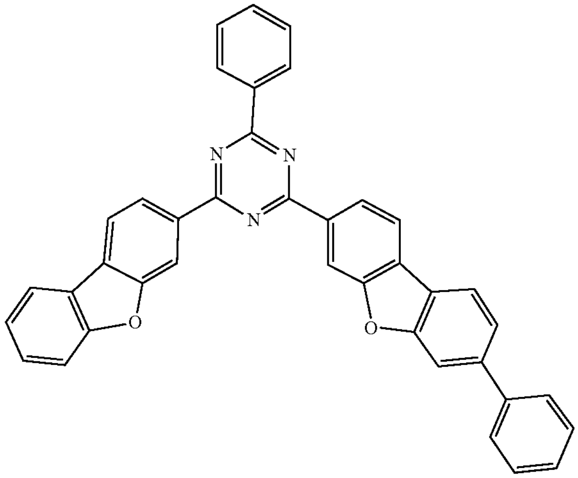
-continued
A-86
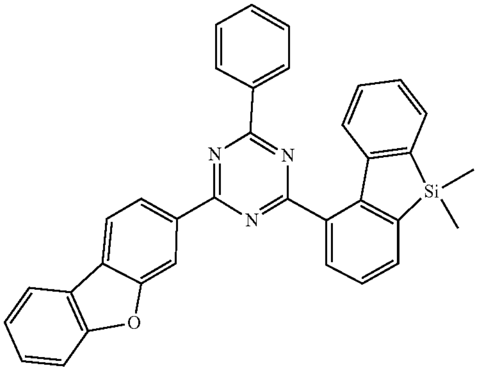
A-87
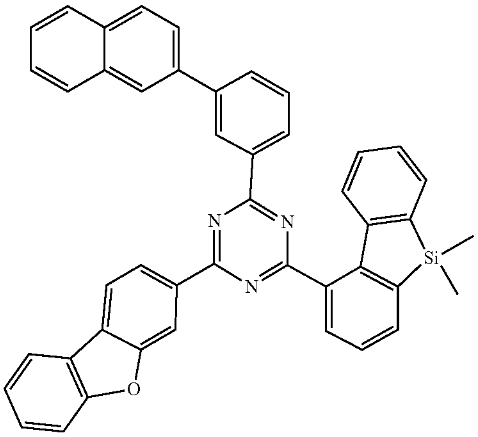
A-88
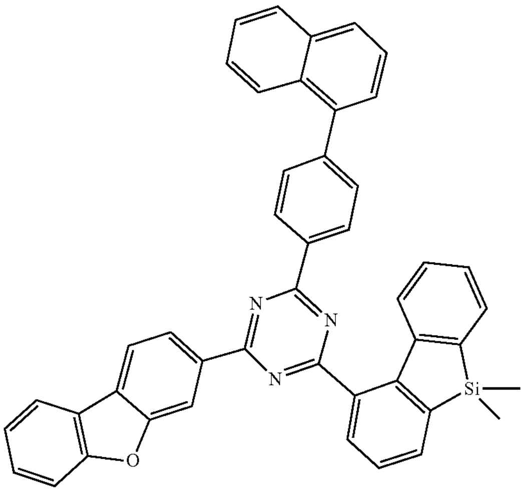

-continued
A-89
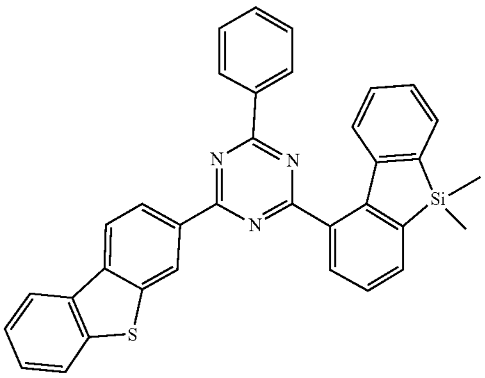
A-90
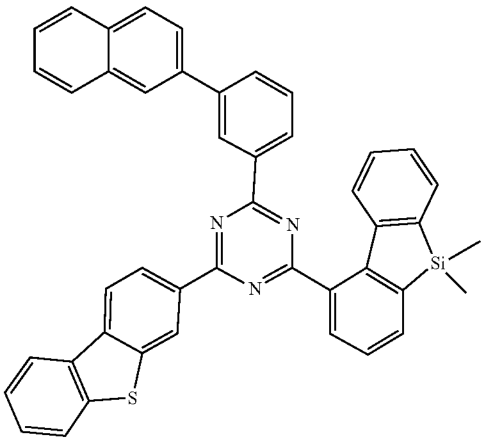
A-91
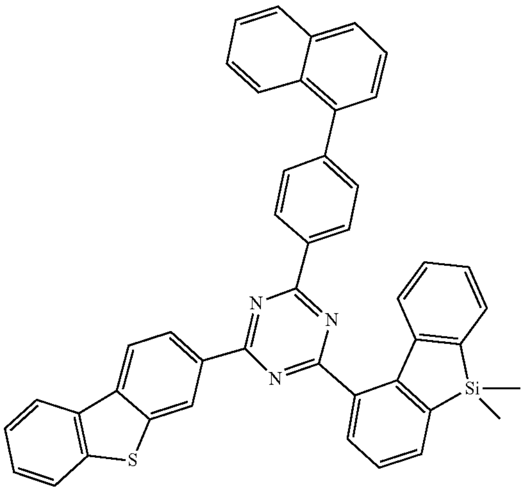
-continued
A-92
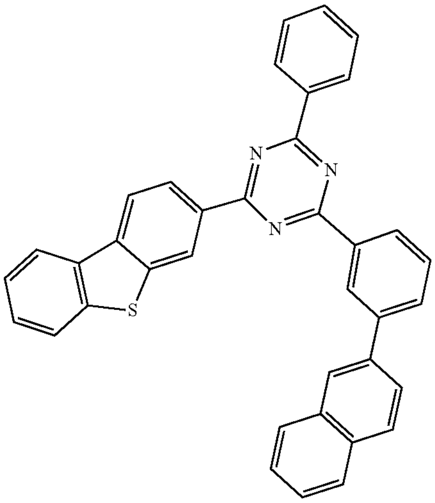
A-93
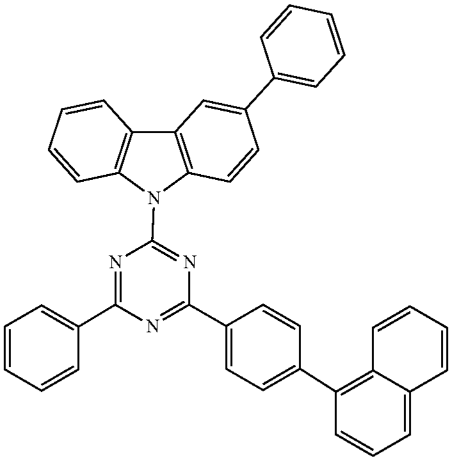
A-94
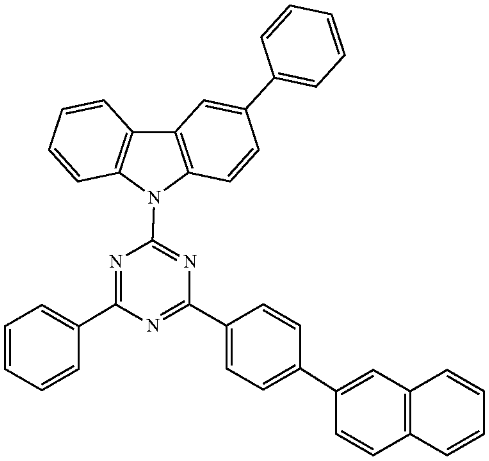

-continued
A-95
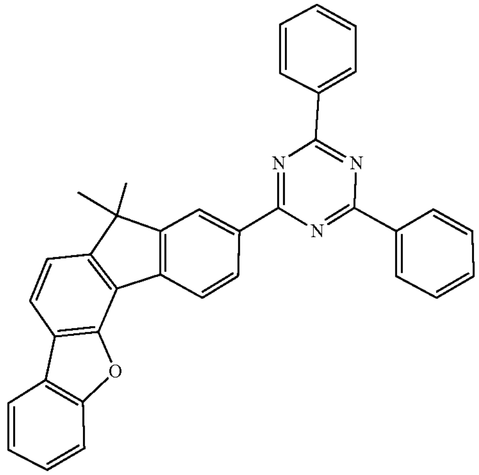
A-96
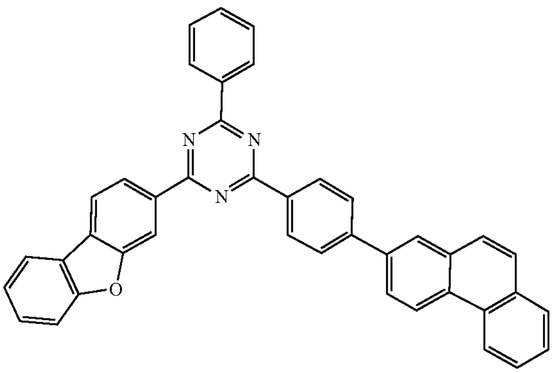
A-97
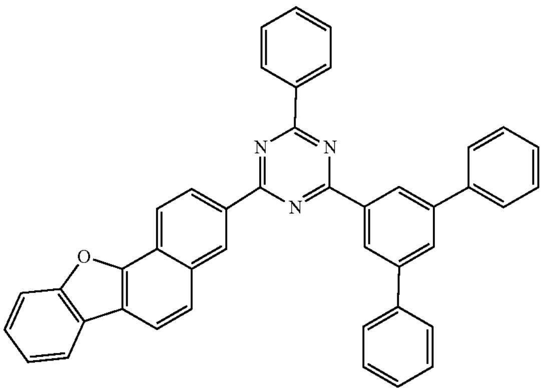
-continued
A-98
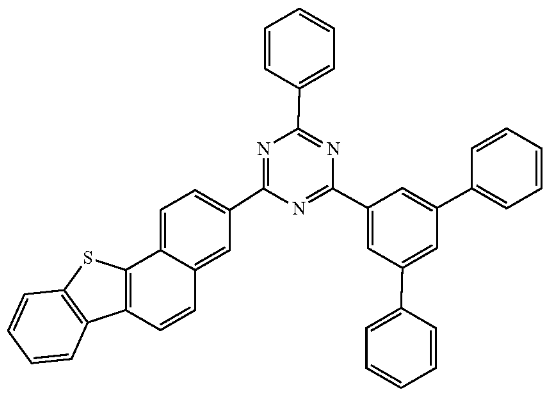
A-99
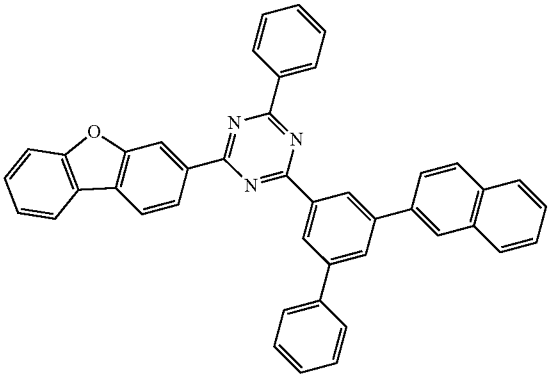
A-100
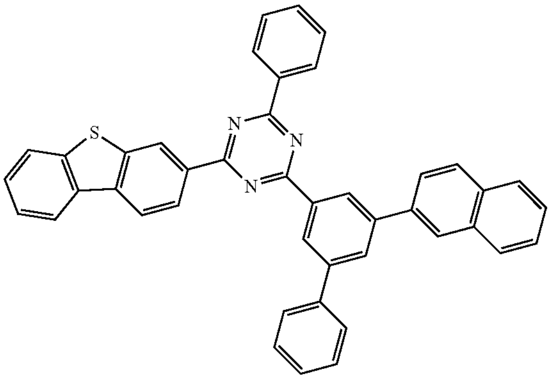
A-101
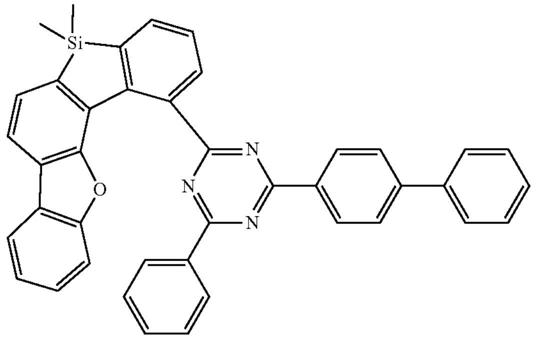

-continued

A-102

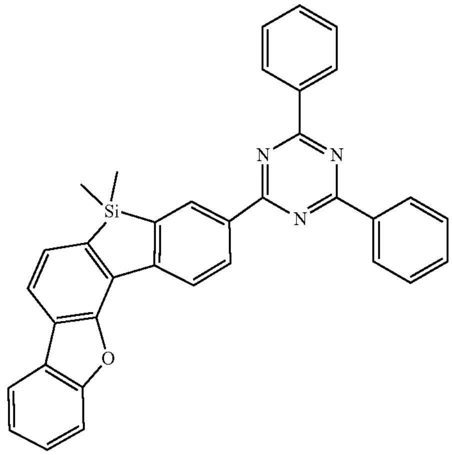

A-103

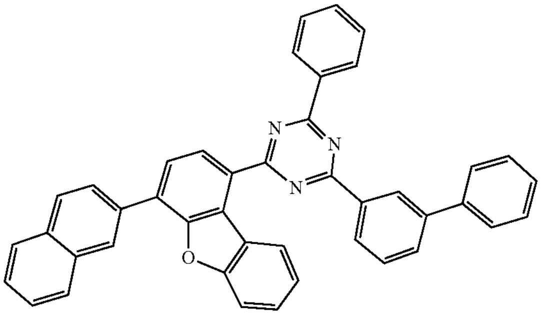

A-104

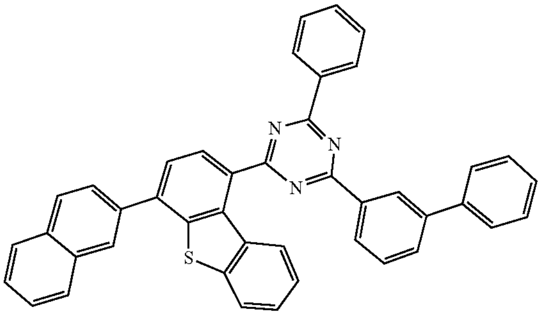

A-105

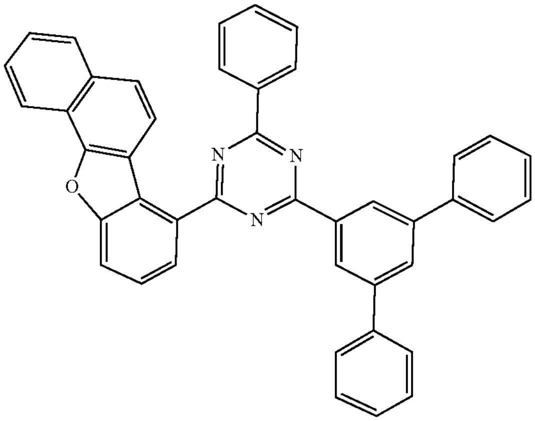

-continued

A-106

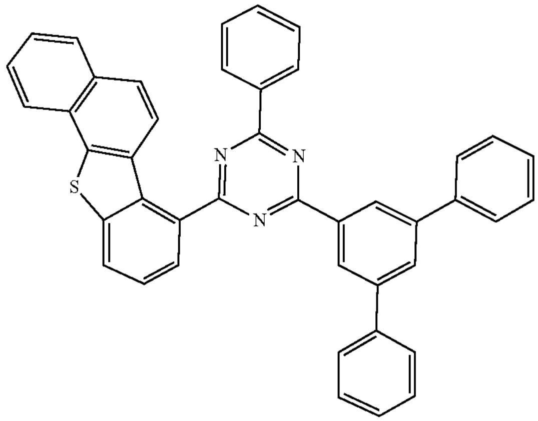

A-107

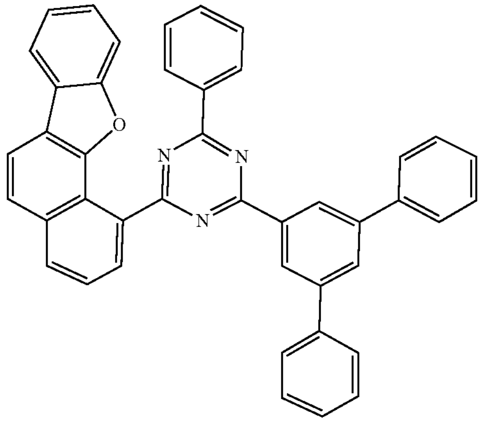

A-108

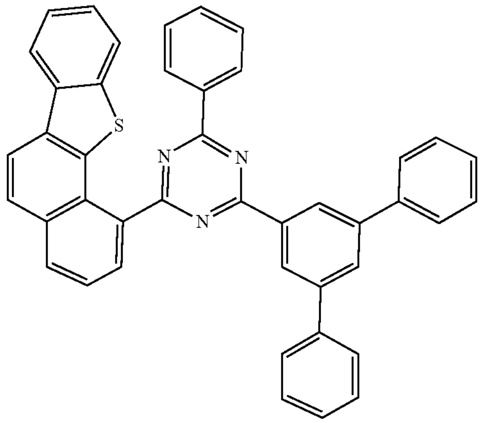

In an implementation, the first compound and the second compound may be included (e.g., mixed) in a weight ratio of, e.g., 1:99 to 99:1. Within the range, a desirable weight ratio may be adjusted using an electron transport capability of the first compound and a hole transport capability of the second compound to realize bipolar characteristics and thus to improve efficiency and life-span. Within the range, they may be, e.g., included in a weight ratio of about 10:90 to 90:10, about 10:90 to 80:20, for example about 10:90 to about 70:30, about 10:90 to about 60:40, and about 10:90 to about 50:50. In an implementation, they may be included in a weight ratio of 20:80, 30:70, 40:60, or 50:50.

One or more compounds may be included in addition to the aforementioned first compound and second compound.

The aforementioned compound for an organic optoelectronic device or composition for an organic optoelectronic device may further include a dopant.

The dopant may be, e.g., a phosphorescent dopant. In an implementation, the dopant may include, e.g., a red, green, or blue phosphorescent dopant. In an implementation, the dopant may include, e.g., a red or green phosphorescent dopant.

The dopant is a material mixed with the compound or composition for an organic optoelectronic device in a small amount to cause light emission, and may be a material such as a metal complex that emits light by multiple excitation into a triplet or more. The dopant may be, e.g., an inorganic, organic, or organic-inorganic compound, and one or more types thereof may be used.

Examples of the dopant may include a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, e.g., a compound represented by Chemical Formula Z.

$L^6MX^4$ [Chemical Formula Z]

In Chemical Formula Z, M may be a metal, and $L^6$ and $X^4$ may each independently be a ligand to form a complex compound with M.

The M may be, e.g., Ir, Pt, Os, Ti, Zr, Hf, Eu, Tb, Tm, Fe, Co, Ni, Ru, Rh, Pd, or a combination thereof and $L^6$ and $X^4$ may be, e.g., a bidendate ligand.

The aforementioned compound for an organic optoelectronic device or composition for an organic optoelectronic device may be formed into a film by a dry film formation method such as chemical vapor deposition (CVD).

Hereinafter, an organic optoelectronic device including the aforementioned compound for an organic optoelectronic device or composition for an organic optoelectronic device is described.

The organic optoelectronic device may be a suitable device to convert electrical energy into photoenergy and vice versa, e.g., an organic photoelectric device, an organic light emitting diode, an organic solar cell, or an organic photo-conductor drum.

Herein, an organic light emitting diode as one example of an organic optoelectronic device is described referring to drawings.

FIGS. 1 to 4 are cross-sectional views of organic light emitting diodes according to embodiments.

Referring to FIG. 1, an organic light emitting diode 100 according to an embodiment may include an anode 120 and a cathode 110 facing each other and an organic layer 105 between the anode 120 and cathode 110.

The anode 120 may be made of a conductor having a large work function to help hole injection, e.g., a metal, a metal oxide, or a conductive polymer. The anode 120 may be, e.g., a metal such as nickel, platinum, vanadium, chromium, copper, zinc, gold, or the like or an alloy thereof; a metal oxide such as zinc oxide, indium oxide, indium tin oxide (ITO), indium zinc oxide (IZO), or the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, or polyaniline.

The cathode 110 may be made of a conductor having a small work function to help electron injection, e.g., a metal, a metal oxide, and/or a conductive polymer. The cathode 110 may be, e.g., a metal such as magnesium, calcium, sodium, potassium, titanium, indium, yttrium, lithium, gadolinium, aluminum silver, tin, lead, cesium, barium, or the like, or an alloy thereof; a multi-layer structure material such as LiF/Al, $LiO_2$/Al, LiF/Ca, LiF/Al, or $BaF_2$/Ca.

The organic layer 105 may include the aforementioned compound for an organic optoelectronic device or composition for an organic optoelectronic device.

The organic layer 105 may include the light emitting layer 130, and the light emitting layer 130 may include the aforementioned compound for an organic optoelectronic device or composition for an organic optoelectronic device.

The composition for an organic optoelectronic device further including a dopant may be, e.g., a red-light emitting composition.

The light emitting layer 130 may include, e.g., the aforementioned first compound and second compound, respectively, as a phosphorescent host.

The organic layer may further include a charge transport region in addition to the light emitting layer.

The charge transport region may be, e.g., the hole transport region 140.

Figure 2:
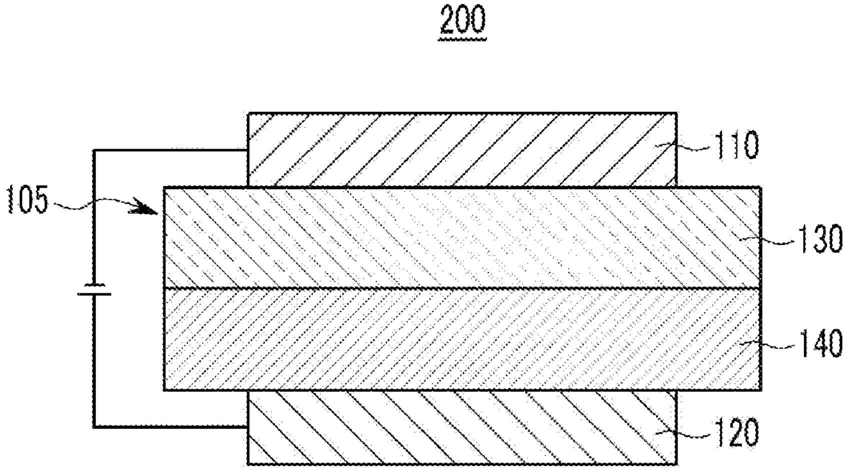

Referring to FIG. 2, the organic light emitting diode 200 may include a hole transport region 140 in addition to the light emitting layer 130. The hole transport region 140 may further increase hole injection and/or hole mobility and block electrons between the anode 120 and the light emitting layer 130. In an implementation, the hole transport region 140 may include a hole transport layer between the anode 120 and the light emitting layer 130, and a hole transport auxiliary layer between the light emitting layer 130 and the hole transport layer, and a compound of Group E may be included in at least one of the hole transport layer and the hole transport auxiliary layer.

[Group E]

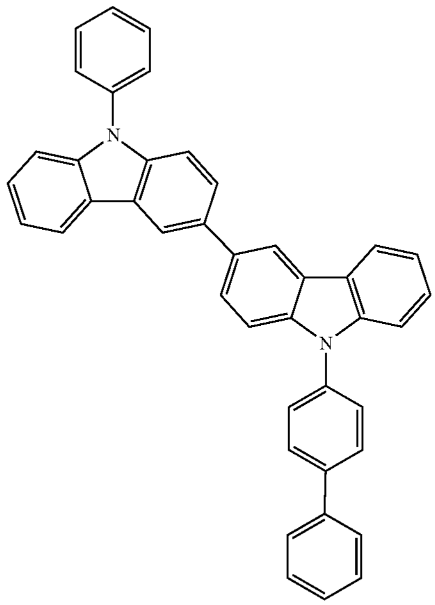

-continued
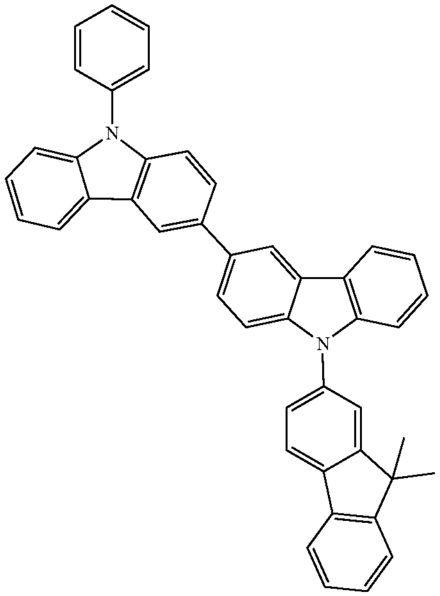
-continued
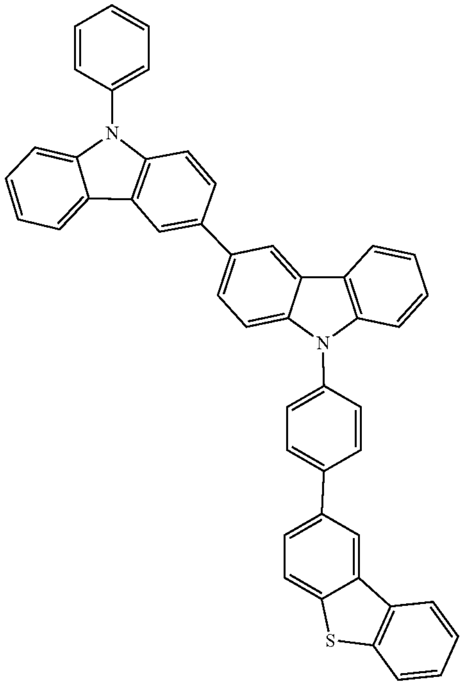
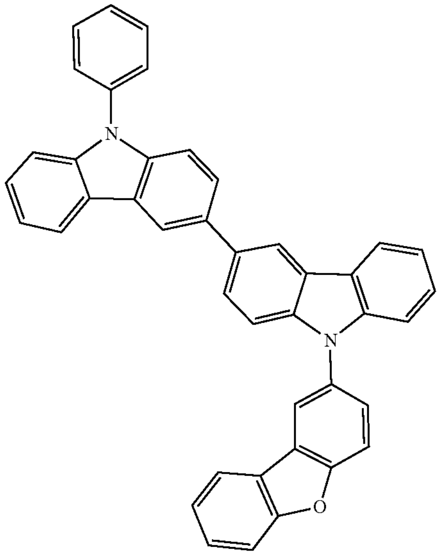
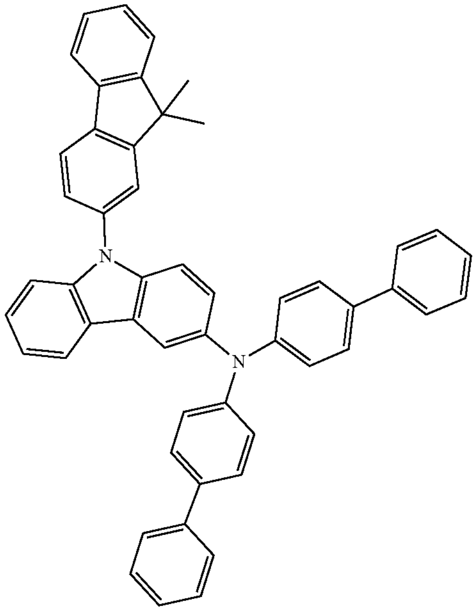

-continued
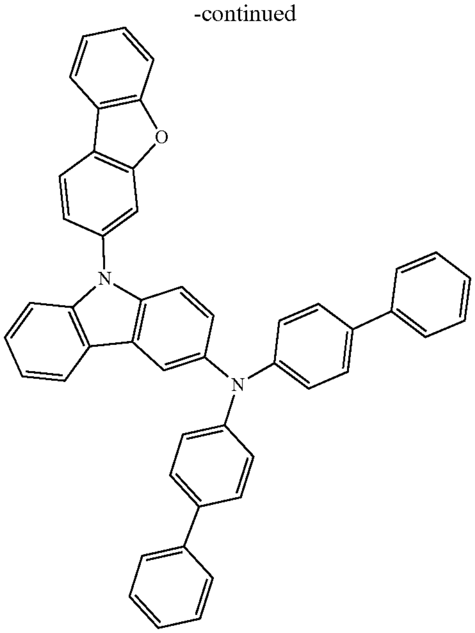
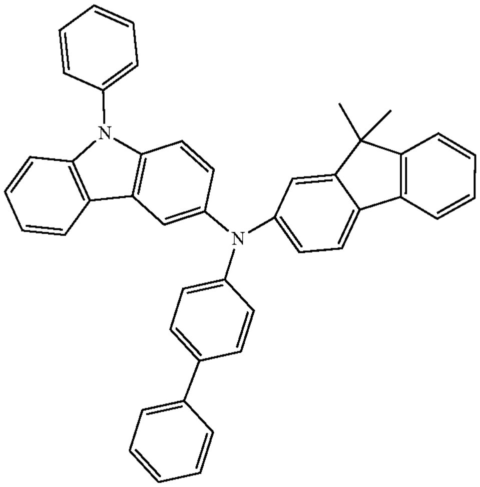
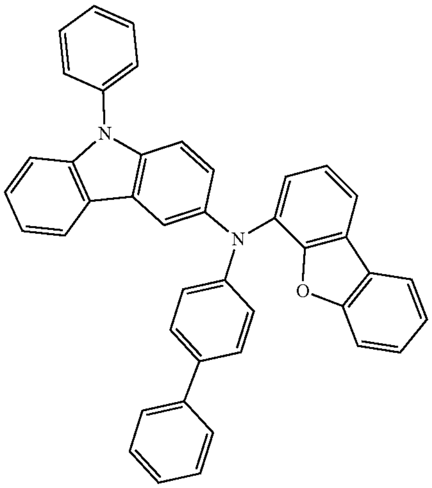
-continued
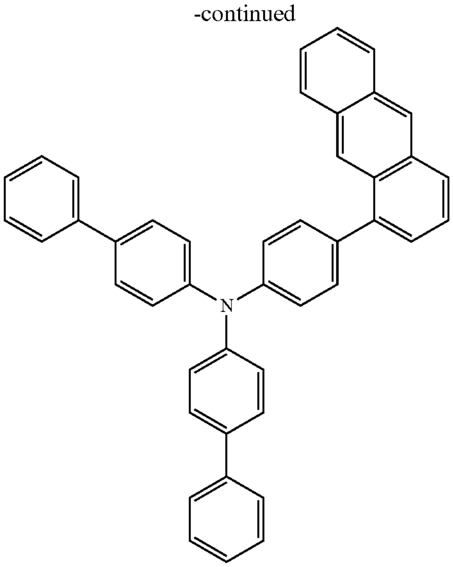
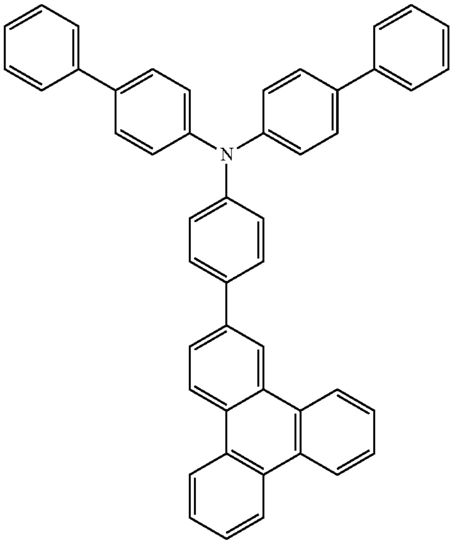
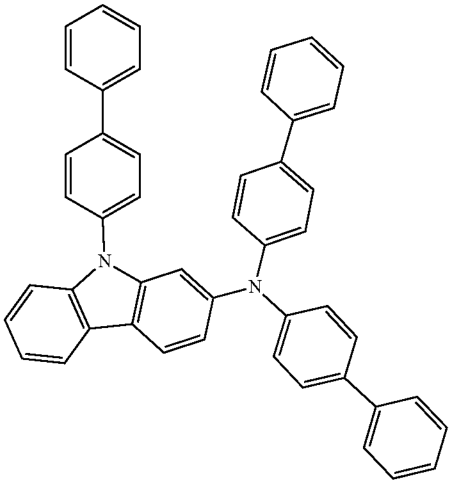

-continued
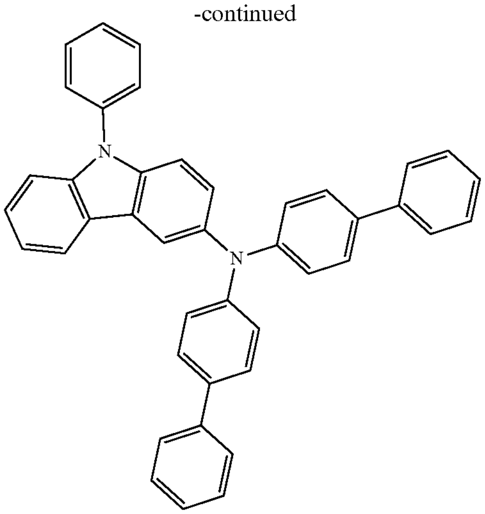
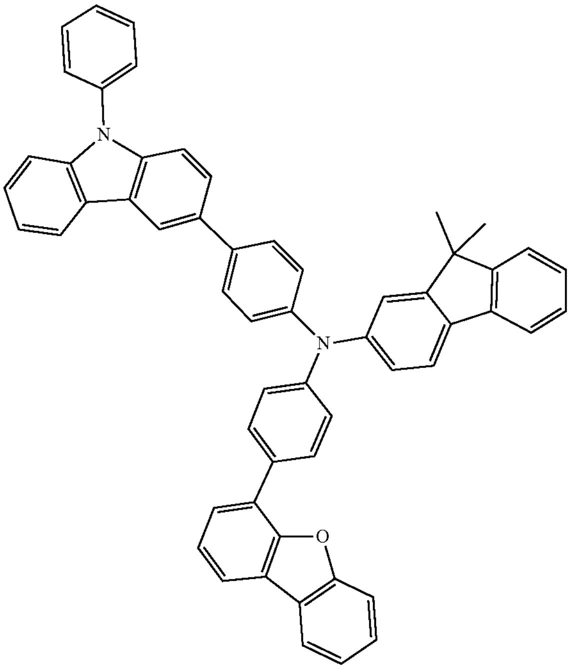
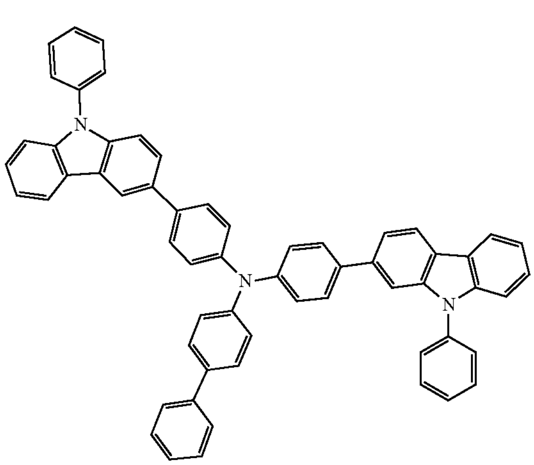
-continued
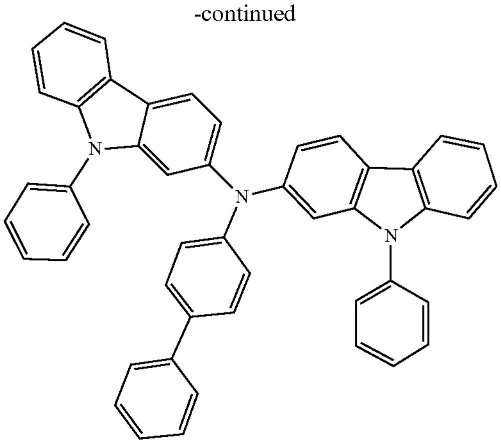
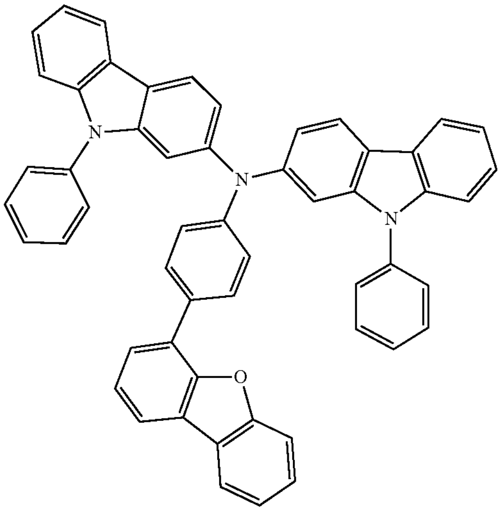
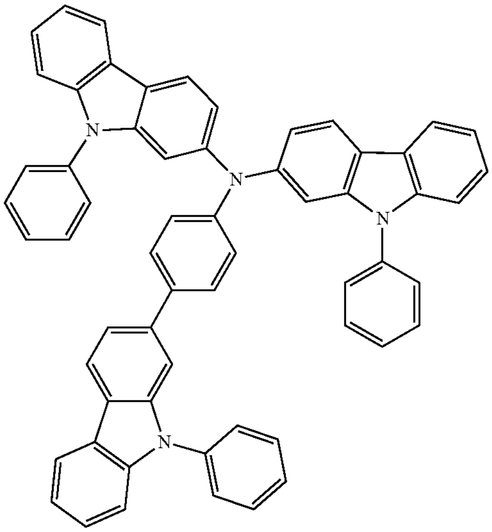

-continued
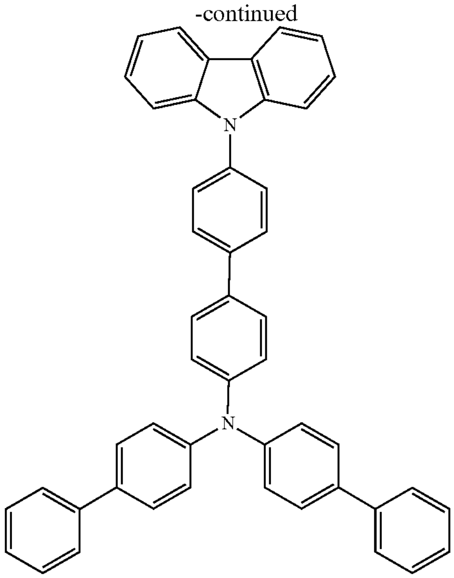
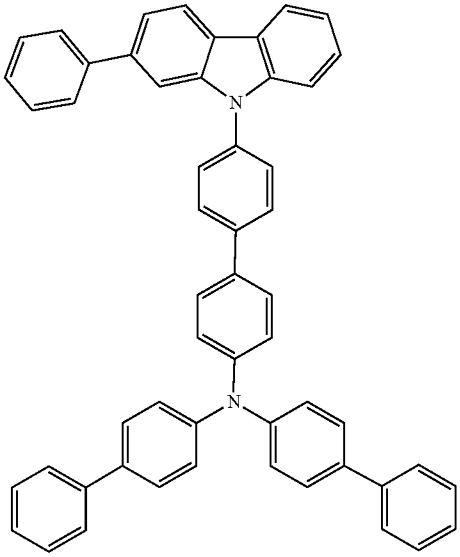
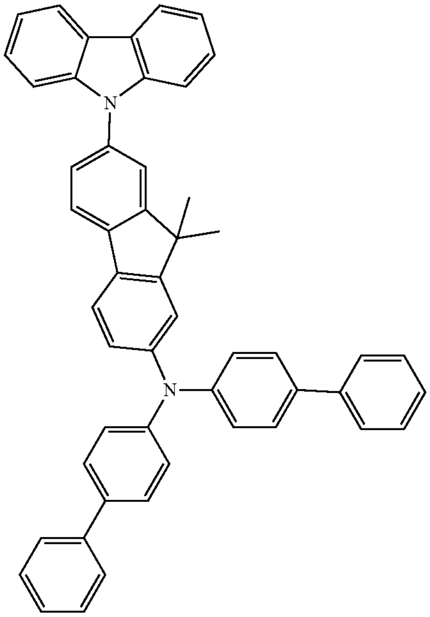
-continued
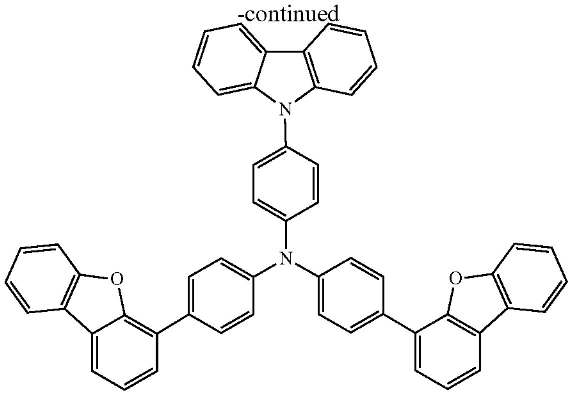
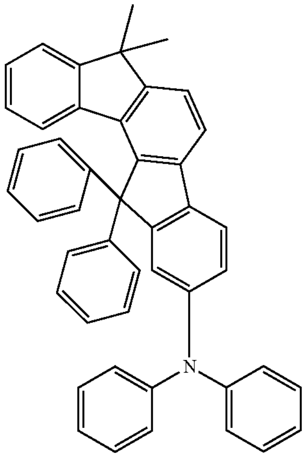
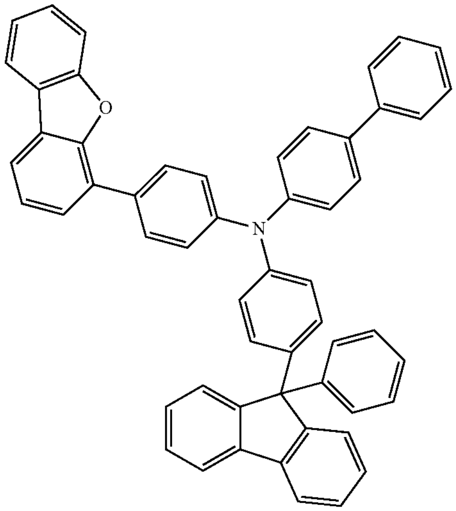

-continued
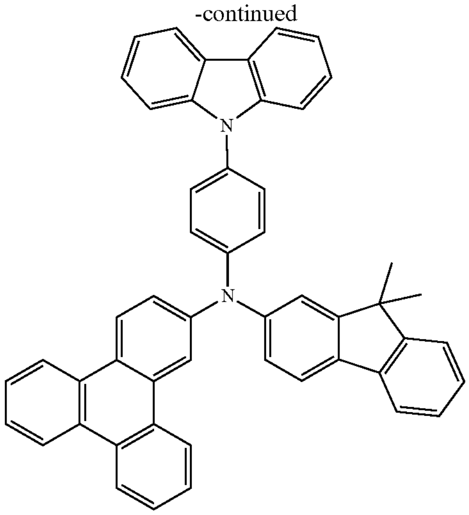
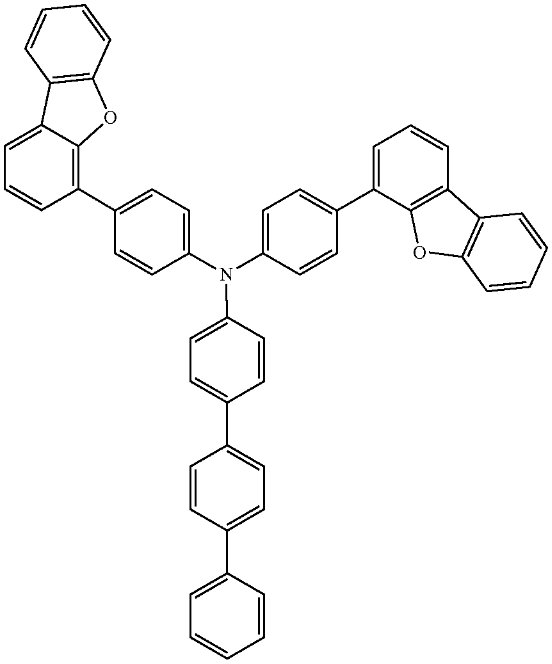
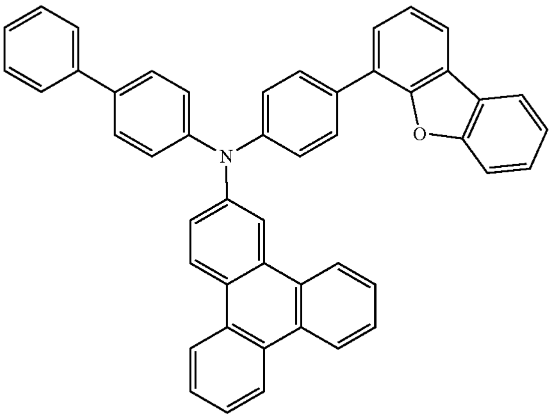
-continued
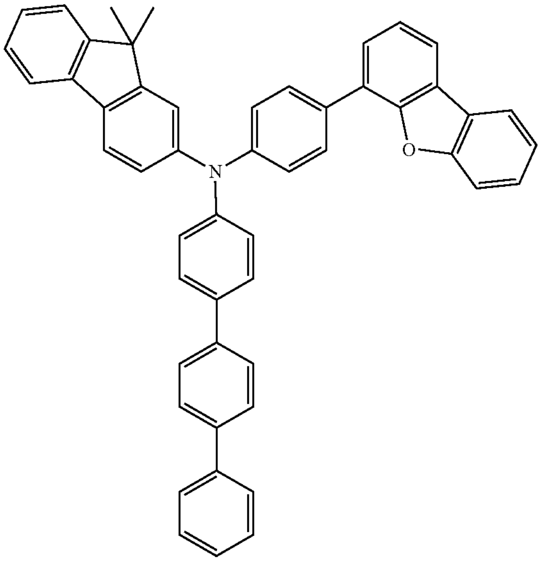
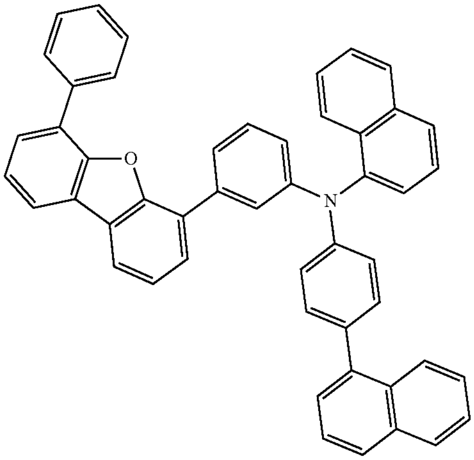
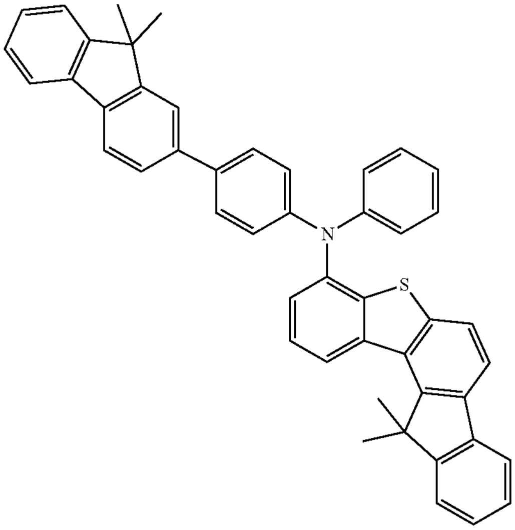

-continued
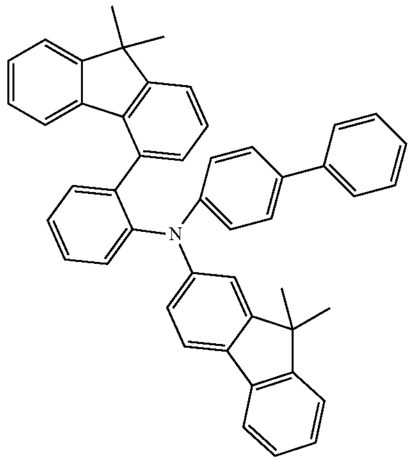
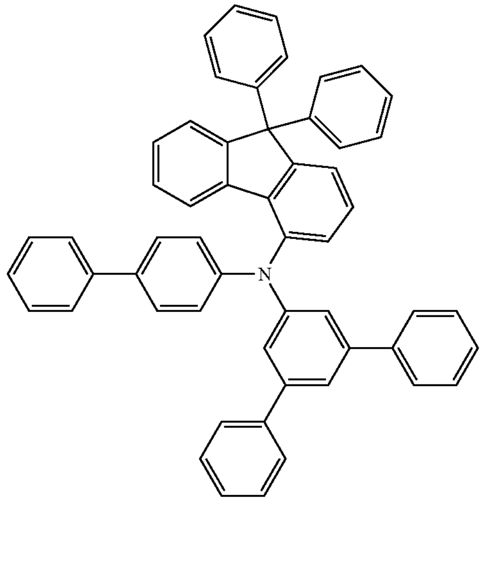
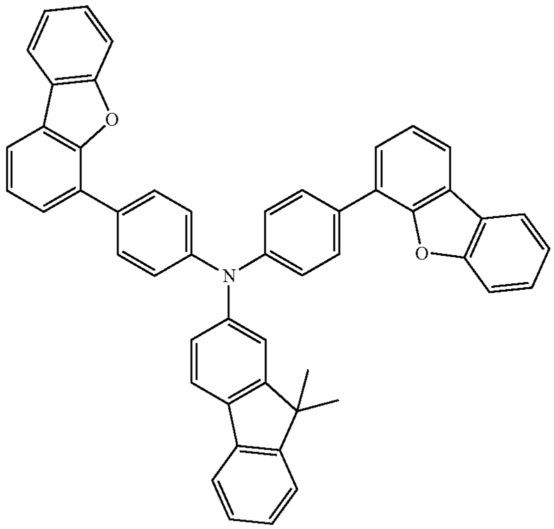
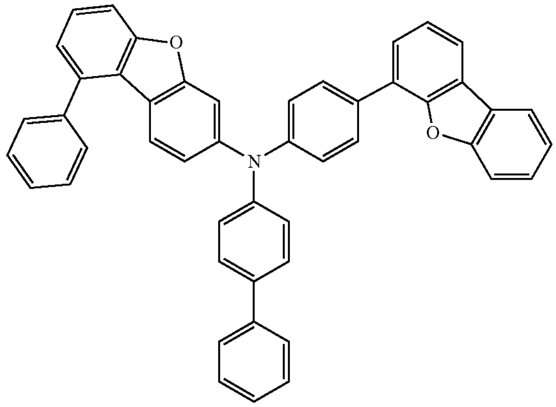
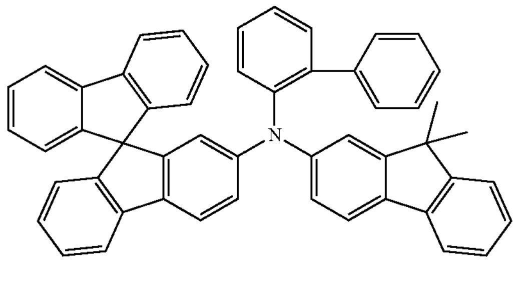
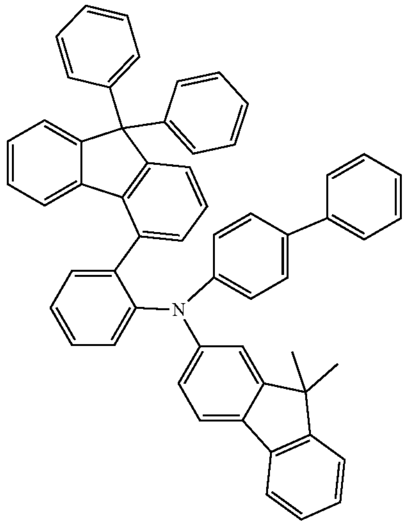
-continued -continued
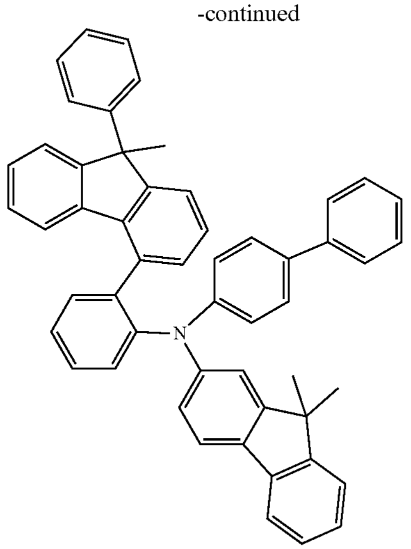
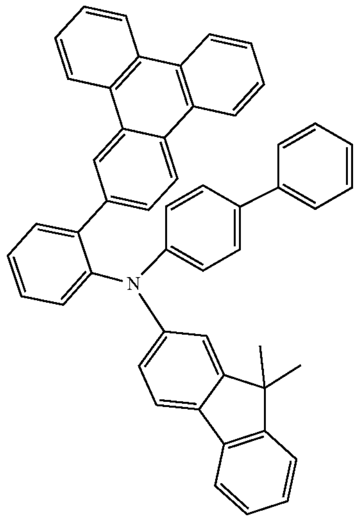
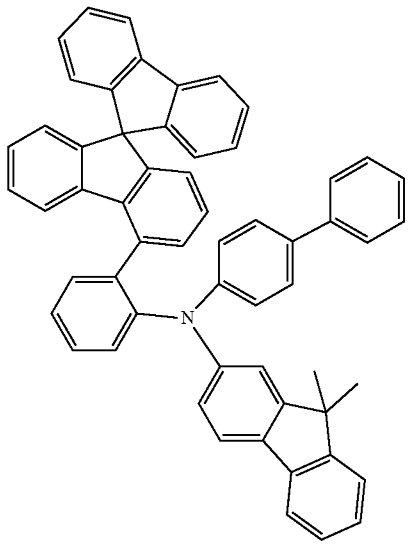
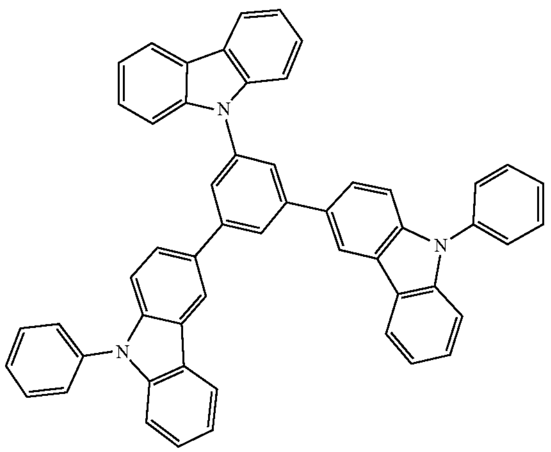
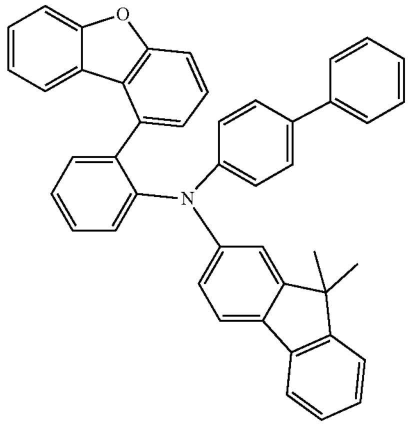
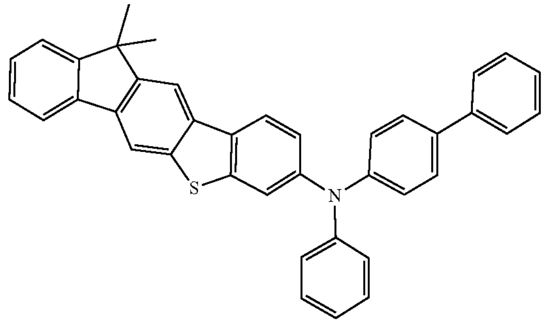

-continued
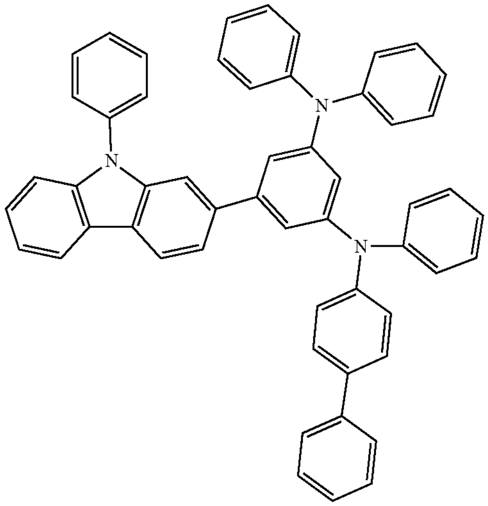
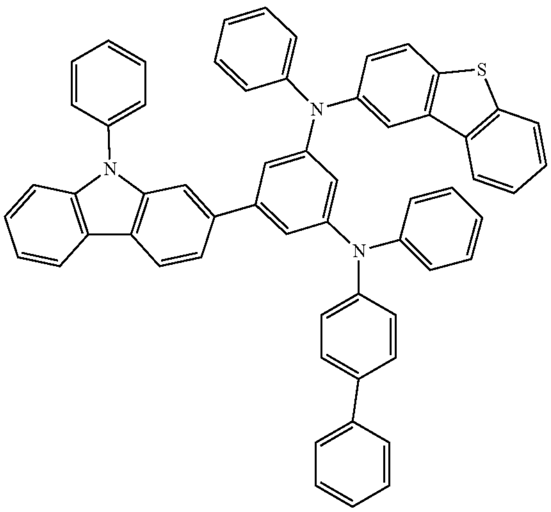
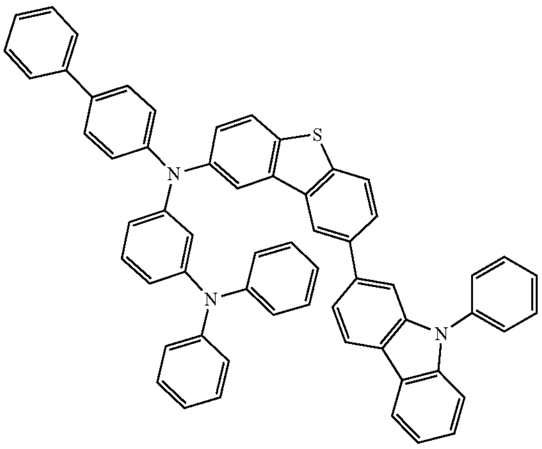
-continued
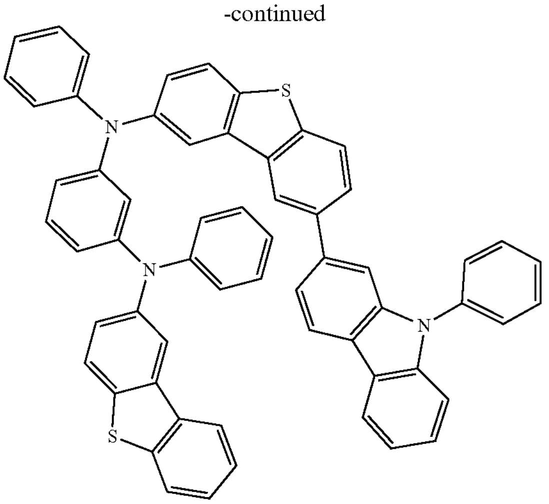
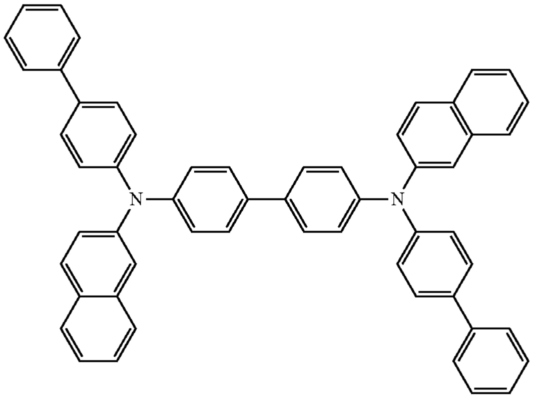
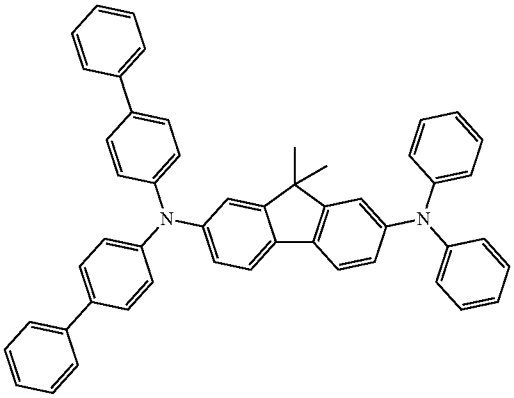
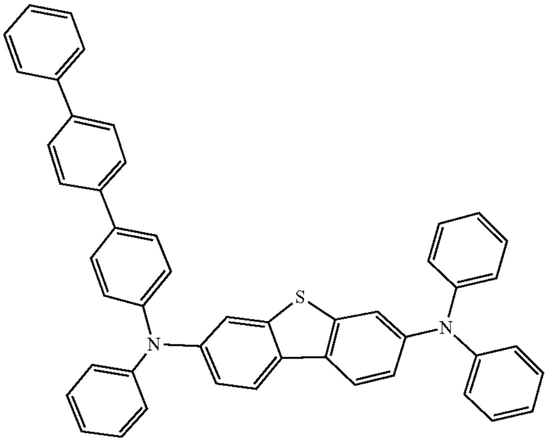

-continued
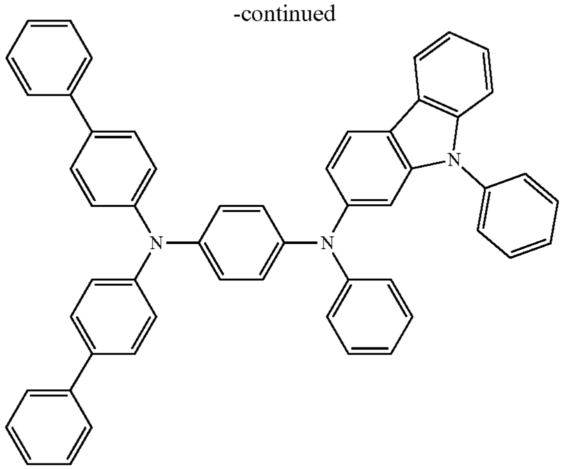
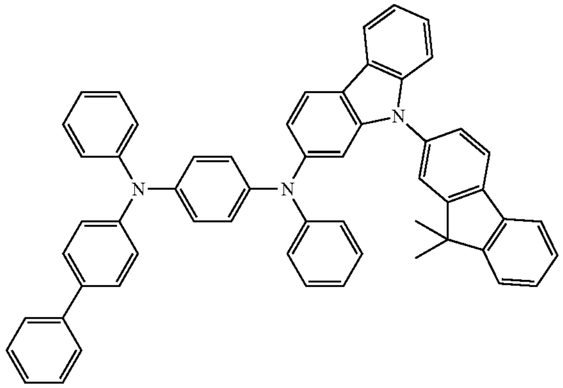
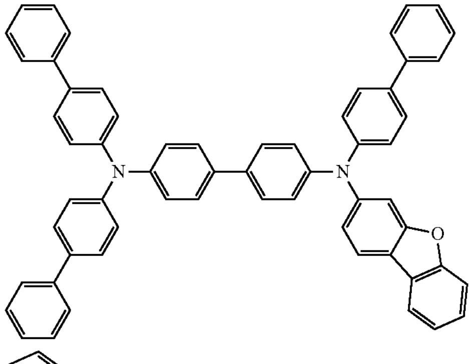
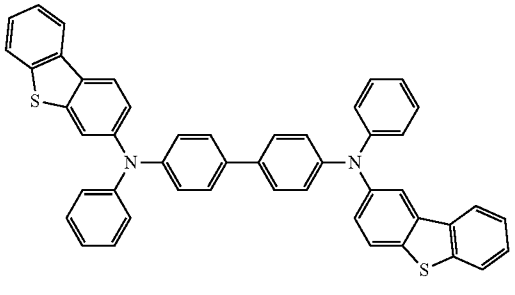
-continued
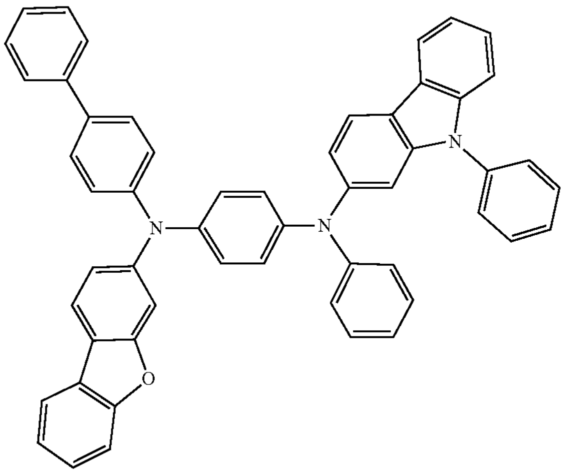
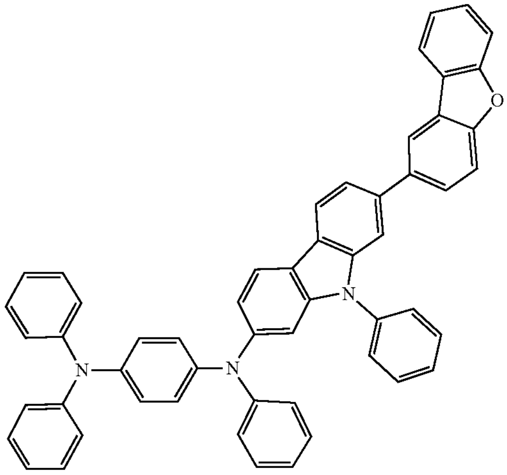
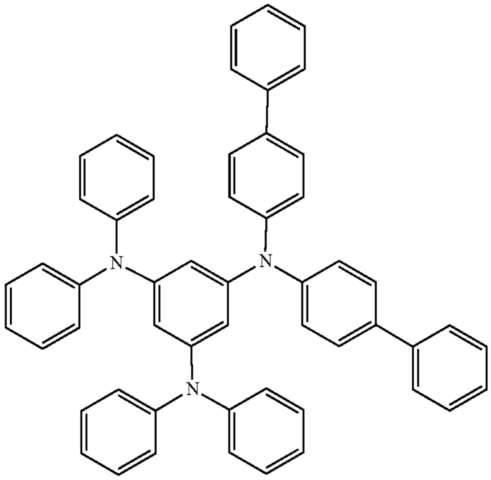

-continued
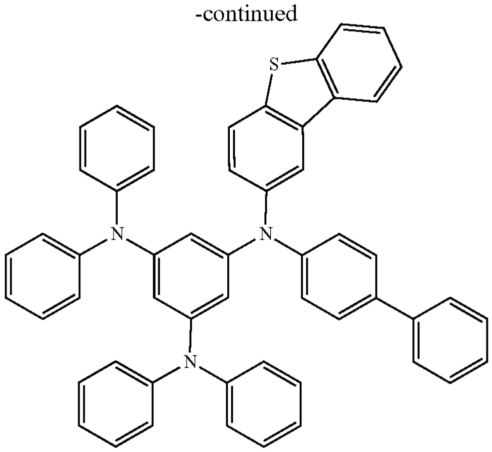
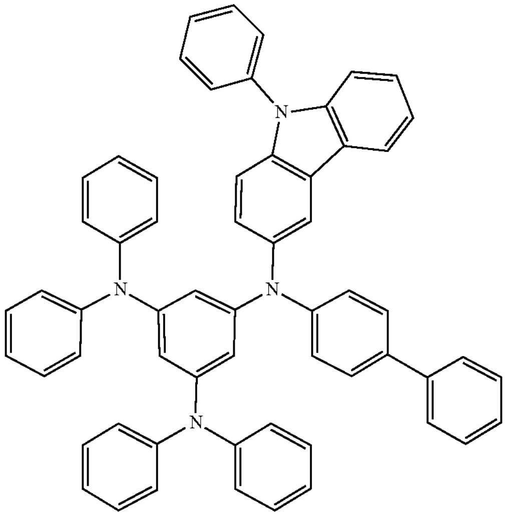
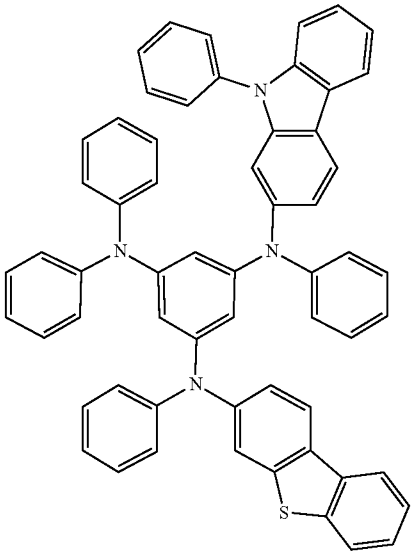
-continued
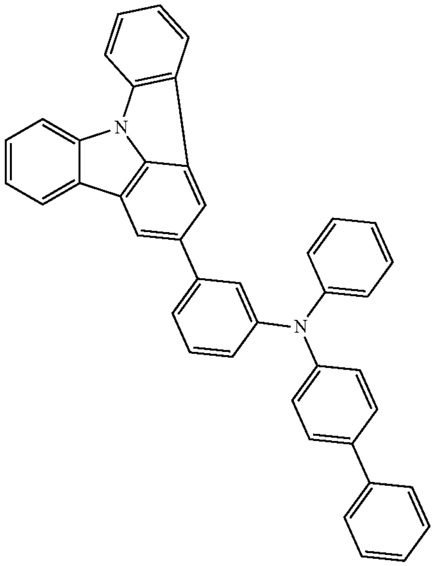
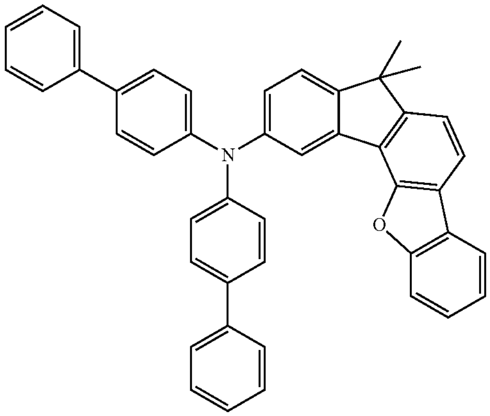
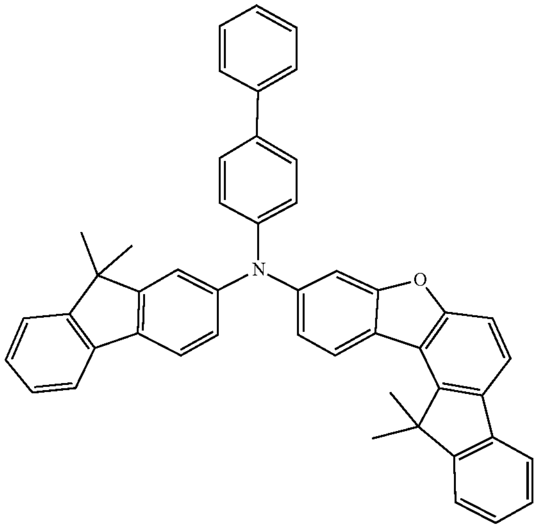

-continued
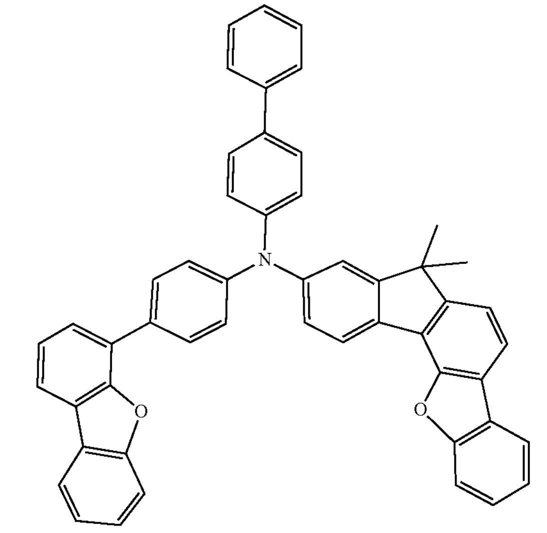
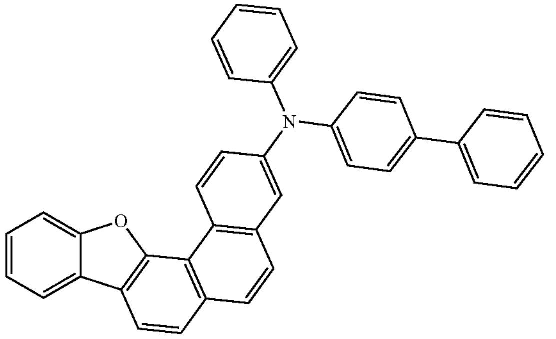
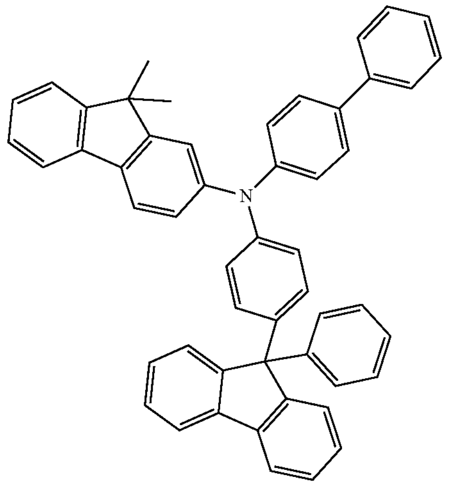
-continued
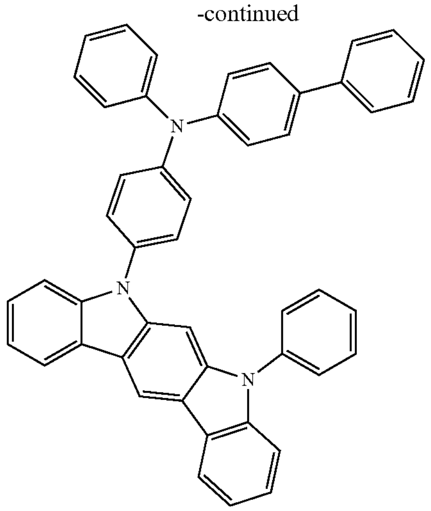
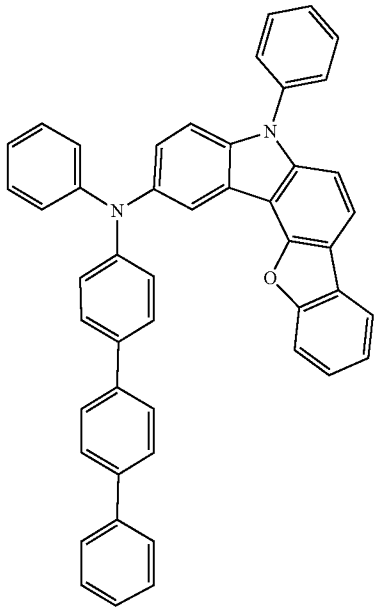
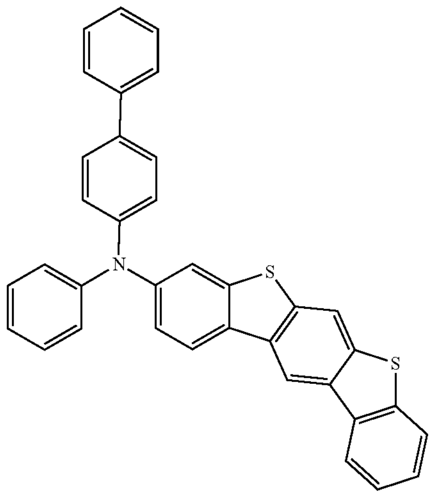

-continued
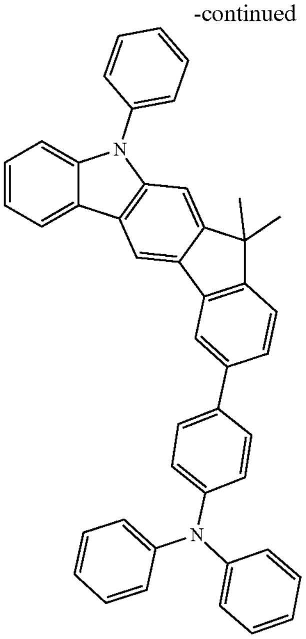
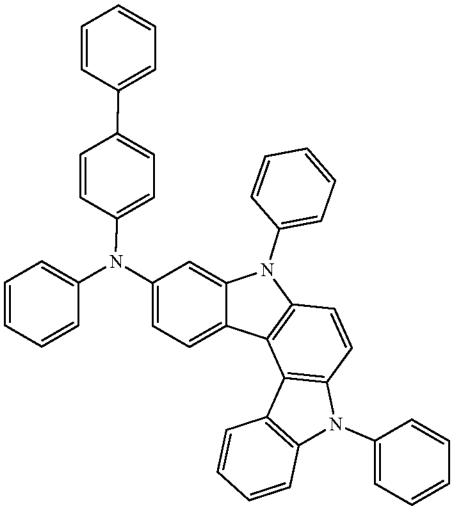
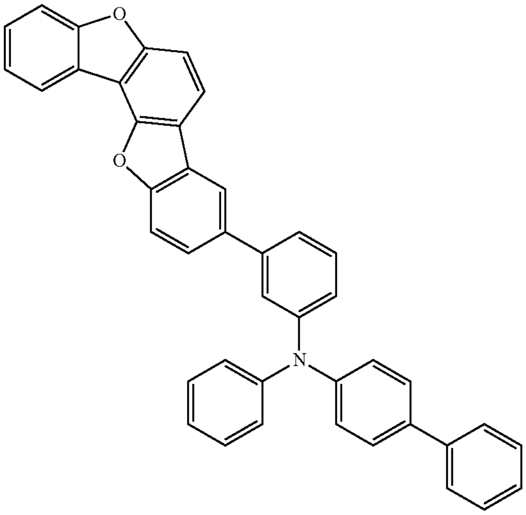
-continued
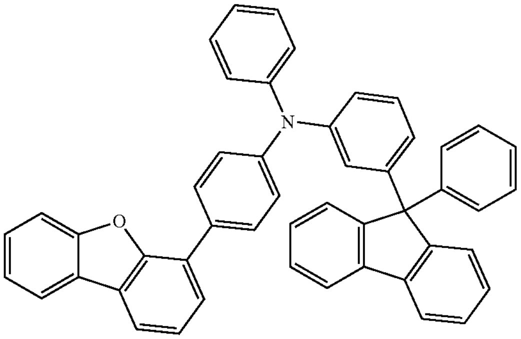
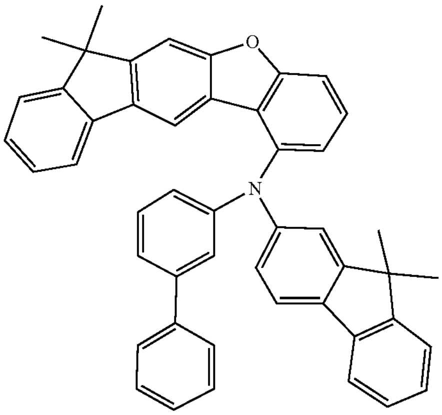
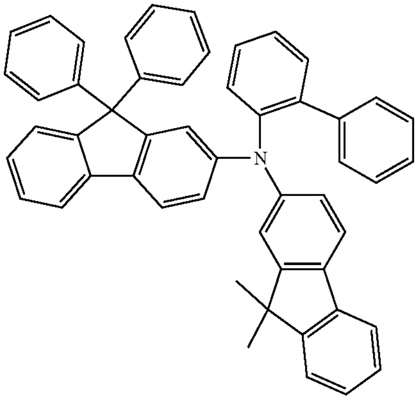
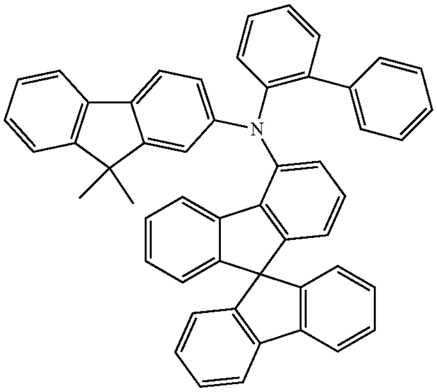

-continued
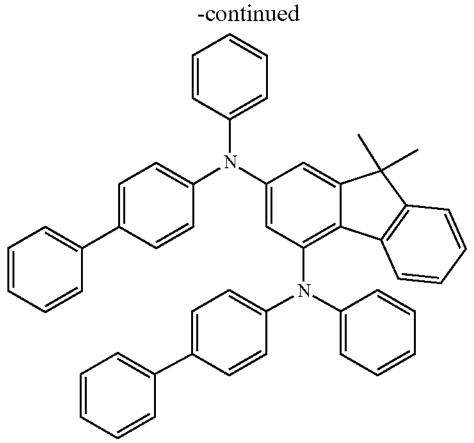
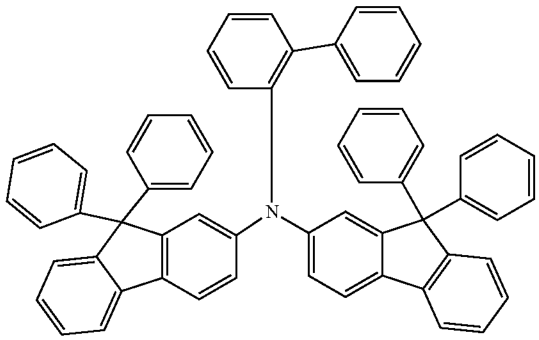
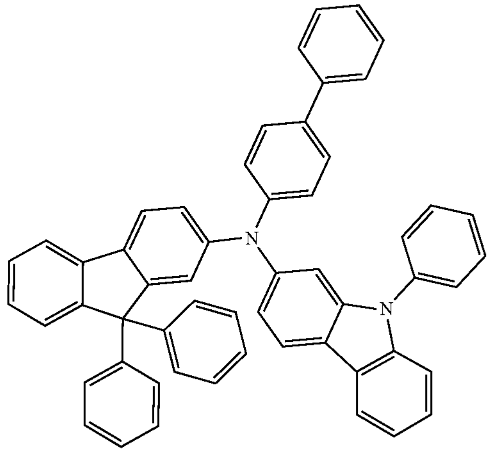
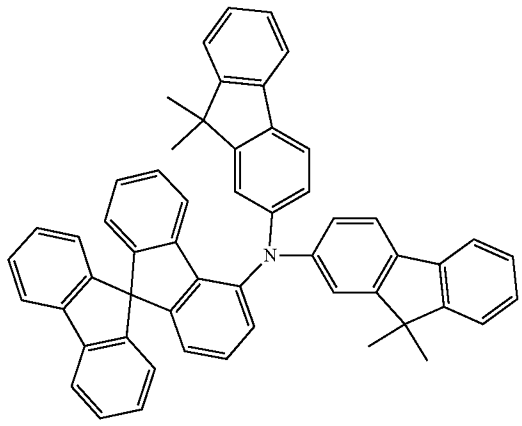
-continued
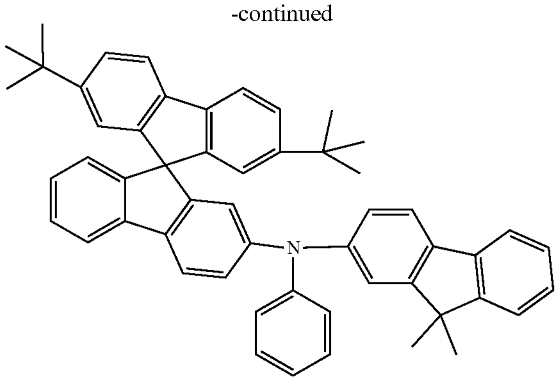
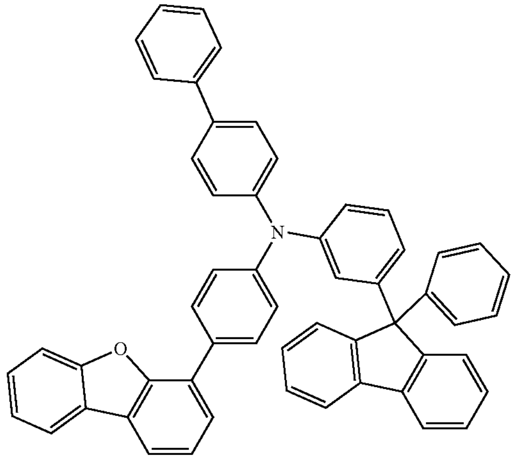
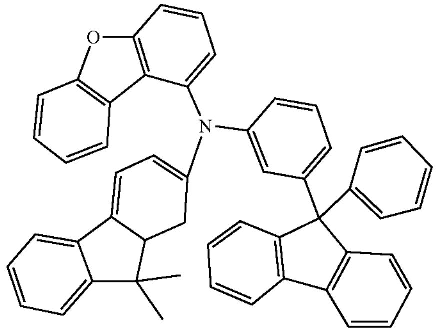
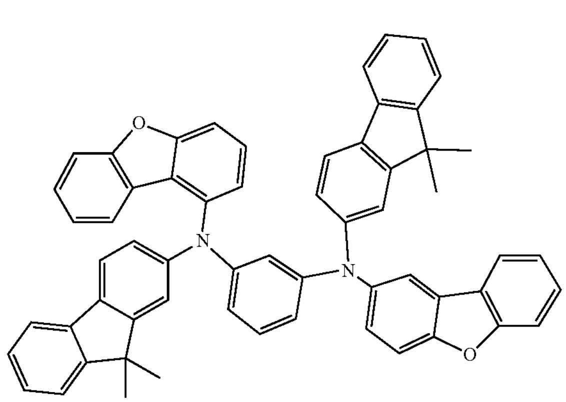

-continued
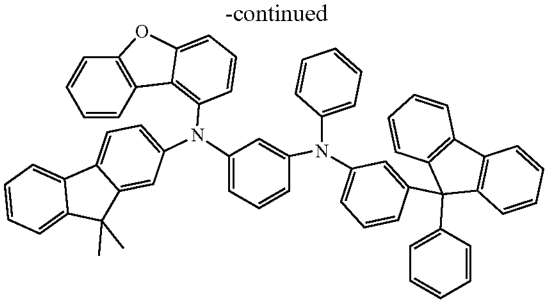
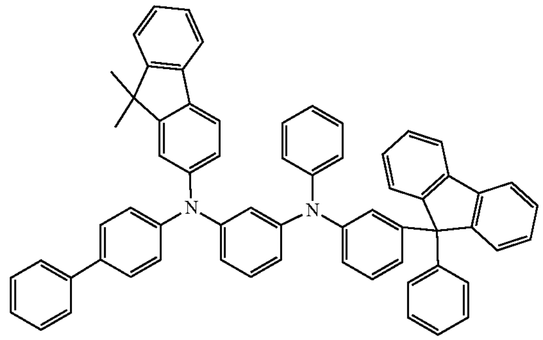
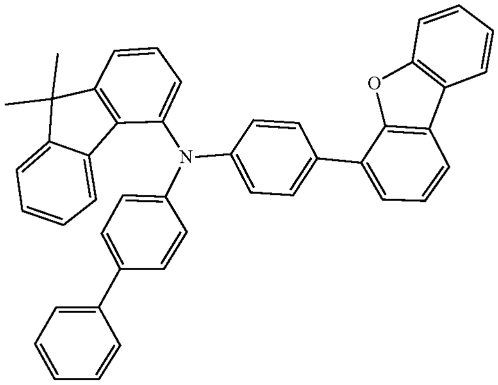
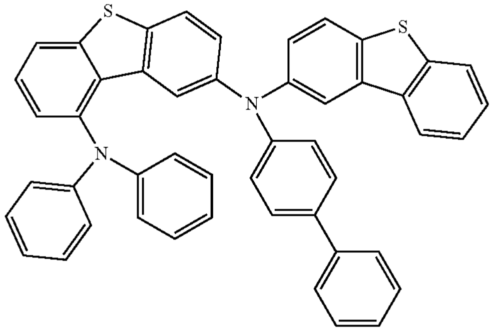
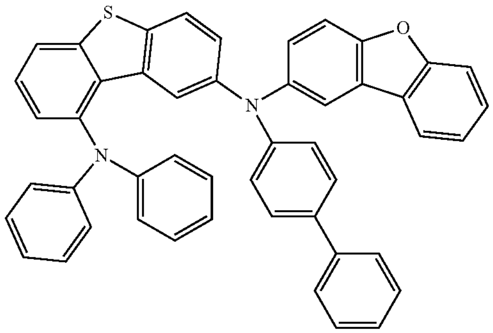
-continued
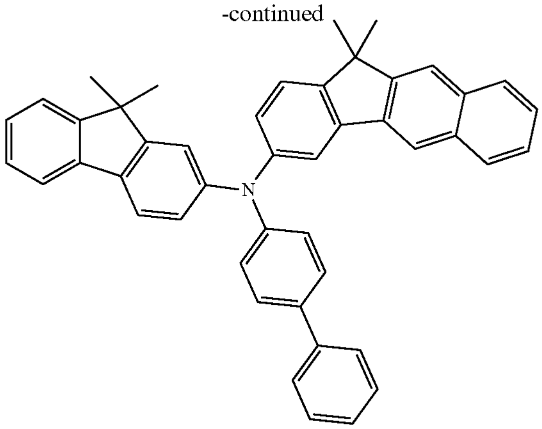
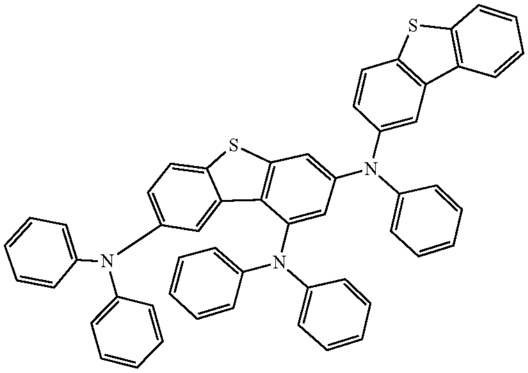
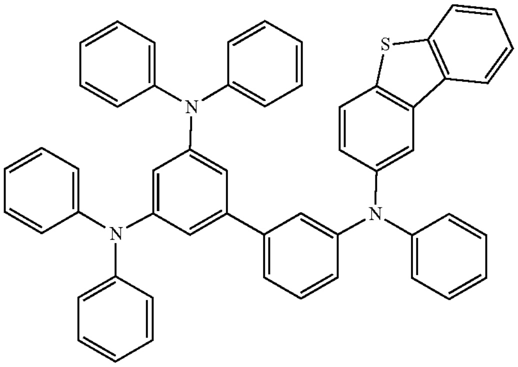
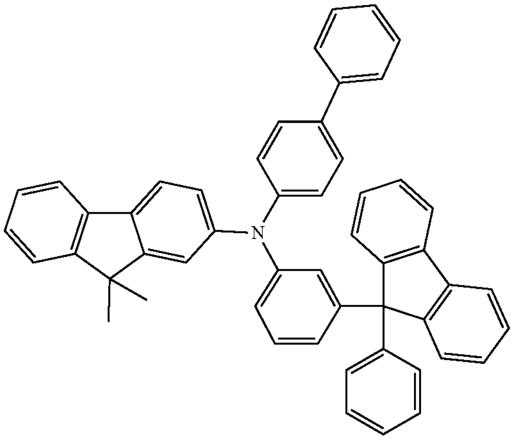
In the hole transport region, other suitable compounds may be used in addition to the aforementioned compound.
In an implementation, the charge transport region may be, e.g., an electron transport region 150.

Figure 3:
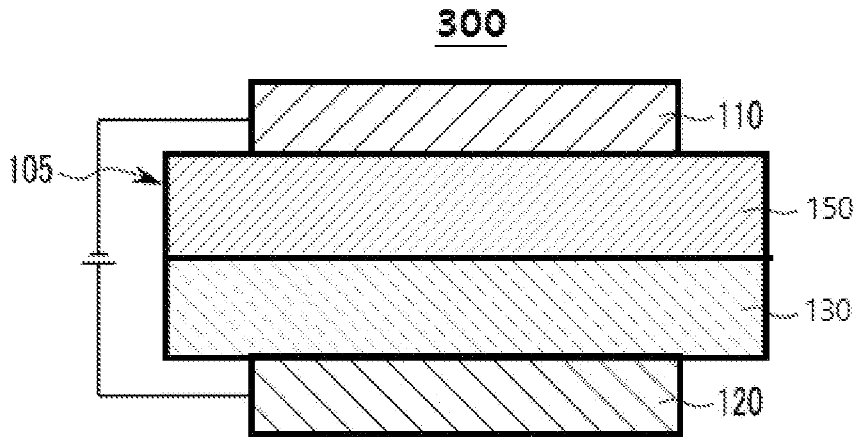

Referring to FIG. 3, the organic light emitting diode 300 may include an electron transport region 150 in addition to the light emitting layer 130. The electron transport region 150 may further increase electron injection and/or electron mobility and block holes between the cathode 110 and the light emitting layer 130.

In an implementation, the electron transport region 150 may include an electron transport layer between the cathode 110 and the light emitting layer 130, and an electron transport auxiliary layer between the light emitting layer 130 and the electron transport layer, and a compound of Group F may be included in at least one of the electron transport layer and the electron transport auxiliary layer.

[Group F]

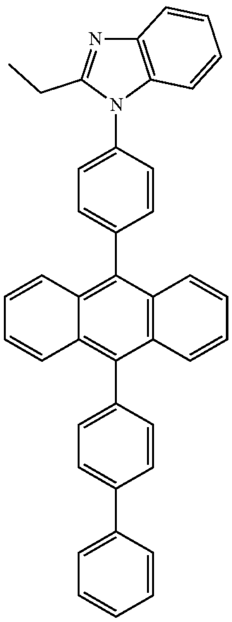

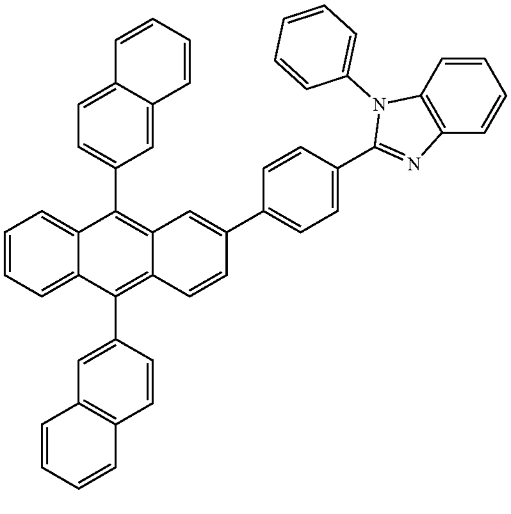

-continued

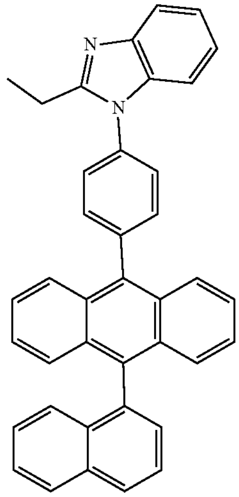

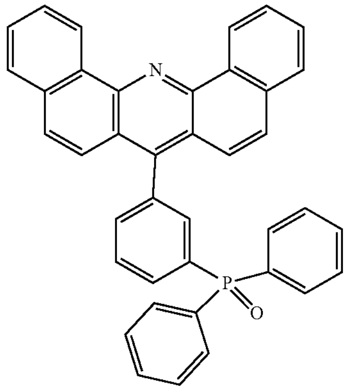

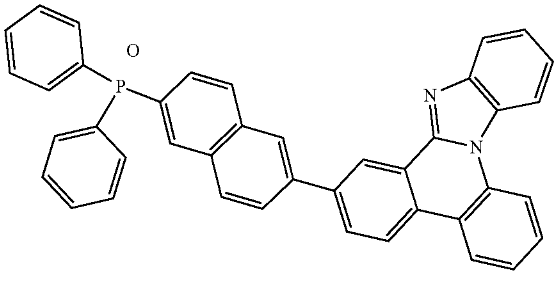

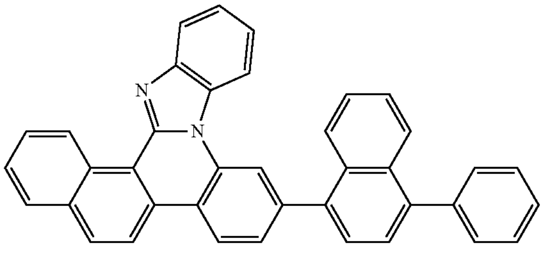

-continued
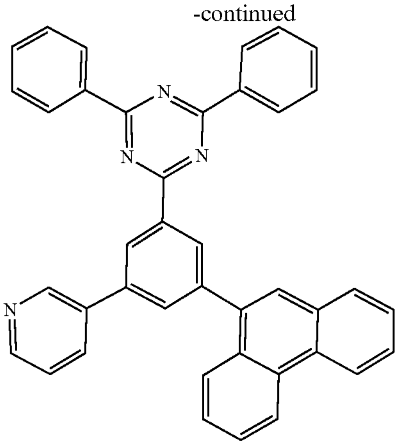
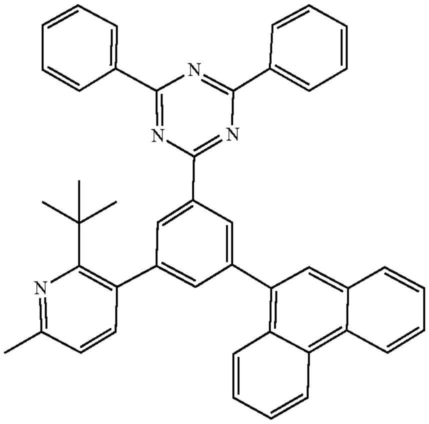
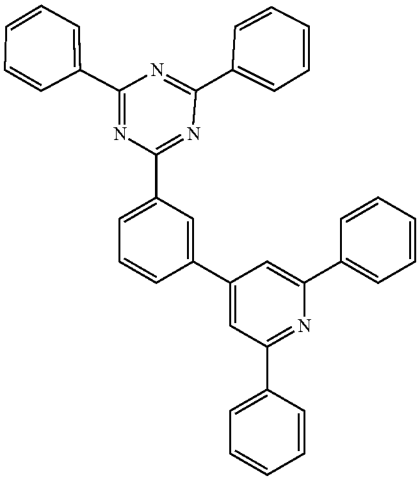
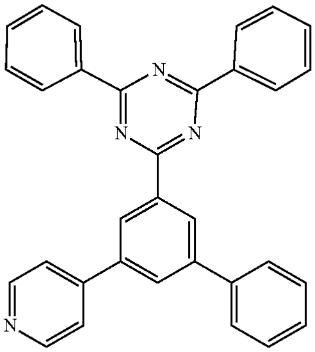
-continued
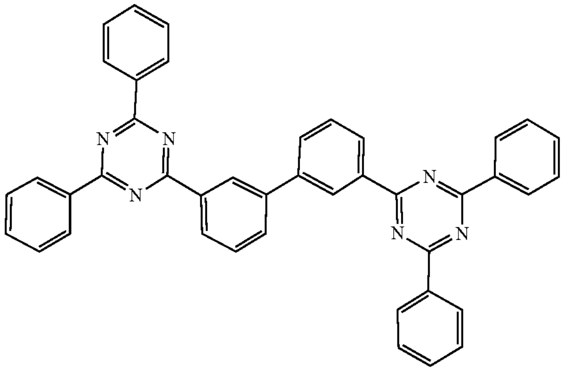
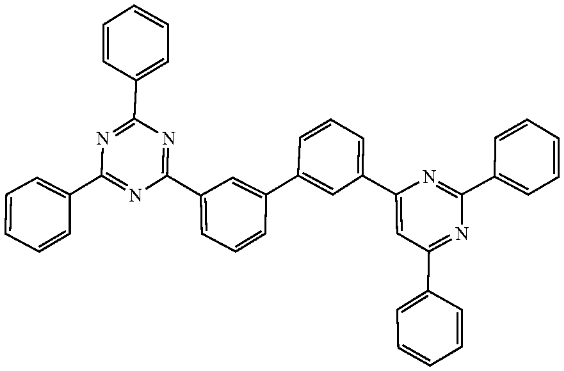
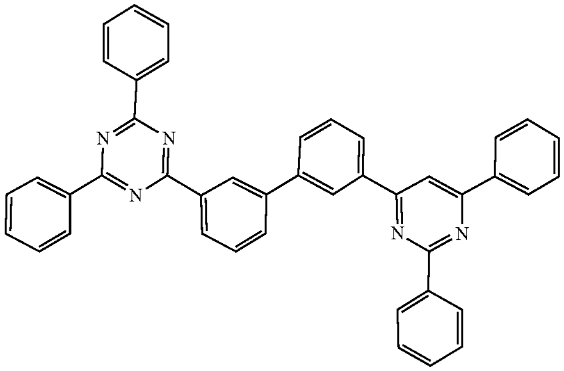
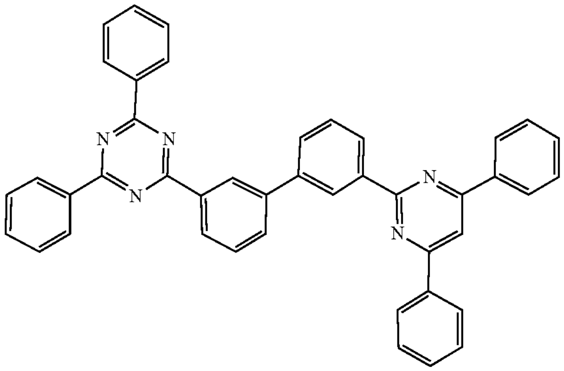

-continued
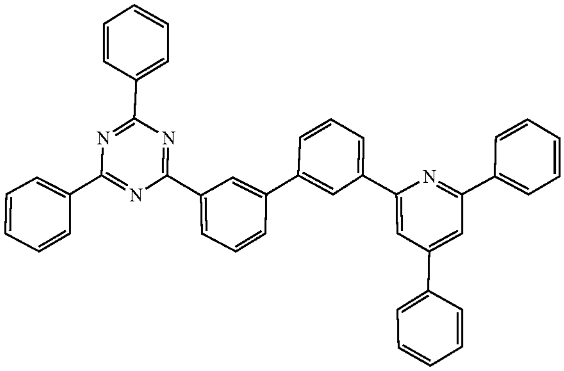
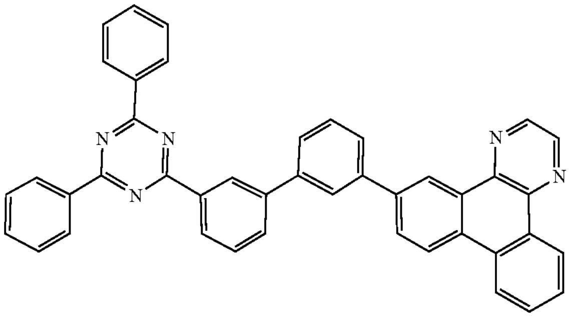
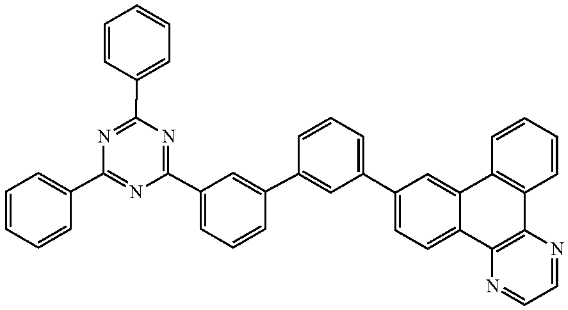
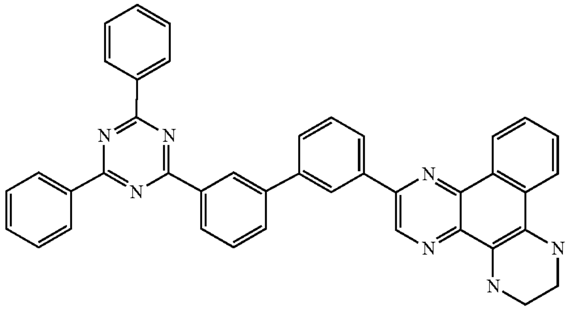
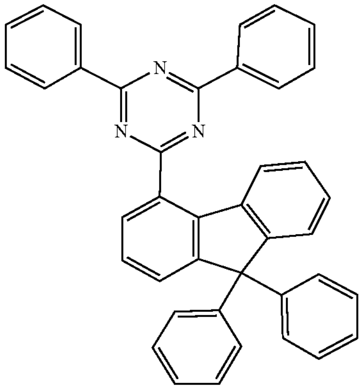
-continued
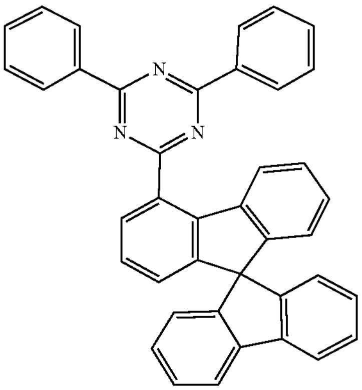
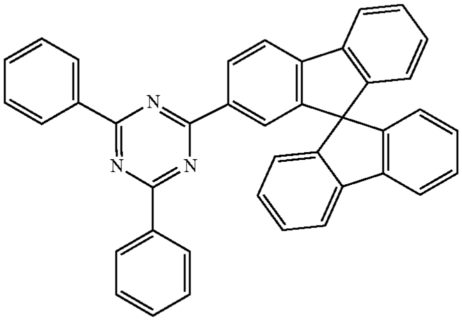
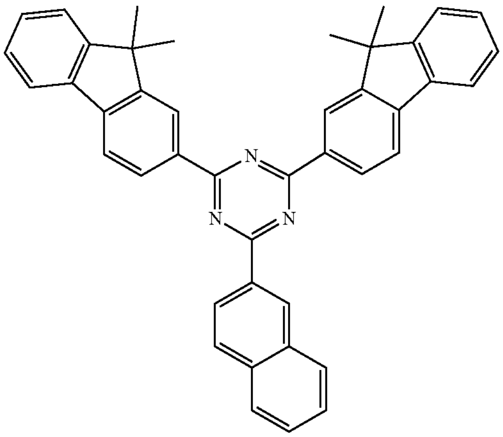
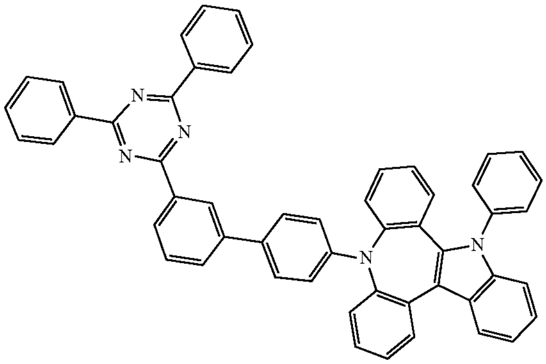

-continued
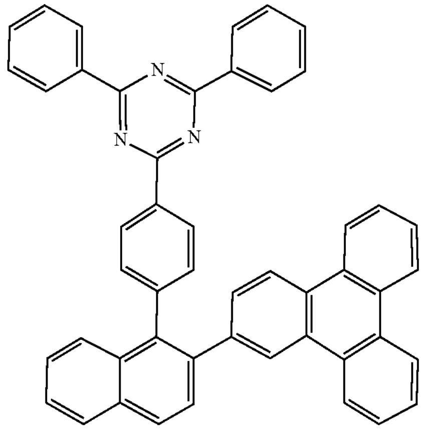
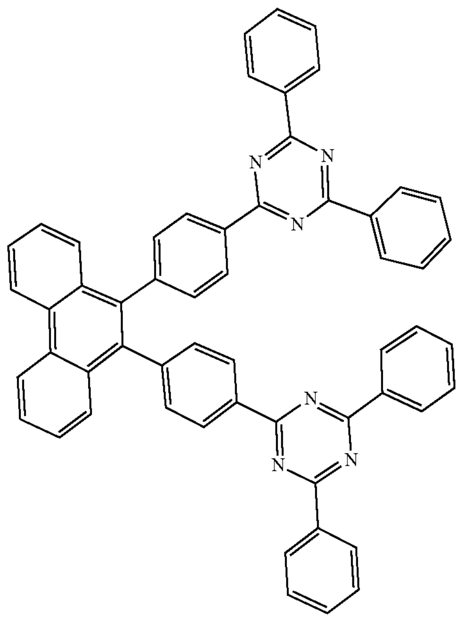
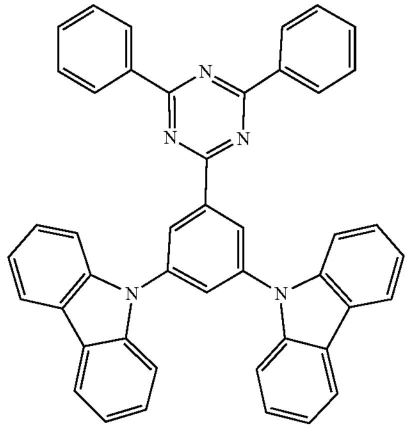
-continued
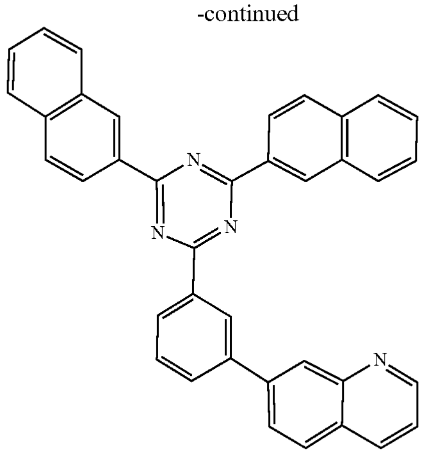
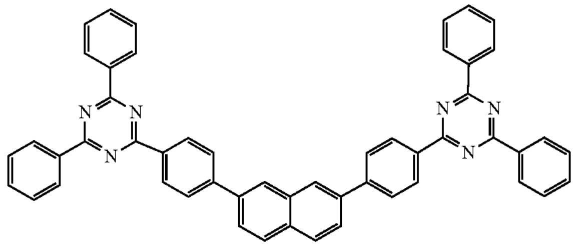
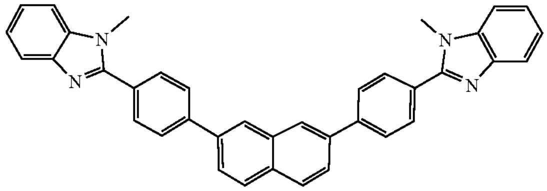
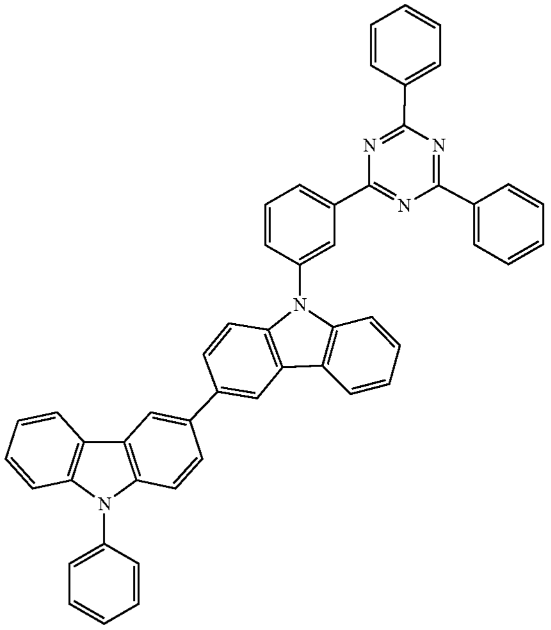

-continued
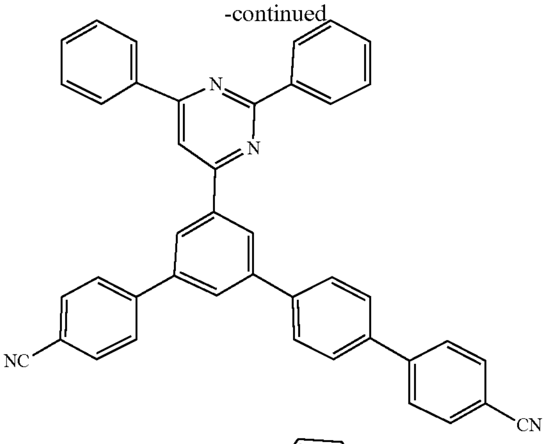
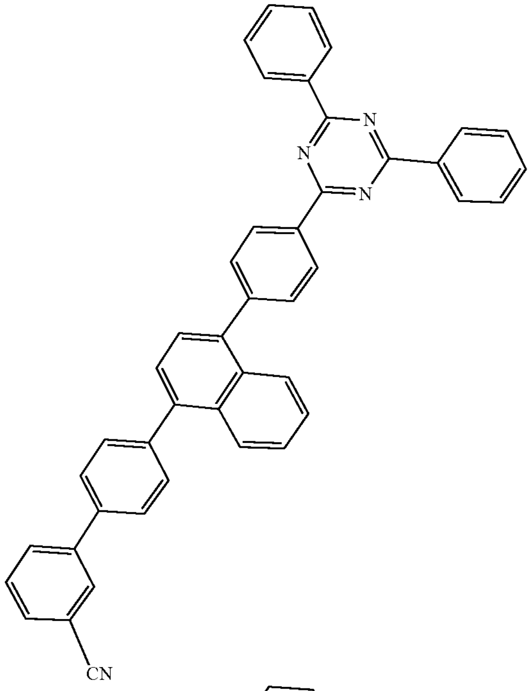
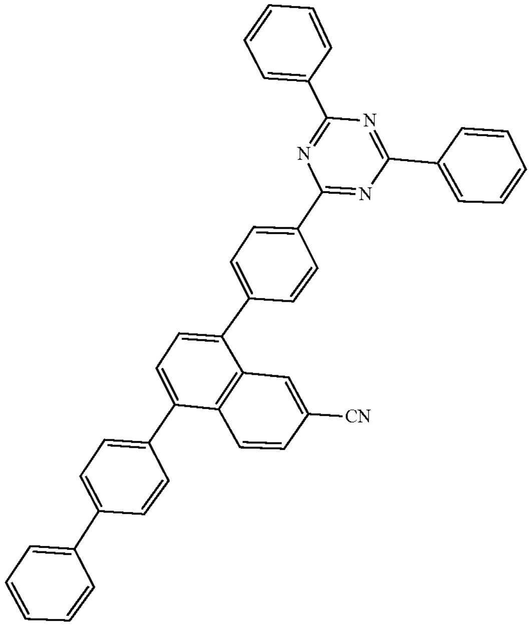
-continued
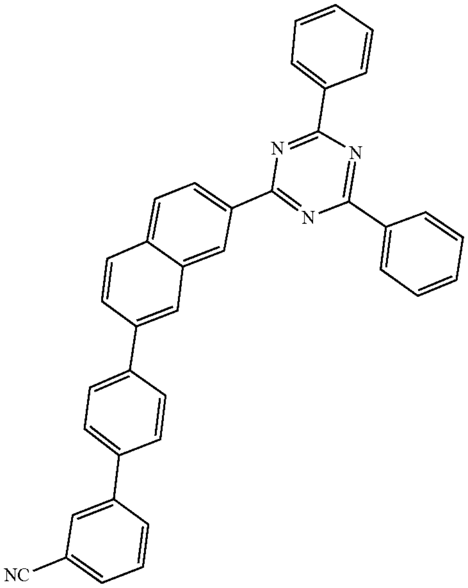
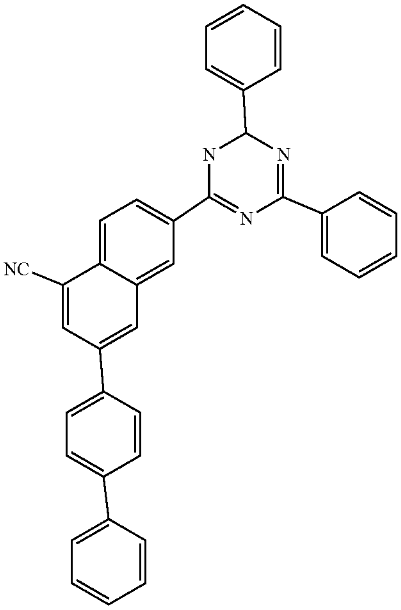

-continued
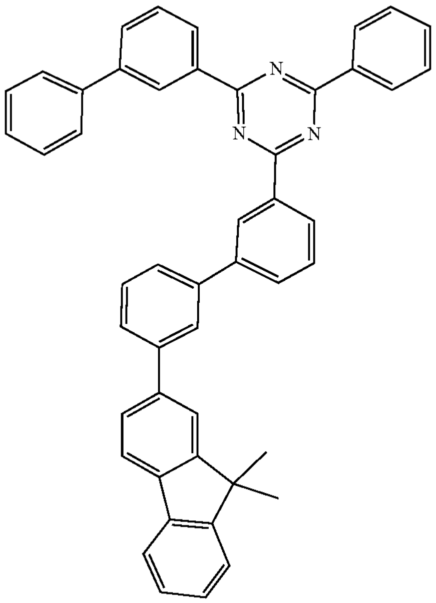
-continued
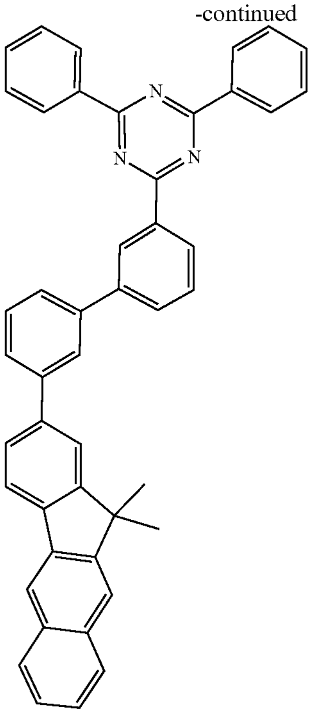
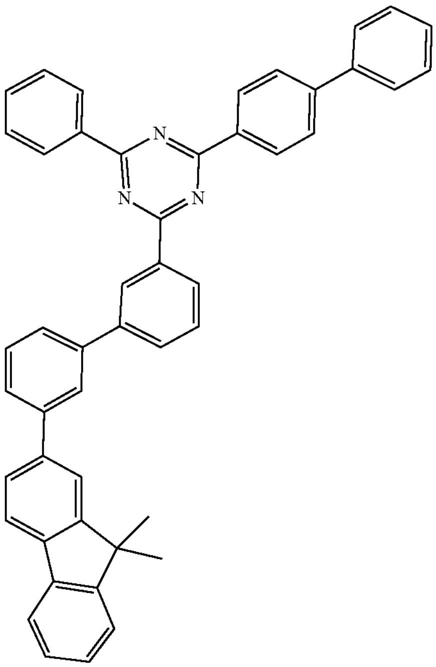
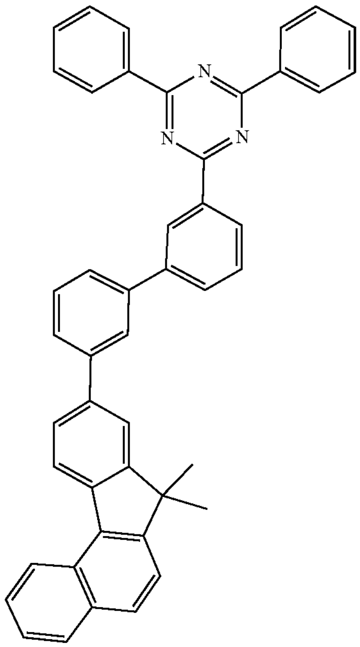

-continued
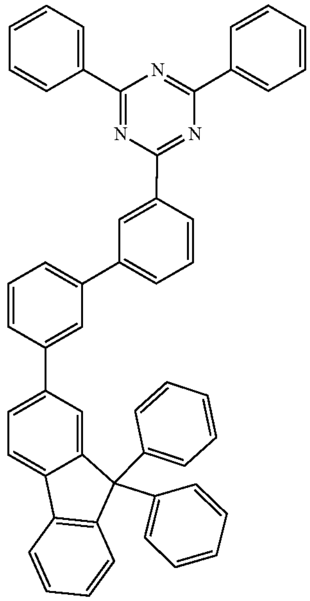
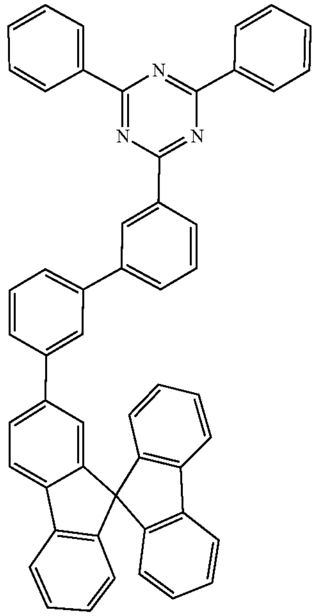
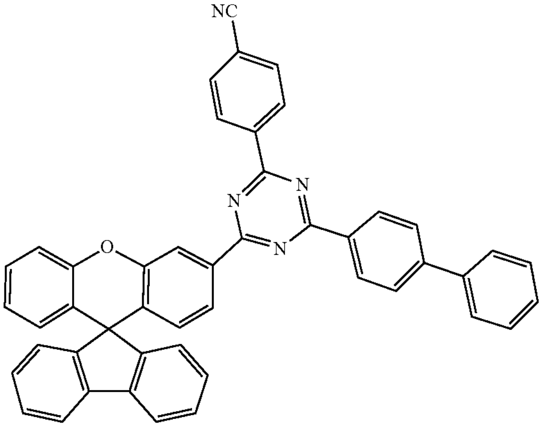
-continued
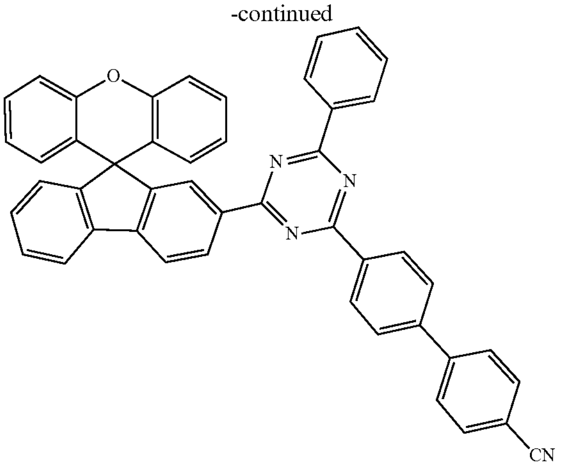
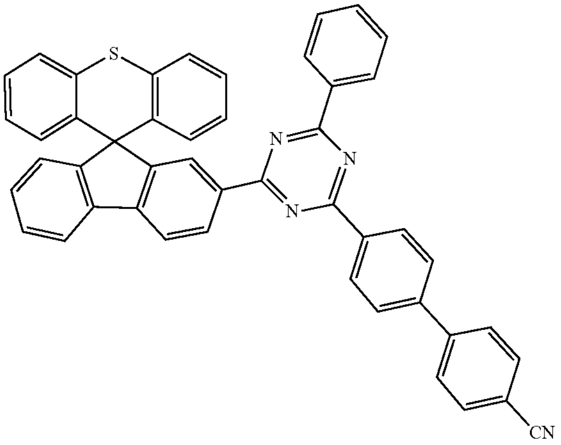
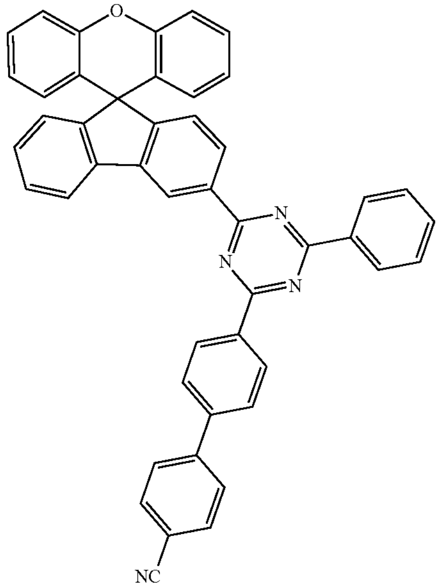

-continued

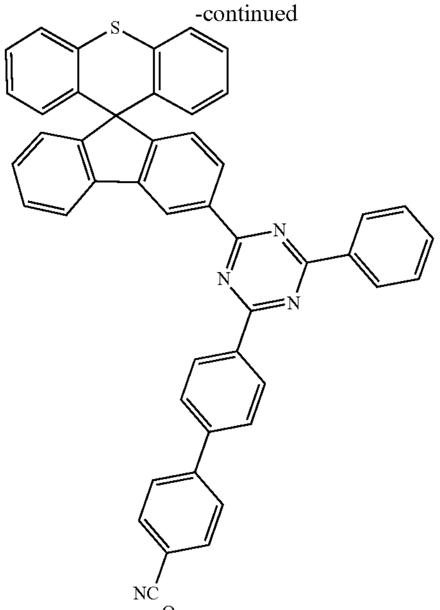

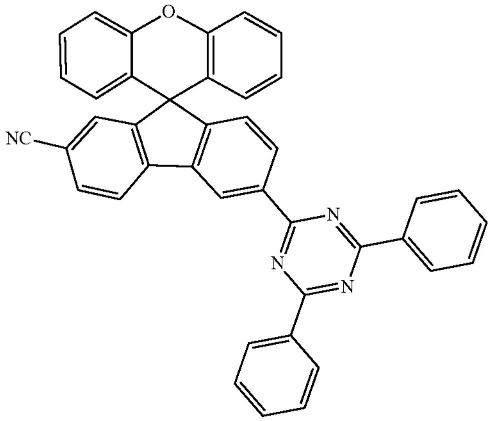

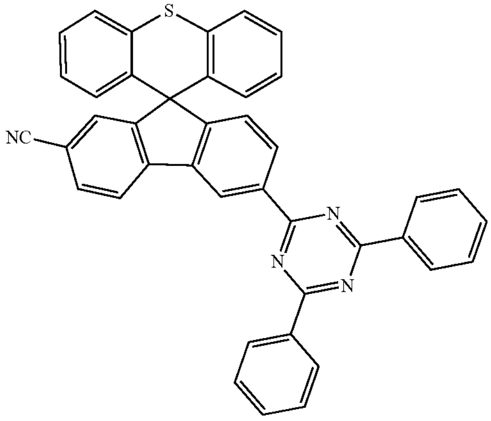

An embodiment may be an organic light emitting diode including the light emitting layer 130 as the organic layer 105 as shown in FIG. 1.

Another embodiment may be an organic light emitting diode including a hole transport region 140 in addition to the light emitting layer 130 as the organic layer 105 as shown in FIG. 2.

Another embodiment may be an organic light emitting diode including an electron transport region 150 in addition to the light emitting layer 130 as the organic layer 105 as shown in FIG. 3.

Figure 4:
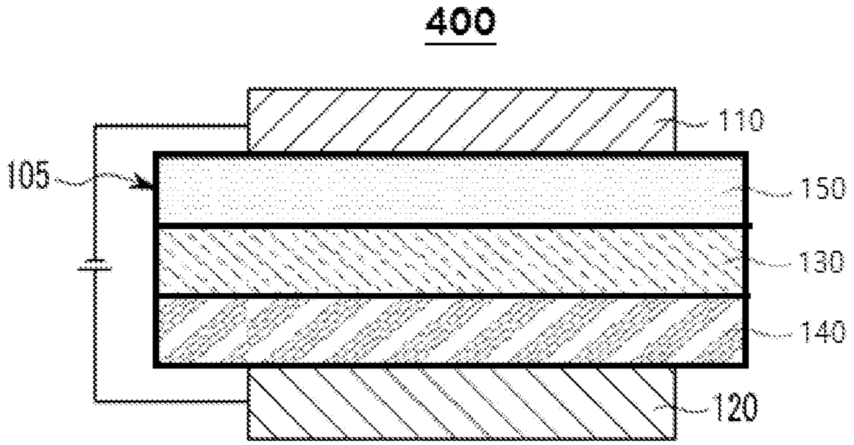

Another embodiment may be an organic light emitting diode including a hole transport region 140 and an electron transport region 150 in addition to the light emitting layer 130 as the organic layer 105 as shown in FIG. 4.

Another embodiment may be an organic light emitting diode further including an electron injection layer, a hole injection layer, or the like, in addition to the light emitting layer 130 as the organic layer 105 in each of FIGS. 1 to 4.

The organic light emitting diodes 100, 200, 300, and 400 may be produced by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in Examples and Synthesis Examples were purchased from Sigma-Aldrich Co. Ltd., TCI Inc., Tokyo chemical industry, or P&H tech, as far as there is no particular comment or were synthesized by suitable methods.

(Preparation of Compound for Organic Optoelectronic Device)

Compounds were synthesized through the following steps.

Synthesis Example 1: Synthesis of Compound B-1

[Reaction Scheme 1]

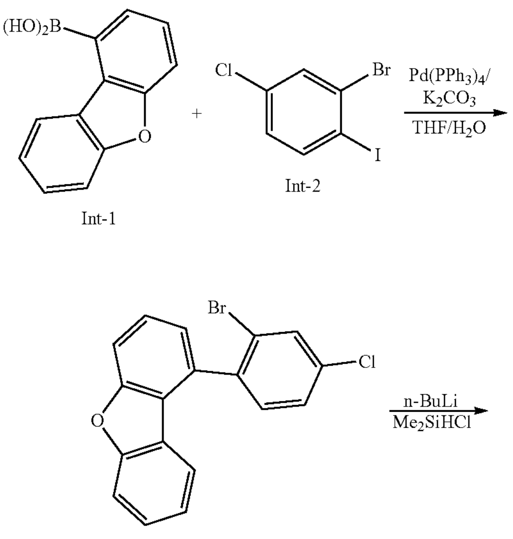

Int-1

Int-2

Int-3

-continued

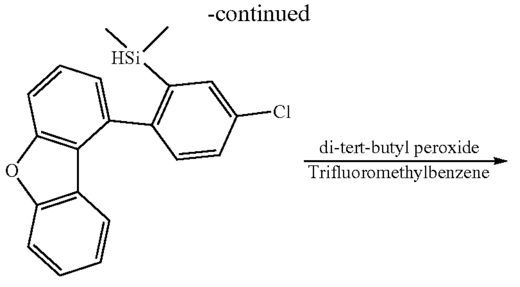

Int-4

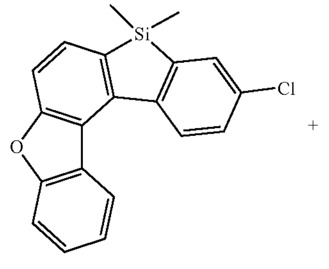

Int-5

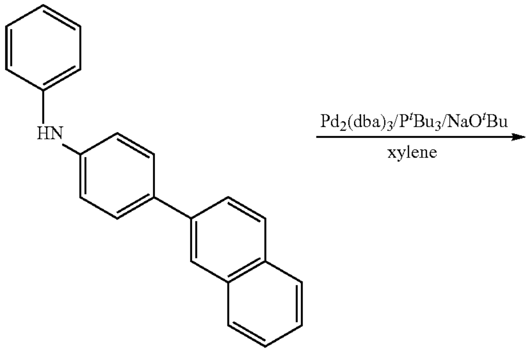

Int-6

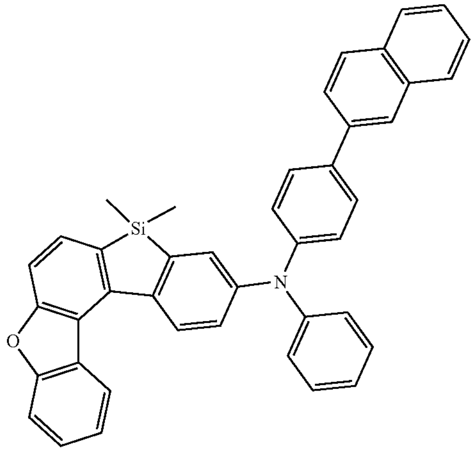

B-1

1$^{st}$ Step: Synthesis of Int-3

Int-2 (2-bromo-4-chloro-1-iodobenzene: 208.74 g, 657.75 mmol) was dissolved in 2.0 L of tetrahydrofuran (THF) and 1.0 L of distilled water, and Int-1 (dibenzofuran-1-boronic acid: 150.00 g, 657.75 mmol) and tetrakis(triphenylphosphine) palladium (22.8 g, 19.73 mmol) were added thereto and then, stirred. Subsequently, potassium carbonate (227.27 g, 1644.38 mmol) saturated in 1,000 ml of water was added thereto and then, heated under reflux at 80° C. for 12 hours. When a reaction was completed, water was added to the reaction solution and then, extracted with ethyl acetate (EA) and treated with anhydrous magnesium sulfate to remove moisture, filtered, and concentrated under a reduced pressure. The obtained residue was separated and purified through flash column chromatography, obtaining 178.78 g (76%) of Int-3.

2$^{nd}$ Step: Synthesis of Int-4

Int-3 (178.00 g 497.72 mmol) was dissolved in 3,000 mL of tetrahydrofuran (THF), and an internal temperature thereof was reduced to −78° C. Subsequently, n-BuLi (238.9 ml, 597.29 mmol) was added thereto in a dropwise fashion, while the internal temperature of −78° C. was maintained, and then, stirred at the temperature for 1 hour.

After slowly adding chlorodimethylsilane (71.31 ml, 622.15 mmol) at −78° C. in a dropwise fashion, the obtained mixture was stirred at ambient temperature for 12 hours. When a reaction was completed, water was added to the reaction solution and then, extracted with ethyl acetate (EA), treated with anhydrous magnesium sulfate to remove moisture, filtered, and concentrated under a reduced pressure. This obtained residue was separated and purified through flash column chromatography, obtaining 92.22 g (55%) of Int-4.

3$^{rd}$ Step: Synthesis of Int-5

Int-4 (92.2 g 273.68 mmol) was dissolved in 1,000 mL of trifluoromethylbenzene, and di-tert-butyl peroxide (153.14 ml g, 821.04 mmol) was slowly added thereto in a dropwise fashion. The obtained mixture was heated under reflux at an internal temperature of 120° C. for 48 hours. When a reaction was completed, the reaction solution was allowed to cool to ambient temperature, and 1,000 ml of water was added thereto and then, stirred for 1 hour. The resultant was extracted with ethyl acetate (EA), treated with anhydrous magnesium sulfate to remove moisture, filtered, and concentrated under a reduced pressure. The obtained residue was separated and purified through flash column chromatography, obtaining 68.74 g (75%) of Int-5.

4$^{th}$ Step: Synthesis of Compound B-1

Int-5 3.38 g (10.1 mmol), Int-6 3.15 g (10.1 mmol), sodium t-butoxide 2.42 g (25.26 mmol), and 0.41 g (1.01 mmol) of tri-tert-butylphosphine were dissolved in 100 ml of xylene, and 0.46 g (0.51 mmol) of $Pd_2(dba)_3$ was added thereto and then, stirred under reflux for 12 hours under a nitrogen atmosphere. When a reaction was completed, after performing extraction with xylene and distilled water, an organic layer therefrom was dried with anhydrous magnesium sulfate and filtered, and a filtrate therefrom was concentrated under a reduced pressure. A product therefrom was purified with normal hexane/dichloromethane (a volume ratio of 2:1) through silica gel column chromatography, obtaining 4.6 g (Yield: 77%) of Compound B-1.

calcd. C42H31NOSi:C, 84.95; H, 5.26; N, 2.36; O, 2.69; Si, 4.73. found: C, 84.95; H, 5.26; N, 2.36; O, 2.69; Si, 4.73.

Synthesis Example 2: Synthesis of Compound C-1

[Reaction Scheme 2]

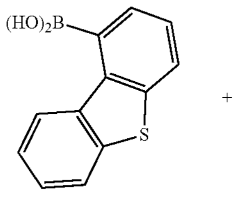

Int-7

-continued

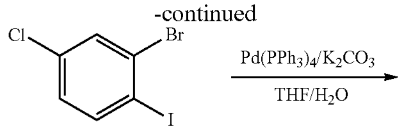

Int-2

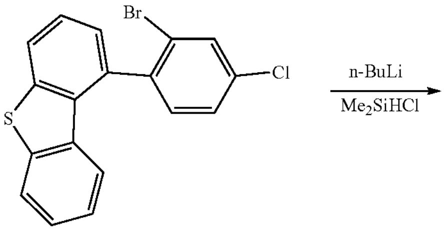

Int-8

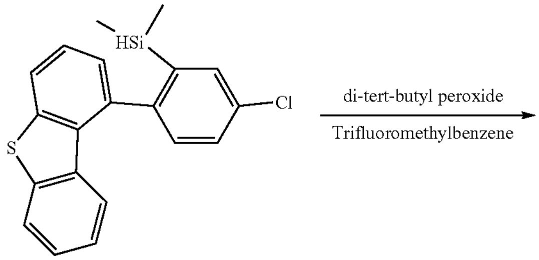

Int-9

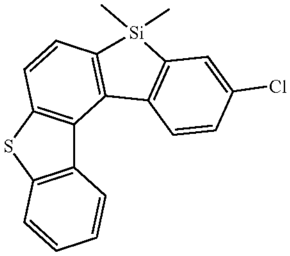

Int-10

+

-continued

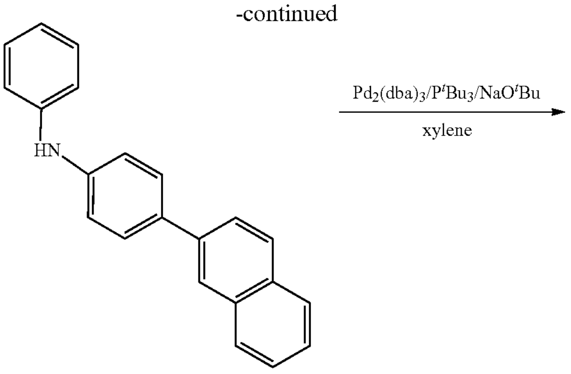

Int-6

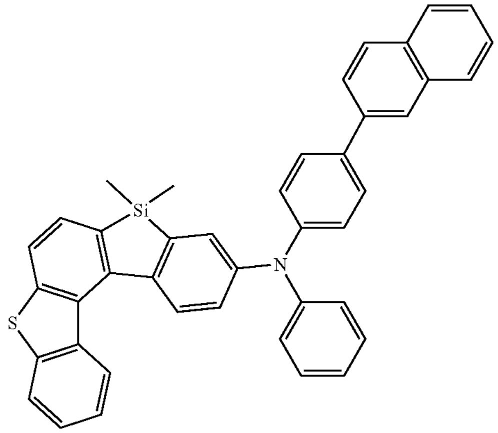

C-1

Compound C-1 was synthesized according to the same method as Synthesis Example 1 except that Int-7 (dibenzothiophene-1-boronic acid) was used instead of Int-1 as shown in Reaction Scheme 2.

calcd. C42H31NSSi:C, 82.72; H, 5.12; N, 2.30; S, 5.26; Si, 4.61. found: C, 82.71; H, 5.12; N, 2.30; S, 5.26; Si, 4.61.

Synthesis of Synthesis Examples 3 to 19

Each compound was synthesized according to the same method as Synthesis Example 1 or Synthesis Example 2 except that Int A of Table 1 was used instead of or as Int-5 of Synthesis Example 1, and Int B of Table 1 was used instead of or as Int-6.

TABLE 1

| Synthesis Examples | Int A | Int B | Final product | Amount (yield) | Property data of final product |
|---|---|---|---|---|---|
| Synthesis Example 3 | Int-5 | Int-14 | Compound B-2 | 5.11 g (69%) | calcd. C48H35NOSi: C, 86.06; H, 5.27; N, 2.09; O, 2.39; Si, 4.19 found: C, 86.06; H, 5.26; N, 2.10; O, 2.39; Si, 4.19 |
| Synthesis Example 4 | Int-5 | Int-15 | Compound B-3 | 5.32 g (72%) | calcd. C48H35NOSi: C, 86.06; H, 5.27; N 2.09; O, 2.39; Si, 4.19 found: C, 86.06; H, 5.26; N, 2.10; O, 2.39; Si, 4.19 |
| Synthesis Example 5 | Int-5 | Int-16 | Compound B-4 | 4.97 g (73%) | calcd. C48H35NOSi: C, 86.06; H, 5.27; N 2.09; O, 2.39; Si, 4.19 found: C, 86.06; H, 5.27; N, 2.10; O, 2.39; Si, 4.18 |
| Synthesis Example 6 | Int-5 | Int-17 | Compound B-5 | 4.63 g (65%) | calcd. C42H31NOSi: C, 86.06; H, 5.27; N, 2.09; O, 2.39; Si, 4.19 found: C, 86.06; H, 5.27; N, 2.11; O, 2.38; Si, 4.19 |

TABLE 1-continued

| Synthesis Examples | Int A | Int B | Final product | Amount (yield) | Property data of final product |
|---|---|---|---|---|---|
| Synthesis Example 7 | Int-5 | Int-18 | Compound B-10 | 5.59 g (63%) | calcd. C48H35NOSi: C, 86.06; H, 5.27; N, 2.09; O, 2.39; Si, 4.19 found: C, 86.07; H, 5.27; N, 2.10; O, 2.38; Si, 4.19 |
| Synthesis Example 8 | Int-5 | Int-19 | Compound B-18 | 5.90 g (68%) | calcd. C48H35NOSi: C, 86.06; H, 5.27; N, 2.09; O, 2.39; Si, 4.19 found: C, 86.05; H, 5.27; N, 2.09; O, 2.40; Si, 4.19 |
| Synthesis Example 9 | Int-5 | Int-20 | Compound B-25 | 4.31 g (70%) | calcd. C48H33NO2Si: C, 84.30; H, 4.86; N, 2.05; O, 4.68; Si, 4.11 found: C, 84.32; H, 4.86; N, 2.04; O, 4.67; Si, 4.11 |
| Synthesis Example 10 | Int-5 | Int-21 | Compound B-29 | 4.01 g (67%) | calcd. C48H33NO2Si: C, 84.30; H, 4.86; N, 2.05; O, 4.68; Si, 4.11 found: C, 84.30; H, 4.85; N, 2.06; O, 4.68; Si, 4.11 |
| Synthesis Example 11 | Int-5 | Int-22 | Compound B-41 | 4.67 g (73%) | calcd. C50H39NOSi2: C, 82.72; H, 5.41; N, 1.93; O, 2.20; Si, 7.74 found: C, 82.73; H, 5.40; N, 1.93; O, 2.20; Si, 7.74 |
| Synthesis Example 12 | Int-5 | Int-23 | Compound B-42 | 5.77 g (75%) | calcd. C50H39NOSi2: C, 82.72; H, 5.41; N, 1.93; O, 2.20; Si, 7.74 found: C, 82.72; H, 5.42; N, 1.92; O, 2.20; Si, 7.74 |
| Synthesis Example 13 | Int-5 | Int-24 | Compound B-49 | 5.22 g (73%) | calcd. C48H33NOSSi: C, 82.37; H, 4.75; N, 2.00; O, 2.29; S, 4.58; Si, 4.01; found: C, 82.37; H, 4.75; N, 2.00; O, 2.29; S, 4.58; Si, 4.01 |
| Synthesis Example 14 | Int-5 | Int-25 | Compound B-69 | 6.84 g (64%) | calcd. C42H29NO2Si: C, 83.00; H, 4.81; N, 2.30; O, 5.26; Si, 4.62; found: C, 83.00; H, 4.82; N, 2.29; O, 5.26; Si, 4.62 |
| Synthesis Example 15 | Int-5 | Int-26 | Compound B-73 | 4.78 g (69%) | calcd. C42H29NO2Si: C, 83.00; H, 4.81; N, 2.30; O, 5.26; Si, 4.62; found: C, 83.01; H, 4.81; N, 2.30; O, 5.26; Si, 4.61 |
| Synthesis Example 16 | Int-11 | Int-6 | Compound B-85 | 7.48 g (76%) | calcd. C42H31NOSi: C, 86.06; H, 5.27; N, 2.09; O, 2.39; Si, 4.19 found: C, 86.06; H, 5.27; N, 2.11; O, 2.38; Si, 4.18 |
| Synthesis Example 17 | Int-12 | Int-6 | Compound B-89 | 5.87 g (71%) | calcd. C42H31NOSi: C, 86.06; H, 5.27; N, 2.09; O, 2.39; Si, 4.19 found: C, 86.05; H, 5.27; N, 2.12; O, 2.38; Si, 4.19 |
| Synthesis Example 18 | Int-13 | Int-6 | Compound B-93 | 5.45 g (69%) | calcd. C42H31NOSi: C, 86.06; H, 5.27; N, 2.09; O, 2.39; Si, 4.19 found: C, 86.06; H, 5.27; N, 2.09; O, 2.39; Si, 4.19 |
| Synthesis Example 19 | Int-5 | Int-27 | Compound B-107 | 4.72 g (65%) | calcd. C54H38N2OSi: C, 85.45; H, 5.05; N, 3.69; O, 2.11; Si, 3.70; found: C, 85.45; H, 5.05; N, 3.69; O, 2.11; Si, 3.70 |
| Synthesis Example 20 | Int-10 | Int-16 | Compound C-4 | 7.33 g (77%) | calcd. C48H35NSSi: C, 84.05; H, 5.14; N, 2.04; S, 4.67; Si, 4.09; found: C, 84.04; H, 5.15; N, 2.04; S, 4.67; Si, 4.09 |
| Synthesis Example 21 | Int-10 | Int-17 | Compound C-5 | 5.08 g (65%) | calcd. C42H31NSSi: C, 82.72; H, 5.12; N, 2.30; S, 5.26; Si, 4.61; found: C, 82.72; H, 5.12; N, 2.30; S, 5.26; Si, 4.61 |
| Synthesis Example 22 | Int-10 | Int-21 | Compound C-29 | 4.45 g (71%) | calcd. C48H33NOSSi: C, 82.37; H, 4.75; N, 2.00; O, 2.29; S, 4.58; Si, 4.01; found: C, 82.38; H, 4.75; N, 2.00; O, 2.29; S, 4.58; Si, 4.00 |
| Synthesis Example 23 | Int-10 | Int-25 | Compound C-69 | 4.94 g (70%) | calcd. C42H29NOSSi: C, 80.86; H, 4.69; N, 2.25; O, 2.56; S, 5.14; Si, 4.50; found: C, 80.86; H, 4.69; N, 2.25; O, 2.55; S, 5.15; Si, 4.50 |
| Synthesis Example 24 | Int-10 | Int-26 | Compound C-73 | 5.57 g (68%) | calcd. C42H29NOSSi: C, 80.86; H, 4.69; N, 2.25; O, 2.56; S, 5.14; Si, 4.50; found: C, 80.86; H, 4.69; N, 2.25; O, 2.56; S, 5.14; Si, 4.50 |

TABLE 1-continued
| Synthesis Examples | Int A | Int B | Final product | Amount (yield) | Property data of final product |
|---|---|---|---|---|---|
[Int A]
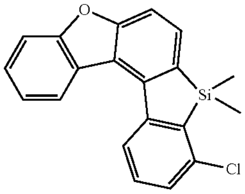
Int-11
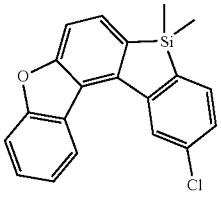
Int-12
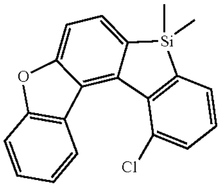
Int-13
[Int B]
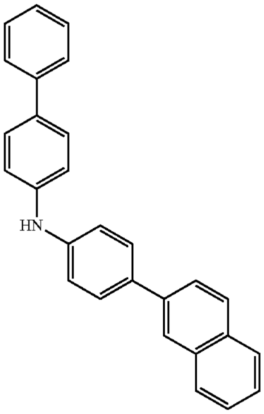
Int-14
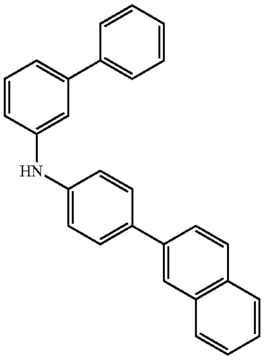
Int-15
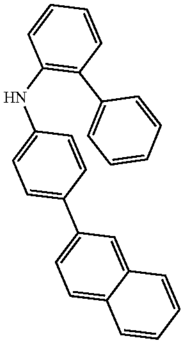
Int-16
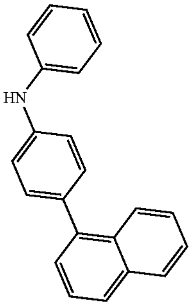
Int-17
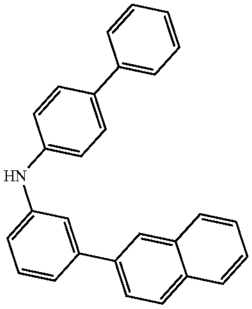
Int-18
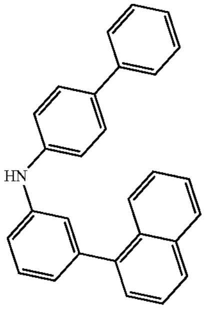
Int-19
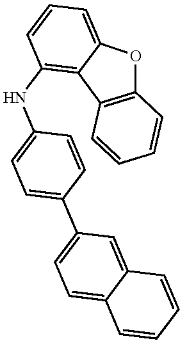
Int-20
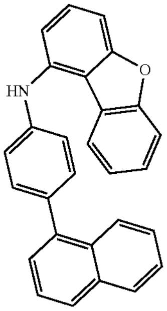
Int-21
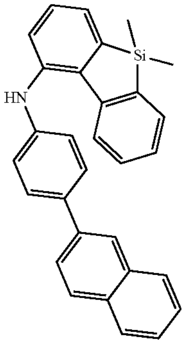
Int-22

TABLE 1-continued
| Synthesis Examples | Int A | Int B | Final product | Amount (yield) | Property data of final product |
|---|---|---|---|---|---|
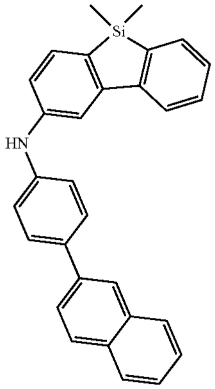
Int-23
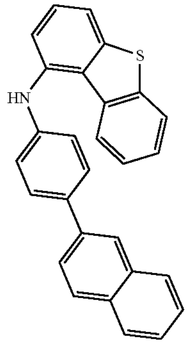
Int-24
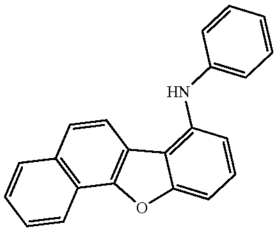
Int-25
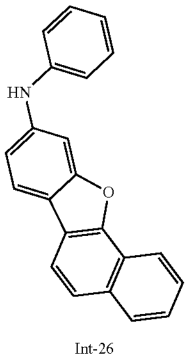
Int-26
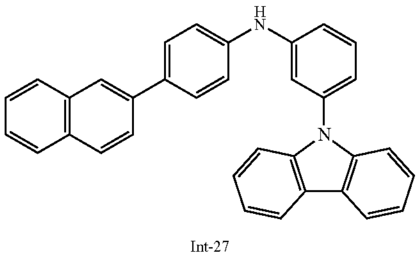
Int-27
Synthesis Example 25: Synthesis of Compound A-3
[Reaction Scheme 3]
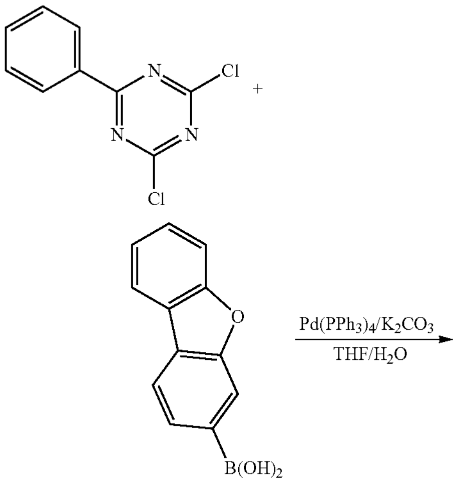
Int-28
-continued
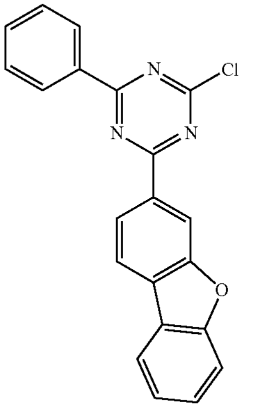
Int-29
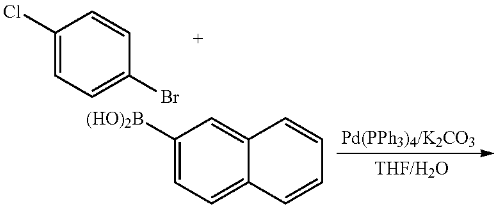

-continued

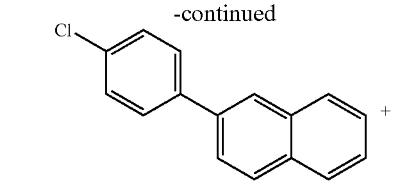

Int-30

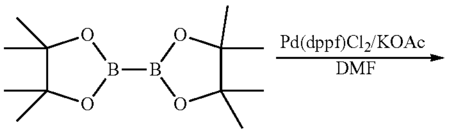

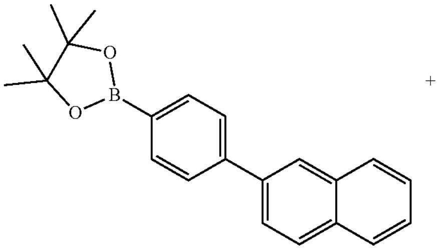

Int-31

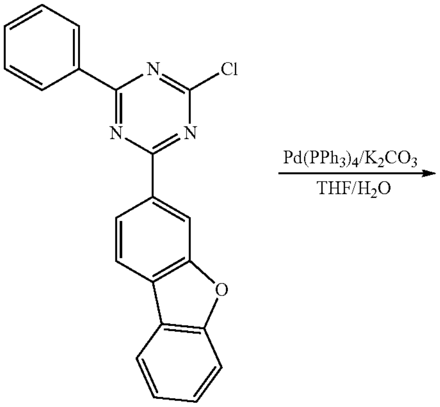

Int-29

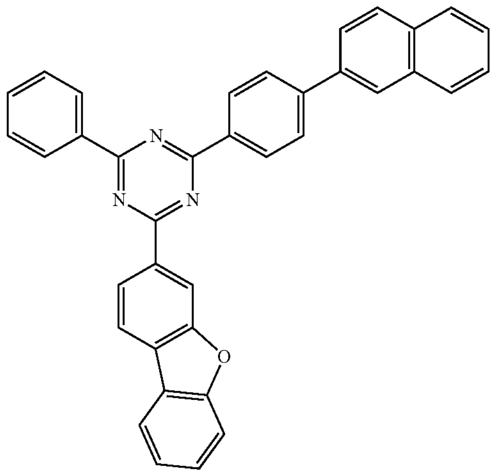

A-3

1st Step: Synthesis of Int-29

In a round-bottomed flask, 22.6 g (100 mmol) of 2,4-dichloro-6-phenyl-1,3,5-triazine was added to 200 mL of tetrahydrofuran and 100 mL of distilled water, and 0.9 equivalents of Int-28 (dibenzofuran-3-boronic acid, CAS No.: 395087-89-5), 0.03 equivalents of tetrakis(triphenylphosphine) palladium, and 2 equivalents of potassium carbonate were added thereto and then, heated under reflux under a nitrogen atmosphere. After 6 hours, the reaction solution was allowed to cool, and after removing an aqueous layer therefrom, an organic layer therefrom was dried under a reduced pressure. The obtained solid was washed with water and hexane and then, recrystallized with 200 mL of toluene, obtaining 21.4 g (Yield: 60%) of Int-29.

2nd Step: Synthesis of Int-30

In a round-bottomed flask, 50.0 g (261.16 mmol) of 1-bromo-4-chloro-benzene, 44.9 g (261.16 mmol) of 2-naphthalene boronic acid, 9.1 g (7.83 mmol) of tetrakis (triphenylphosphine) palladium, and 71.2 g (522.33 mmol) of potassium carbonate were dissolved in 1,000 mL of tetrahydrofuran and 500 mL of distilled water and then, heated under reflux under a nitrogen atmosphere. After 6 hours, the reaction solution was allowed to cool, and after removing an aqueous layer therefrom, an obtained organic layer therefrom was dried under a reduced pressure. The obtained solid was washed with water and hexane and then, recrystallized with 200 mL of toluene, obtaining 55.0 g (Yield: 88%) of Int-30.

3rd Step: Synthesis of Int-31

In a round-bottomed flask, 100.0 g (418.92 mmol) of the synthesized Int-30 was added to 1,000 mL of DMF, and 17.1 g (20.95 mmol) of dichlorodiphenylphosphinoferrocene palladium, 127.7 g (502.70 mmol) of bis(pinacolato) diboron, and 123.3 g (1256.76 mmol) of potassium acetate were added thereto and then, heated under reflux for 12 hours under a nitrogen atmosphere. The reaction solution was allowed to cool and added dropwise to 2 L of water, catching a solid. The solid was dissolved in boiling toluene and then, filtered through silica gel, and a filtrate therefrom was concentrated. After stirring the concentrated solid with a small amount of hexane, a solid was filtered therefrom, obtaining 28.5 g (Yield: 70%) of Int-31.

4th Step: Synthesis of Compound A-3

In a round-bottomed flask, 10.0 g (27.95 mmol) of Int-31, 11.1 g (33.54 mmol) of Int-29, 1.0 g (0.84 mmol) of tetrakis(triphenylphosphine) palladium, and 7.7 g (55.90 mmol) of potassium carbonate were dissolved in 150 mL of tetrahydrofuran and 75 mL of distilled water and then, heated under reflux under a nitrogen atmosphere. After 12 hours, the reaction solution was allowed to cool, and after removing an aqueous layer, an organic layer therefrom was dried under a reduced pressure. The obtained solid was washed with water and methanol and recrystallized with 200 mL of toluene, obtaining 13.4 g (Yield: 91%) of Compound A-3.

calcd. C37H23N3O:C, 84.55; H, 4.41; N, 7.99; O, 3.04. found: C, 84.55; H, 4.41; N, 8.00; O, 3.03.

Synthesis Example 26: Synthesis of Compound A-71

[Reaction Scheme 4]

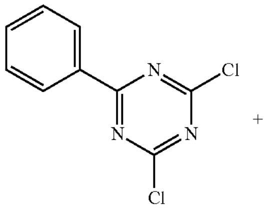

-continued

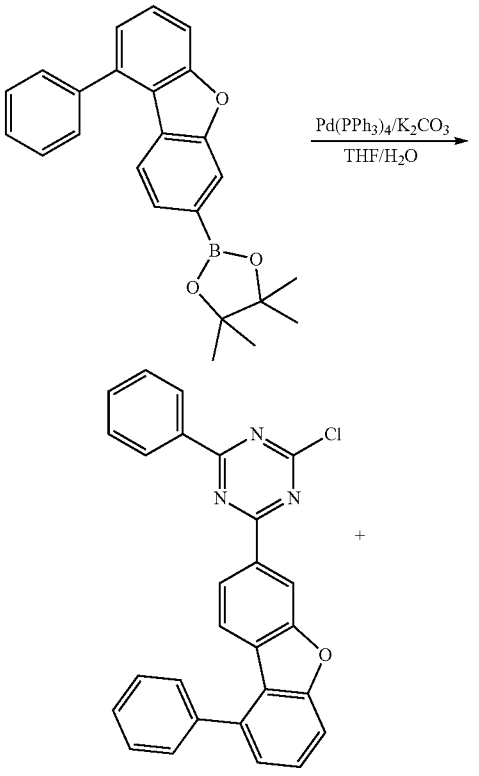

Int-32

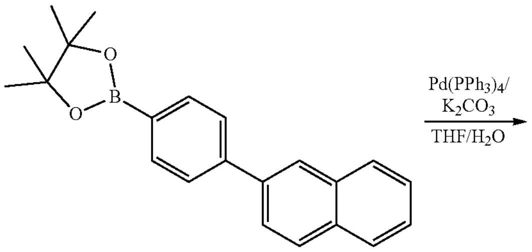

Int-31

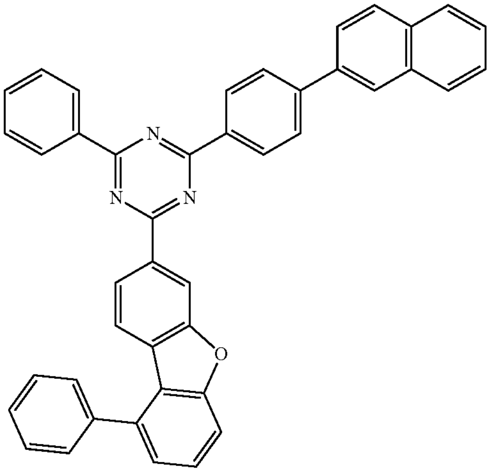

A-71

1st Step: Synthesis of Int-32

Int-32 was synthesized according to the same method as Int-29 of Synthesis Example 25 except that 2,4-dichloro-6-phenyl-1,3,5-triazine and 1-phenyl-7-(4,4,5,5-tetramethyl-[1,3,2]dioxaborolan-2-yl)-dibenzofuran were respectively used in amounts corresponding with 1.0 equivalent.

2nd Step: Synthesis of Compound A-71

Compound A-71 was synthesized according to the same method as the 4th step of Synthesis Example 25 except that Int-32 and Int-31 were respectively used in amounts corresponding with 1.0 equivalent.

calcd. C43H27N3O:C, 85.83; H, 4.52; N, 6.98; O, 2.66. found: C, 85.83; H, 4.52; N, 6.98; O, 2.66.

Synthesis Example 27: Synthesis of Compound A-61

[Reaction Scheme 5]

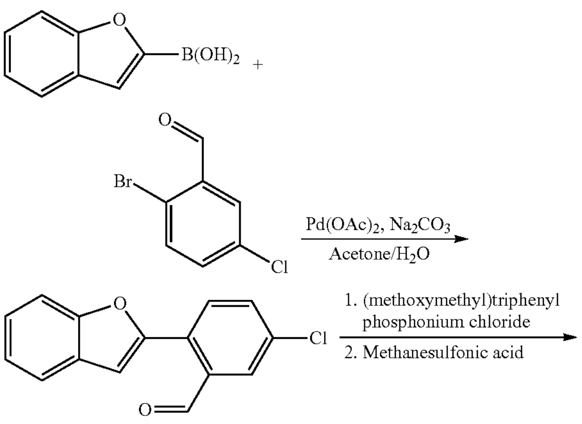

Int-33

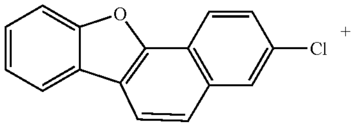

Int-34

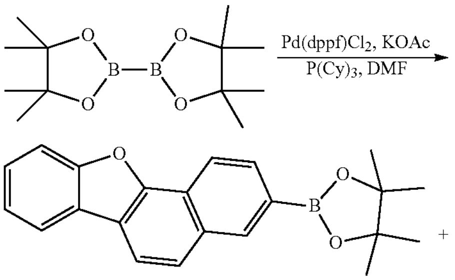

Int-35

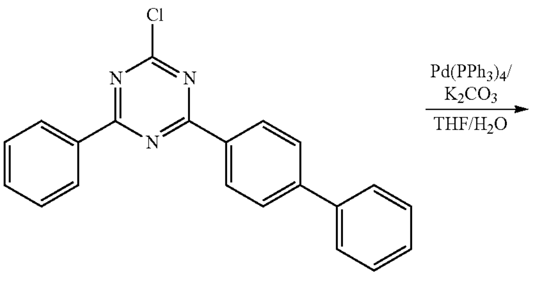

Int-36

-continued

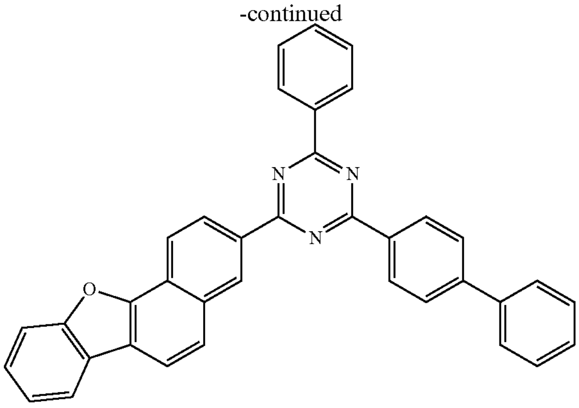

A-61

1st Step: Synthesis of Int-33

In a round-bottomed flask, 21.95 g (135.53 mmol) of 2-benzofuranylboronic acid, 26.77 g (121.98 mmol) of 2-bromo-5-chlorobenzaldehyde, 2.74 g (12.20 mmol) of $Pd(OAc)_2$, and 25.86 g (243.96 mmol) of $Na_2CO_3$ were suspended in 200 ml of acetone/220 ml of distilled water and then, stirred for 12 hours at ambient temperature. When a reaction was completed, the resultant was concentrated and then, extracted with methylene chloride, and an organic layer therefrom was silica gel-columned, obtaining 21.4 g (Yield: 68%) of Int-33.

2nd Step: Synthesis of Int-34

20.4 g (79.47 mmol) of Int-33 and 29.97 g (87.42 mmol) of (methoxymethyl)triphenylphosphonium chloride were suspended in 400 ml of THF, and 10.70 g (95.37 mmol) of potassium tert-butoxide was added thereto and then, stirred for 12 hours at ambient temperature. When a reaction was completed, 400 ml of distilled water was added thereto and then, extracted, an organic layer therefrom was concentrated and re-extracted with methylene chloride, magnesium sulfate was added to the organic layer and then, stirred for 30 minutes and filtered, and then, a filtrate therefrom was concentrated. After adding 100 ml of methylene chloride again to the concentrated filtrate, 10 ml of methane sulfonic acid was added thereto and then, stirred for 1 hour.

When a reaction was completed, a solid produced therein was filtered and then, dried with distilled water and methyl alcohol, obtaining 21.4 g (Yield: 65%) of Int-34.

3rd Step: Synthesis of Int-35

12.55 g (49.66 mmol) of Int-34, 2.43 g (2.98 mmol) of $Pd(dppf)Cl_2$, 15.13 g (59.60 mmol) of bis(pinacolato) diboron, 14.62 g (148.99 mmol) of KOAc, and 3.34 g (11.92 mmol) of $P(Cy)_3$ were suspended in 200 ml of DMF and then, stirred under reflux for 12 hours. When a reaction was completed, 200 ml of distilled water was added thereto to filter a solid produced therein and then, extracted with methylene chloride, and an organic layer therefrom was columned with hexane:EA=4:1 (v/v), obtaining 13 g (Yield: 76%) of Int-35.

4th Step: Synthesis of Compound A-61

Compound A-61 was synthesized according to the same method as the 4th step of Synthesis Example 25 except that Int-35 and Int-36 were respectively used in amounts corresponding with 1.0 equivalent.

calcd. C37H23N3O:C, 84.55; H, 4.41; N, 7.99; O, 3.04. found: C, 84.55; H, 4.41; N, 7.99; O, 3.04.

Synthesis Example 28: Synthesis of Compound A-17

[Reaction Scheme 6]

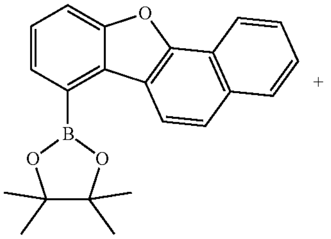

Int-37

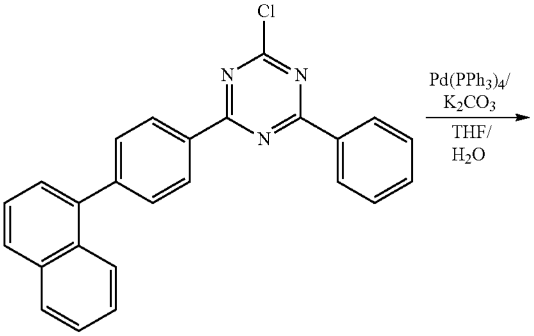

Int-38

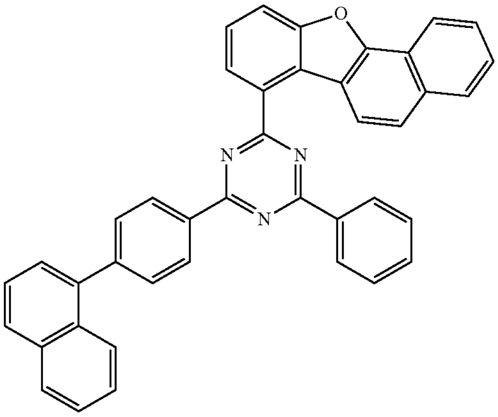

A-17

Compound A-17 was synthesized according to the same method as the 4th step of Synthesis Example 25 except that Int-37 and Int-38 were respectively used in amounts corresponding with 1.0 equivalent.

calcd. C41H25N3O:C, 85.54; H, 4.38; N, 7.30; O, 2.78. found: C, 85.53; H, 4.38; N, 7.30; O, 2.77.

Synthesis Example 29: Synthesis of Compound A-37

[Reaction Scheme 7]

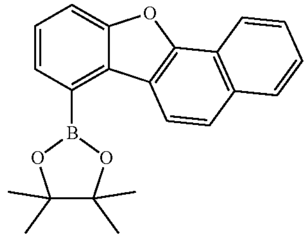

+

Int-37

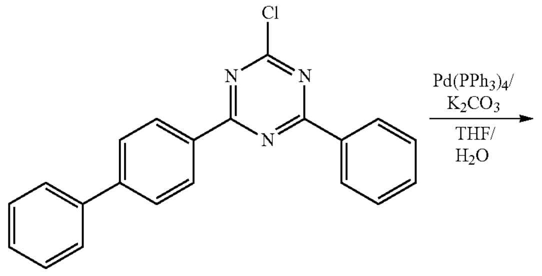

Int-36

-continued

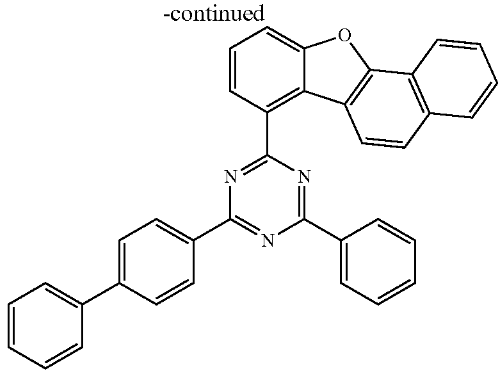

A-37

Compound A-37 was synthesized according to the same method as the 4th step of Synthesis Example 25 except that Int-37 and Int-36 were respectively used in amounts corresponding with 1.0 equivalent.

calcd. C37H23N3O:C, 84.55; H, 4.41; N, 7.99; O, 3.04. found: C, 84.57; H, 4.40; N, 7.99; O, 3.03.

Synthesis of Synthesis Examples 30 to 32

Each compound was synthesized according to the same method as the 4th step of Synthesis Example 25 except that Int C of Table 2 instead of Int-31 and Int D of Table 2 instead of Int-29 were used.

TABLE 2

| Synthesis Example | Int C | Int D | Final product | Amount (yield) | Property data of final product |
|---|---|---|---|---|---|
| Synthesis Example 30 | Int-39 | Int-38 | Compound A-24 | 8.33 g (74%) | calcd. C41H25N3S: C, 83.22; H, 4.26; N, 7.10; S, 5.42 found: C, 83.22; H, 4.26; N, 7.10; S, 5.42 |
| Synthesis Example 31 | Int-40 | Int-42 | Compound A-77 | 6.29 g (71%) | calcd. C37H23N3S: C, 82.04; H, 4.28; N, 7.76; S, 5.92 found: C, 82.04; H, 4.28; N, 7.76; S, 5.92 |
| Synthesis Example 32 | Int-41 | Int-43 | Compound A-35 | 7.67 g (71%) | calcd. C41H25N3O: C, 85.54; H, 4.38; N, 7.30; O, 2.78 found: C, 85.55; H, 4.38; N, 7.29; O, 2.7 |

[Int C]

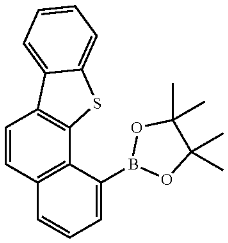

Int-39

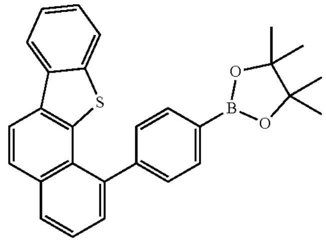

Int-40

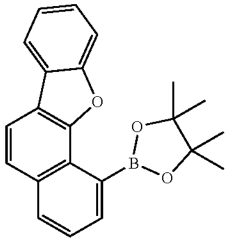

Int-41

TABLE 2-continued

| Synthesis Example | Int C | Int D | Final product | Amount (yield) | Property data of final product |
|---|---|---|---|---|---|

[Int D]

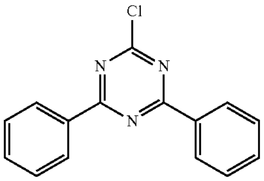

Int-42

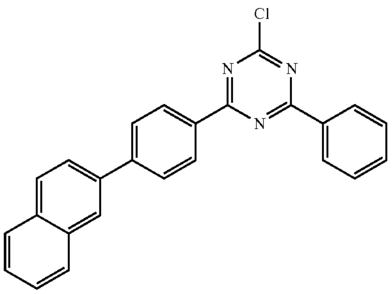

Int-43

Comparative Synthesis Example 1: Synthesis of Comparative Compound 1

[Reaction Scheme 8]

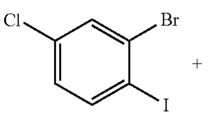

Int-2

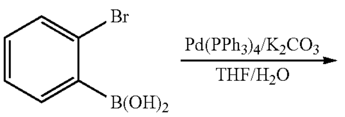

Int-44

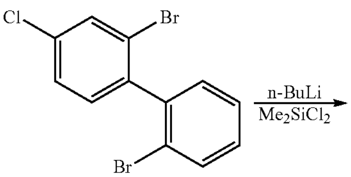

Int-45

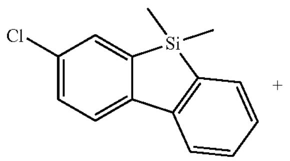

Int-46

-continued

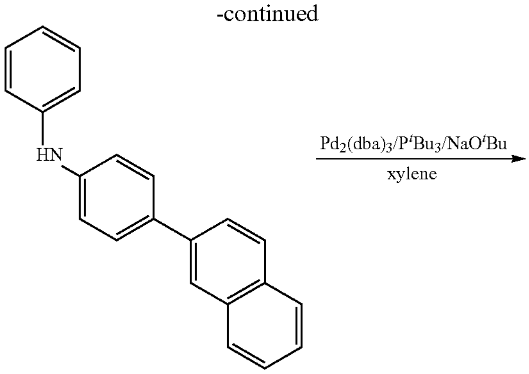

Int-6

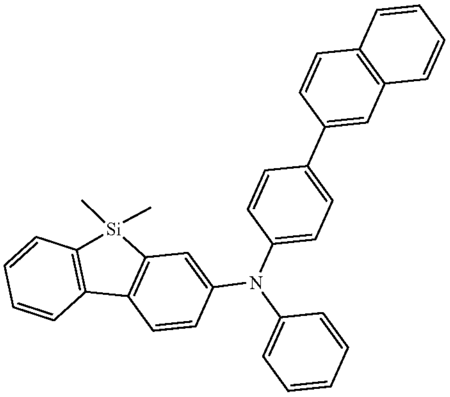

Comparative Compound 1

1st Step: Synthesis of Int-45

Int-2 (100 g, 315.11 mmol) was dissolved in 1.0 L of tetrahydrofuran (THF), and Int-44 (63.28 g, 315.11 mmol) and tetrakis(triphenylphosphine) palladium (10.92 g, 9.45 mmol) were added thereto and then, stirred. Subsequently, potassium carbonate (108.88 g, 787.77 mmol) saturated in 500 ml of water was heated under reflux at 80° C. for 12 hours. When a reaction was completed, water was added to the reaction solution and then, extracted with ethyl acetate (EA), treated with anhydrous magnesium sulfate to remove moisture, filtered, and concentrated under a reduced pressure. This obtained residue was separated and purified through flash column chromatography, obtaining 86.24 g (79%) of Int-45.

$2^{nd}$ Step: Synthesis of Int-46

Int-45 (86.24 g, 248.92 mmol) was dissolved in 600 mL of tetrahydrofuran (THF), and an internal temperature was decreased to −78° C. Subsequently, n-BuLi (288.75 ml, 721.88 mmol) was slowly added thereto in a dropwise fashion, while the internal temperature of −78° C. was maintained, and then, stirred at the temperature for 1 hour.

After slowly adding dichlorodimethylsilane (104.31 ml, 871.24 mmol) thereto in a dropwise fashion, while the −78° C. was maintained, the obtained mixture was stirred at room temperature for 12 hours. When a reaction was completed, water was added to the reaction solution and then, extracted with ethyl acetate (EA), treated with anhydrous magnesium sulfate to remove moisture, filtered, and concentrated under a reduced pressure. The obtained residue was separated and purified through flash column chromatography, obtaining 43.12 g (71%) of Int-46.

$3^{rd}$ Step: Synthesis of Comparative Compound 1

Comparative Compound 1 (5.69 g, 72%) was synthesized according to the same method as Synthesis Example 1 except that Int-46 was used instead of Int-5.

calcd. C36H29NSi:C, 85.84; H, 5.80; N, 2.78; Si, 5.58. found: C, 85.84; H, 5.80; N, 2.78; Si, 5.58.

Comparative Synthesis Example 2: Synthesis of Comparative Compound 2

[Reaction Scheme 9]

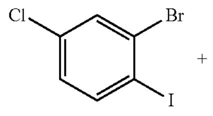

Int-2

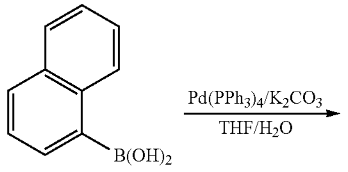

Int-47

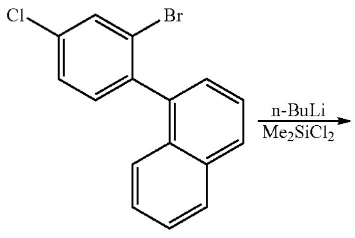

Int-48

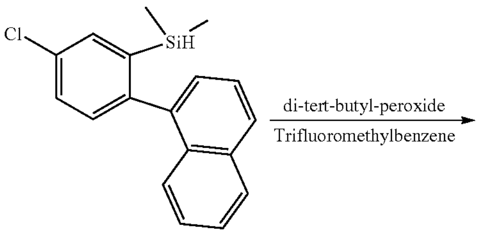

Int-49

-continued

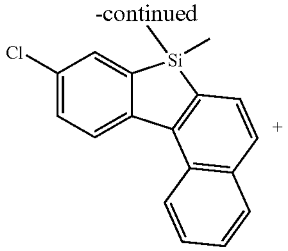

Int-50

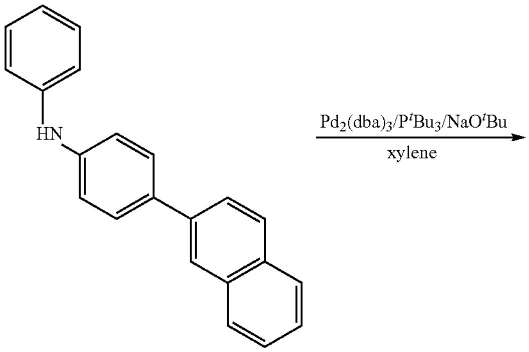

Int-6

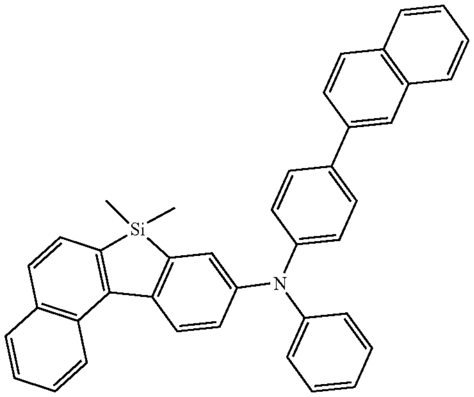

Comparative Compound 2

Comparative Compound 2 (4.86 g, 76%) was synthesized according to the same method as Synthesis Example 1 except that Int-50 was used instead of Int-5.

calcd. C40H31NSi:C, 86.76; H, 5.64; N, 2.53; Si, 5.07. found: C, 86.77; H, 5.64; N, 2.53; Si, 5.06.

Comparative Synthesis Example 3: Synthesis of Comparative Compound 3

[Reaction Scheme 10]

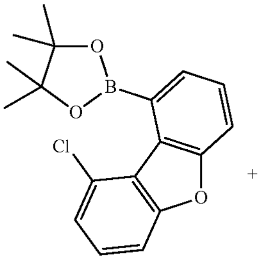

Int-51

-continued

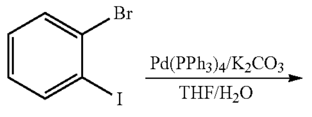

Int-52

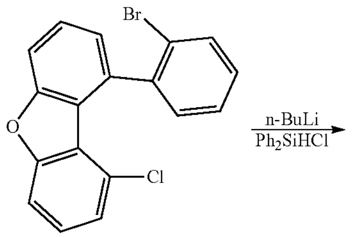

Int-53

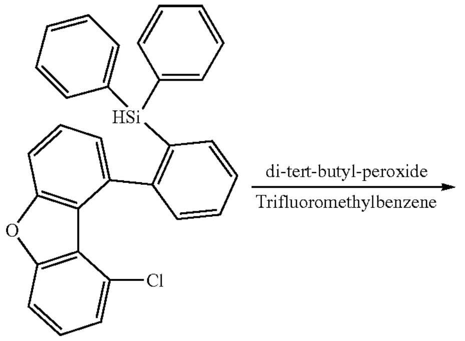

Int-54

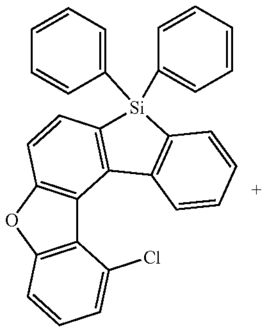

Int-55

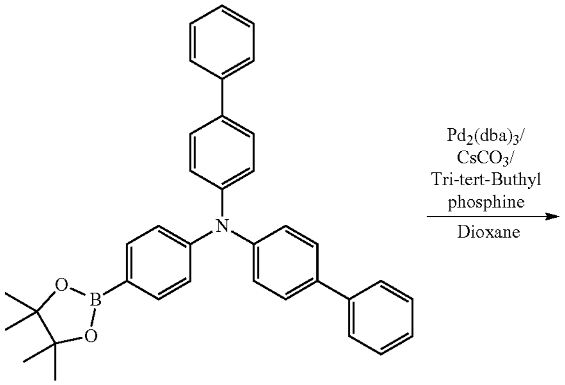

Int-56

-continued

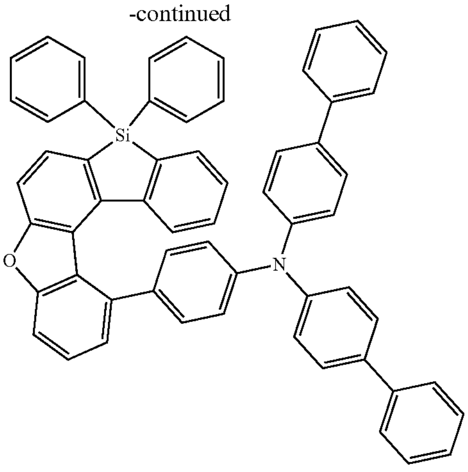

Comparative Compound 3

1st to 3rd Step: Synthesis of Int-55

Int-55 (8.20 g, 56%) was synthesized according to the same method as Int-5 of Synthesis Example 1.

4th Step: Synthesis of Comparative Compound 3

In a round-bottomed flask, 8.67 g (17.19 mmol) of Int-55, 9.28 g (17.19 mmol) of Int-56, 22.41 g (34.39 mmol) of cesium carbonate, and 0.31 g (1.55 mmol) of tri-tert-butylphosphine were dissolved in 170 ml of 1,4-dioxane, and 0.47 g (0.52 mmol) of $Pd_2(dba)_3$ was added thereto and heated under reflux under a nitrogen atmosphere. After 12 hours, the reaction solution was allowed to cool, and an organic layer therefrom was dried under a reduced pressure. A solid obtained therefrom was washed with water and methanol and recrystallized with 70 mL of toluene, obtaining Comparative Compound 3 (8.34 g, 59%).

calcd. C60H41NOSi:C, 87.88; H, 5.04; N, 1.71; O, 1.95; Si, 3.42. found: C, 87.89; H, 5.04; N, 1.71; O, 1.94; Si, 3.42.

(Manufacture of Organic Light Emitting Diode)—Single Host

Example 1

The glass substrate coated with ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 1% NDP-9 (available from Novaled) was vacuum-deposited on the ITO substrate to form a 100 Å-thick hole injection layer, and Compound A was deposited on the hole injection layer to form a 1,300 Å-thick hole transport layer. Compound B was deposited on the hole transport layer to form a 600 Å-thick hole transport auxiliary layer. On the hole transport auxiliary layer, 400 Å-thick light emitting layer was formed by using Compound B-1 of Synthesis Example 1 as a host and doping 10 wt % of $[Ir(piq)_2acac]$ as a dopant. Subsequently, Compound C was deposited on the light emitting layer to form a 50 Å-thick electron transport auxiliary layer, and Compound D and LiQ were simultaneously vacuum-deposited at a weight ratio of 1:1 to form a 300 Å-thick electron transport layer. LiQ (15 Å) and Al (1,200 Å) were sequentially vacuum-deposited on the electron transport layer to form a cathode, thereby manufacturing an organic light emitting diode.

ITO/Compound A (1% NDP-9 doping, 100 Å)/Compound A (1,300 Å)/Compound B (600 Å)/EML [Compound B-1 (98 wt %): [$Ir(piq)_2acac$] (2 wt %)] (400 Å)/Compound C (50 Å)/Compound D:LiQ (300 Å)/LiQ (15 Å)/Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinolone

Examples 2 to 24 and Comparative Examples 1 to 3

Diodes of Examples 2 to 24 and Comparative Examples 1 to 3 were manufactured in the same manner as in Example 1, except that the host was changed as shown in Table 3.

(Manufacture of Organic Light Emitting Diode)—Two Hosts

Example 25

The glass substrate coated with ITO (Indium tin oxide) was washed with distilled water and ultrasonic waves. After washing with the distilled water, the glass substrate was ultrasonically washed with isopropyl alcohol, acetone, or methanol, and dried and then, moved to a plasma cleaner, cleaned by using oxygen plasma for 10 minutes, and moved to a vacuum depositor. This obtained ITO transparent electrode was used as an anode, Compound A doped with 1% NDP-9 (available from Novaled) was vacuum-deposited on the ITO substrate to form a 100 Å-thick hole injection layer, and Compound A was deposited on the hole injection layer to form a 1,300 Å-thick hole transport layer. Compound B was deposited on the hole transport layer to form a 600 Å-thick hole transport auxiliary layer. On the hole transport auxiliary layer, 400 Å-thick light emitting layer was formed by using Compound B-1 of Synthesis Example 1 and Compound A-3 of Synthesis Example 25 simultaneously as a host and doping 2 wt % of [$Ir(piq)_2acac$] as a dopant. Herein, Compound B-1 and Compound A-3 were used in a weight ratio of 5:5. Subsequently, Compound C was deposited on the light emitting layer to form a 50 Å-thick electron transport auxiliary layer, and Compound D and LiQ were simultaneously vacuum-deposited at a weight ratio of 1:1 to form a 300 Å-thick electron transport layer. LiQ (15 Å) and Al (1,200 Å) were sequentially vacuum-deposited on the electron transport layer to form a cathode, thereby manufacturing an organic light emitting diode.

ITO/Compound A (1% NDP-9 doping, 100 Å)/Compound A (1,300 Å)/Compound B (600 Å)/EML [98 wt % host (Compound B-1: Compound A-3=5:5), 2 wt % of dopant ($Ir(piq)_2acac$)] (400 Å)/Compound C (50 Å)/Compound D:LiQ (300 Å)/LiQ (15 Å)/Al (1,200 Å).

Compound A: N-(biphenyl-4-yl)-9,9-dimethyl-N-(4-(9-phenyl-9H-carbazol-3-yl)phenyl)-9H-fluoren-2-amine Compound B: N,N-di([1,1'-biphenyl]-4-yl)-7,7-dimethyl-7H-fluoreno[4,3-b]benzofuran-10-amine Compound C: 2-(3-(3-(9,9-dimethyl-9H-fluoren-2-yl)phenyl)phenyl)-4,6-diphenyl-1,3,5-triazine Compound D: 8-(4-(4,6-di(naphthalen-2-yl)-1,3,5-triazin-2-yl)phenyl)quinolone

Examples 26 to 43 and Comparative Examples 4 to 6

Diodes of Examples 26 to 43 and Comparative Examples 4 to 6 were manufactured in the same manner as in Example 25, except that the host was changed as shown in Table 4.

Evaluations

The driving voltages, luminous efficiency, and life-span characteristics of the organic light emitting diodes according to Examples 1 to 43 and Comparative Examples 1 to 6 were evaluated. Specific measurement methods are as follows.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000 A), while the voltage of the organic light emitting diodes was increased from 0 V to 10 V.

(3) Measurement of Luminous Efficiency

Luminous efficiency (cd/A) at the same current density (10 $mA/cm^2$) were calculated by using the luminance and current density from the items (1) and (2).

(4) Measurement of Life-Span (T90)

The results were obtained by measuring a time when current efficiency (cd/A) was decreased down to 90%, while luminance ($cd/m^2$) was maintained to be 5,000 $cd/m^2$.

(5) Measurement of Driving Voltage

The driving voltage of each diode was measured at 15 $mA/cm^2$ using a current-voltmeter (Keithley 2400) to obtain the results.

(6) Calculation of T90 Life-Span Ratio (%)

Using the T90(h) of Comparative Example 2 of Table 3 and T90(h) of Comparative Example 5 of Table 4 as each reference value, relative comparative values for each T90(h) value were calculated, and are shown in Tables 3 and 4.

(7) Calculation of Driving Voltage Ratio (%)

Using the driving voltages of Comparative Example 2 of Table 3 and Comparative Example 5 of Table 4 as each reference value, relative comparative values for each driving voltage were calculated and shown in Tables 3 and 4.

(8) Calculation of Luminous Efficiency Ratio (%)

Using the luminous efficiency (cd/A) of Comparative Example 2 of Table 3 and Comparative Example 5 of Table 4 as each reference value, the relative comparative values for each luminous efficiency (cd/A) were calculated and are shown in Tables 3 and 4.

TABLE 3

| | First host | Driving voltage ratio | Luminous efficiency ratio | Life-spanT90 ratio |
|---|---|---|---|---|
| Example 1 | B-1 | 95% | 107% | 118% |
| Example 2 | B-2 | 92% | 107% | 127% |
| Example 3 | B-3 | 93% | 109% | 128% |
| Example 4 | B-4 | 93% | 106% | 125% |
| Example 5 | B-5 | 94% | 110% | 116% |
| Example 6 | B-10 | 92% | 109% | 128% |
| Example 7 | B-18 | 94% | 111% | 124% |
| Example 8 | B-25 | 91% | 109% | 126% |
| Example 9 | B-29 | 94% | 110% | 121% |
| Example 10 | B-41 | 94% | 108% | 120% |
| Example 11 | B-42 | 91% | 106% | 124% |

TABLE 3-continued

| | First host | Driving voltage ratio | Luminous efficiency ratio | Life-spanT90 ratio |
|---|---|---|---|---|
| Example 12 | B-49 | 95% | 105% | 113% |
| Example 13 | B-69 | 93% | 108% | 124% |
| Example 14 | B-73 | 93% | 107% | 127% |
| Example 15 | B-85 | 95% | 106% | 111% |
| Example 16 | B-89 | 95% | 107% | 114% |
| Example 17 | B-93 | 96% | 110% | 110% |
| Example 18 | B-107 | 92% | 111% | 117% |
| Example 19 | C-1 | 95% | 108% | 118% |
| Example 20 | C-4 | 94% | 106% | 125% |
| Example 21 | C-5 | 95% | 109% | 115% |
| Example 22 | C-29 | 93% | 109% | 121% |
| Example 23 | C-69 | 94% | 108% | 120% |
| Example 24 | C-73 | 94% | 106% | 125% |
| Comparative Example 1 | Comparative Compound 1 | 109% | 92% | 92% |
| Comparative Example 2 | Comparative Compound 2 | 100% | 100% | 100% |
| Comparative Example 3 | Comparative Compound 3 | 107% | 94% | 93% |

TABLE 4

| | First host | Second host | Driving voltage ratio | Luminous efficiency ratio | Life-span T90 ratio |
|---|---|---|---|---|---|
| Example 25 | B-1 | A-3 | 93% | 112% | 123% |
| Example 26 | B-2 | | 88% | 115% | 135% |
| Example 27 | B-3 | | 91% | 117% | 135% |
| Example 28 | B-4 | | 91% | 115% | 132% |
| Example 29 | B-10 | | 90% | 118% | 137% |
| Example 30 | B-18 | | 92% | 120% | 129% |
| Example 31 | B-25 | | 92% | 119% | 132% |
| Example 32 | B-69 | | 93% | 117% | 135% |
| Example 33 | B-73 | | 91% | 116% | 139% |
| Example 34 | C-1 | | 95% | 110% | 119% |
| Example 35 | C-4 | | 93% | 114% | 129% |
| Example 36 | C-69 | | 94% | 116% | 128% |
| Example 37 | B-25 | A-71 | 92% | 116% | 126% |
| Example 38 | | A-61 | 91% | 124% | 138% |
| Example 39 | | A-17 | 88% | 120% | 135% |
| Example 40 | | A-37 | 87% | 121% | 138% |
| Example 41 | | A-24 | 93% | 115% | 128% |
| Example 42 | | A-77 | 94% | 114% | 123% |
| Example 43 | | A-35 | 93% | 117% | 130% |
| Comparative Example 4 | Comparative Compound 1 | A-3 | 114% | 89% | 78% |
| Comparative Example 5 | Comparative Compound 2 | | 100% | 100% | 100% |
| Comparative Example 6 | Comparative Compound 3 | | 111% | 92% | 85% |

Referring to Tables 3 and 4, the compounds according to the Examples exhibited significantly improved driving voltage, efficiency, and life-span, compared with the Comparative Examples.

One or more embodiments may provide a compound for an organic optoelectronic device capable of realizing an organic optoelectronic device having high efficiency and long life-span.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by Chemical Formula 1:

[Chemical Formula 1]

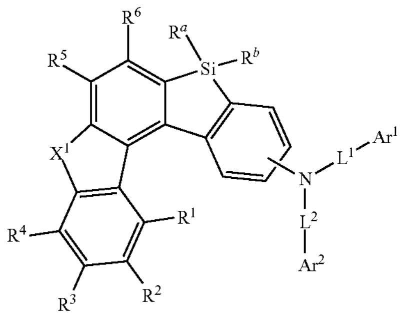

wherein, in Chemical Formula 1, $X^1$ is O or S, $Ar^1$ and $Ar^2$ are each independently a substituted or unsubstituted C6 to C30 aryl group or a substituted or unsubstituted C2 to C30 heterocyclic group, $L^1$ and $L^2$ are each independently a single bond, a substituted or unsubstituted C6 to C30 arylene group, or a substituted or unsubstituted C2 to C30 heteroarylene group, $R^1$ to $R^4$ are each independently hydrogen, deuterium, a cyano group, a halogen, a substituted or unsubstituted amine group, a substituted or unsubstituted C1 to C30 alkyl group, a substituted or unsubstituted C6 to C30 aryl group, or a substituted or unsubstituted C2 to C30 heterocyclic group, $R^5$ and $R^6$ are each independently hydrogen, deuterium, a cyano group, a halogen, a substituted or unsubstituted C1 to C30 alkyl group, a substituted or unsubstituted C6 to C30 aryl group, or a substituted or unsubstituted C2 to C30 heterocyclic group, and $R^a$ and $R^b$ are each independently a substituted or unsubstituted C1 to C30 alkyl group or a substituted or unsubstituted C6 to C30 aryl group.

2. The compound for an organic optoelectronic device as claimed in claim 1, wherein:

Chemical Formula 1 is represented by one of Chemical Formula 1-1 to Chemical Formula 1-4:

[Chemical Formula 1-1]

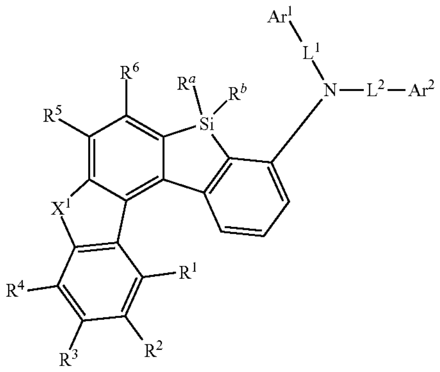

[Chemical Formula 1-2]

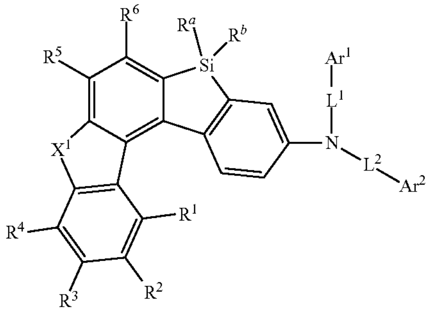

[Chemical Formula 1-3]

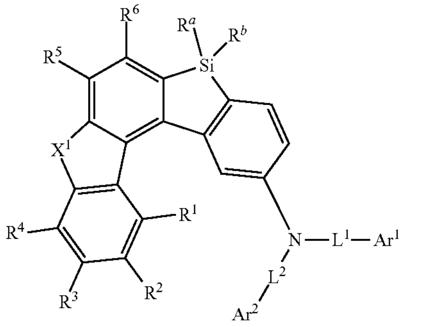

[Chemical Formula 1-4]

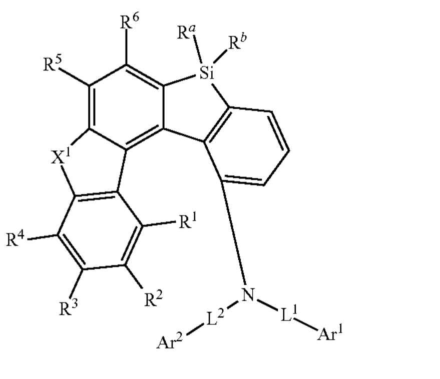

in Chemical Formula 1-1 to Chemical Formula 1-4, $X^1$, $Ar^1$, $Ar^2$, $L^1$, $L^2$, $R^1$ to $R^6$, $R^a$, and $R^b$ are defined the same as those of Chemical Formula 1.

3. The compound for an organic optoelectronic device as claimed in claim 1, wherein $Ar^1$ and $Ar^2$ are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted fluorenyl group, a substituted or unsubstituted chrysenyl group, a substituted or unsubstituted carbazolyl group, a substituted or unsubstituted dibenzofuranyl group, a substituted or unsubstituted dibenzothiophenyl group, a substituted or unsubstituted dibenzosilolyl group a substituted or unsubstituted benzonaphthofuranyl group, a substituted or unsubstituted benzonaphthothiophenyl group, or a substituted or unsubstituted benzoxazolyl group.

4. The compound for an organic optoelectronic device as claimed in claim 1, wherein:

moieties *-$L^1$-$Ar^1$ and *-$L^2$-$Ar^2$ are each independently a group of Group I:

[Group I]

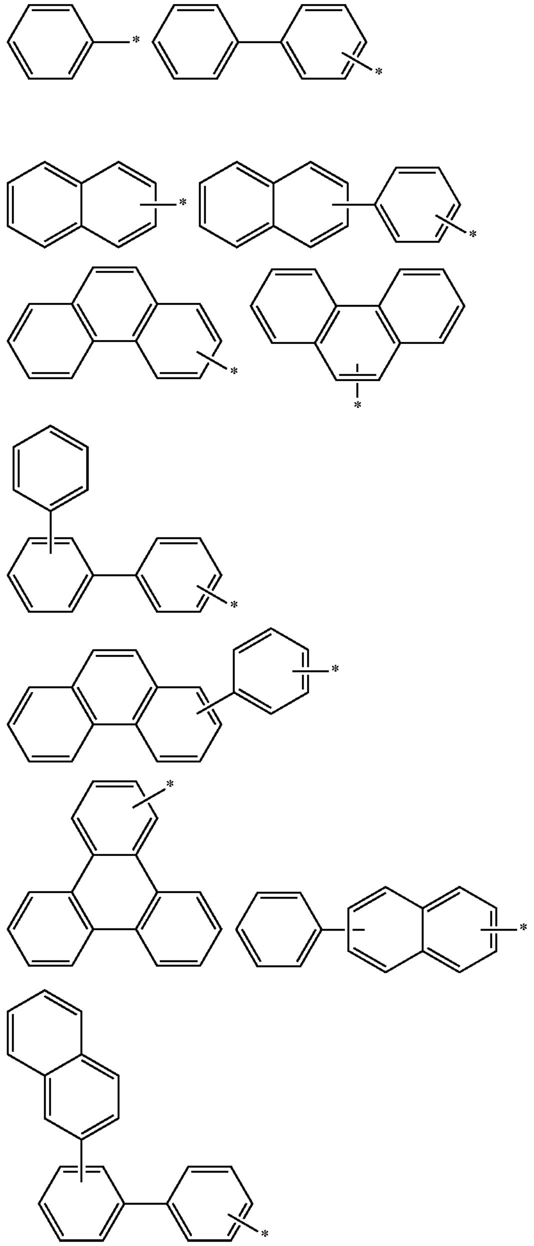

-continued
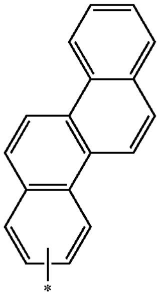
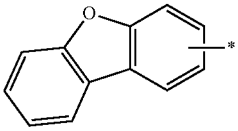
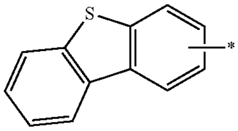
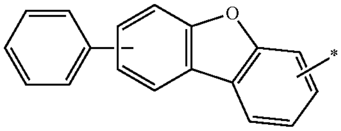
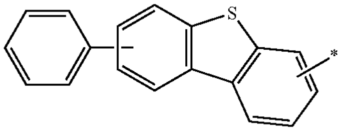
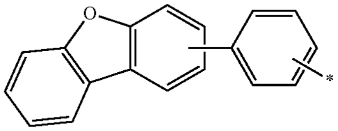
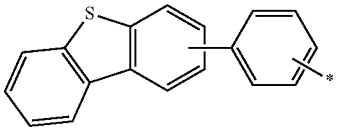
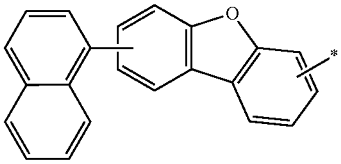
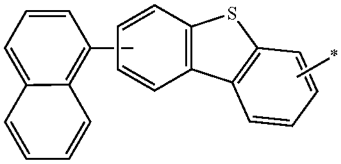
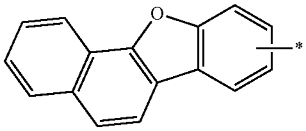
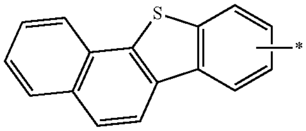
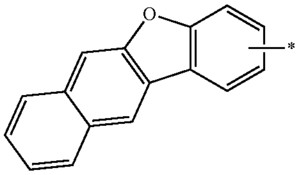
-continued
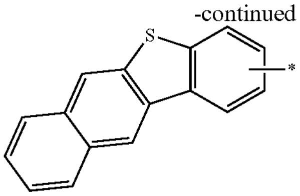
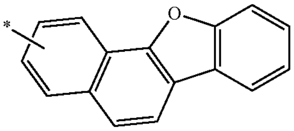
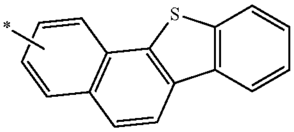
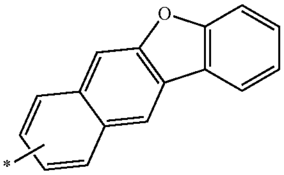
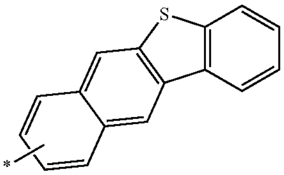
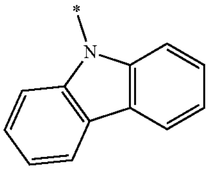
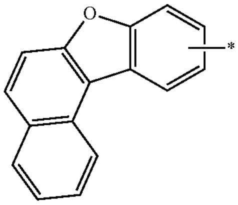
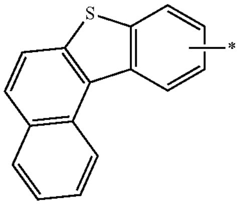
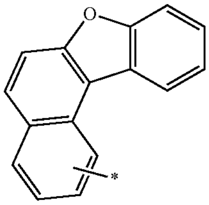
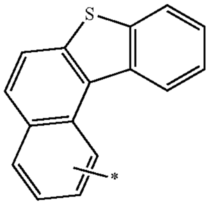
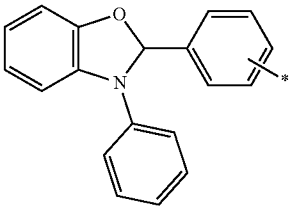
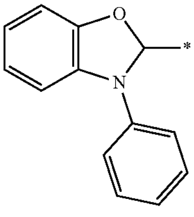
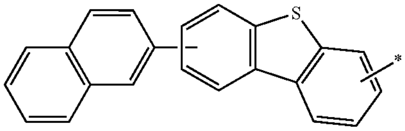
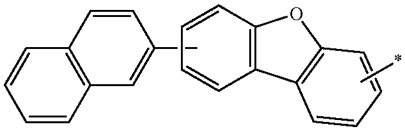

-continued

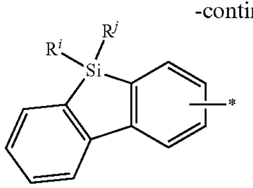

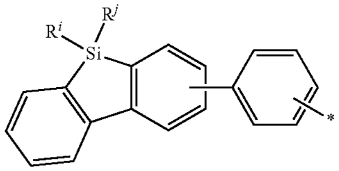

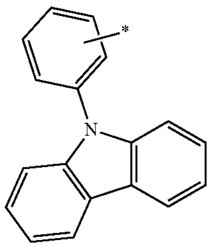

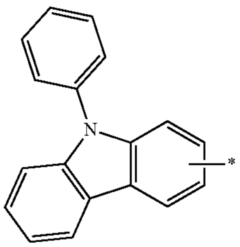

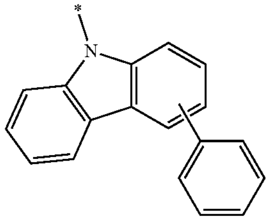

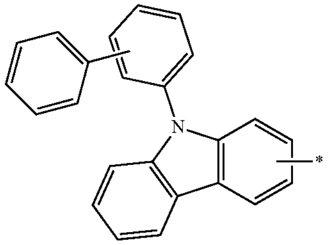

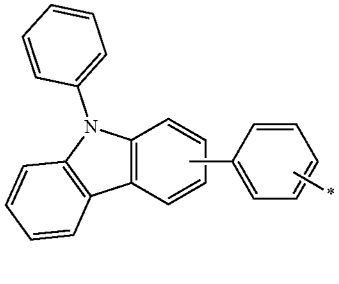

in Group I, $R^i$ and $R^j$ are independently a substituted or unsubstituted C1 to C10 alkyl group or a substituted or unsubstituted C6 to C12 aryl group, and

* is a linking point.

5. The compound for an organic optoelectronic device as claimed in claim 1, wherein:

$Ar^1$ and $Ar^2$ are each independently a substituted or unsubstituted phenyl group, a substituted or unsubstituted biphenyl group, a substituted or unsubstituted naphthyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group, and at least one of $Ar^1$ and $Ar^2$ is a substituted or unsubstituted biphenyl group, a substituted or unsubstituted naphthyl group, a substituted or unsubstituted carbazolyl group, a substituted or unsubstituted dibenzofuranyl group, a substituted or unsubstituted dibenzothiophenyl group, a substituted or unsubstituted dibenzosilolyl group, a substituted or unsubstituted benzonaphthofuranyl group, or a substituted or unsubstituted benzonaphthothiophenyl group.

6. The compound for an organic optoelectronic device as claimed in claim 1, wherein $R^a$ and $R^b$ are each independently an unsubstituted methyl group, an unsubstituted ethyl group, an unsubstituted propyl group, a substituted or unsubstituted phenyl group, or a substituted or unsubstituted biphenyl group.

7. The compound for an organic optoelectronic device as claimed in claim 1, wherein the compound is one of the compounds of Group 1:

[Group 1]

B-1

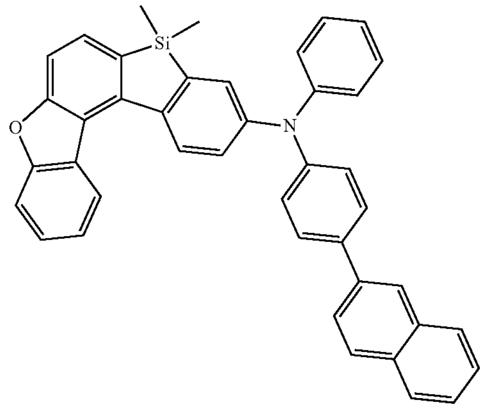

B-2

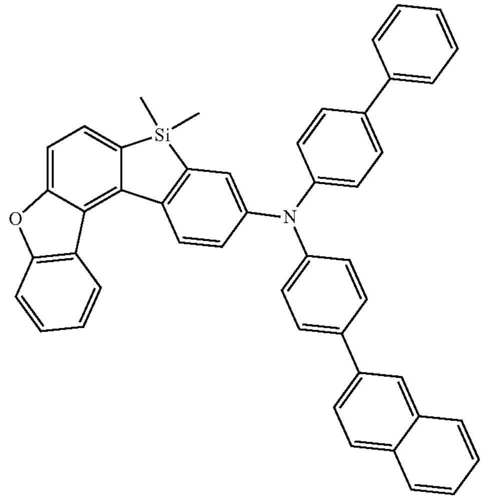

-continued
B-3
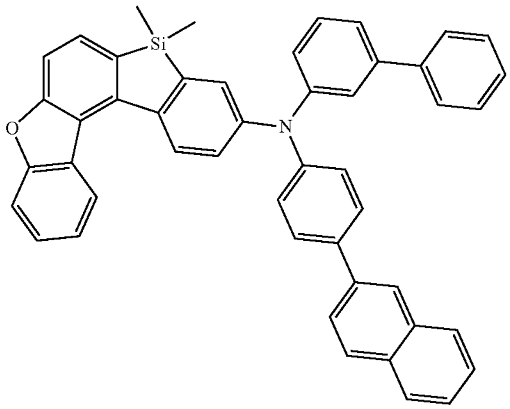
B-4
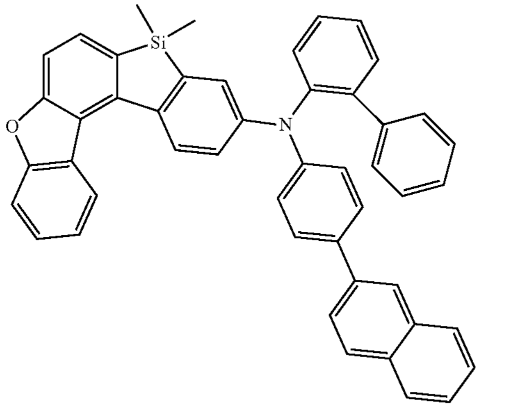
B-5
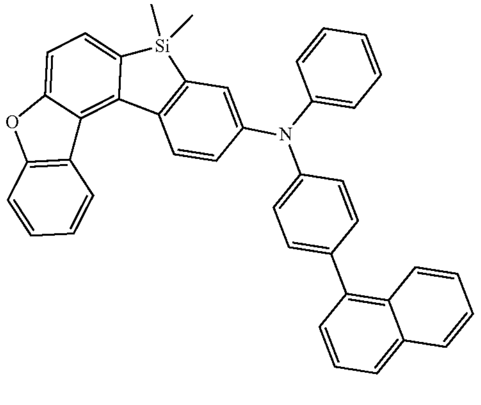
-continued
B-6
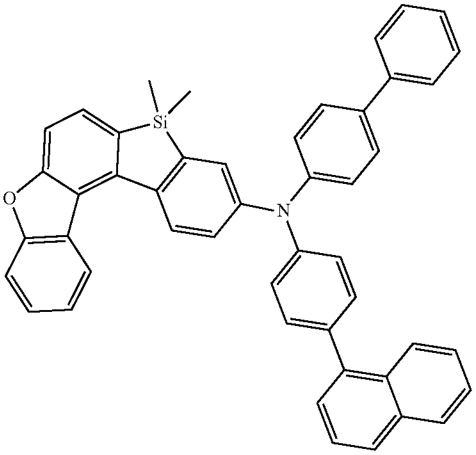
B-7
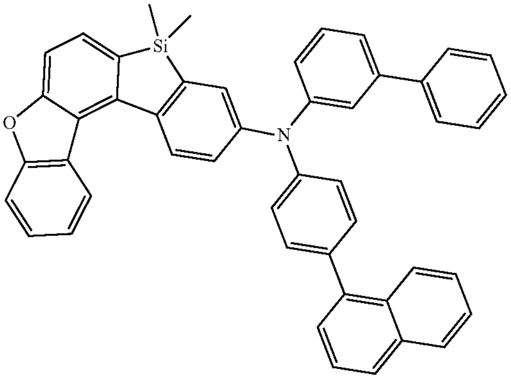
B-8
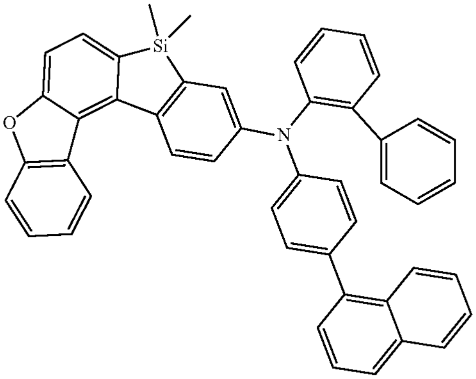
B-9
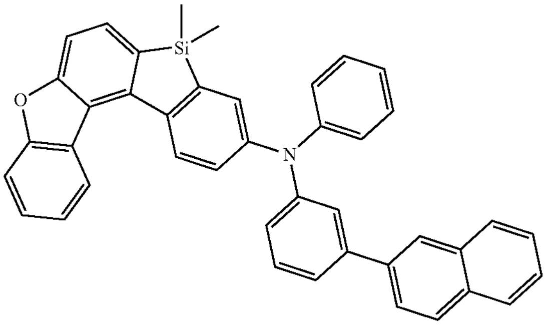

-continued
B-10
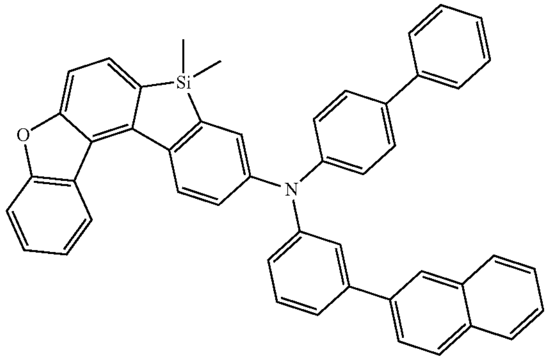
B-11
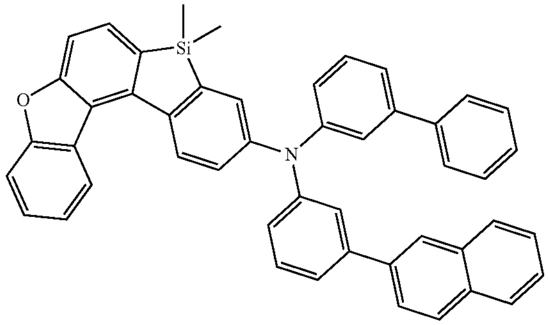
B-12
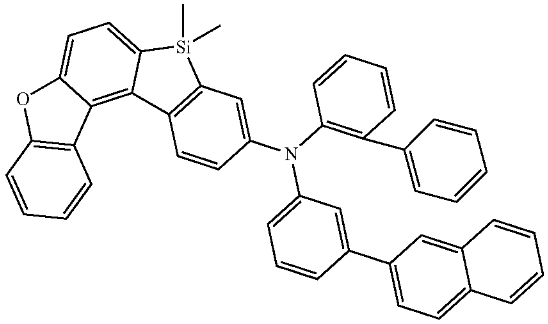
B-13
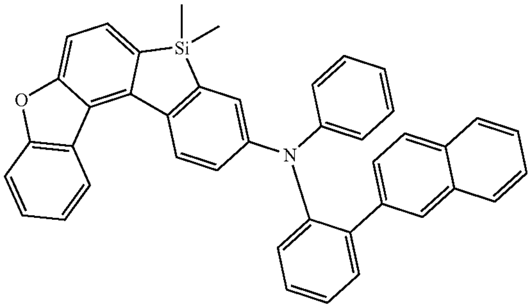
-continued
B-14
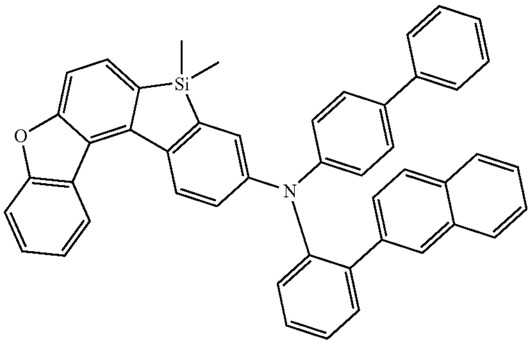
B-15
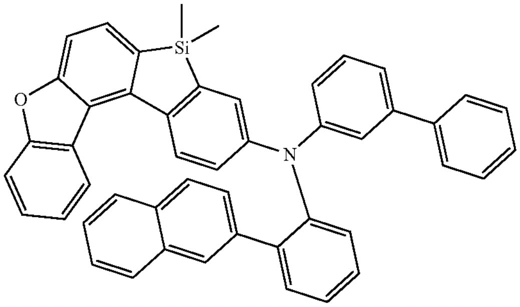
B-16
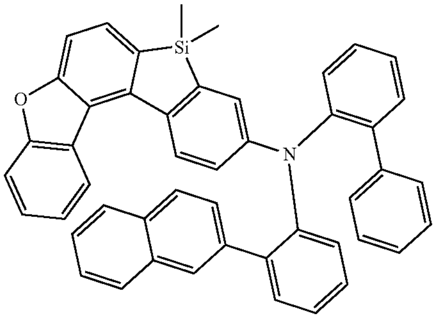
B-17
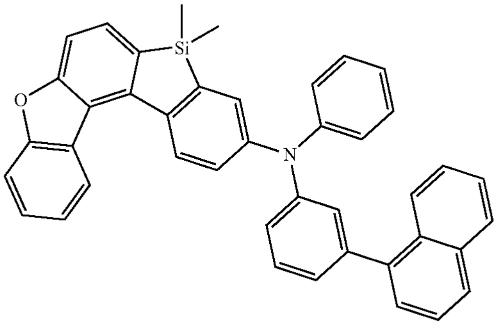

-continued
B-18
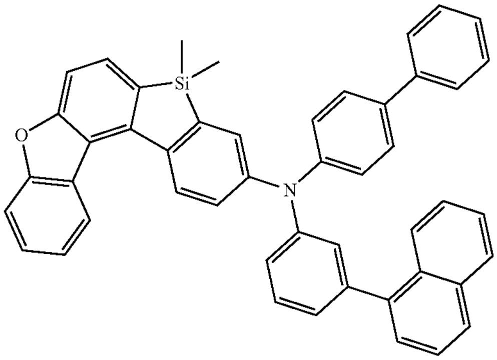
B-19
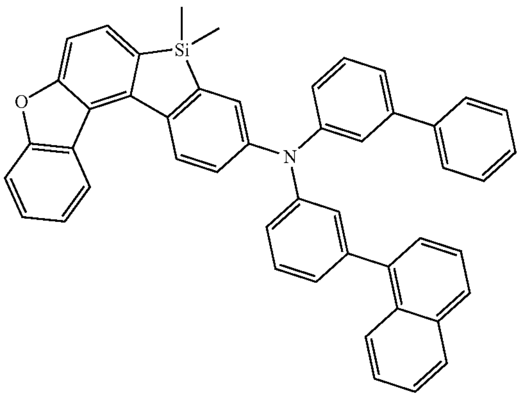
B-20
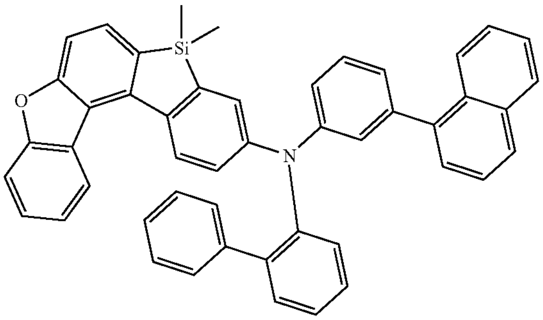
B-21
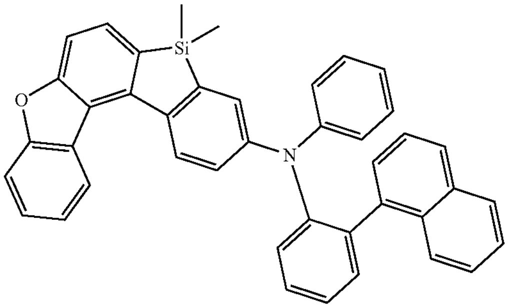
-continued
B-22
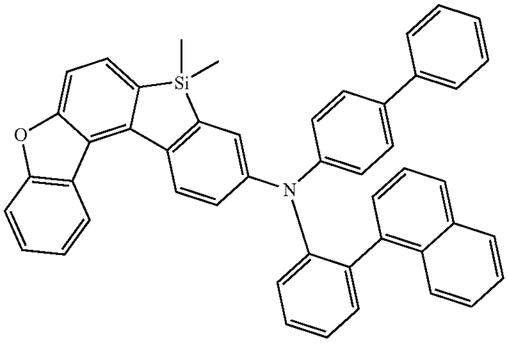
B-23
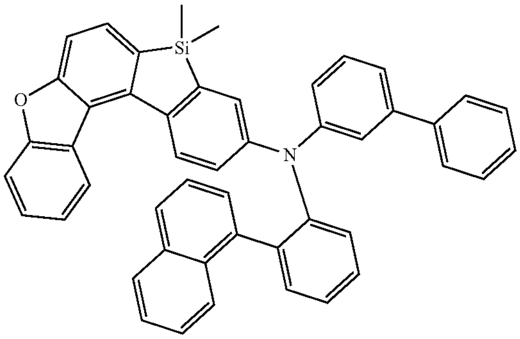
B-24
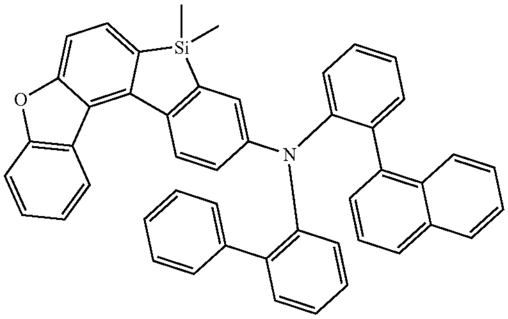
B-25
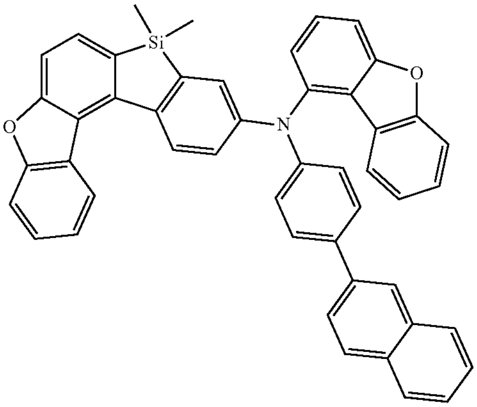

-continued
B-26
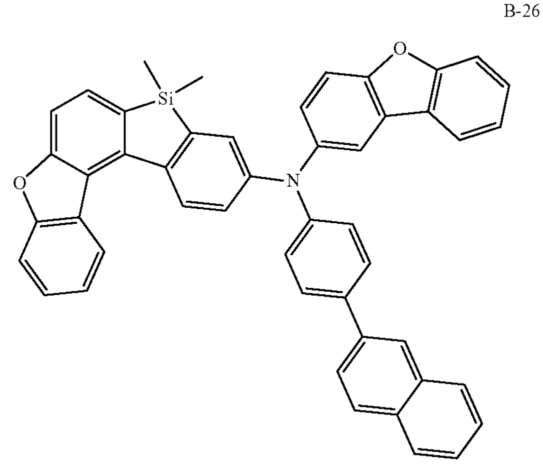
B-27
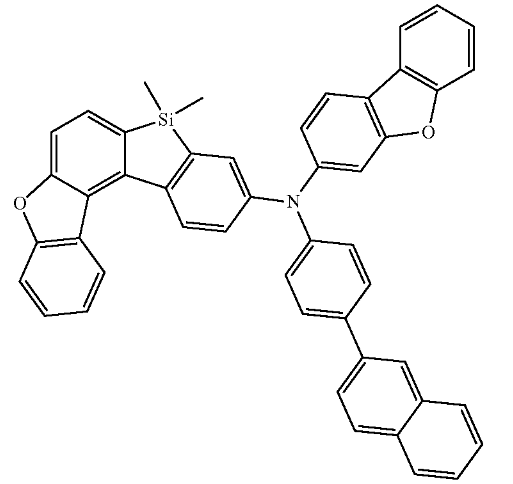
B-28
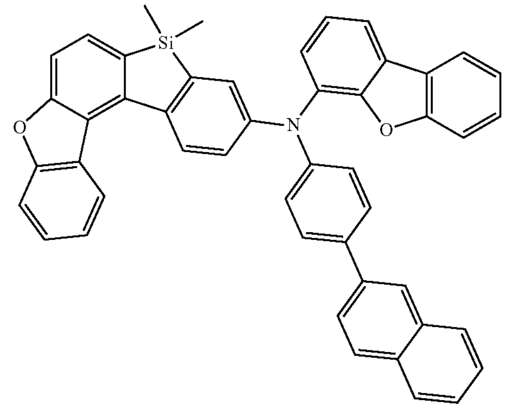
-continued
B-29
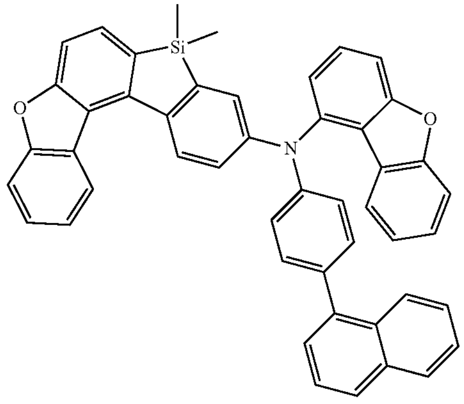
B-30
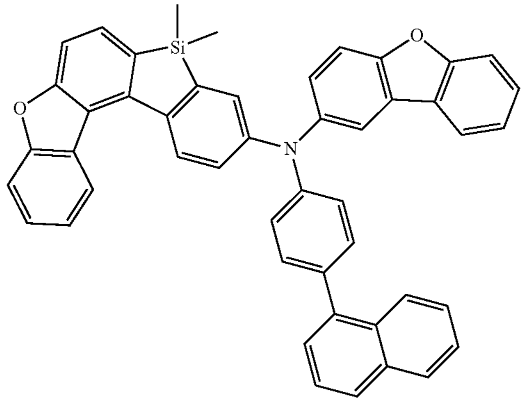
B-31
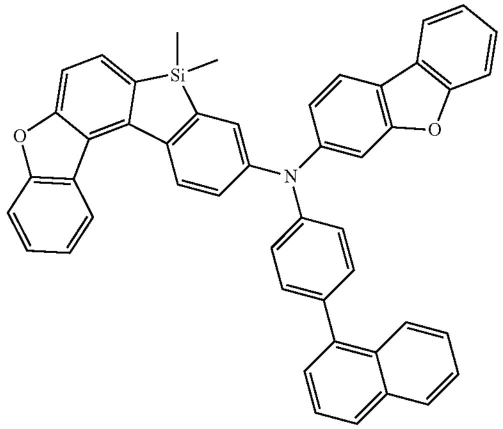

B-32
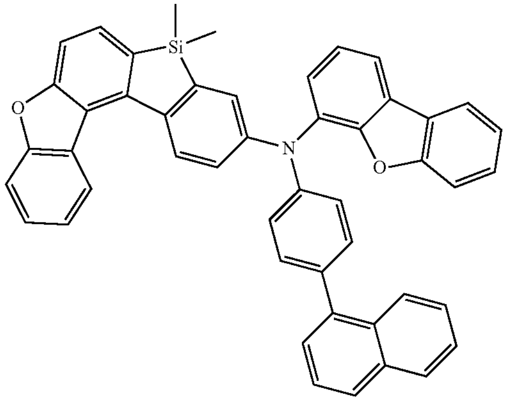
B-33
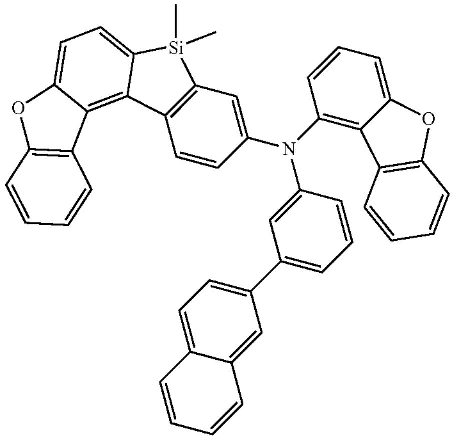
B-34
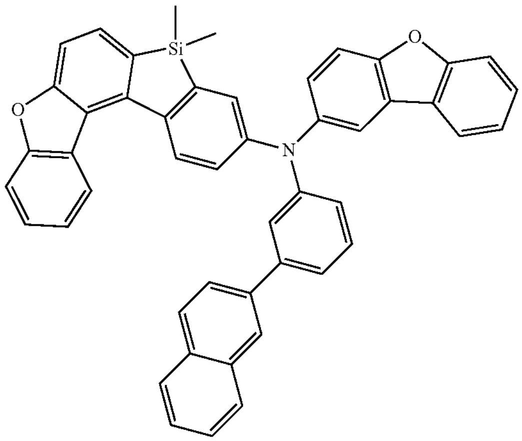
B-35
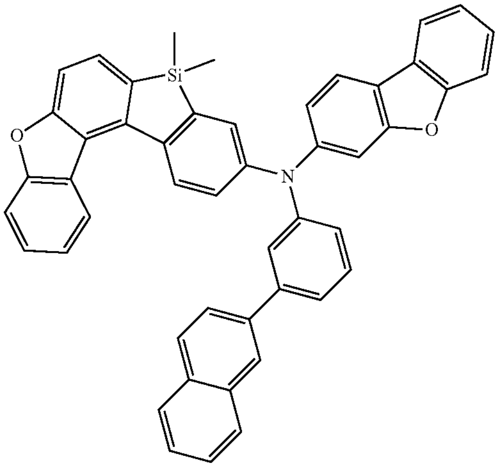
B-36
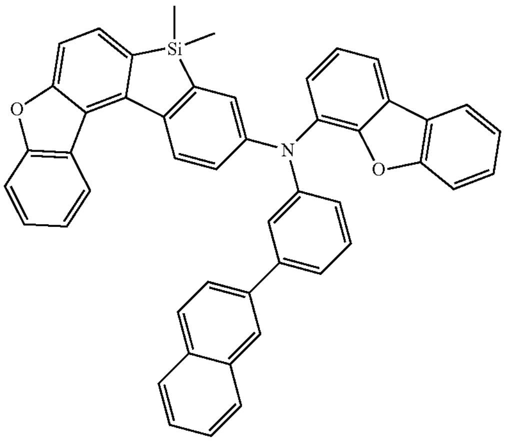
B-37
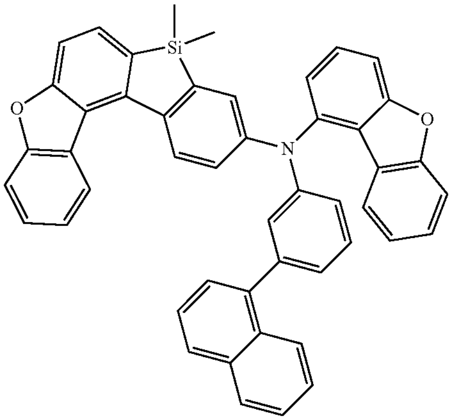

-continued
B-38
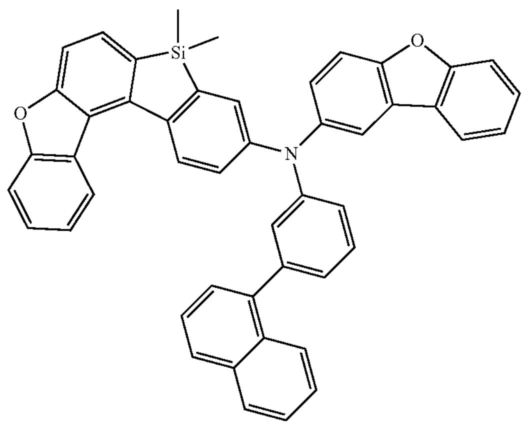
B-39
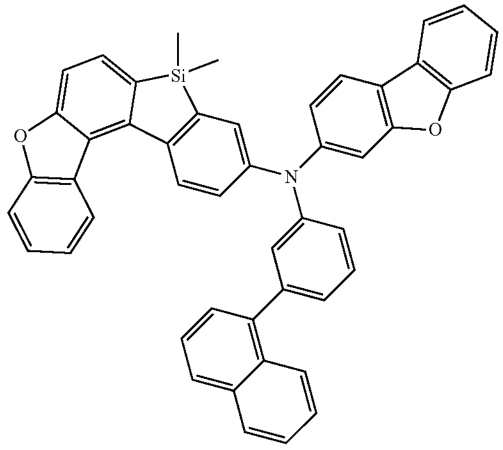
B-40
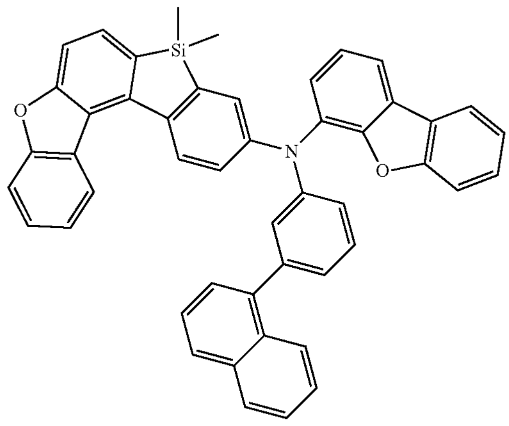
-continued
B-41
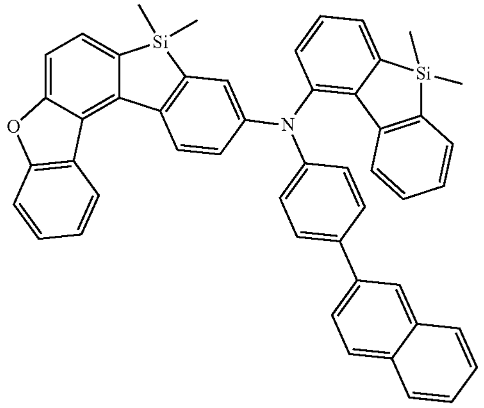
B-42
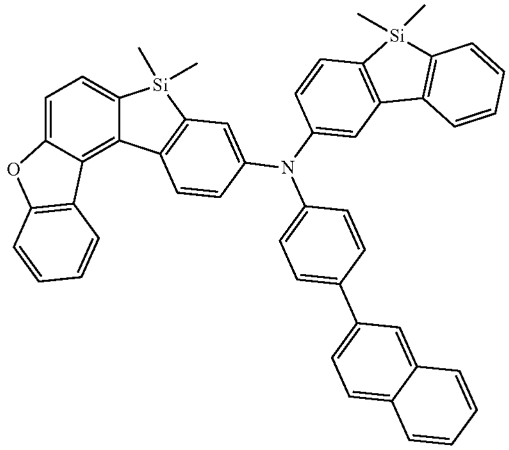
B-43
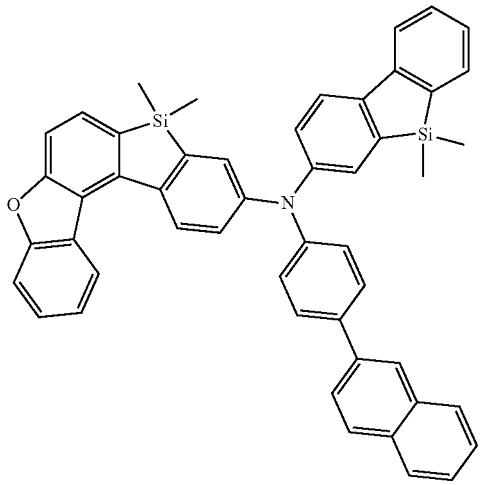

-continued
B-44
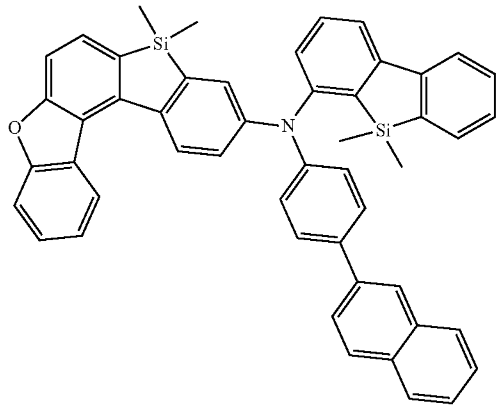
B-45
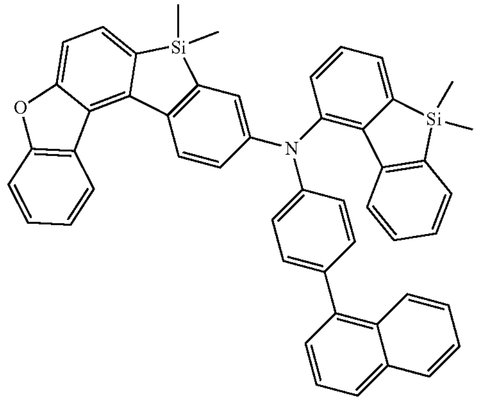
B-46
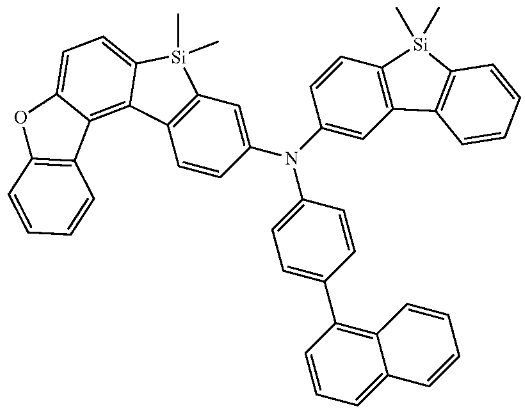
-continued
B-47
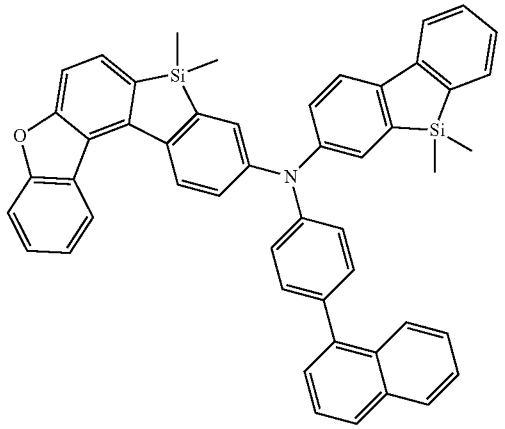
B-48
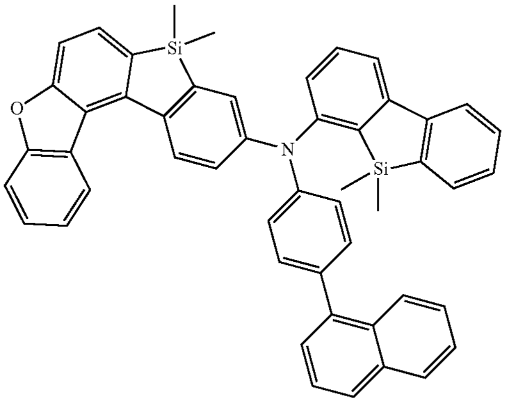
B-49
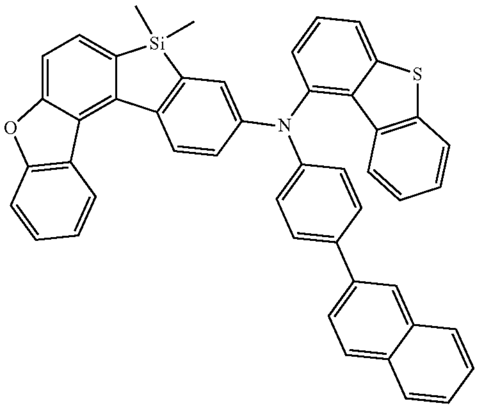

B-50
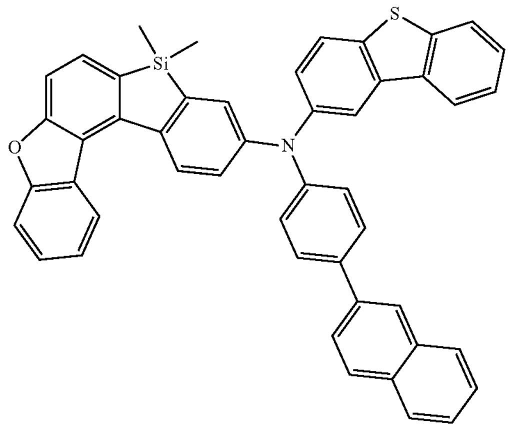
B-51
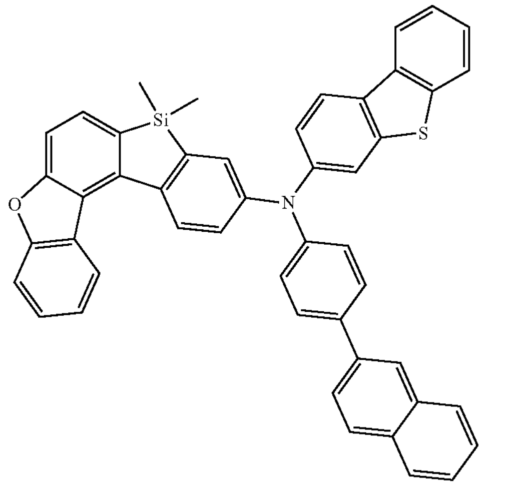
B-52
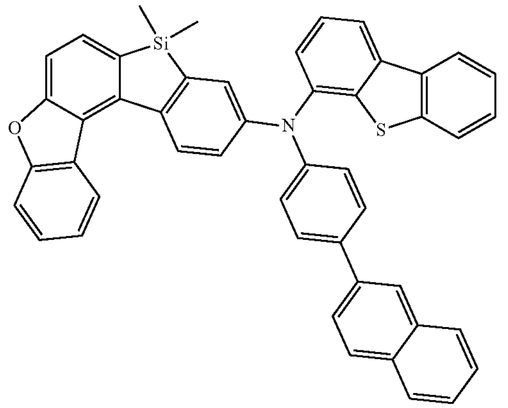
B-53
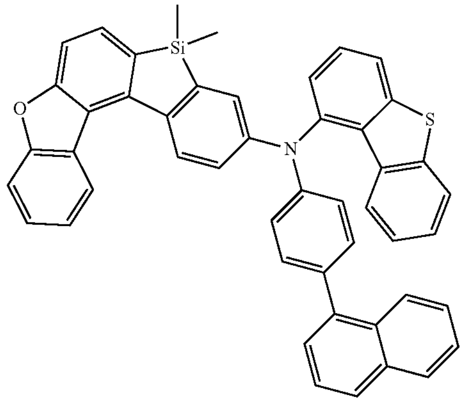
B-54
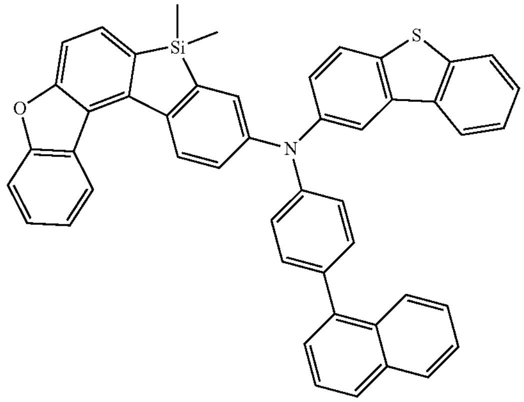
B-55
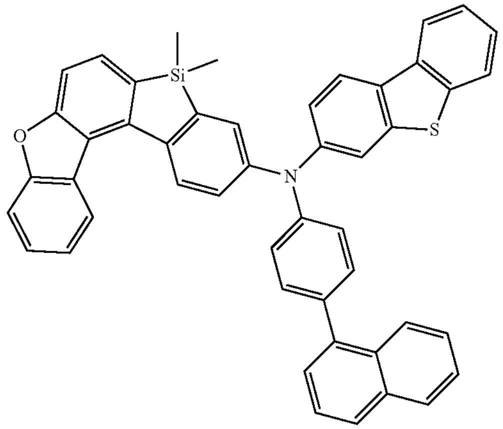

-continued
B-56
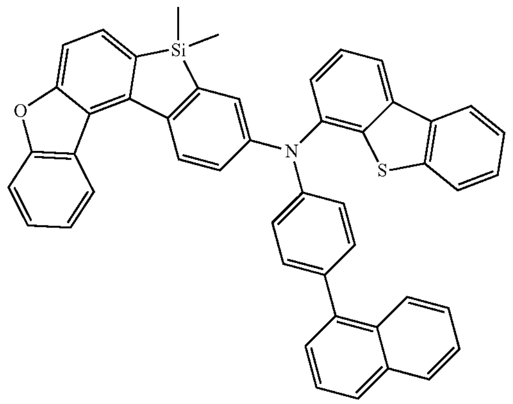
B-57
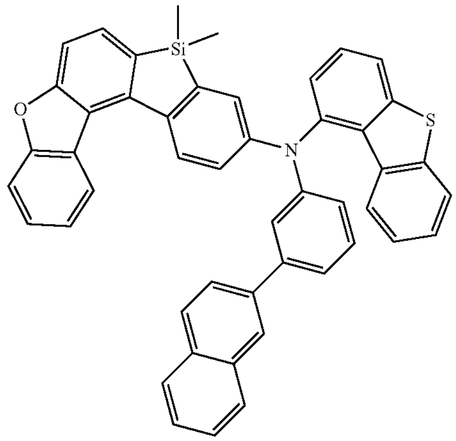
B-58
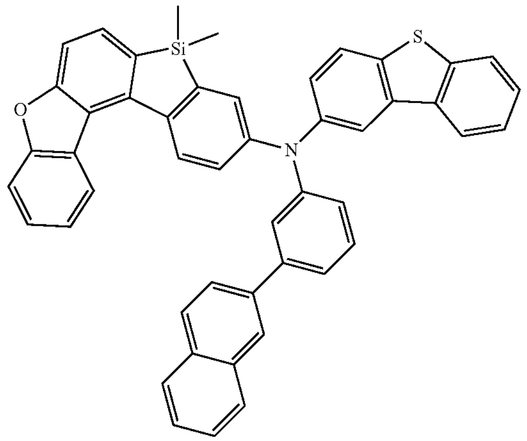
-continued
B-59
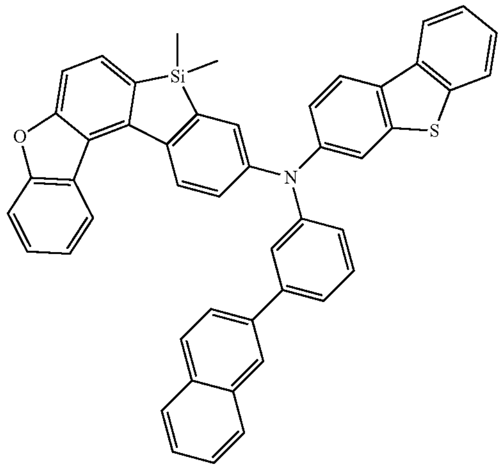
B-60
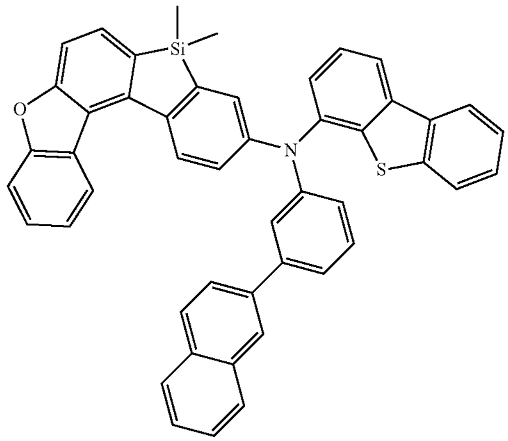
B-61
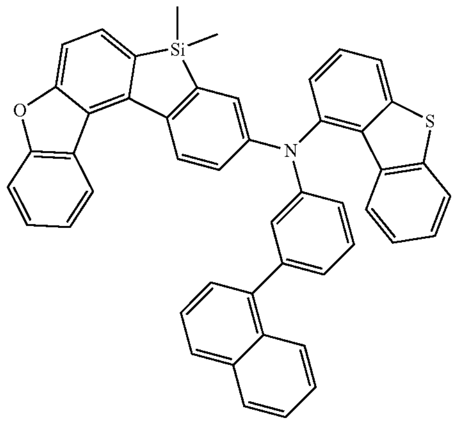

-continued
B-62
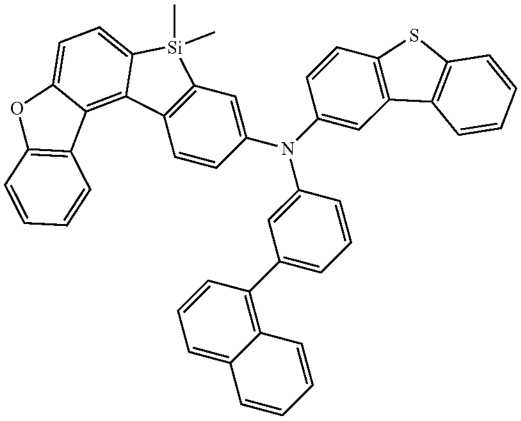
B-63
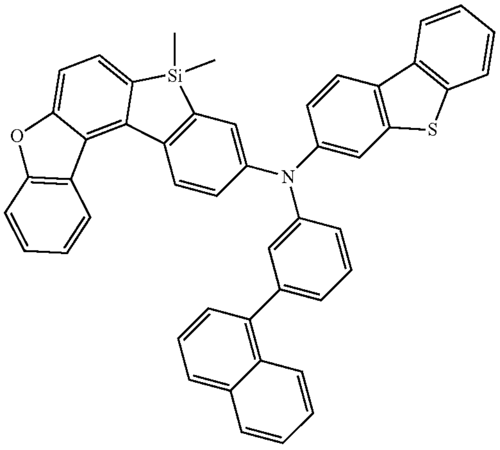
B-64
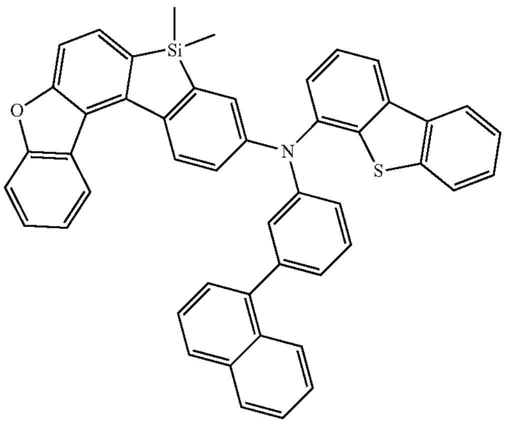
-continued
B-65
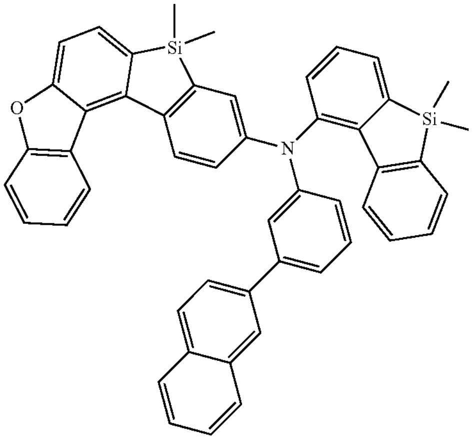
B-66
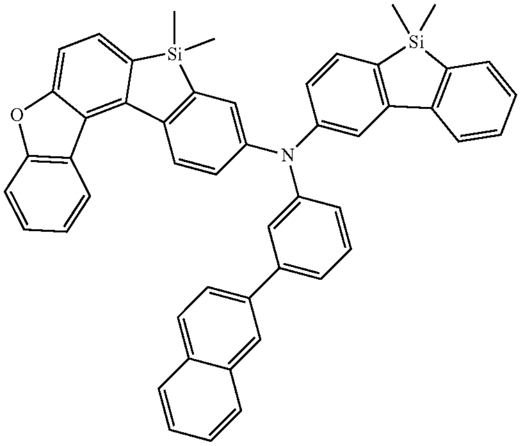
B-67
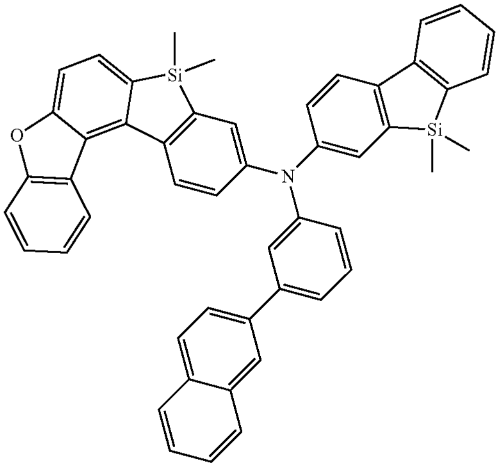

-continued
B-68
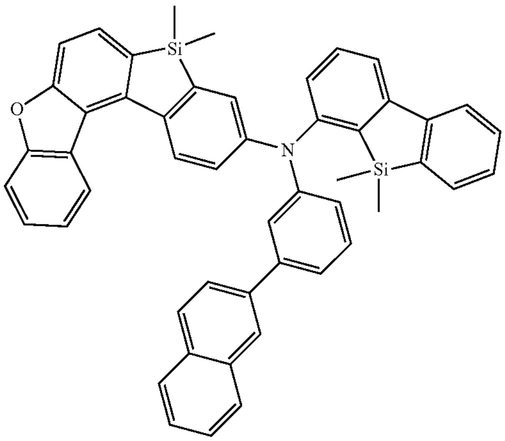
B-69
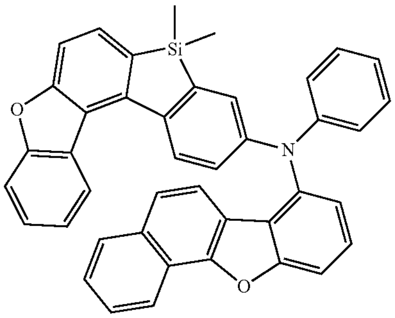
B-70
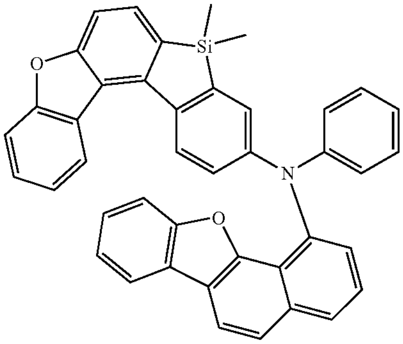
B-71
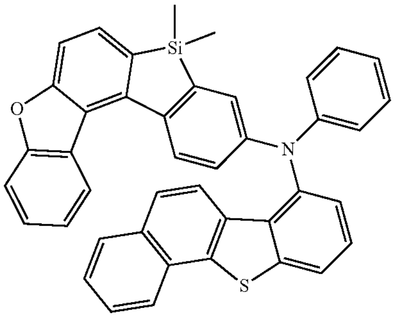
-continued
B-72
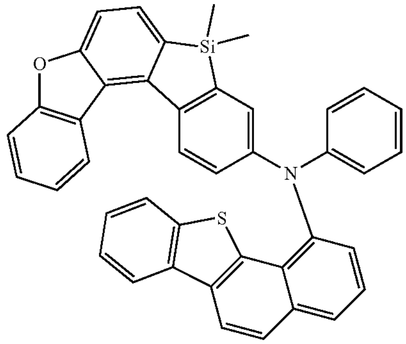
B-73
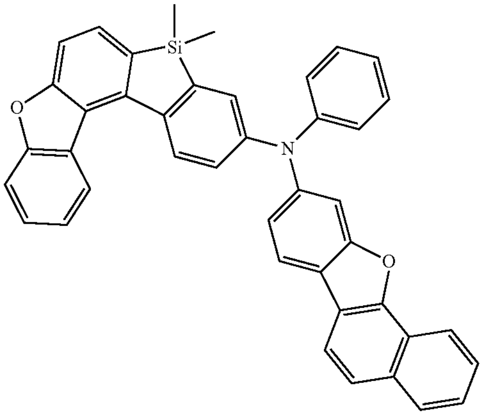
B-74
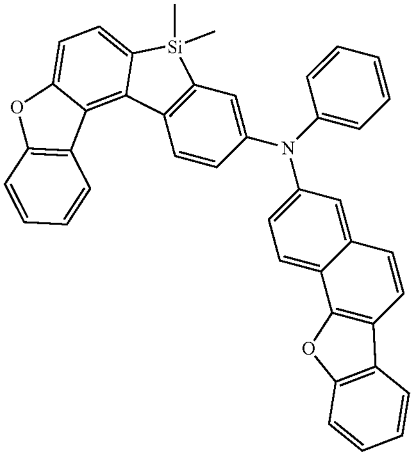

-continued
B-75
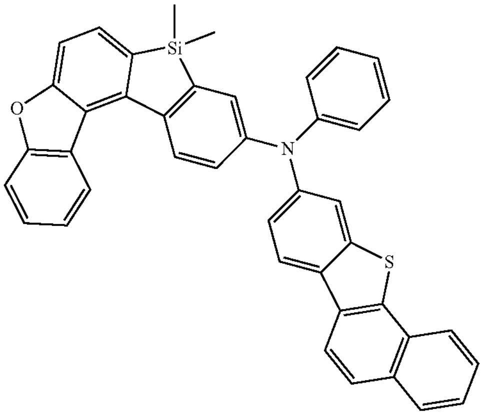
B-76
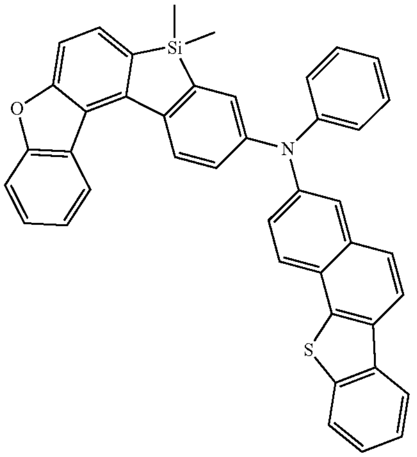
B-77
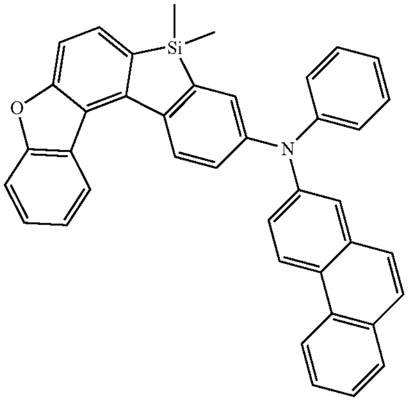
B-78
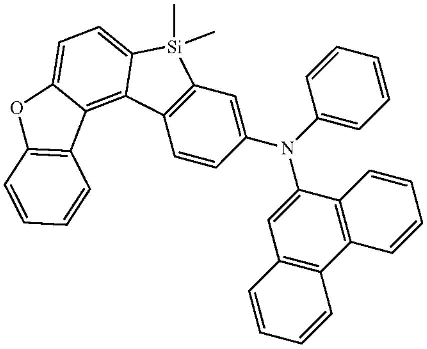
-continued
B-79
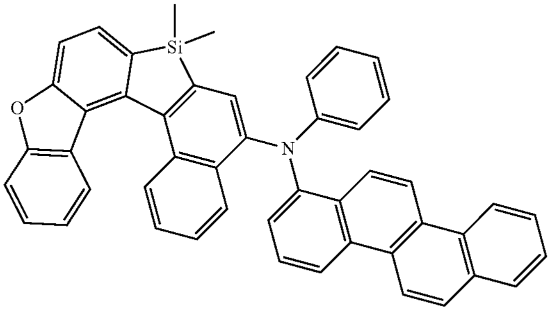
B-80
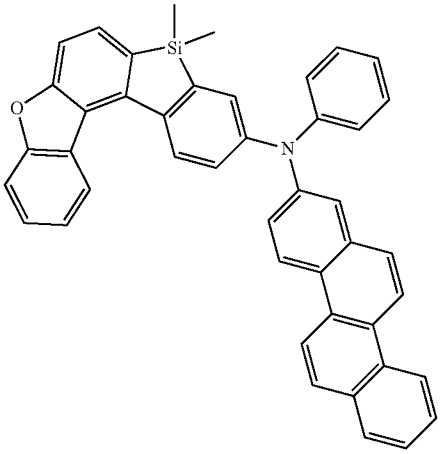
B-81
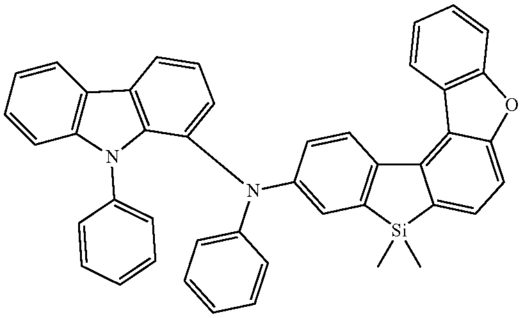
B-82
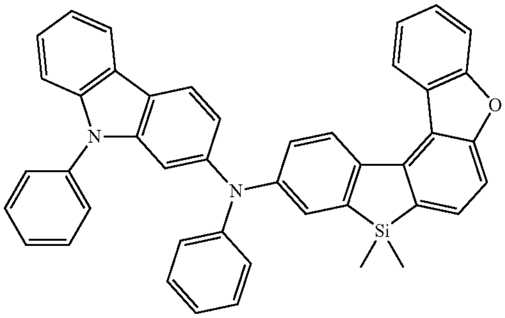

-continued
B-83
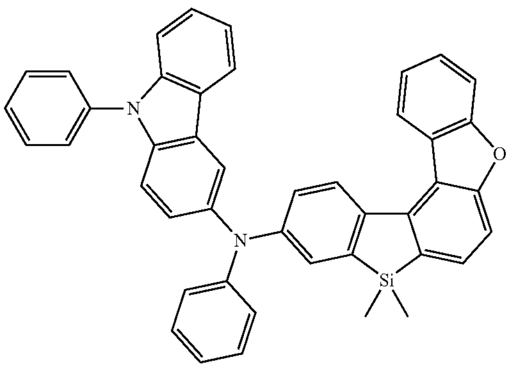
B-84
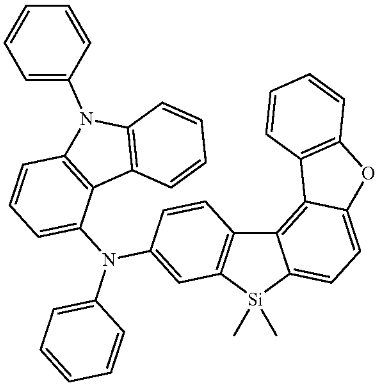
B-85
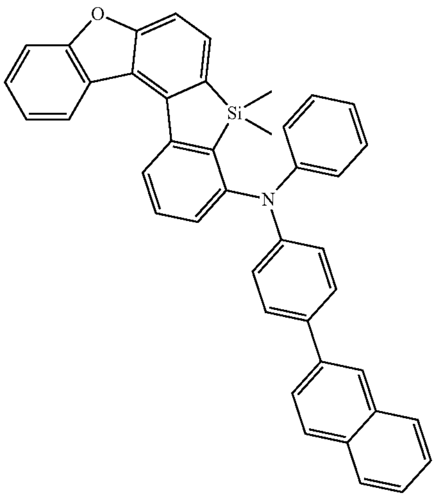
-continued
B-86
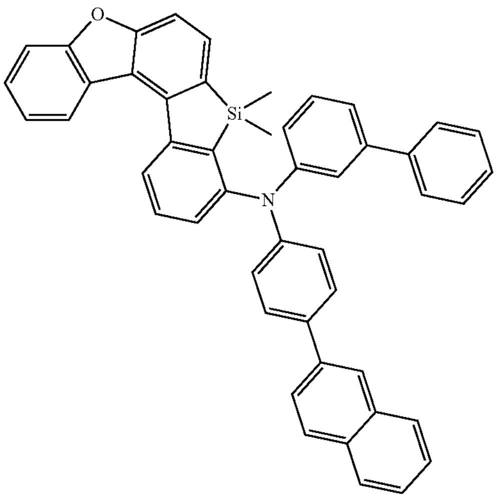
B-87
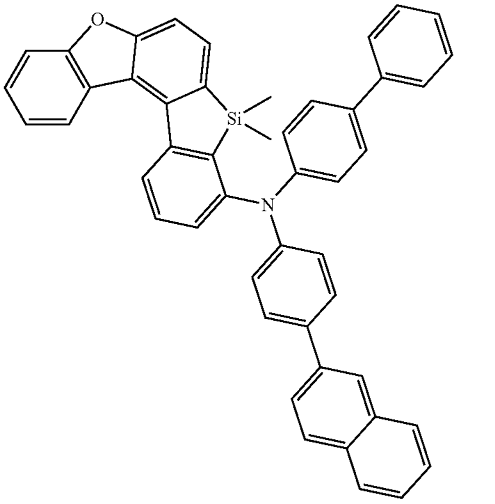
B-88
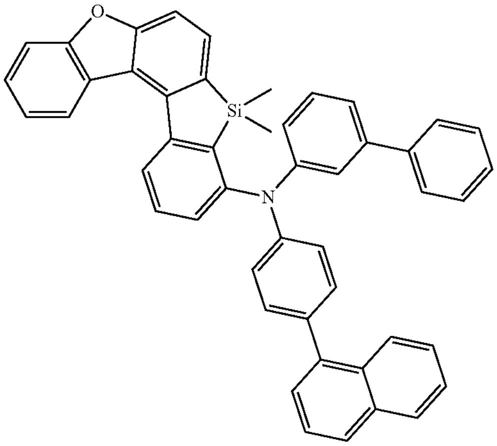

-continued
B-89
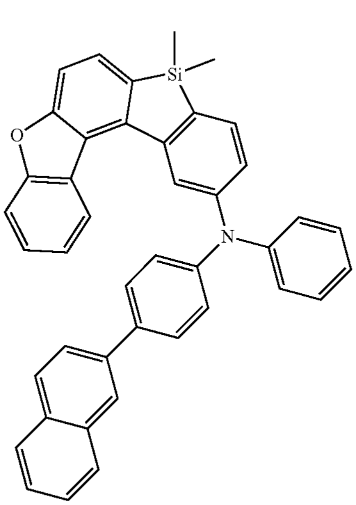
B-90
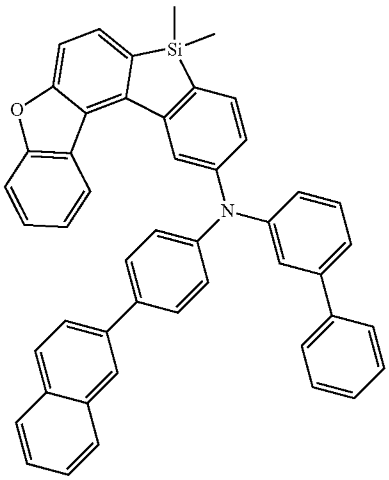
B-91
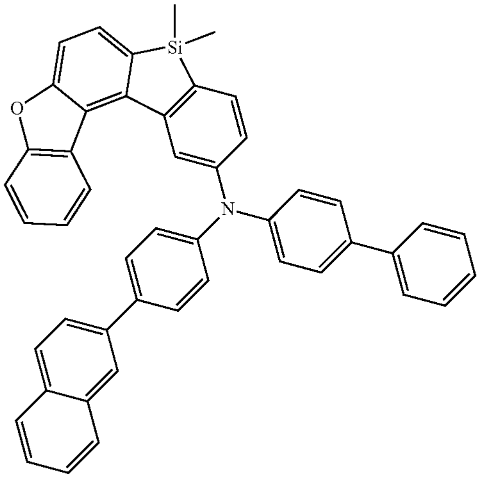
-continued
B-92
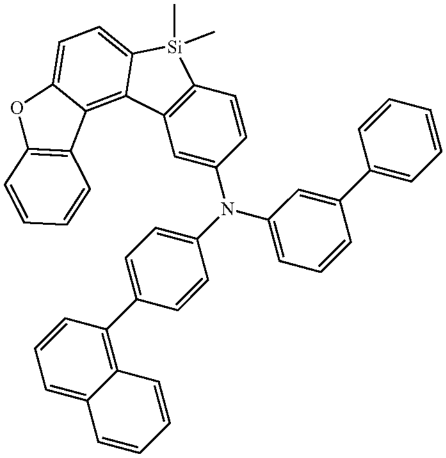
B-93
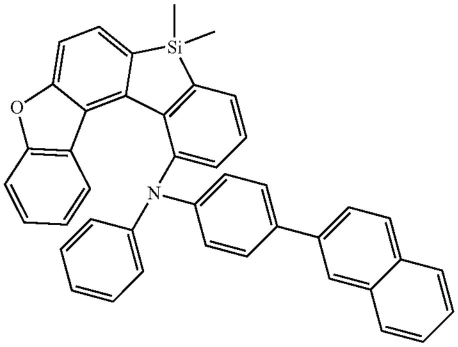
B-94
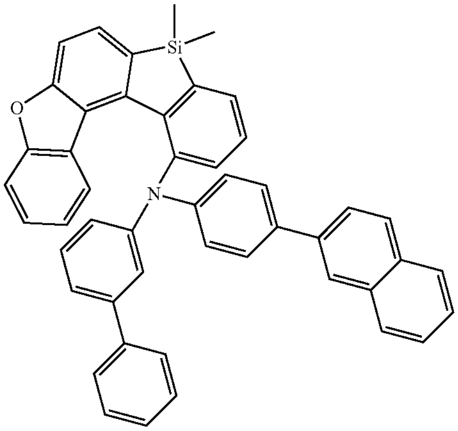

-continued
B-95
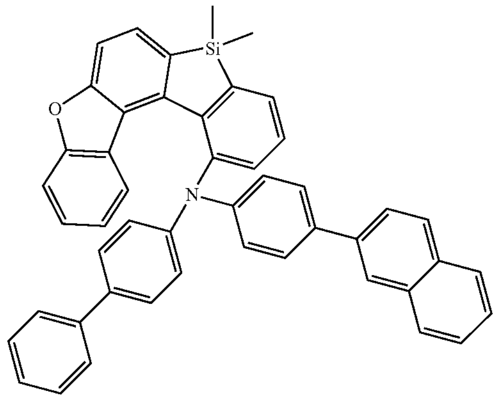
B-96
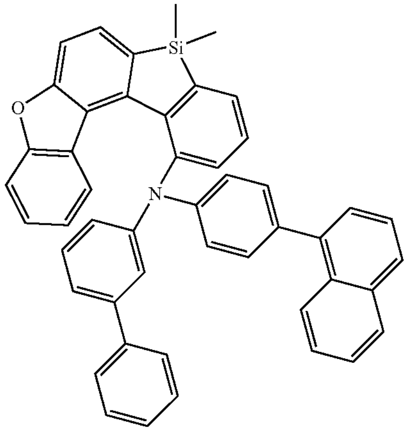
B-97
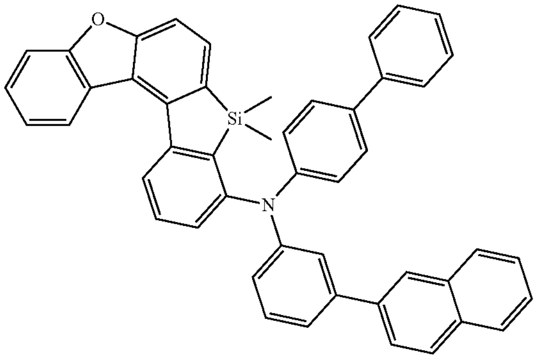
-continued
B-98
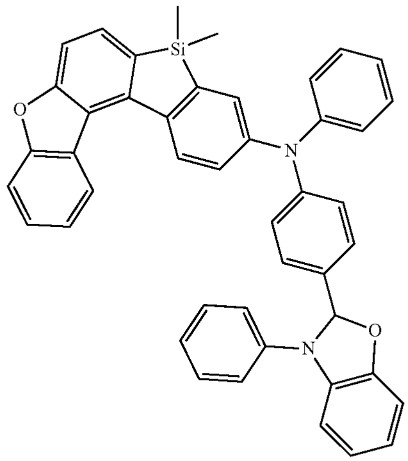
B-99
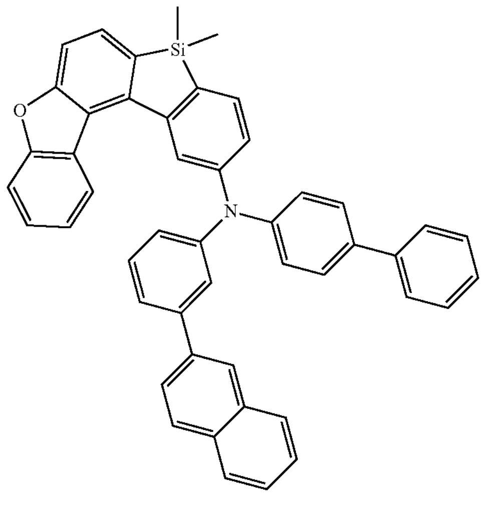
B-100
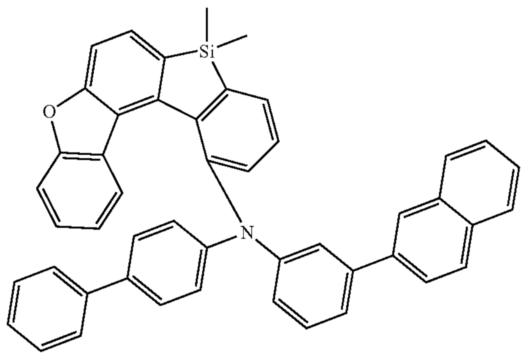

B-101
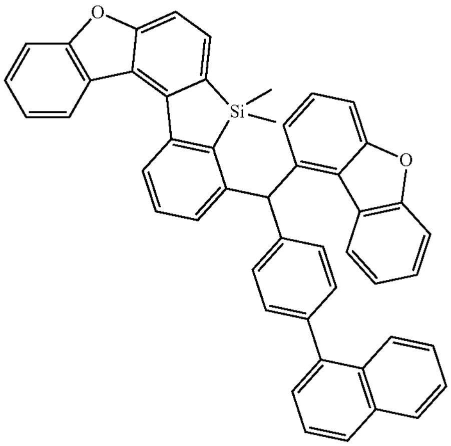
B-102
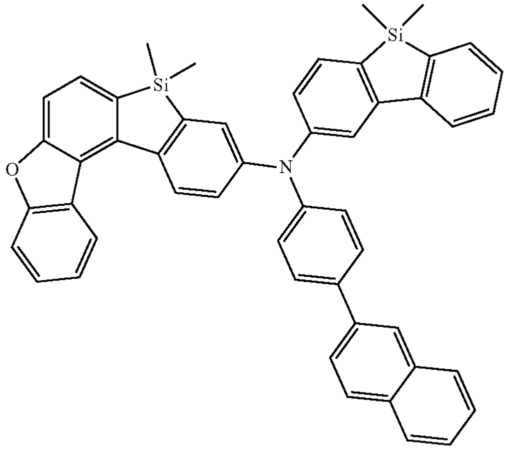
B-103
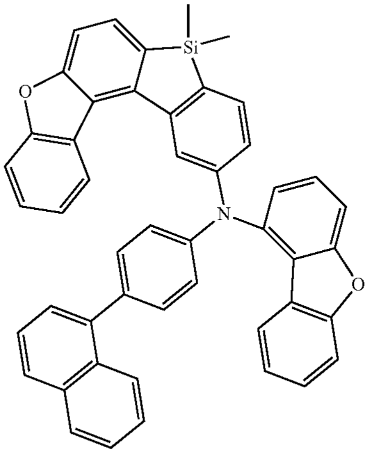
-continued
B-104
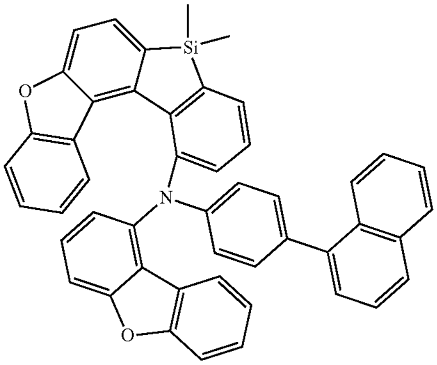
B-105
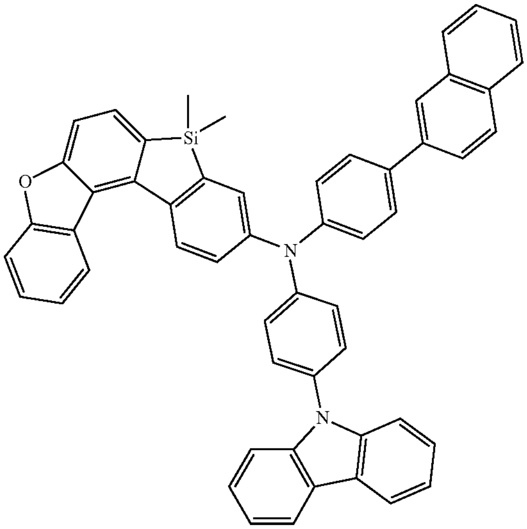
B-106
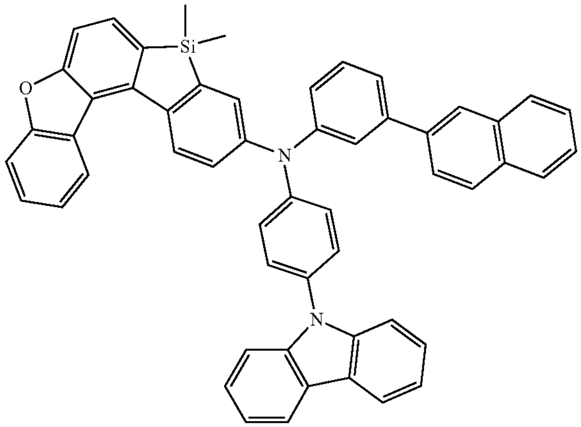

-continued
B-107
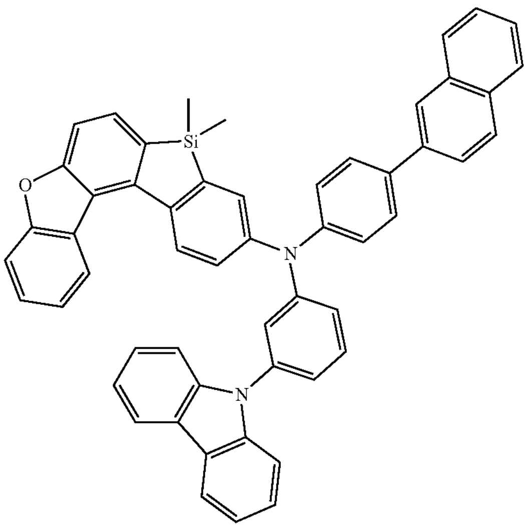
B-108
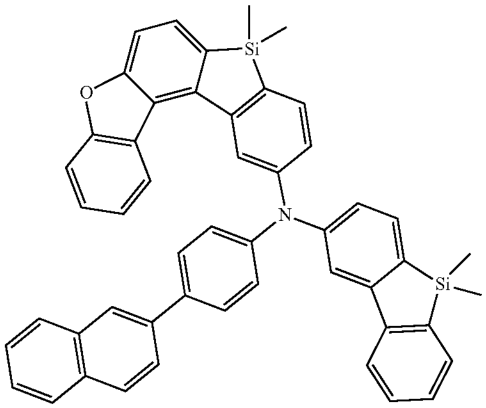
C-1
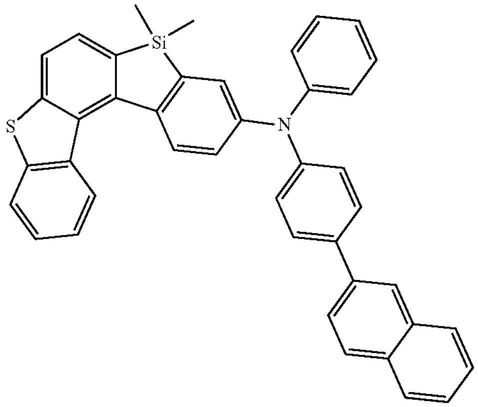
-continued
C-2
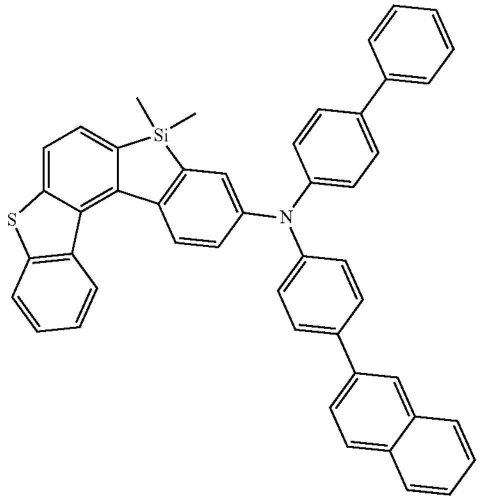
C-3
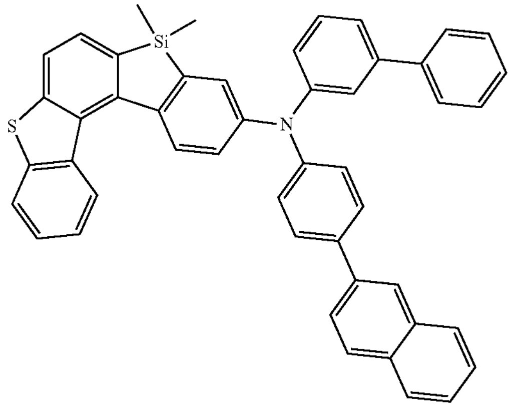
C-4
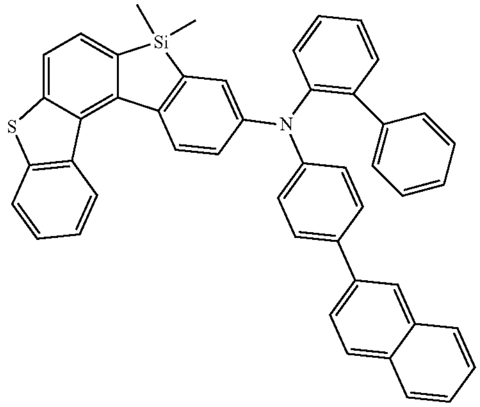

C-5
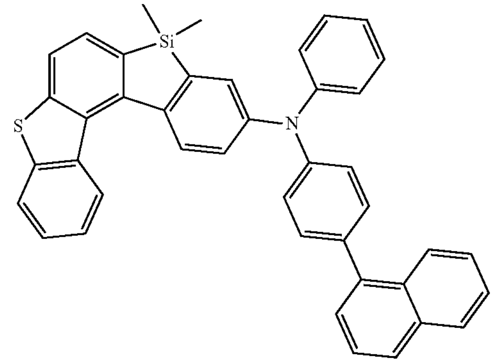
C-6
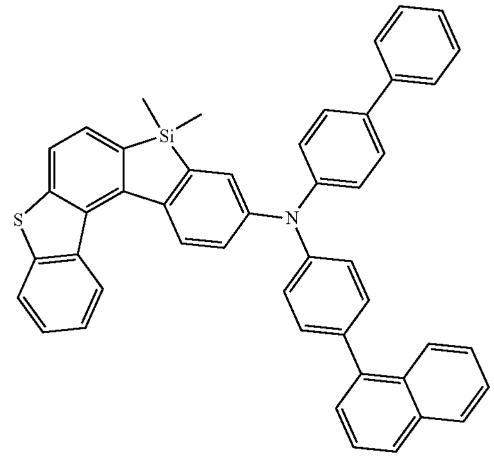
C-7
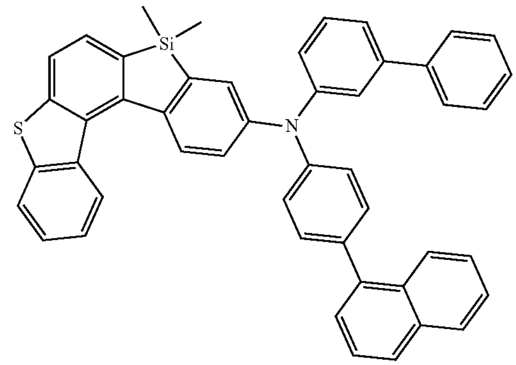
C-8
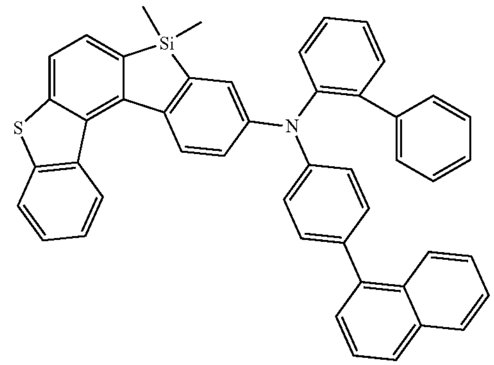
C-9
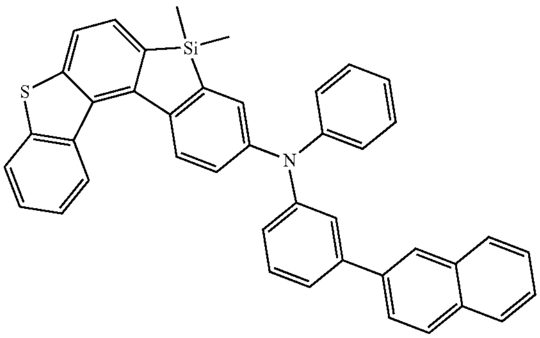
C-10
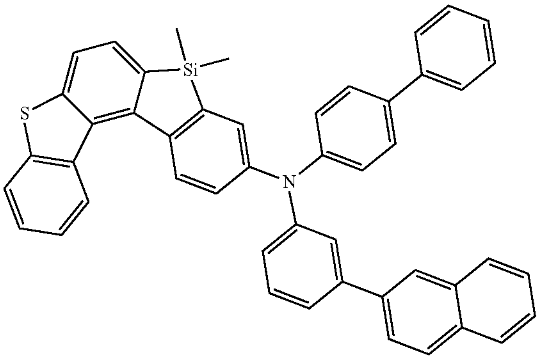
C-11
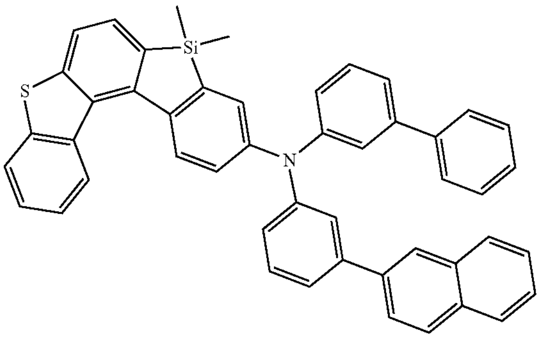
C-12
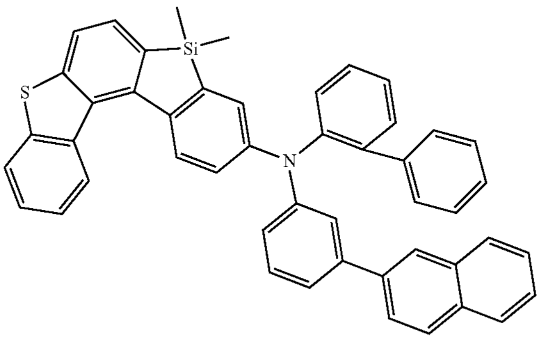

-continued
C-13
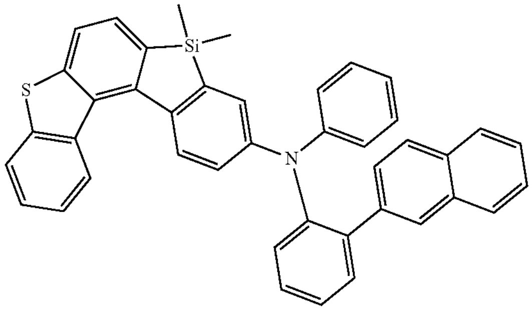
C-14
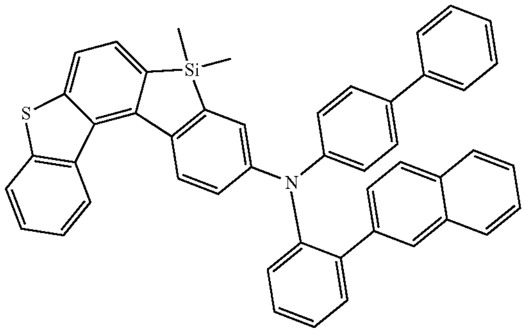
C-15
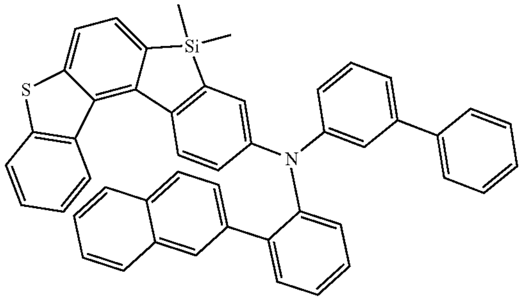
C-16
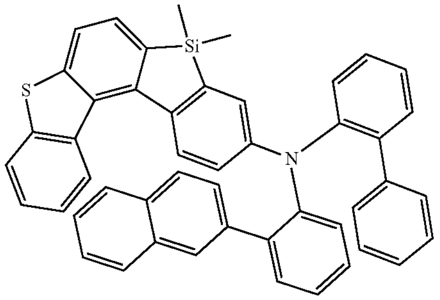
-continued
C-17
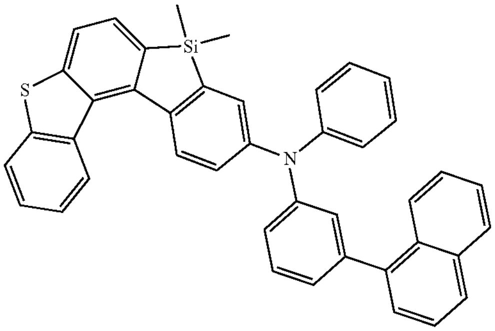
C-18
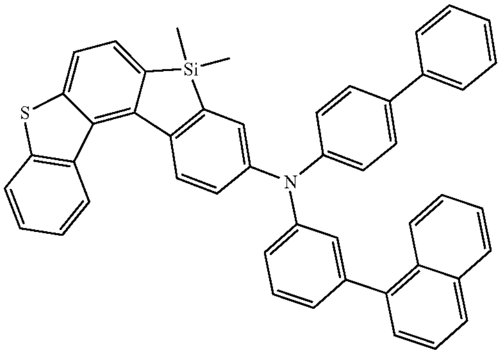
C-19
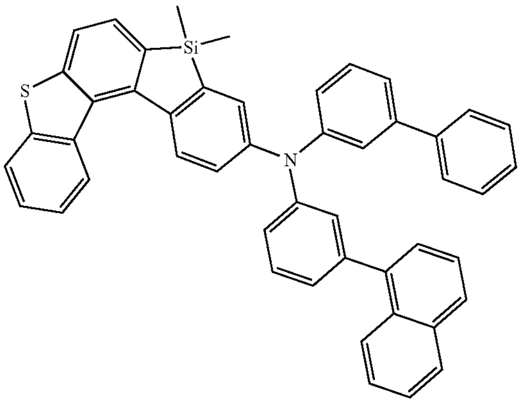
C-20
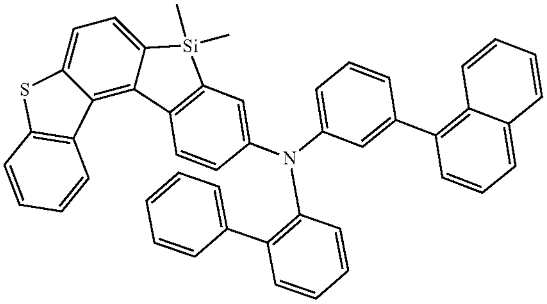

-continued
C-21
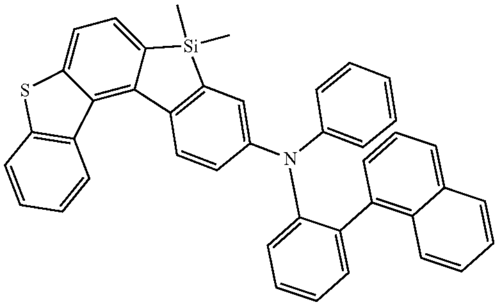
C-22
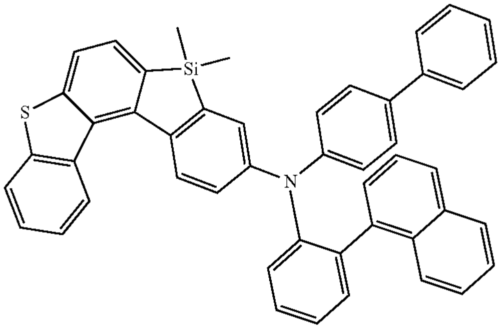
C-23
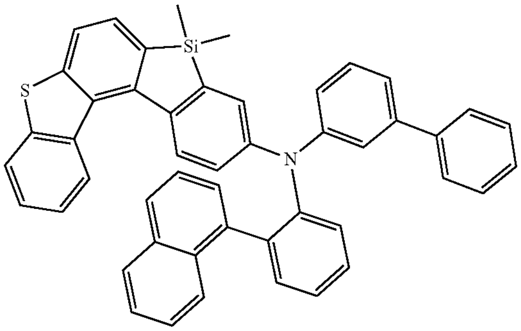
C-24
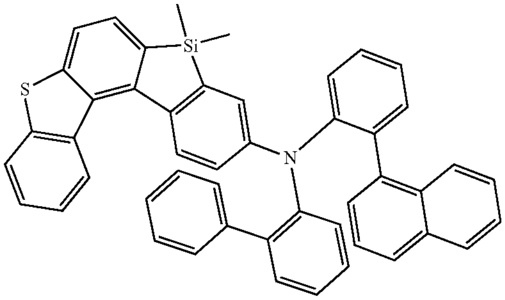
-continued
C-25
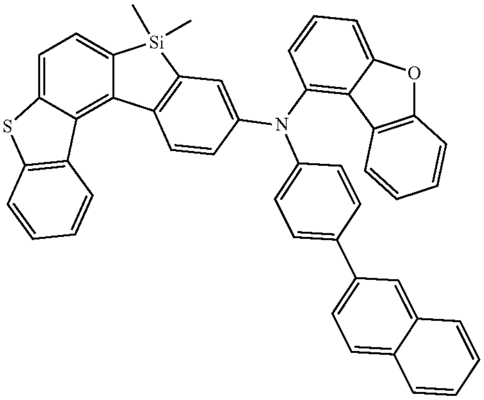
C-26
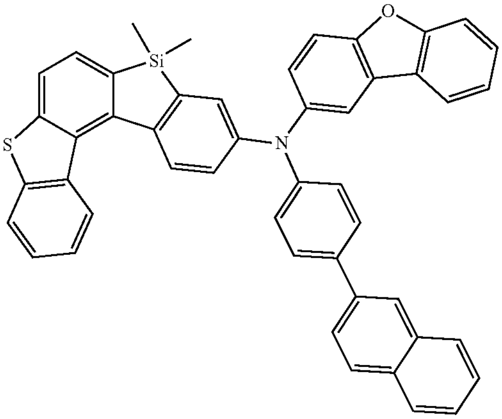
C-27
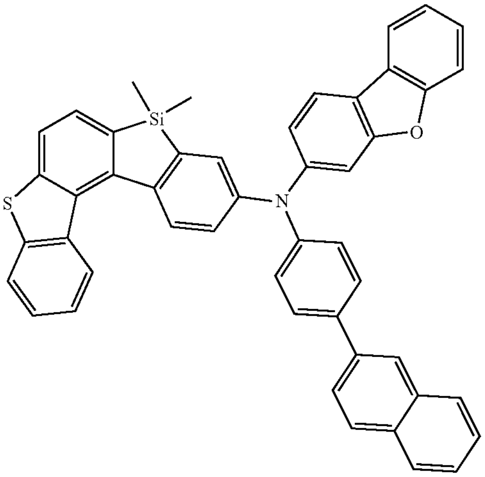

-continued
C-28
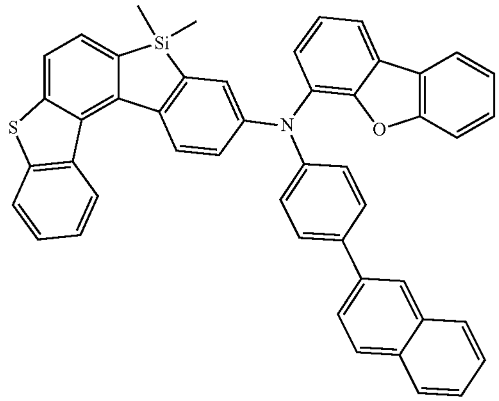
C-29
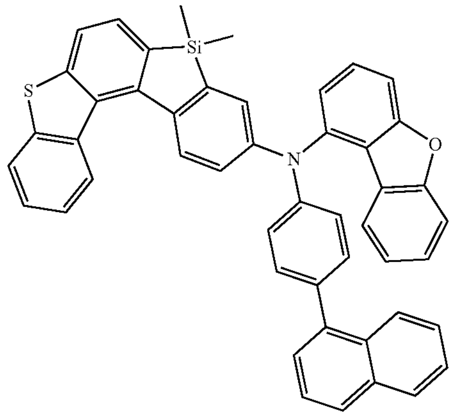
C-30
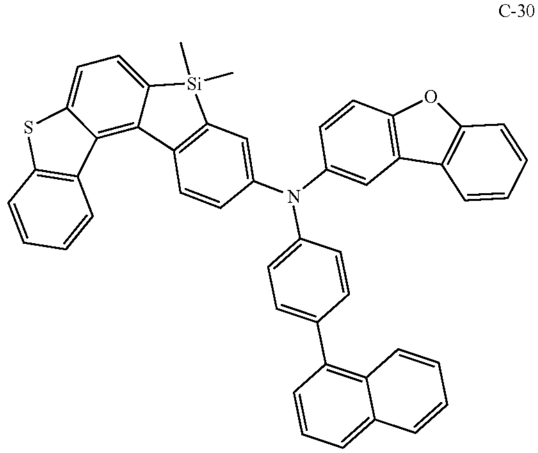
-continued
C-31
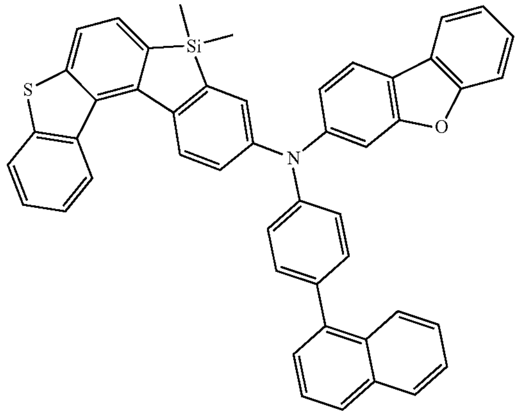
C-32
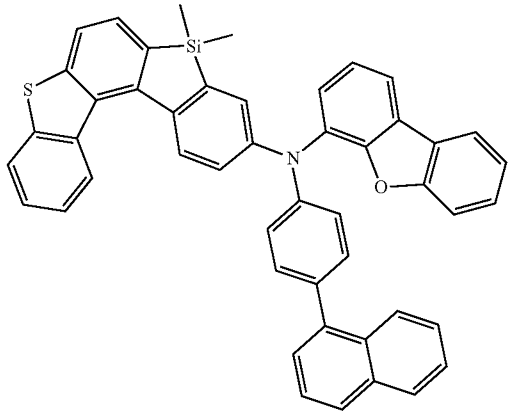
C-33
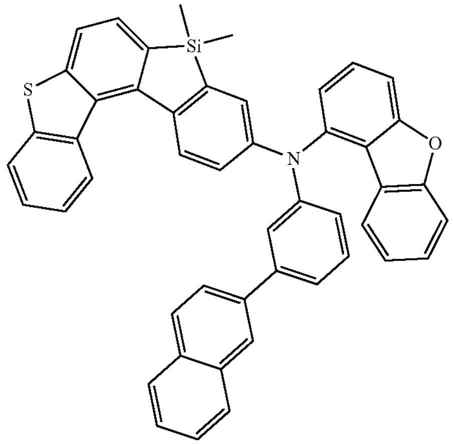

-continued
C-34
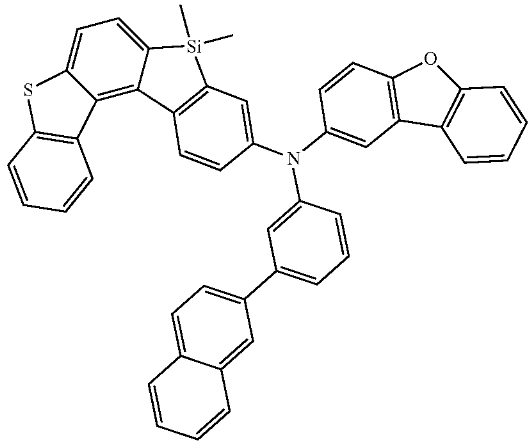
C-35
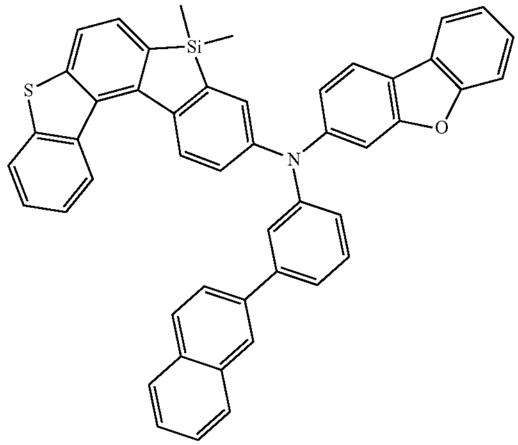
C-36
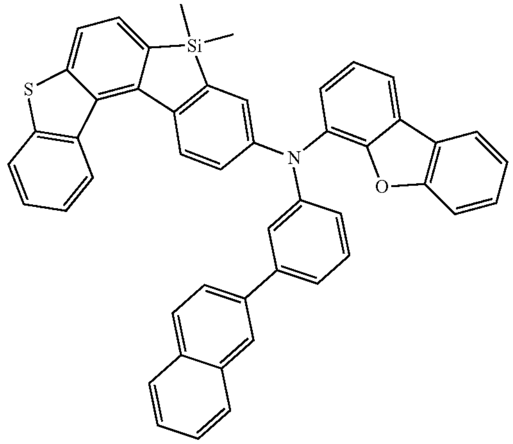
-continued
C-37
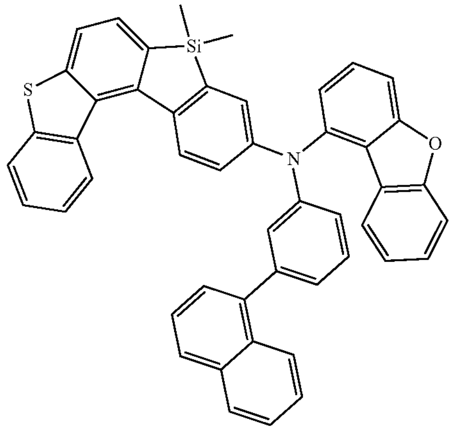
C-38
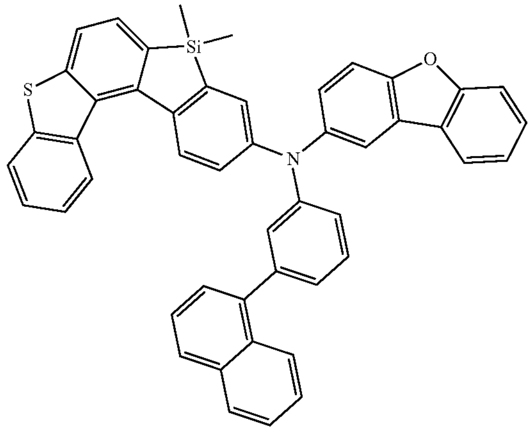
C-39
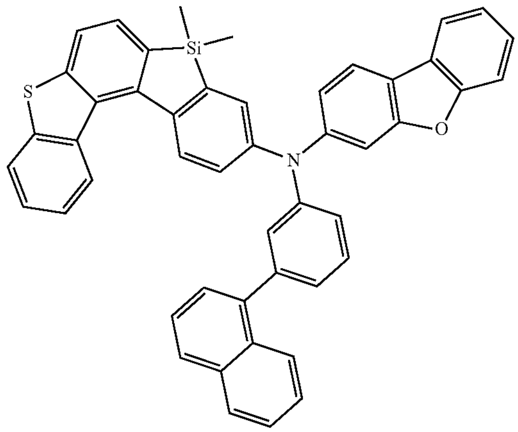

-continued
C-40
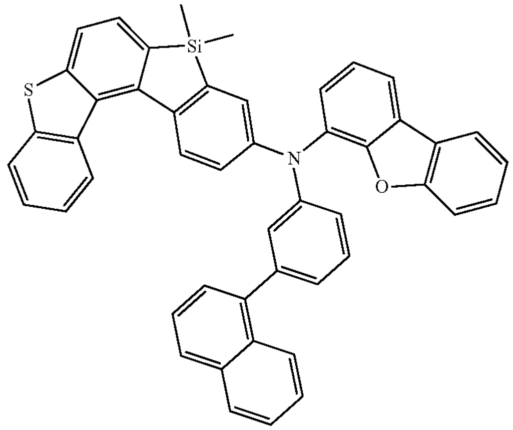
C-41
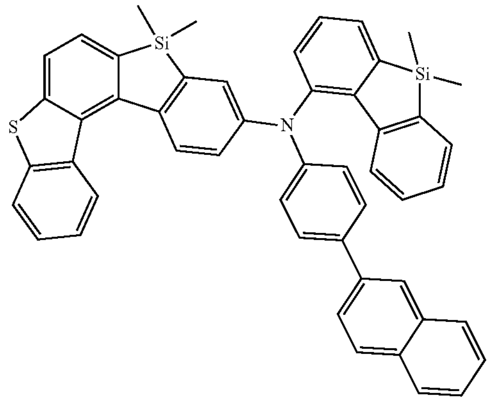
C-42
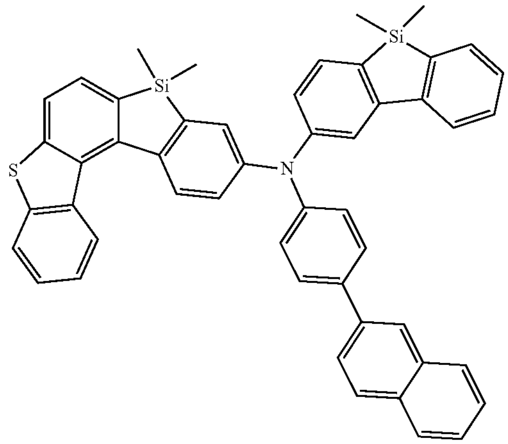
-continued
C-43
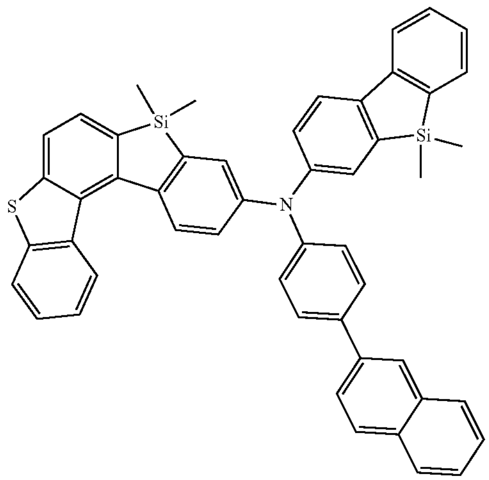
C-44
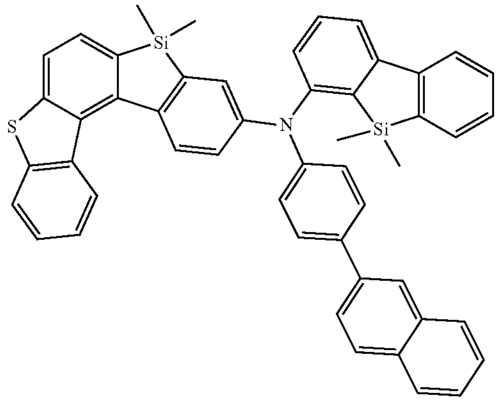
C-45
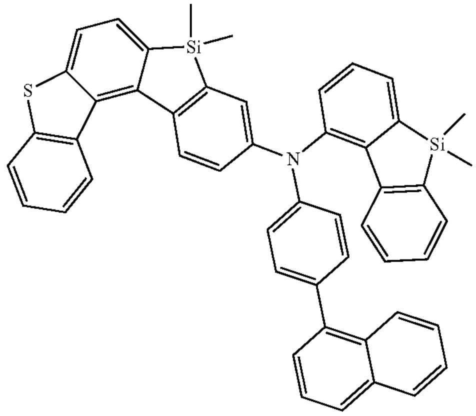

-continued
C-46
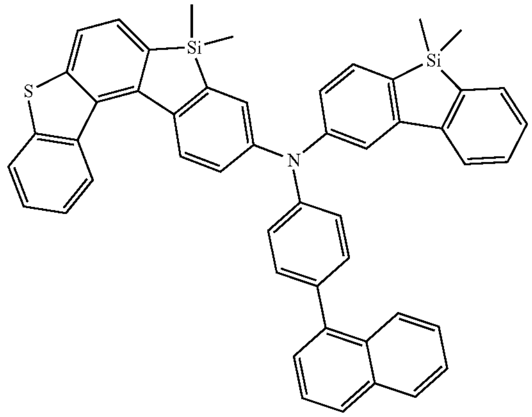
C-47
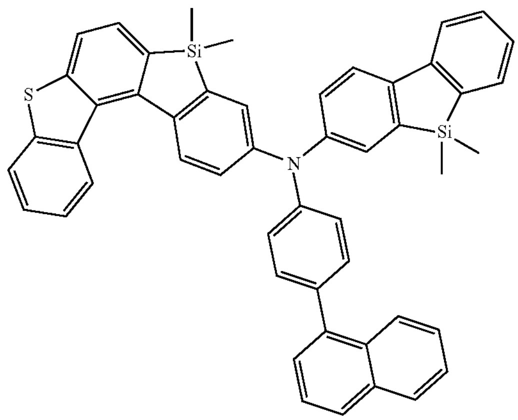
C-48
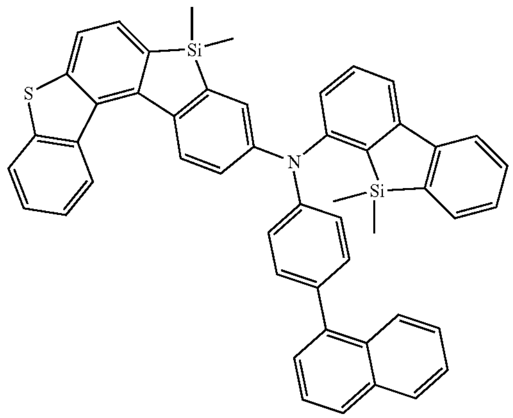
-continued
C-49
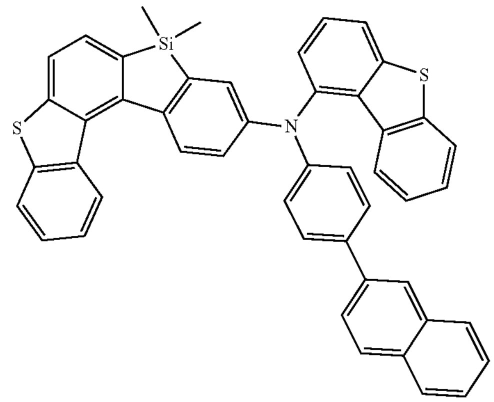
C-50
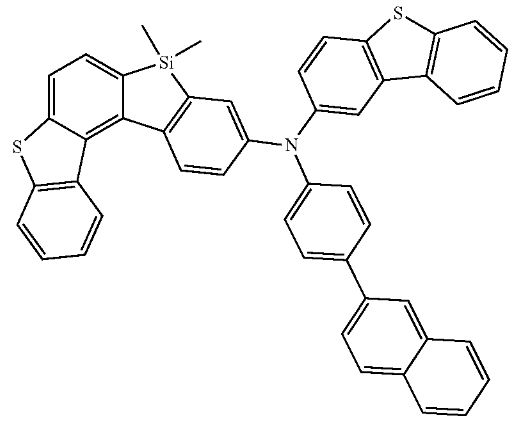
C-51
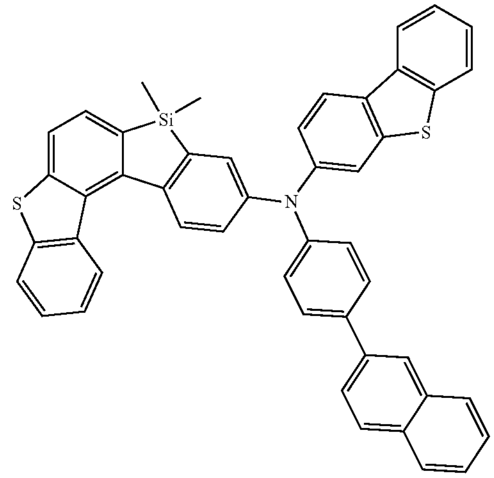

-continued
C-52
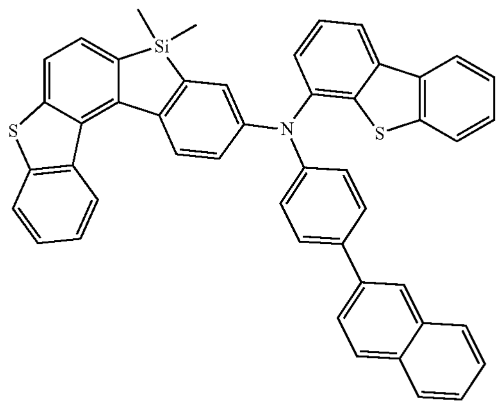
C-53
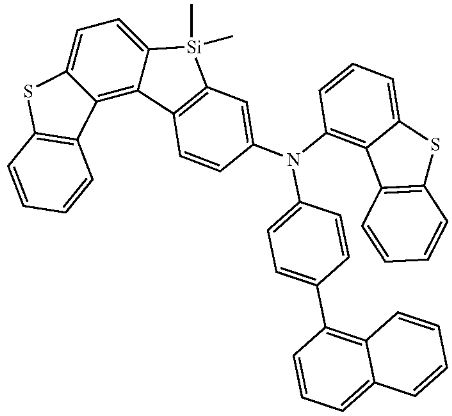
C-54
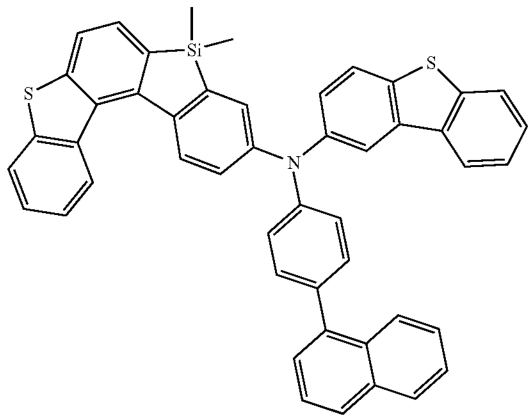
-continued
C-55
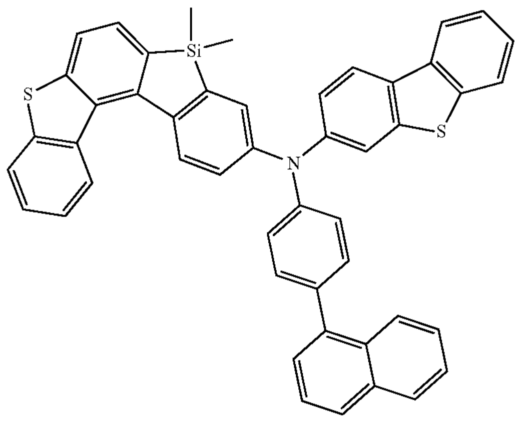
C-56
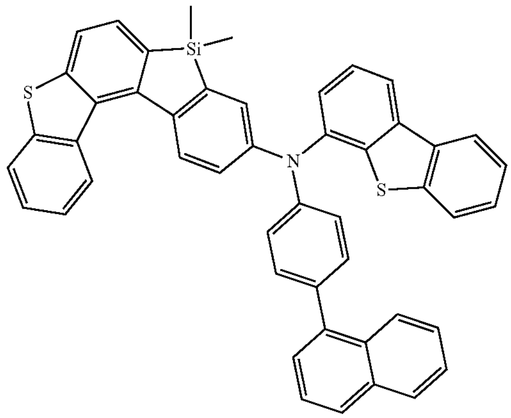
C-57
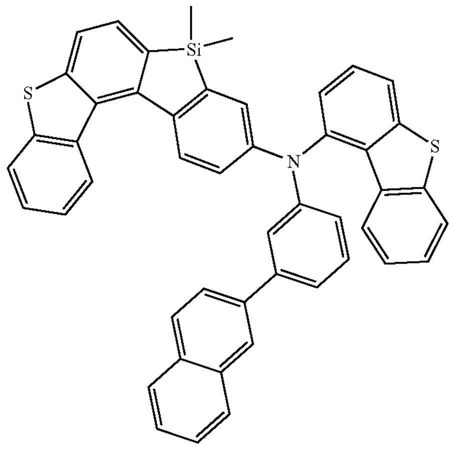

-continued
C-58
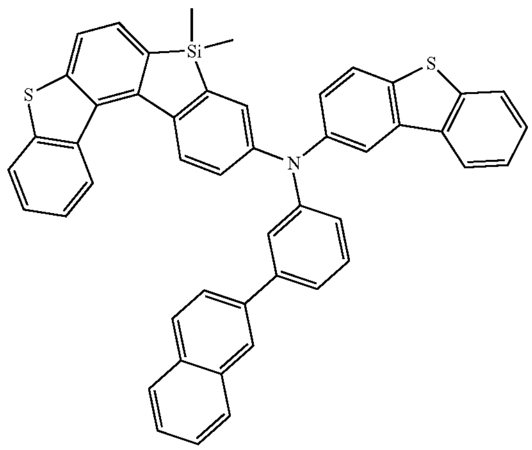
C-59
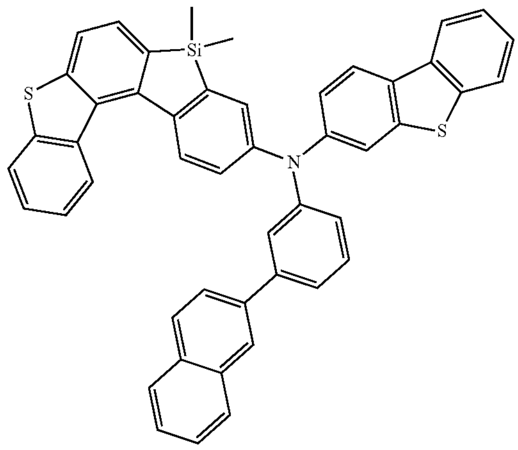
C-60
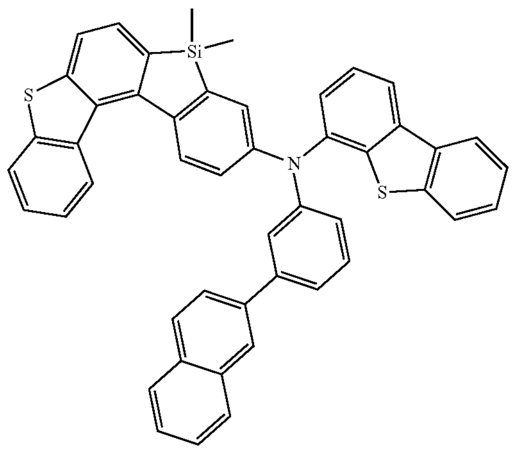
-continued
C-61
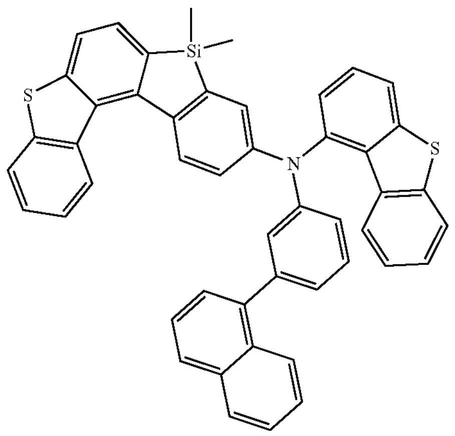
C-62
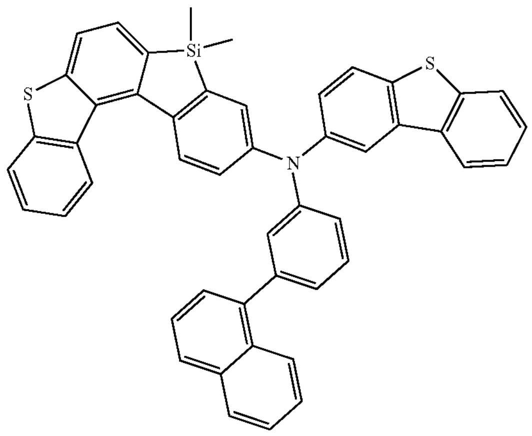
C-63
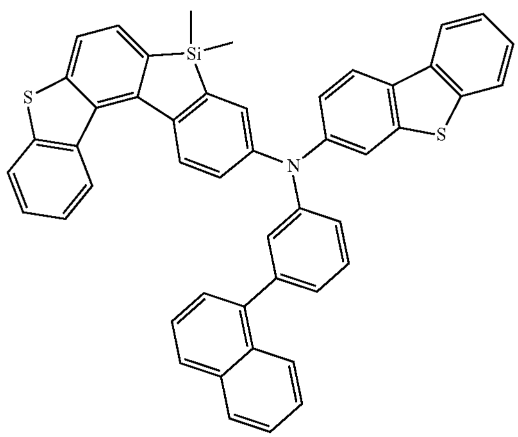

-continued
C-64
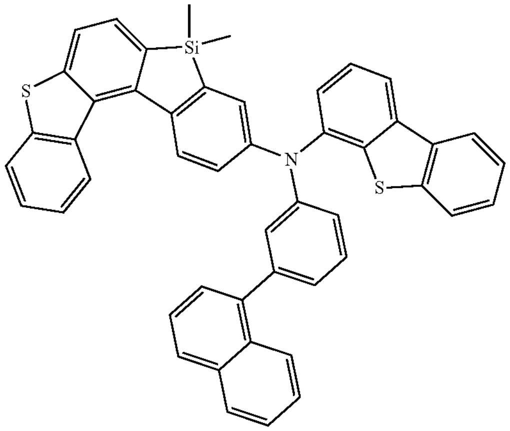
C-65
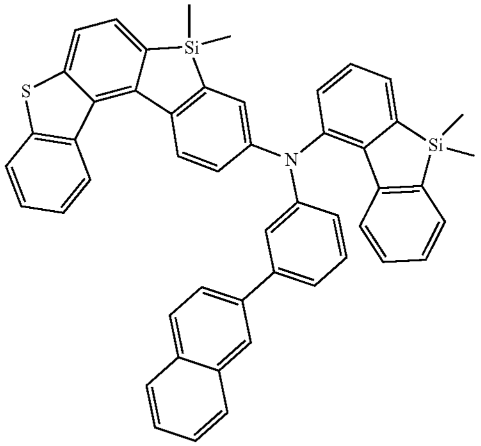
C-66
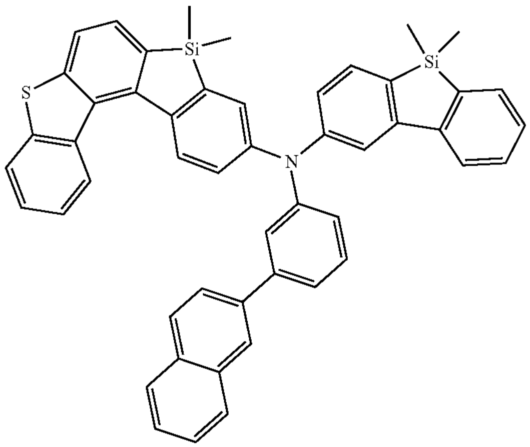
-continued
C-67
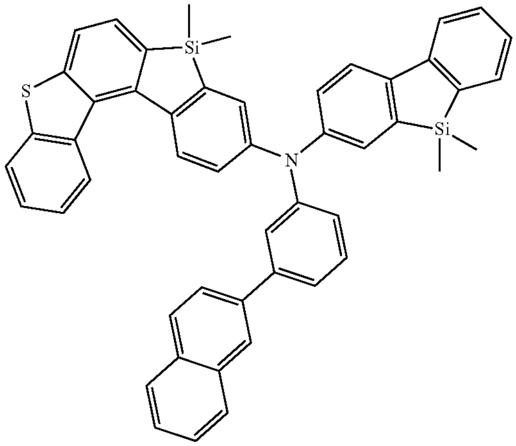
C-68
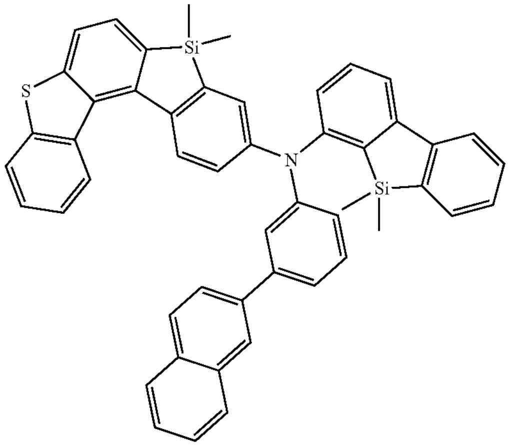
C-69
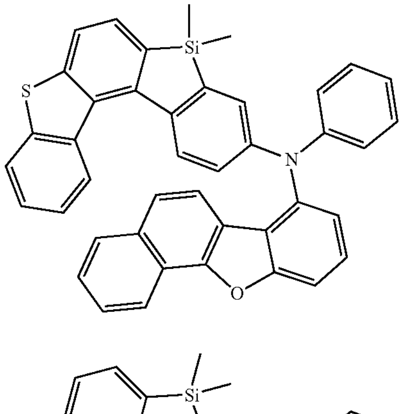
C-70
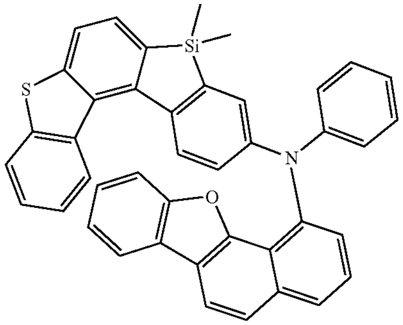

-continued
C-71
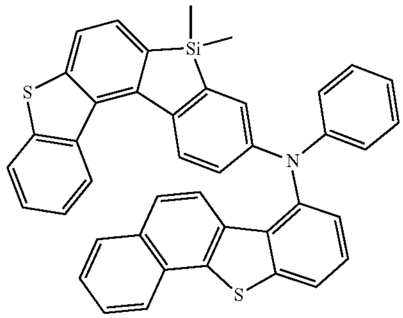
C-72
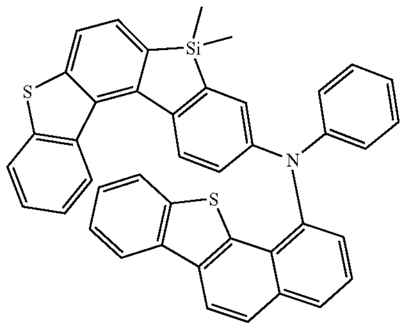
C-73
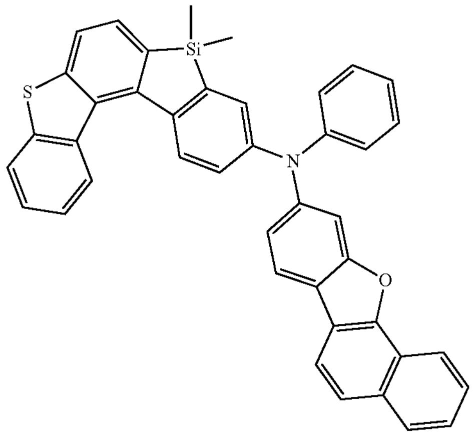
C-74
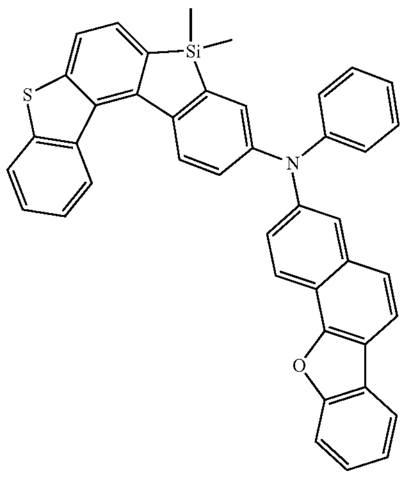
-continued
C-75
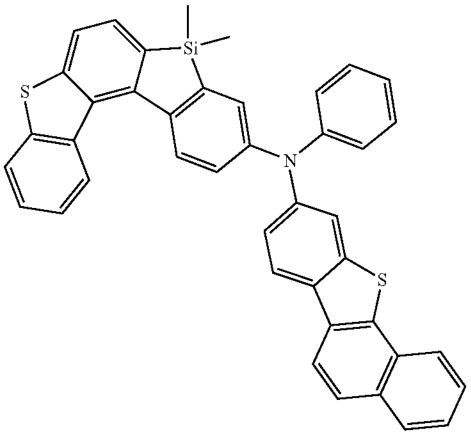
C-76
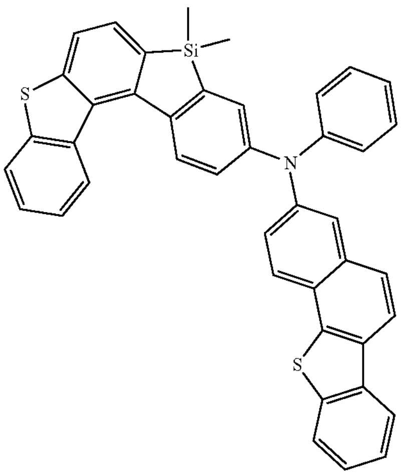
C-77
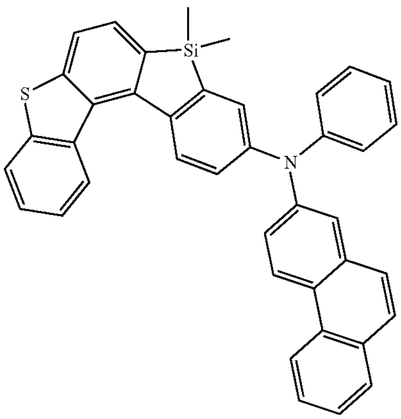

-continued
C-78
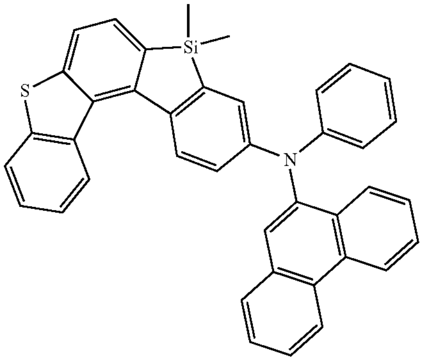
C-79
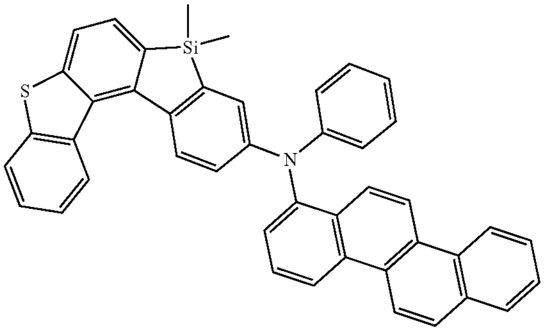
C-80
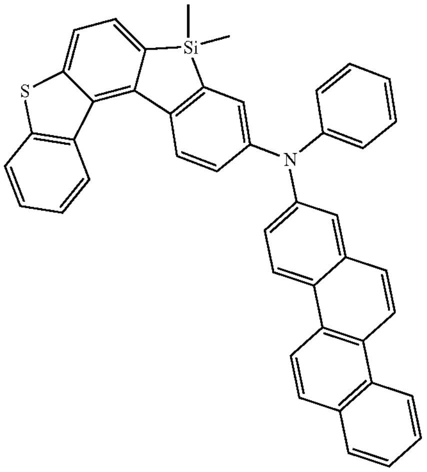
C-81
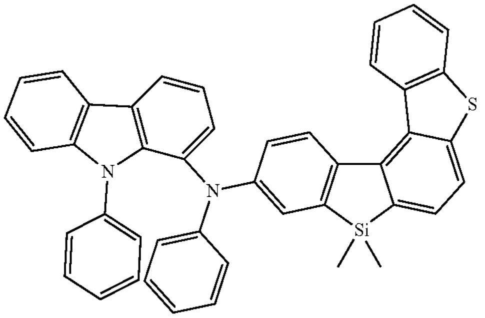
-continued
C-82
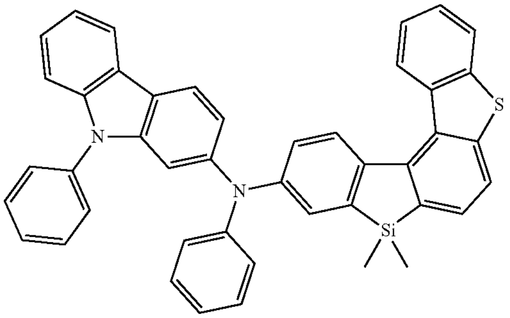
C-83
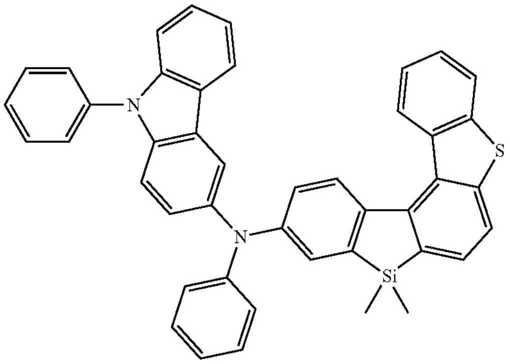
C-84
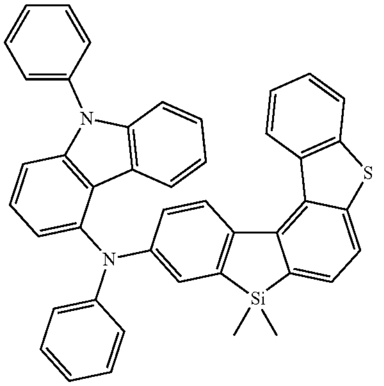
C-85
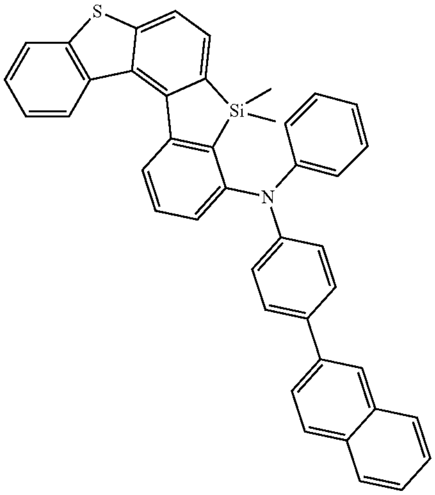

-continued
C-86
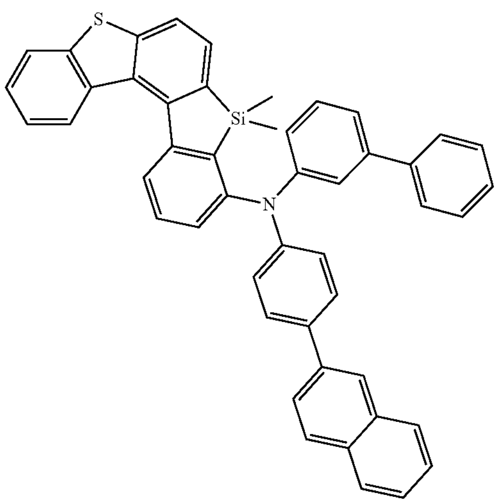
C-87
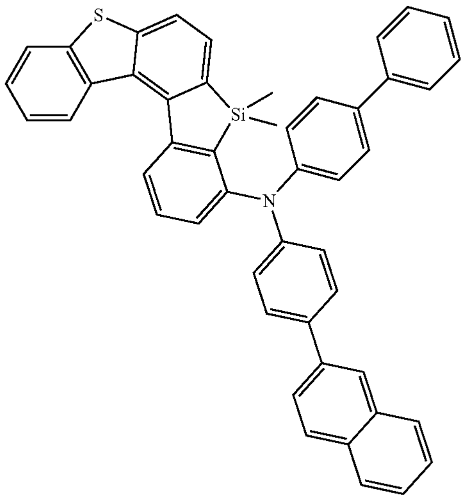
C-88
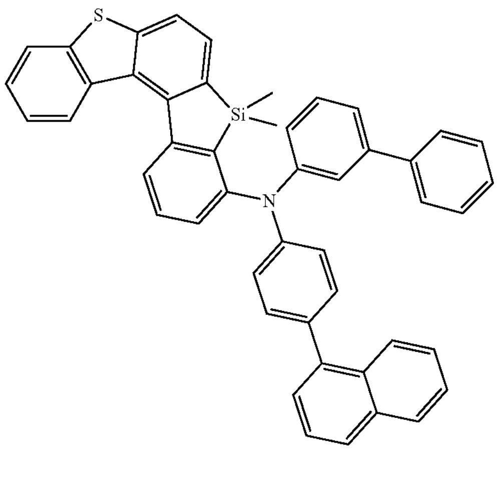
-continued
C-89
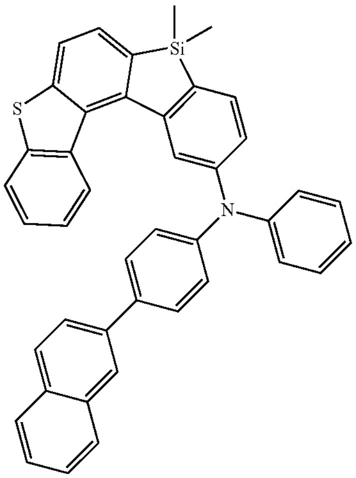
C-90
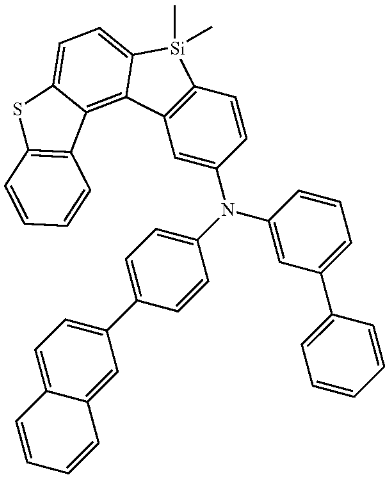
C-91
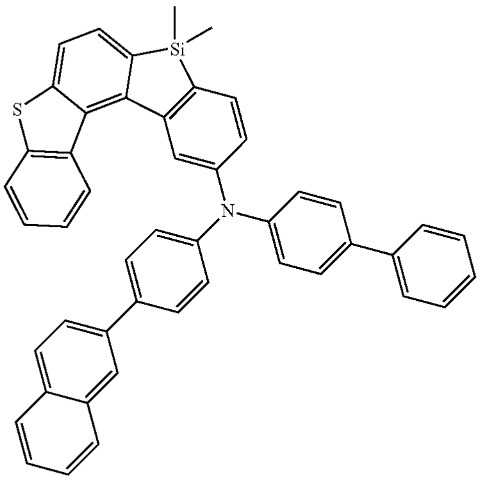

-continued
C-92
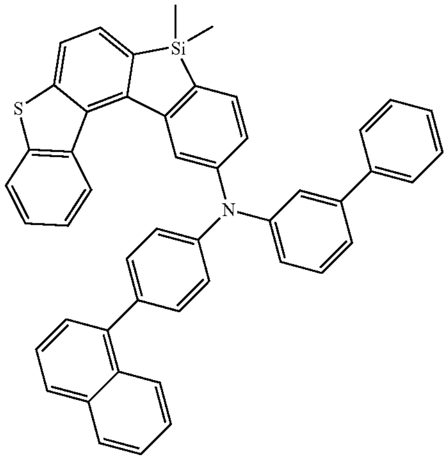
C-93
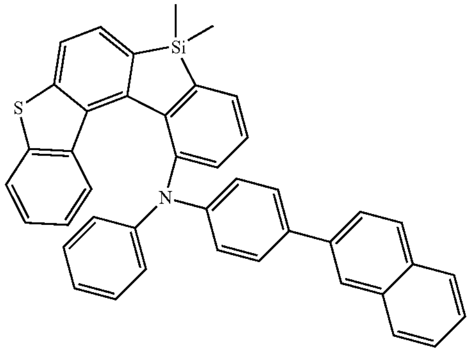
C-94
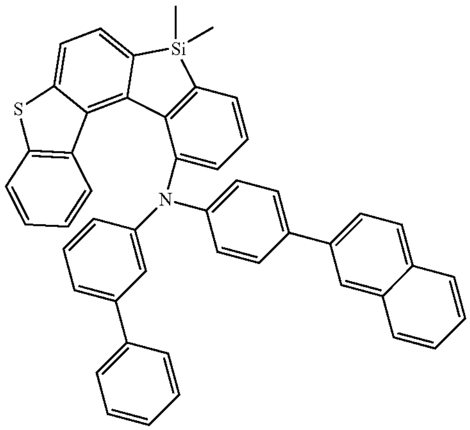
-continued
C-95
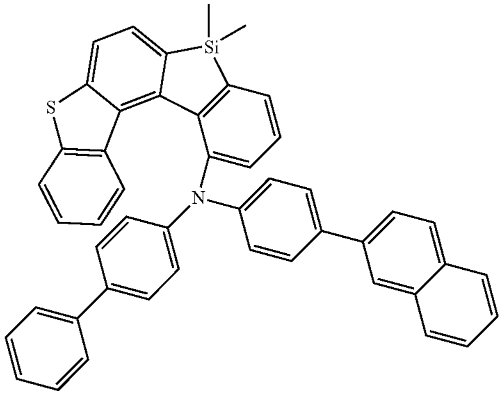
C-96
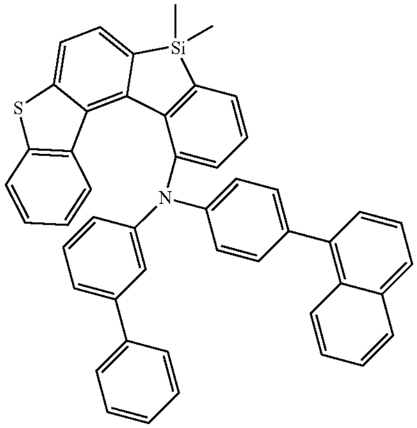
C-97
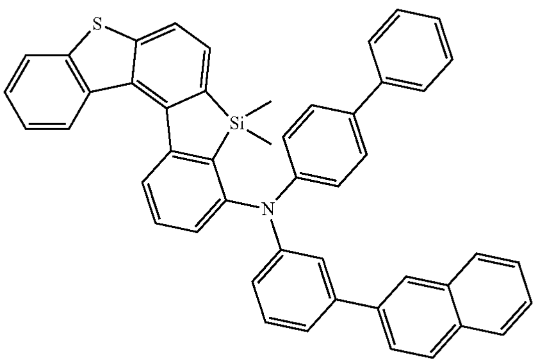

-continued
C-98
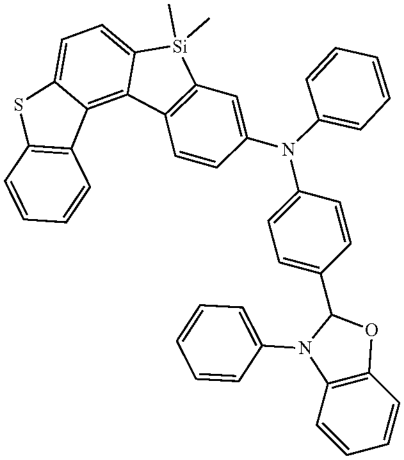
C-99
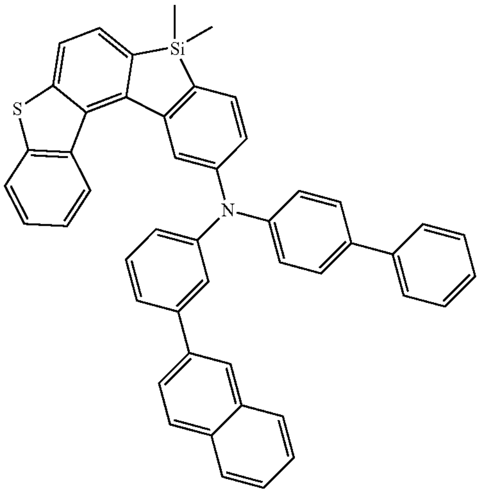
C-100
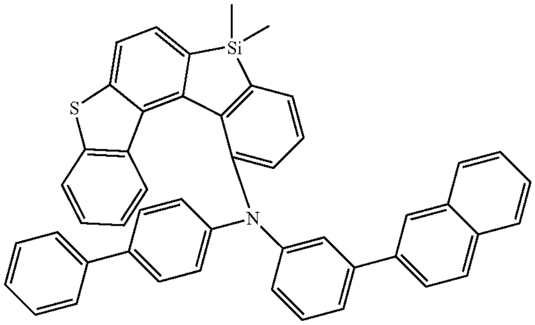
-continued
C-101
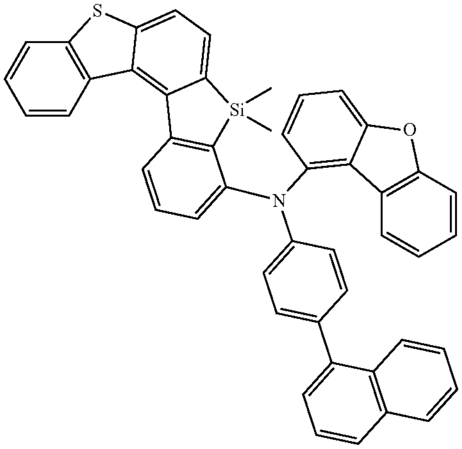
C-102
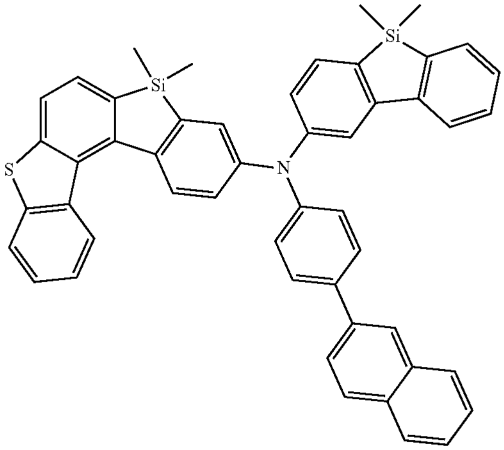
C-103
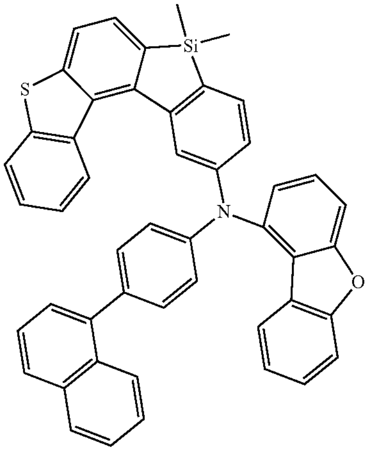

-continued

C-104

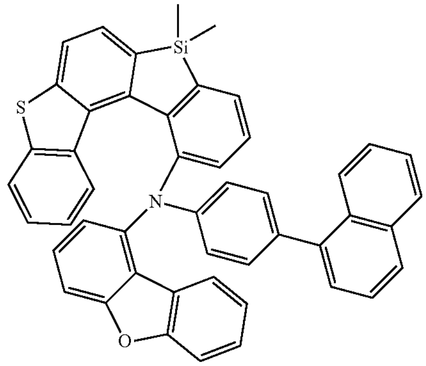

C-105

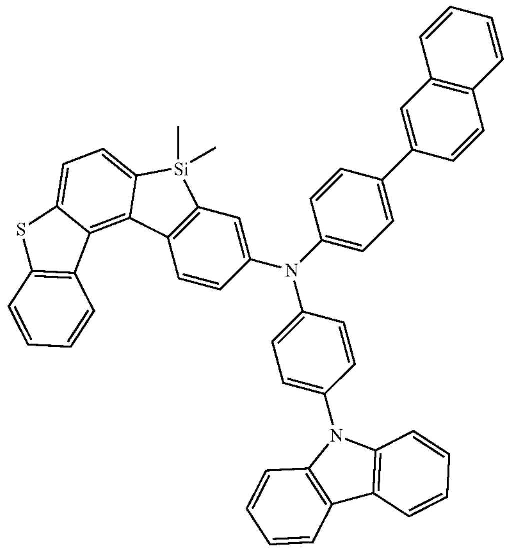

C-106

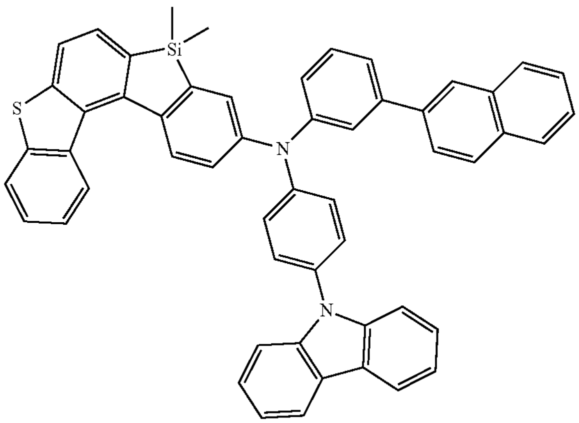

-continued

C-107

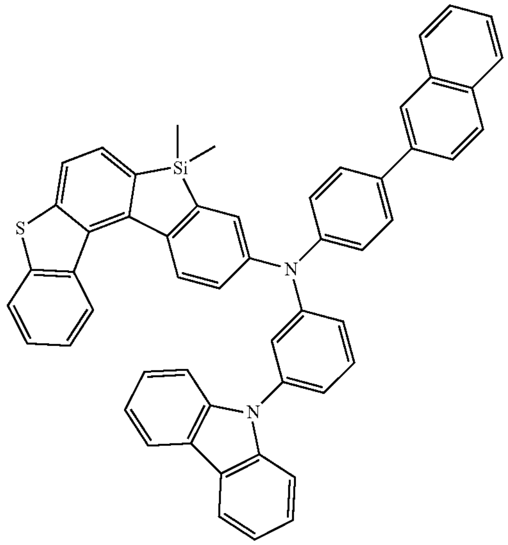

C-108

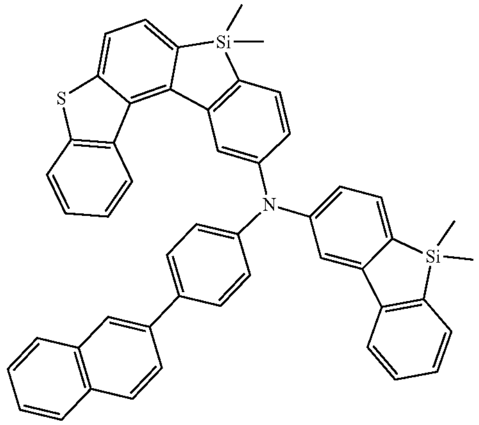

.

8. A composition for an organic optoelectronic device, the composition comprising a first compound and a second compound, wherein:

the first compound is the compound for an organic optoelectronic device as claimed in claim 1, the second compound is represented by Chemical Formula 2:

[Chemical Formula 2]

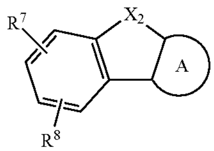

in Chemical Formula 2, $X^2$ is O, S, N-$L^a$-$R^c$, $CR^dR^e$, or $SiR^fR^g$, $L^a$ is a single bond or a substituted or unsubstituted C6 to C12 arylene group, $R^c$ is a substituted or unsubstituted C6 to C20 aryl group or a substituted or unsubstituted C2 to C30 heterocyclic group, $R^d$, $R^e$, $R^f$, and $R^g$ are each independently a substituted or unsubstituted C1 to C30 alkyl group or a substituted or unsubstituted C6 to C30 aryl group, $R^7$ and $R^8$ are each independently hydrogen, deuterium, a cyano group, a halogen, a substituted or unsubstituted C1 to C30 alkyl group, a substituted or unsubstituted C6 to C30 aryl group, or a substituted or unsubstituted C2 to C30 heterocyclic group, and A is a ring of Group II,

[Group II]

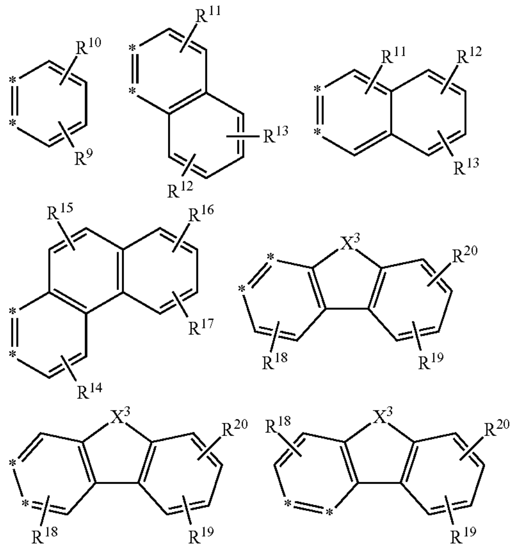

in Group II,

* is a linking point, $X^3$ is O or S, $R^9$ to $R^{20}$ are each independently hydrogen, deuterium, a substituted or unsubstituted C6 to C20 aryl group, or a substituted or unsubstituted C2 to C30 heterocyclic group, and at least one of $R^c$ and $R^7$ to $R^{20}$ is a group represented by Chemical Formula a,

[Chemical Formula a]

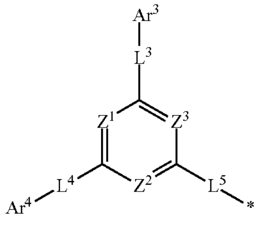

in Chemical Formula a, $Z^1$ to $Z^3$ are each independently N or $CR^h$, at least two of $Z^1$ to $Z^3$ being N, $R^h$ is hydrogen, deuterium, a substituted or unsubstituted C1 to C30 alkyl group, or a substituted or unsubstituted C6 to C30 aryl group, $L^3$ to $L^5$ are each independently a single bond or a substituted or unsubstituted C6 to C30 arylene group, $Ar^3$ and $Ar^4$ are each independently a substituted or unsubstituted C6 to C30 aryl group or a substituted or unsubstituted C2 to C30 heteroaryl group, and

* is a linking point.

9. The composition for an organic optoelectronic device as claimed in claim 8, wherein:

the second compound is represented by one of Chemical Formula 2A to Chemical Formula 2J:

[Chemical Formula 2A]

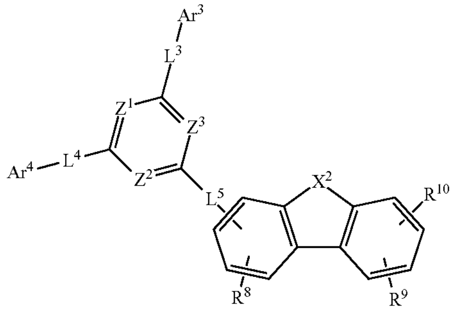

[Chemical Formula 2B]

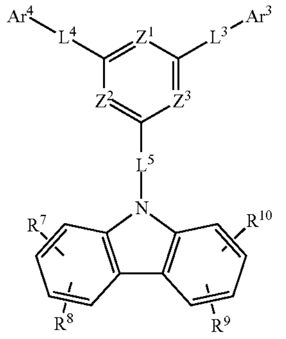

[Chemical Formula 2C]

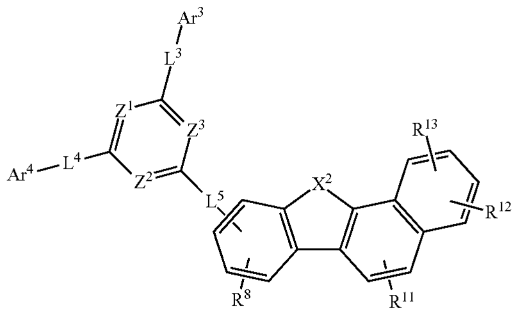

[Chemical Formula 2D]

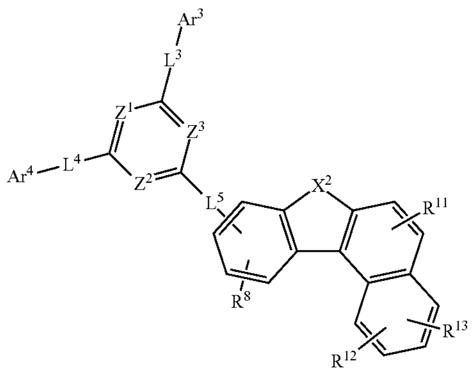

-continued

[Chemical Formula 2E]

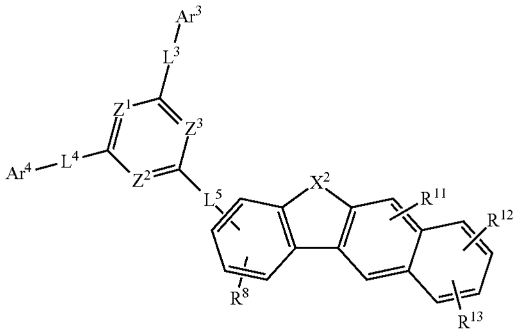

[Chemical Formula 2F]

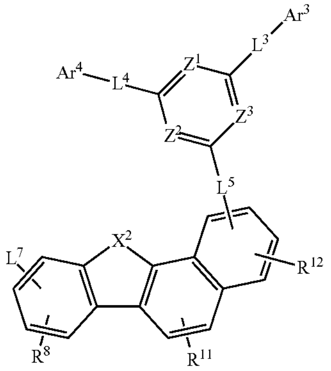

[Chemical Formula 2G]

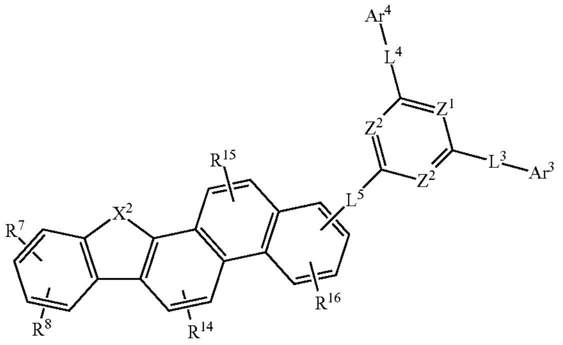

[Chemical Formula 2H]

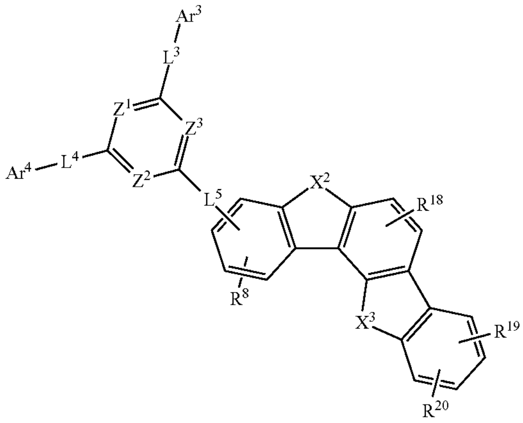

-continued

[Chemical Formula 2I]

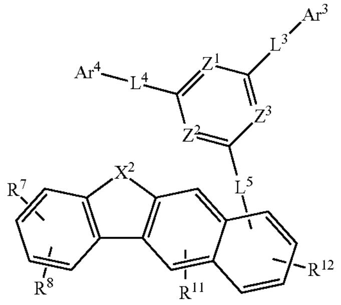

[Chemical Formula 2J]

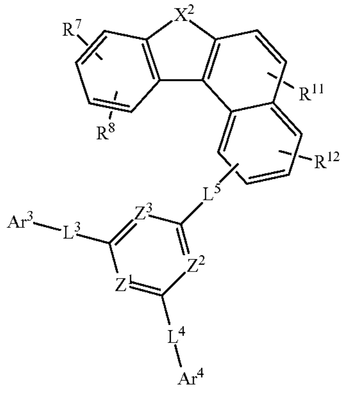

in Chemical Formula 2A to Chemical Formula 2J, $X^2$, $X^3$, $Z^1$ to $Z^3$, $R^7$ to $R^{16}$, $R^{18}$ to $R^{20}$, $L^3$ to $L^5$, $Ar^3$, and $Ar^4$ are defined the same as those of Chemical Formula 2.

10. The composition for an organic optoelectronic device as claimed in claim 9, wherein the second compound is represented by Chemical Formula 2A, Chemical Formula 2C, or Chemical Formula 2F.

11. The composition for an organic optoelectronic device as claimed in claim 9, wherein:

the second compound is represented by Chemical Formula 2A-3, Chemical Formula 2C-1, Chemical Formula 2F-1, or Chemical Formula 2F-3:

[Chemical Formula 2A-3]

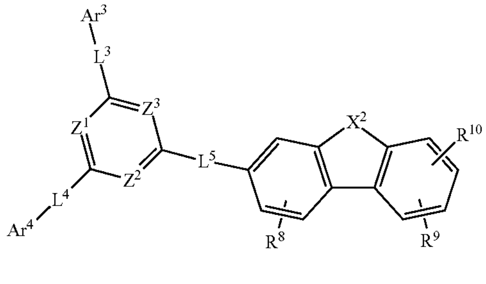

-continued

[Chemical Formula 2C-1]

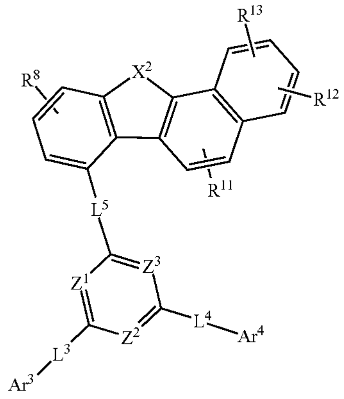

[Chemical Formula 2F-1]

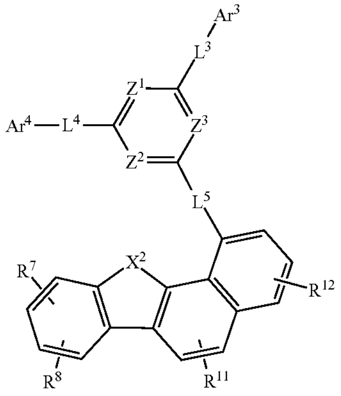

[Chemical Formula 2F-3]

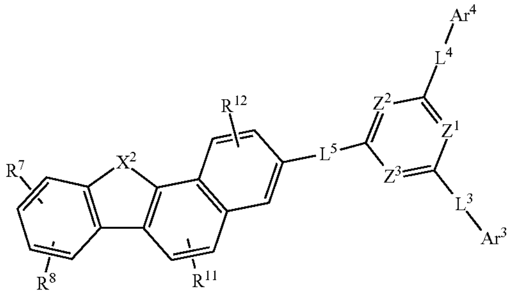

in Chemical Formula 2A-3, Chemical Formula 2C-1, Chemical Formula 2F-1, and Chemical Formula 2F-3, $X^2$, $Z^1$ to $Z^3$, $R^7$ to $R^{13}$, $L^3$ to $L^5$, $Ar^3$, and $Ar^4$ are defined the same as those of Chemical Formula 2.

12. The composition for an organic optoelectronic device as claimed in claim 8, wherein $Ar^3$ and $Ar^4$ of Chemical Formula a are each independently a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, a substituted or unsubstituted triphenylene group, a substituted or unsubstituted carbazolyl group, a substituted or unsubstituted dibenzofuranyl group, a substituted or unsubstituted dibenzothiophenyl group, or a substituted or unsubstituted dibenzosilolyl group.

13. The composition for an organic optoelectronic device as claimed in claim 8, wherein the second compound is a compound of Group 2:

[Group 2]

A-1

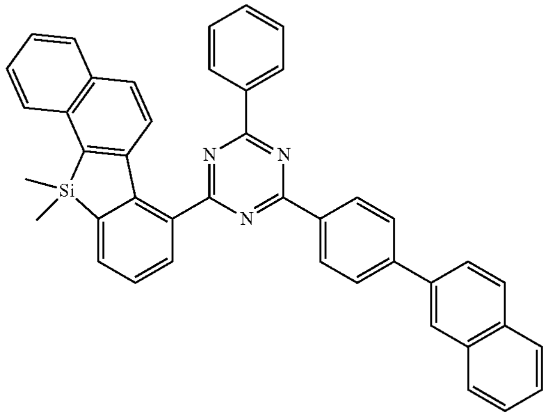

A-2

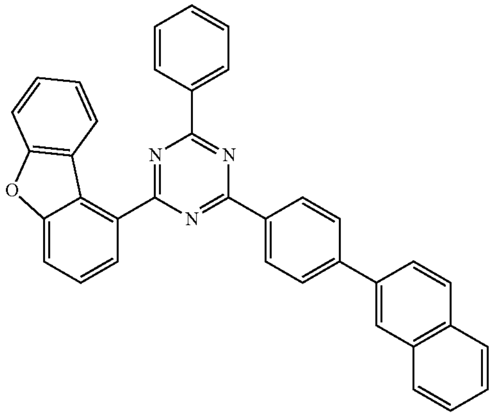

A-3

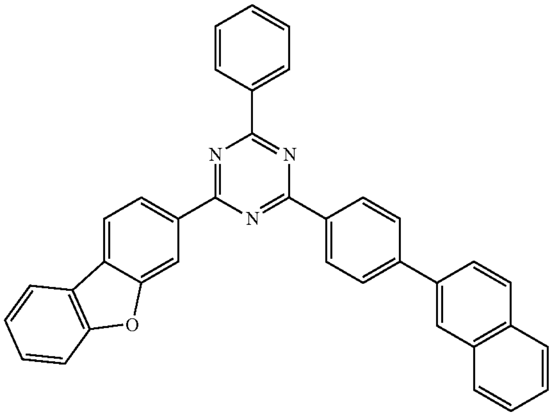

-continued
A-4
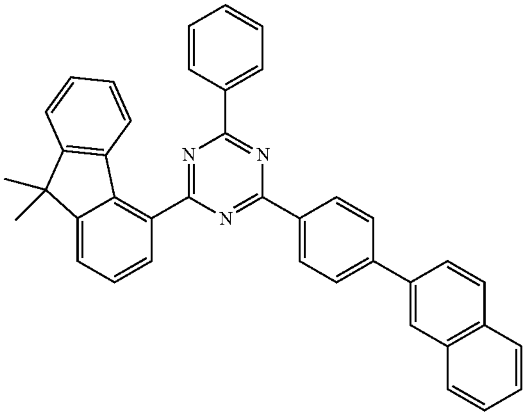
A-5
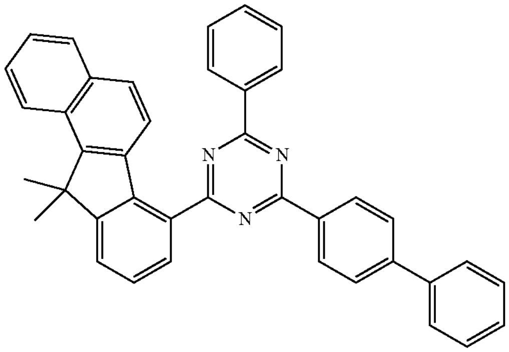
A-6
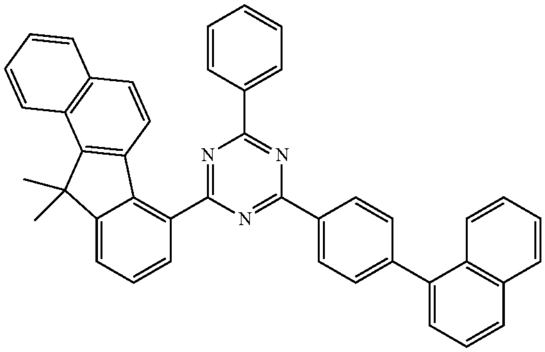
A-7
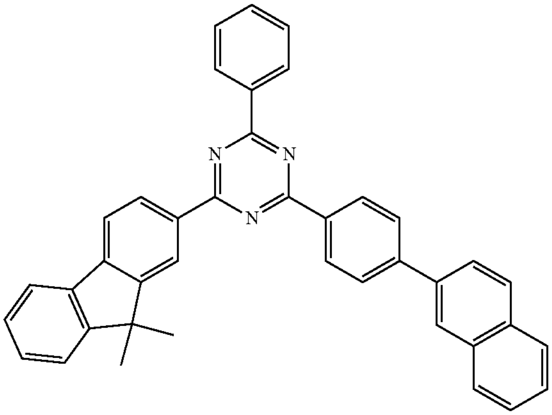
-continued
A-8
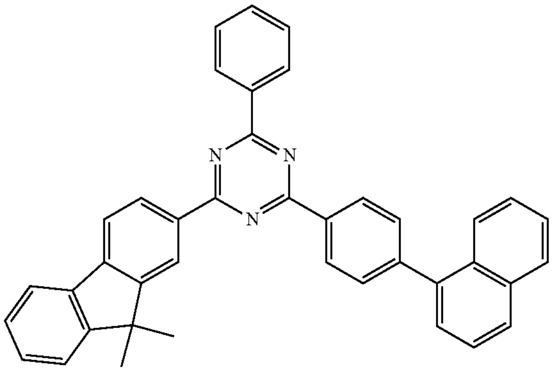
A-9
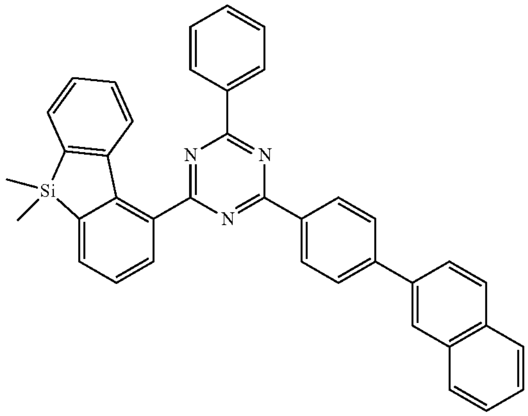
A-10
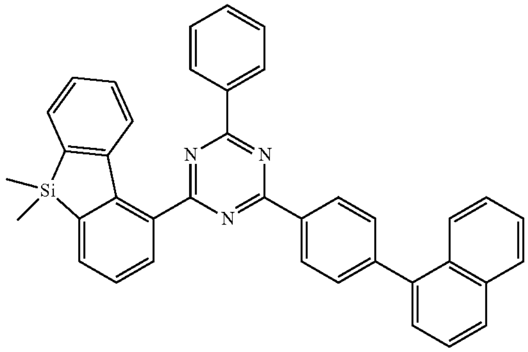
A-11
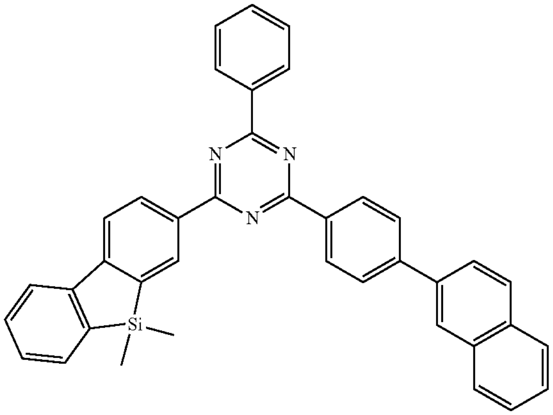

-continued
A-12
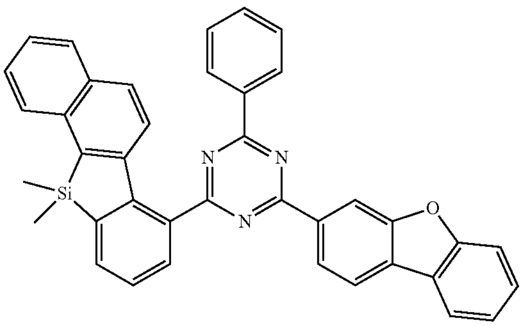
A-13
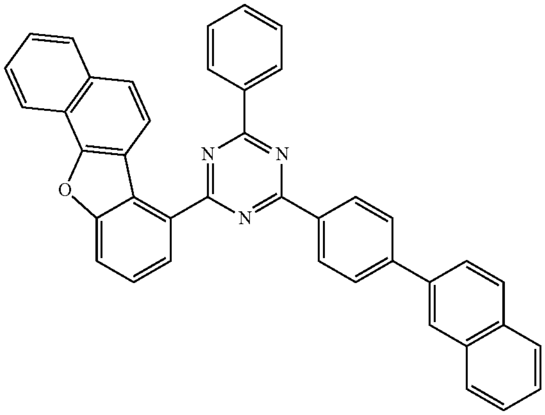
A-14
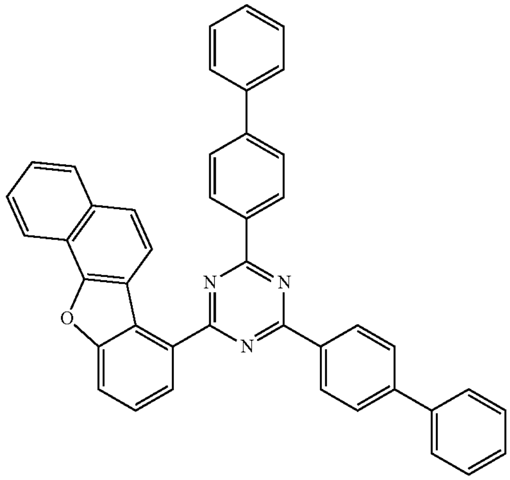
-continued
A-15
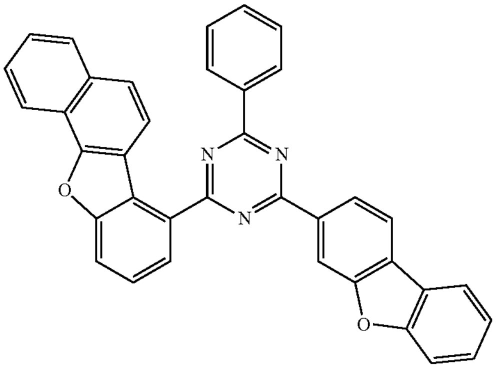
A-16
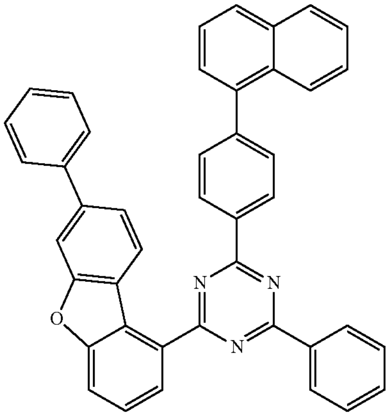
A-17
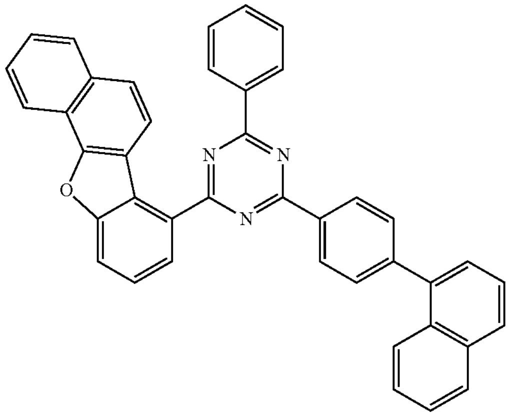
A-18
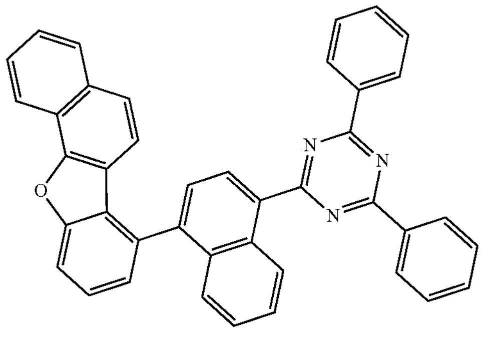

-continued
A-19
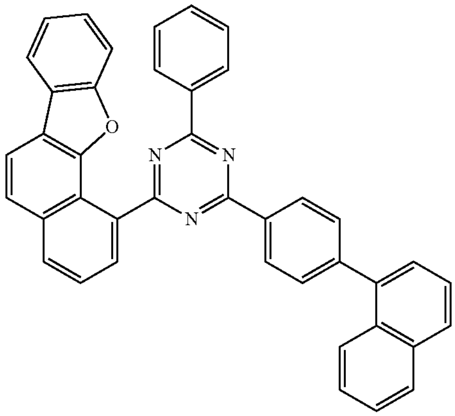
A-20
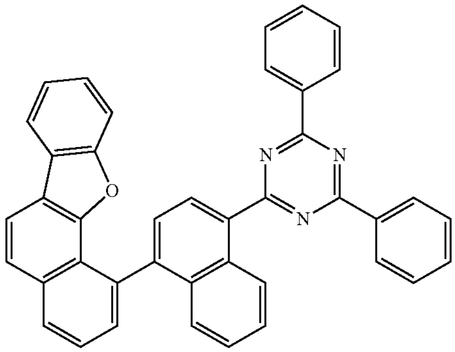
A-21
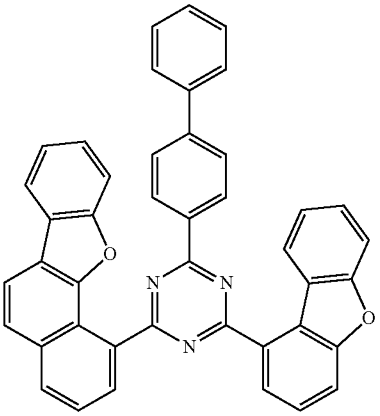
A-22
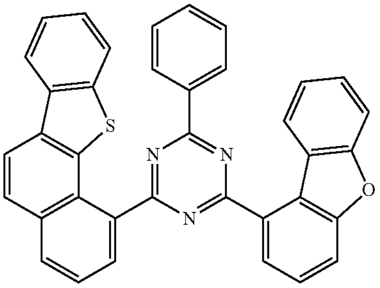
-continued
A-23
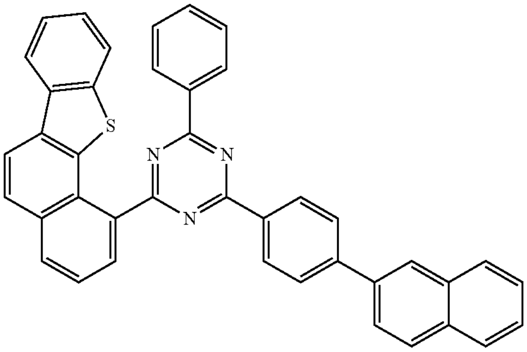
A-24
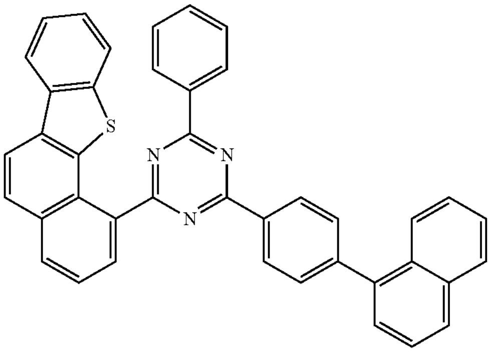
A-25
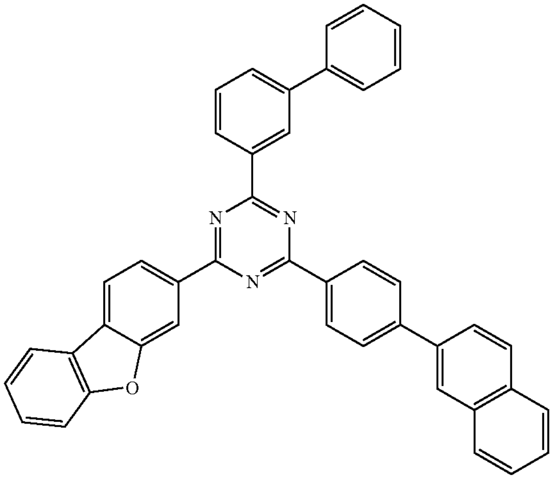

-continued
A-26
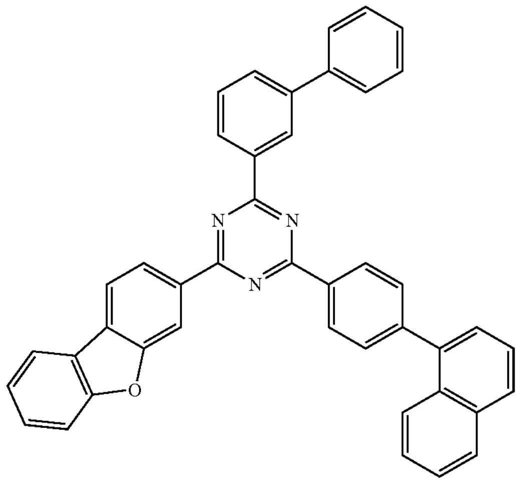
A-27
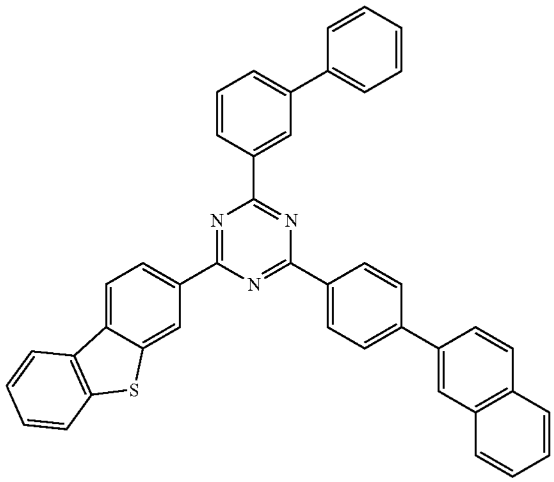
A-28
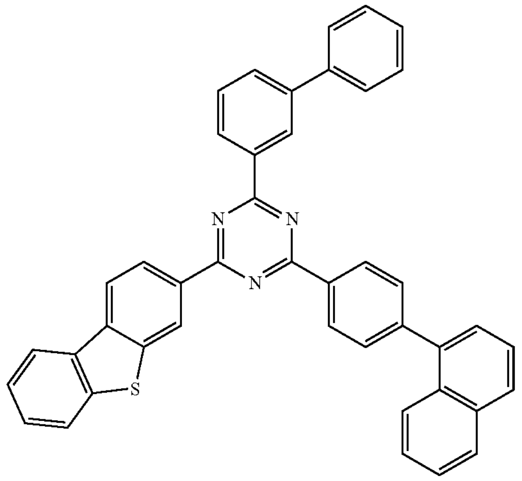
-continued
A-29
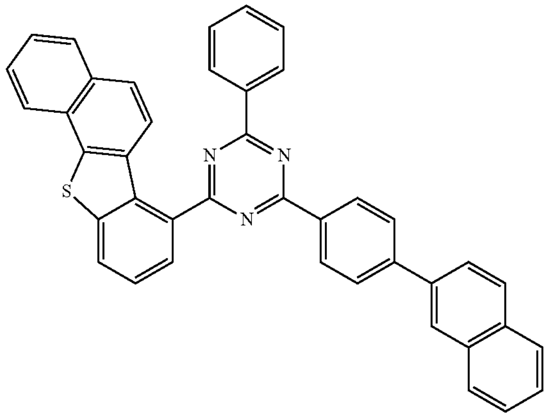
A-30
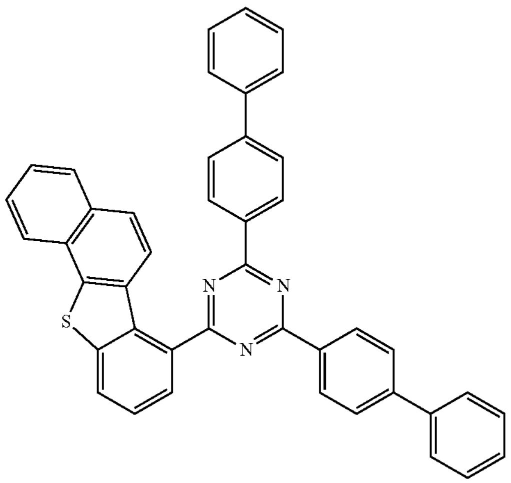
A-31
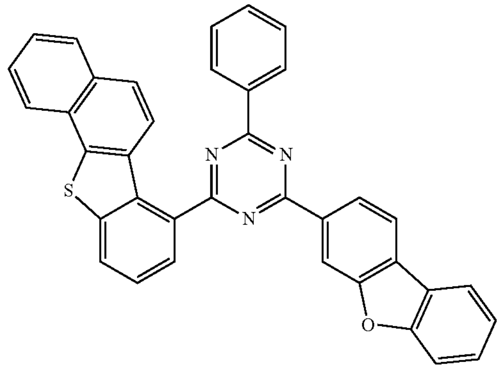

-continued
A-32
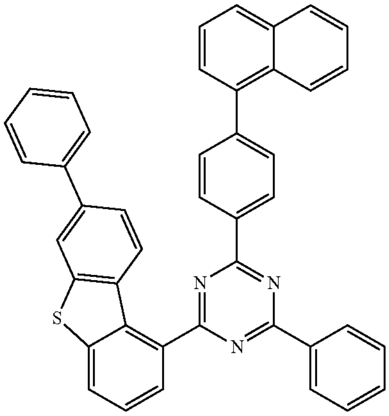
A-33
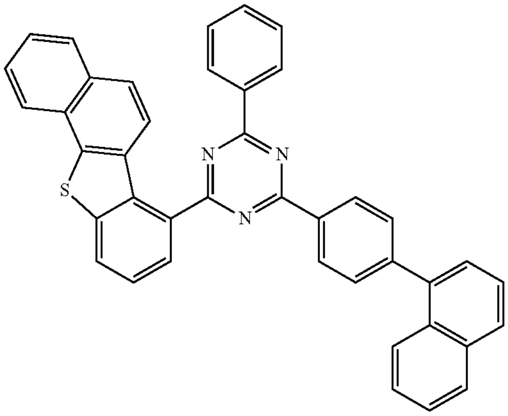
A-34
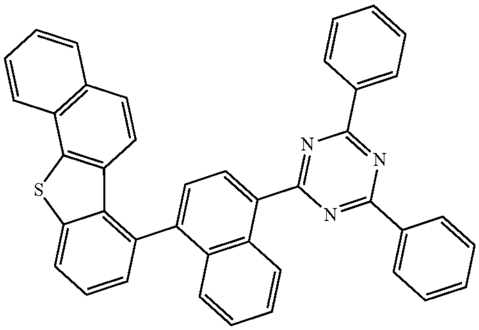
A-35
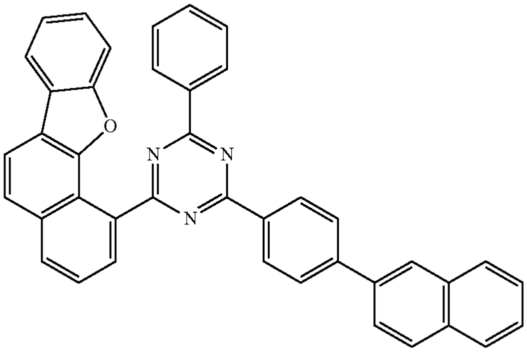
-continued
A-36
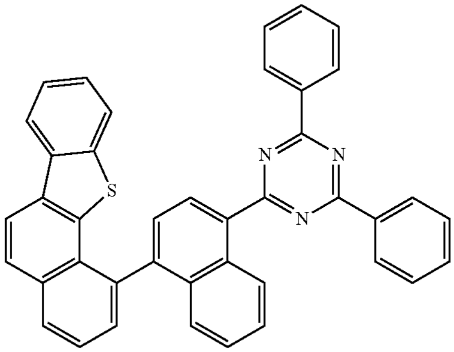
A-37
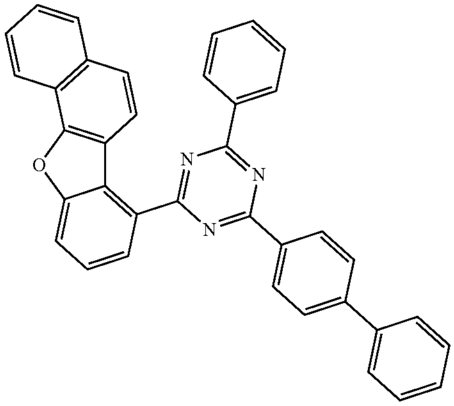
A-38
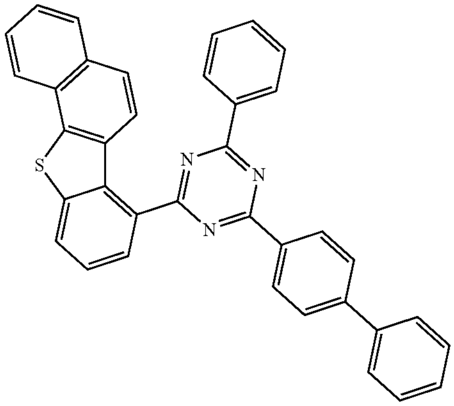
A-39
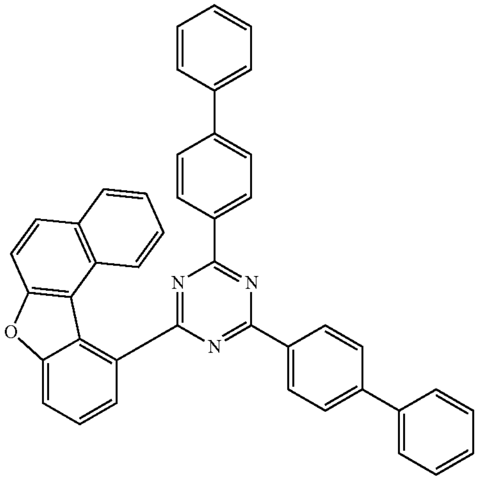

-continued
A-40
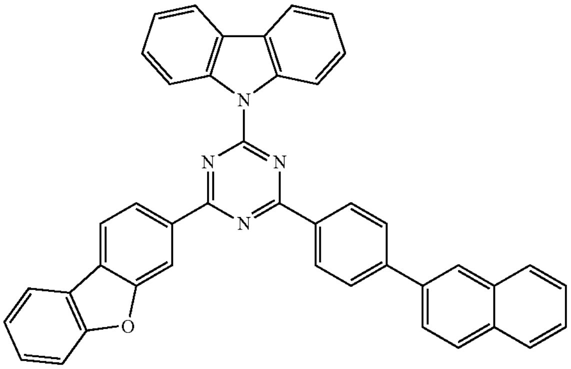
A-41
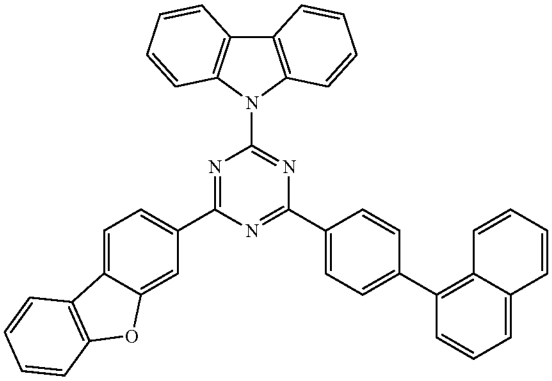
A-42
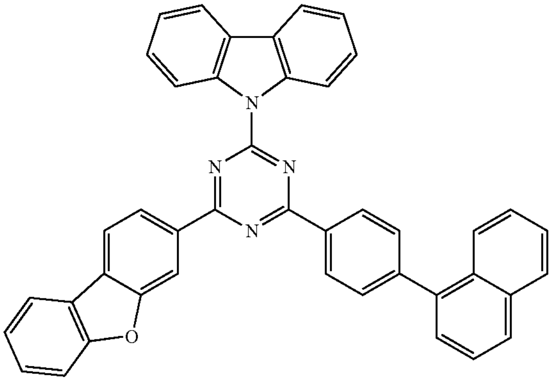
-continued
A-43
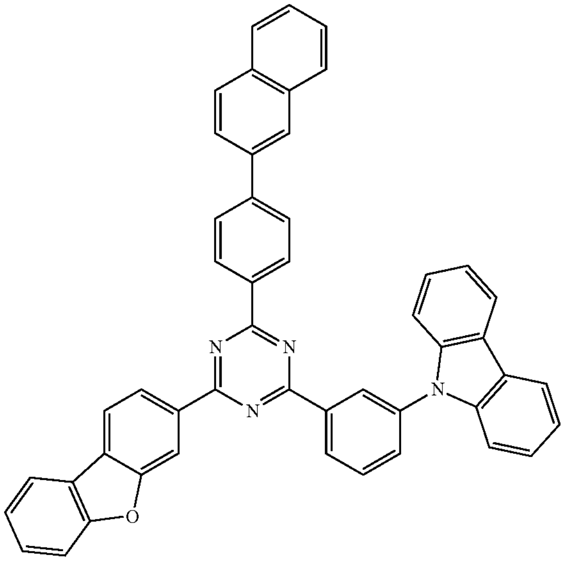
A-44
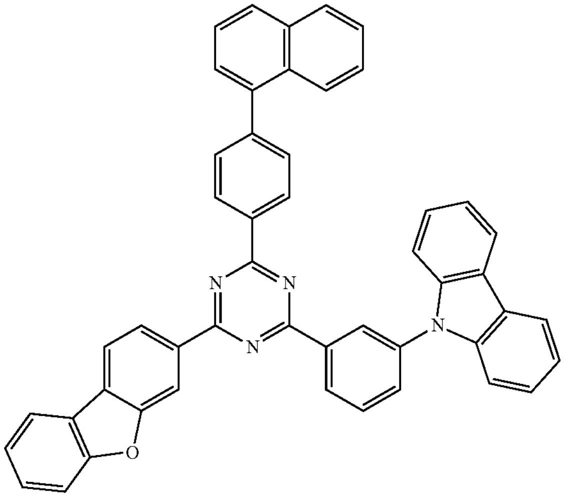
A-45
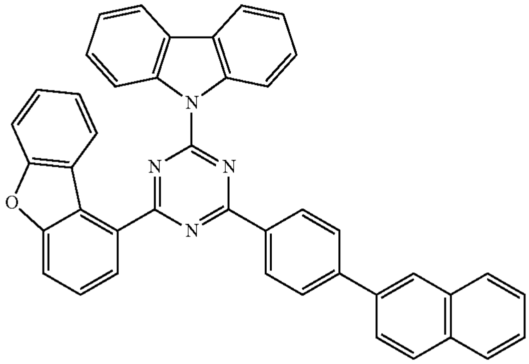

-continued
A-46
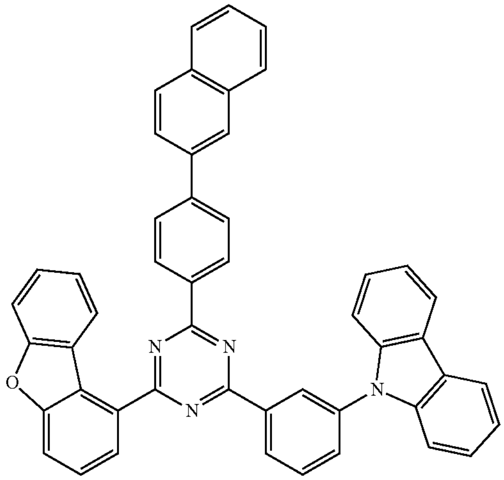
A-47
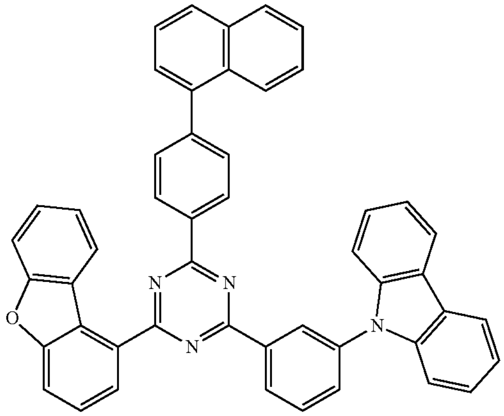
A-48
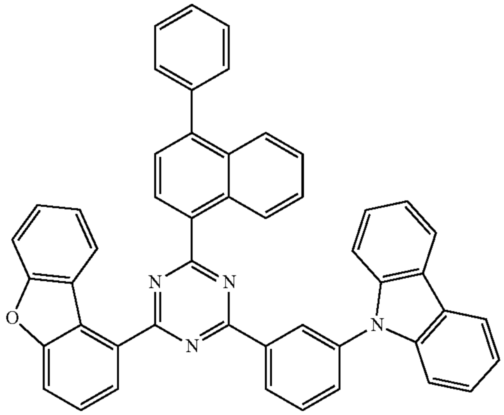
-continued
A-49
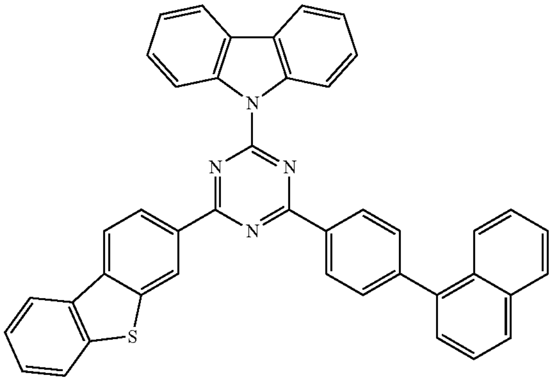
A-50
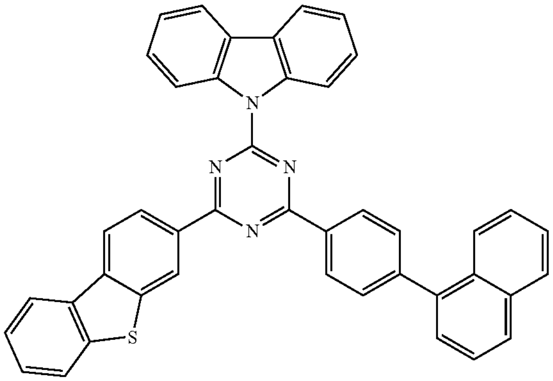
A-51
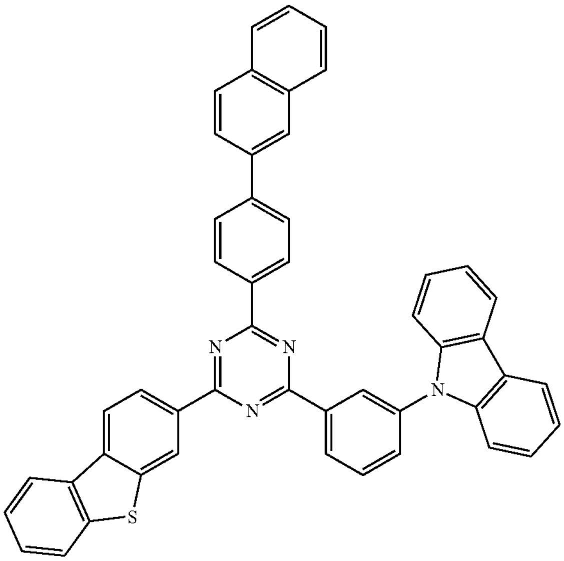

-continued
A-52
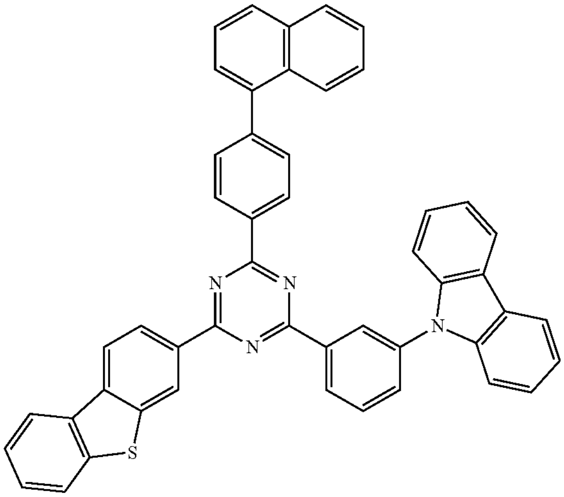
A-53
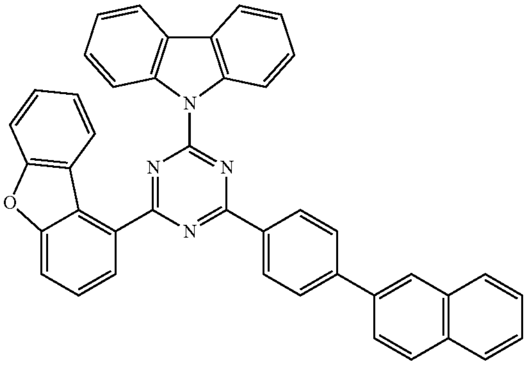
A-54
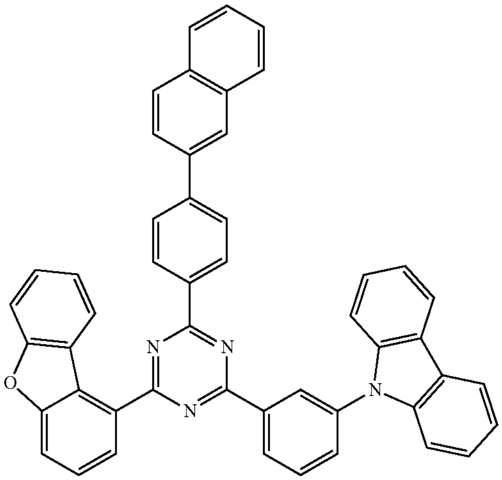
-continued
A-55
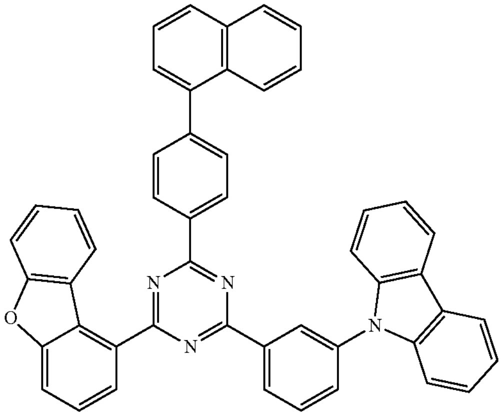
A-56
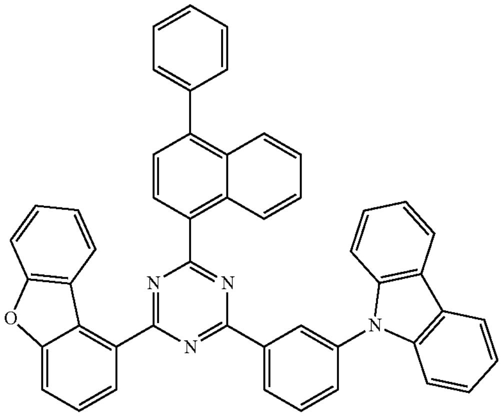
A-57
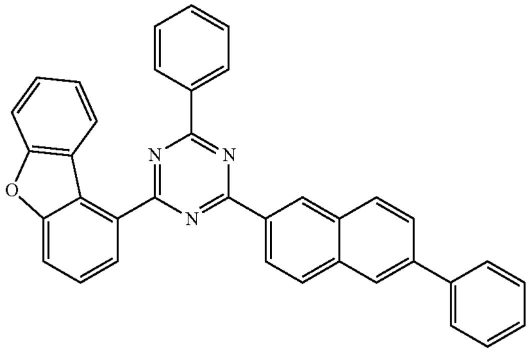
A-58
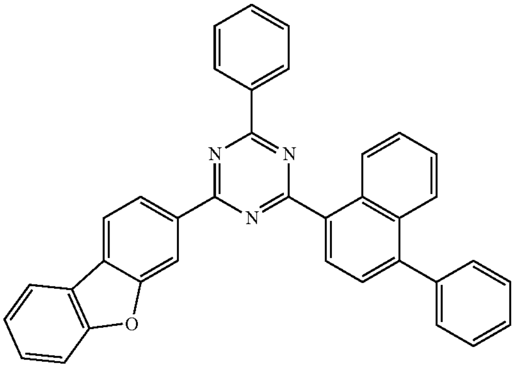

-continued
A-59
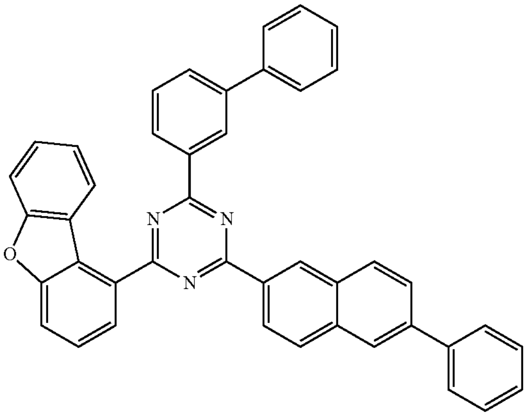
A-60
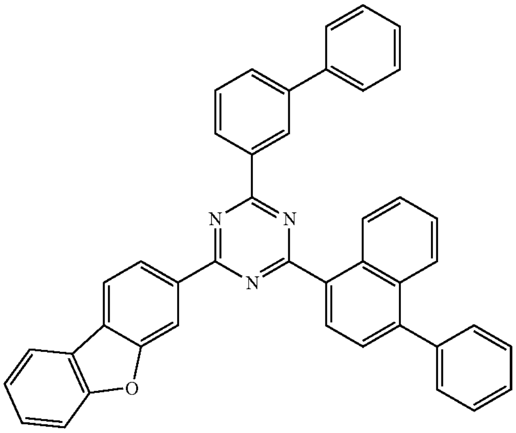
A-61
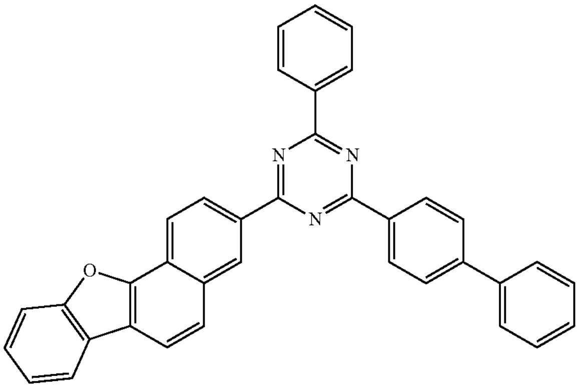
-continued
A-62
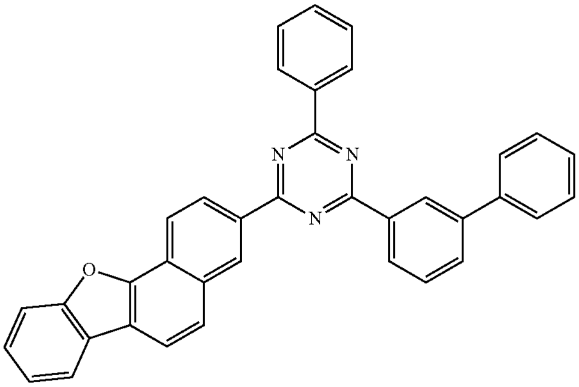
A-63
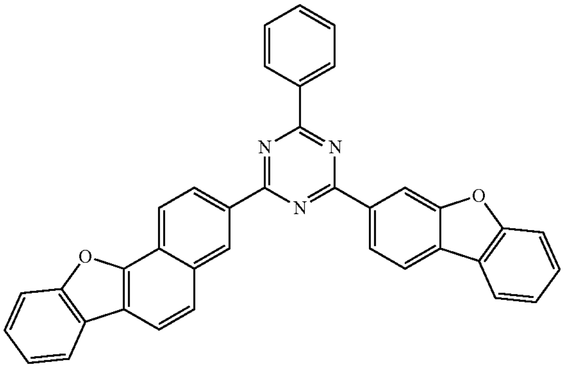
A-64
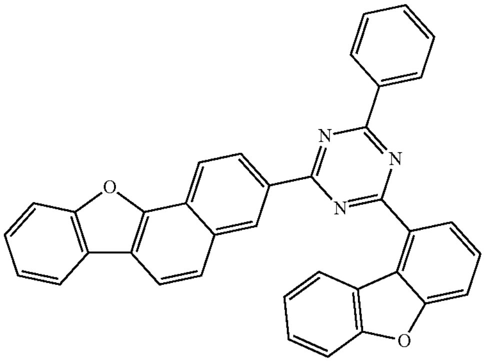
A-65
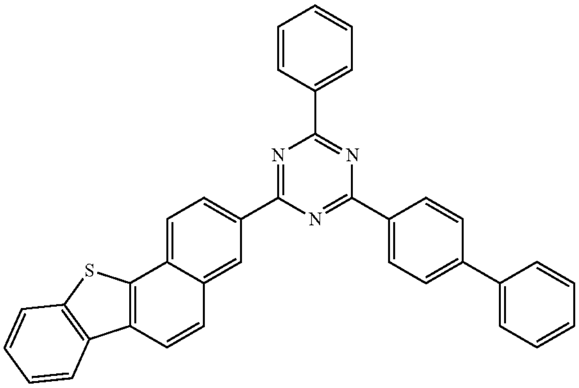

-continued
A-66
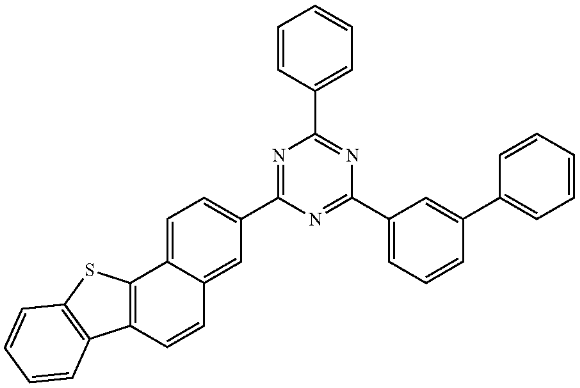
A-67
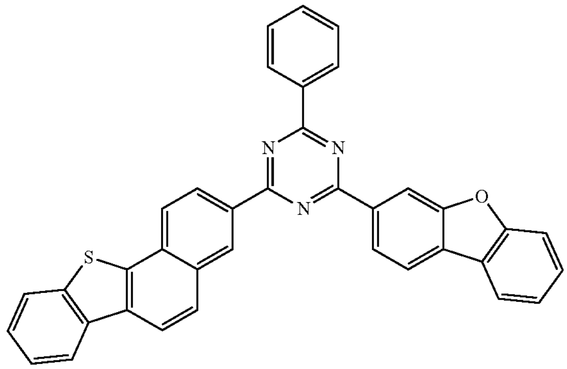
A-68
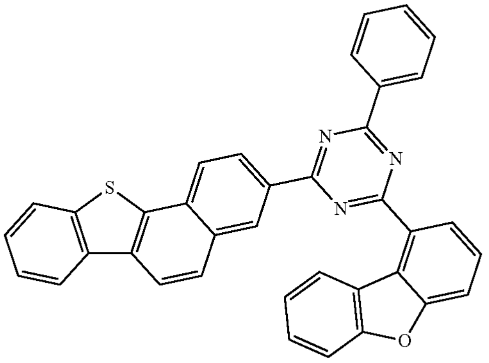
-continued
A-69
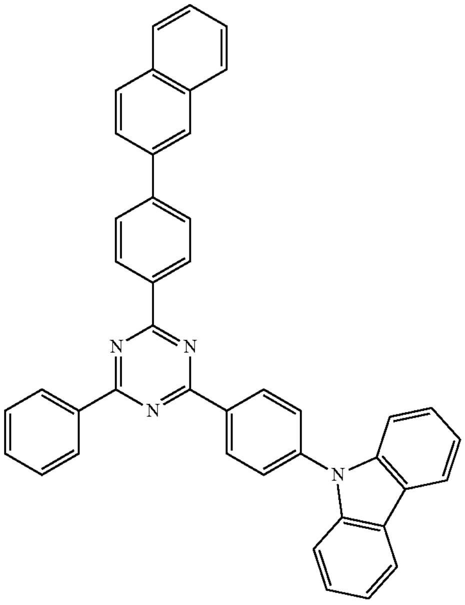
A-70
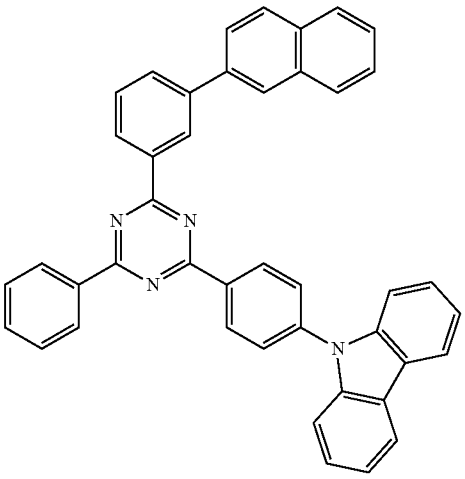
A-71
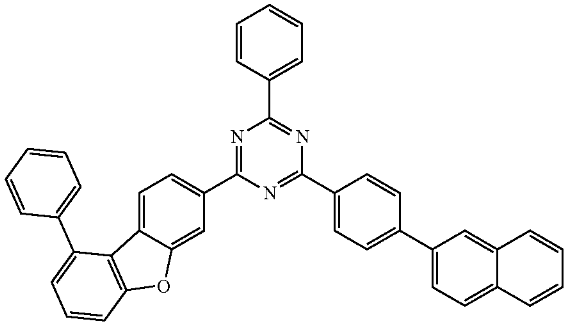

-continued
A-72
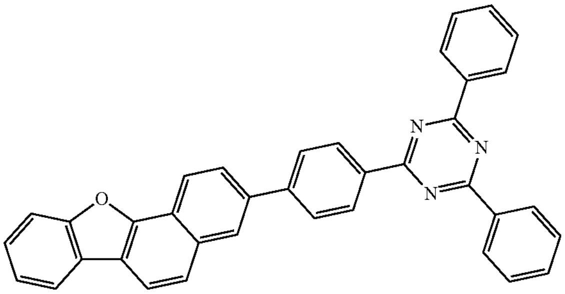
A-73
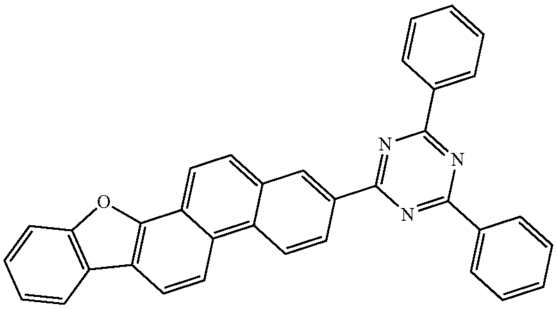
A-74
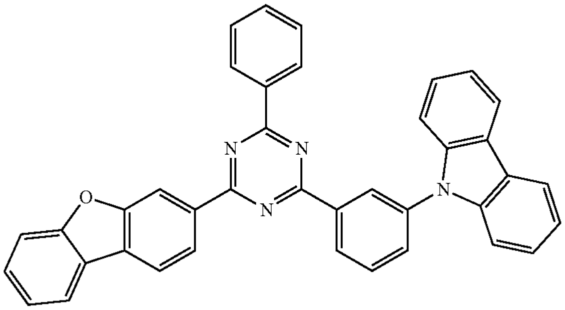
A-75
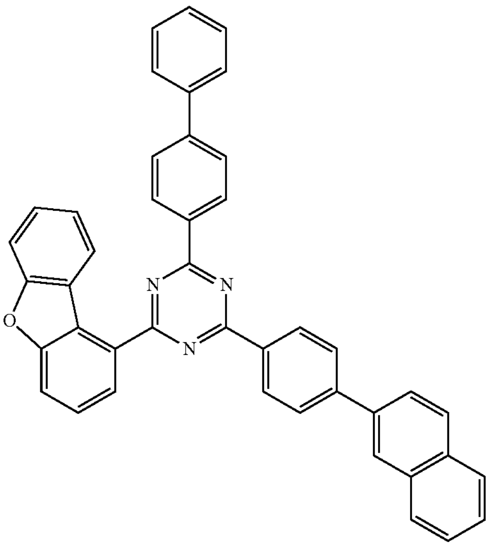
-continued
A-76
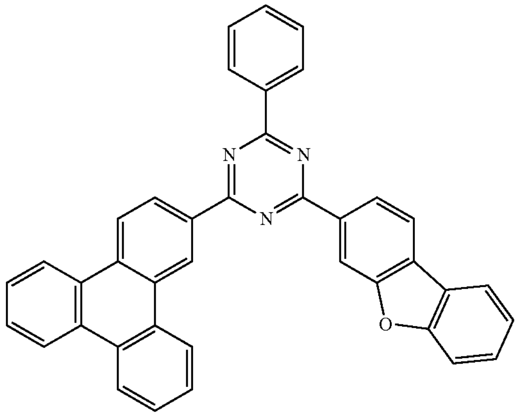
A-77
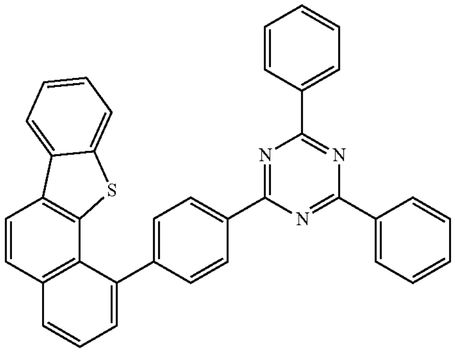
A-78
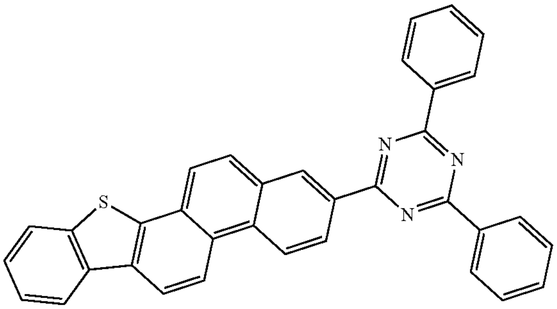
A-79
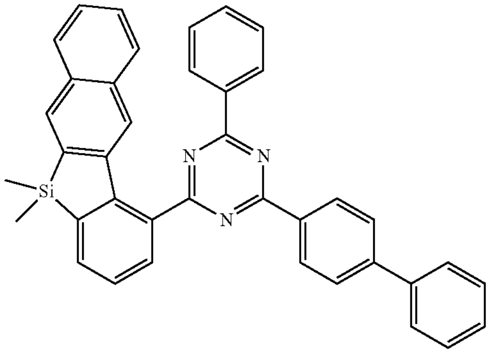

-continued
A-80
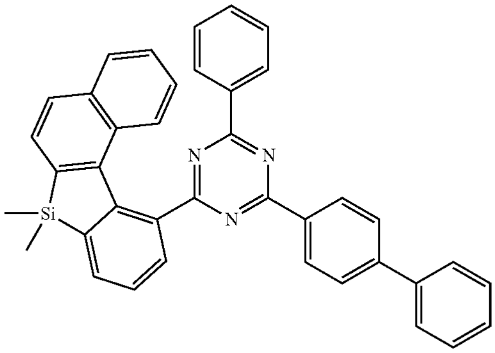
A-81
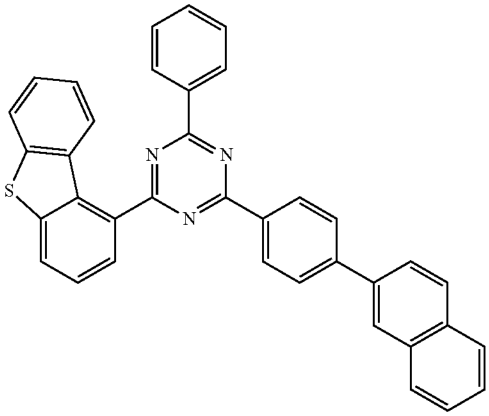
A-82
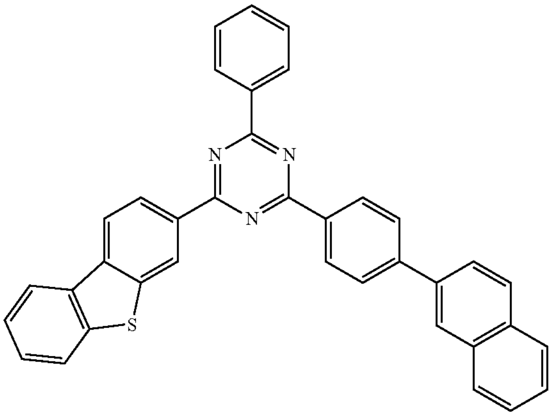
A-83
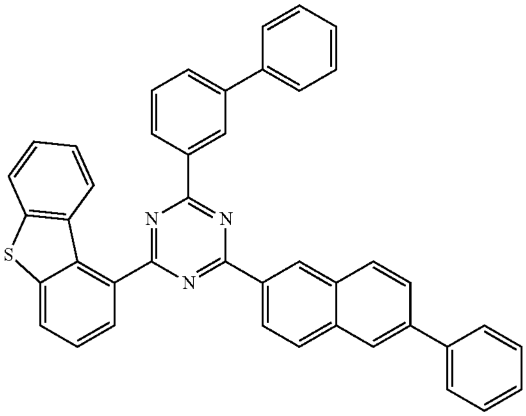
-continued
A-84
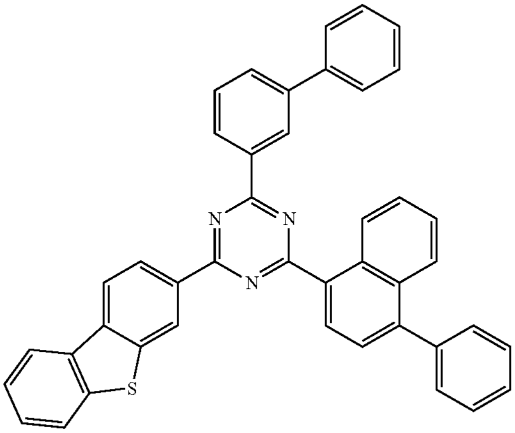
A-85
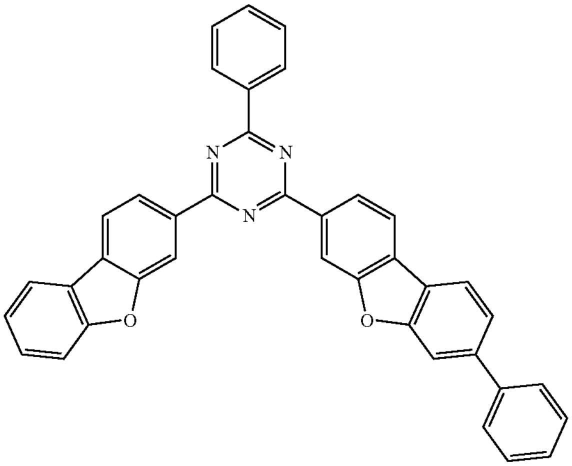
A-86
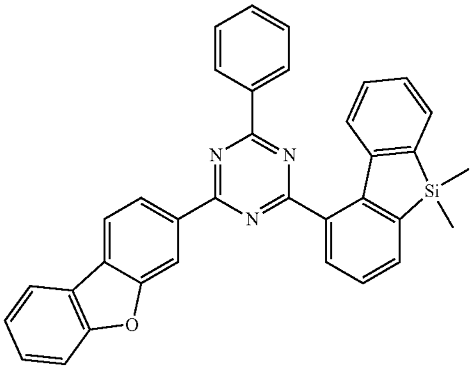

-continued
A-87
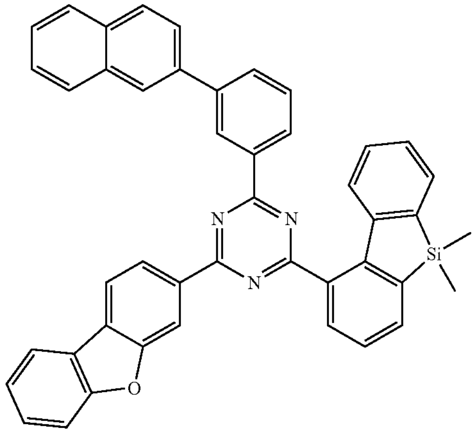
A-88
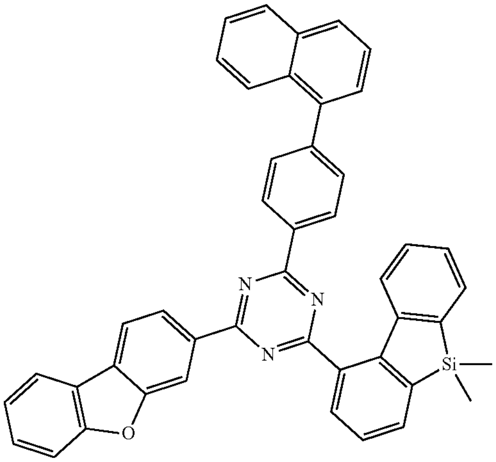
A-89
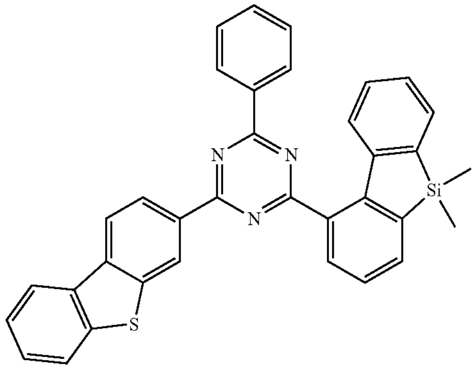
-continued
A-90
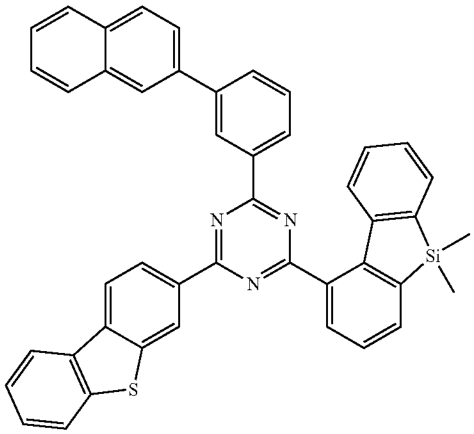
A-91
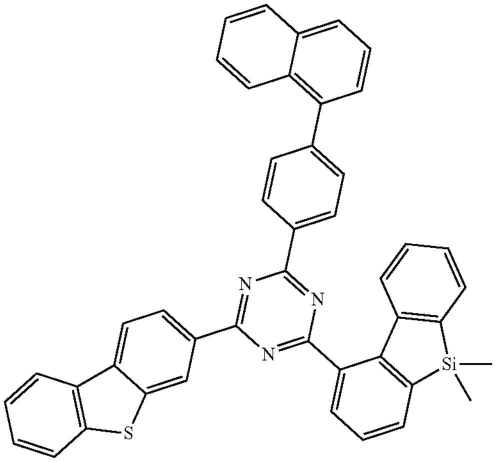
A-92
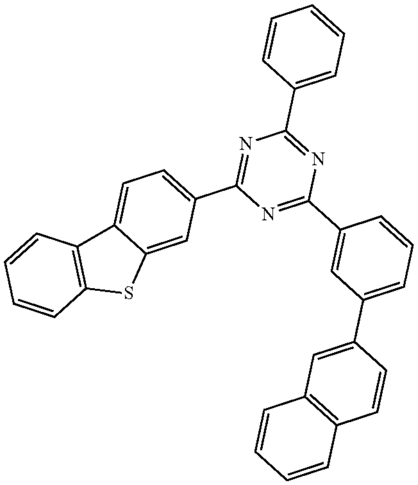

-continued
A-93
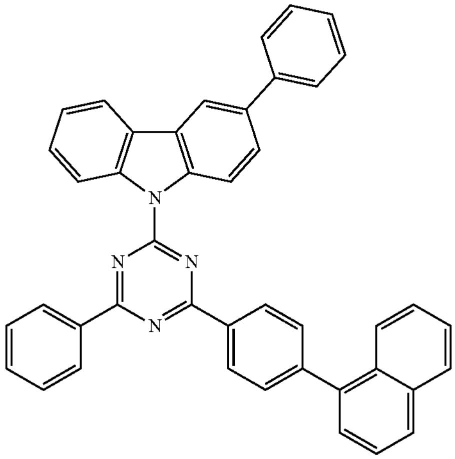
A-94
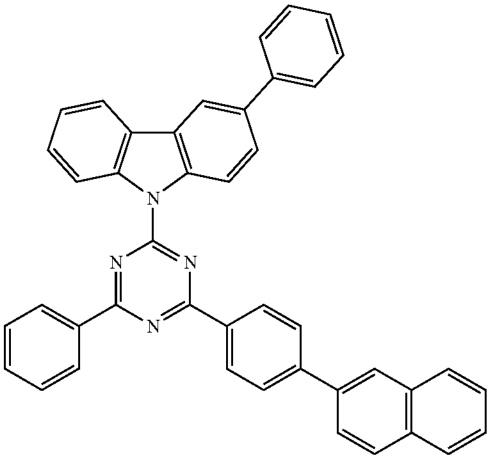
A-95
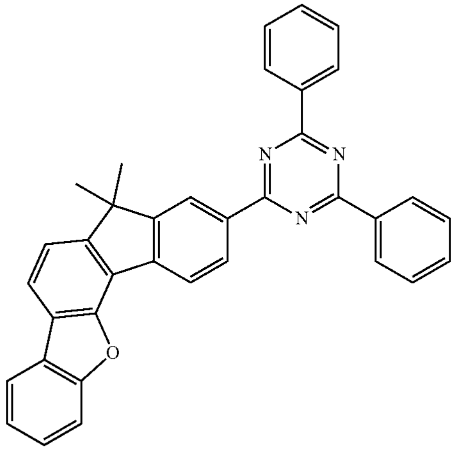
-continued
A-96
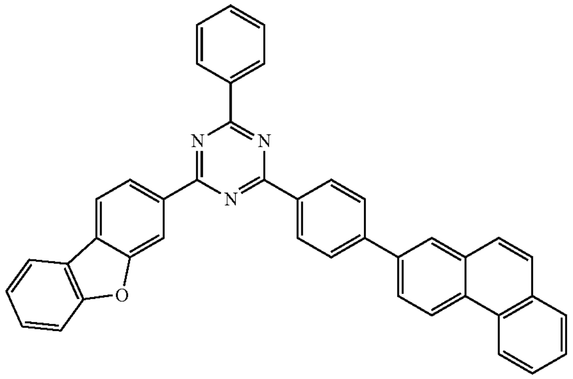
A-97
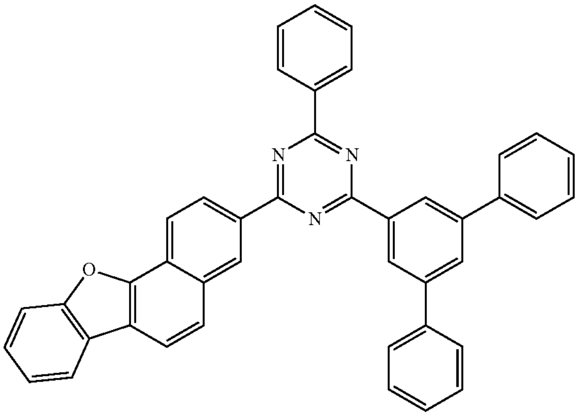
A-98
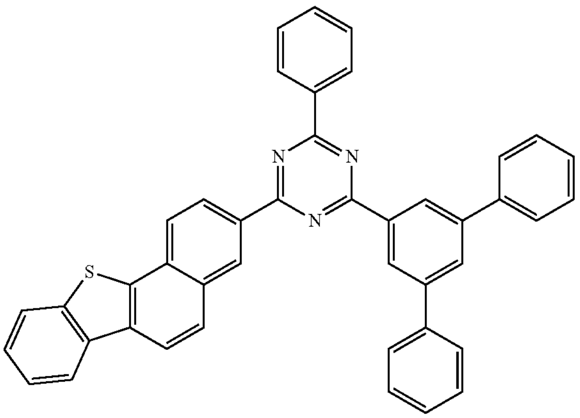

-continued
A-99
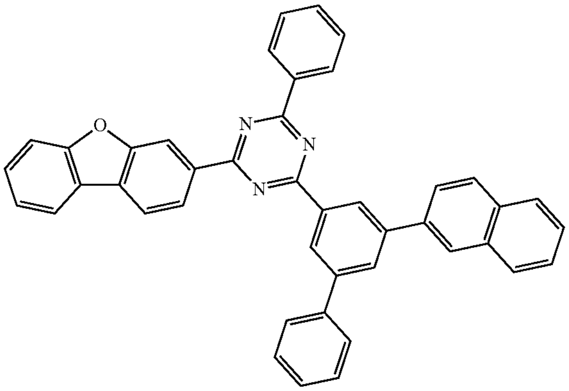
A-100
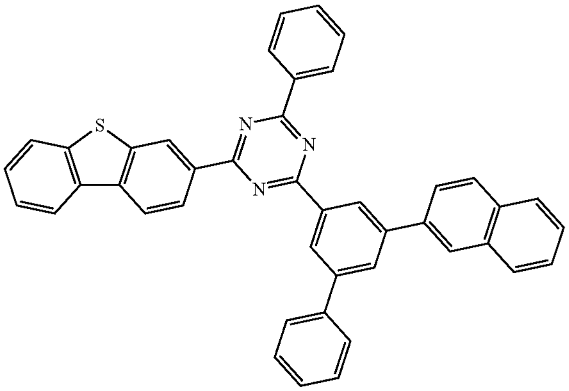
A-101
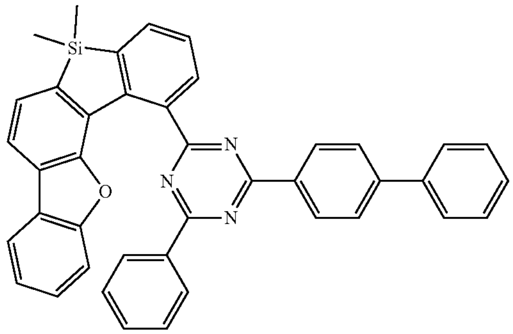
A-102
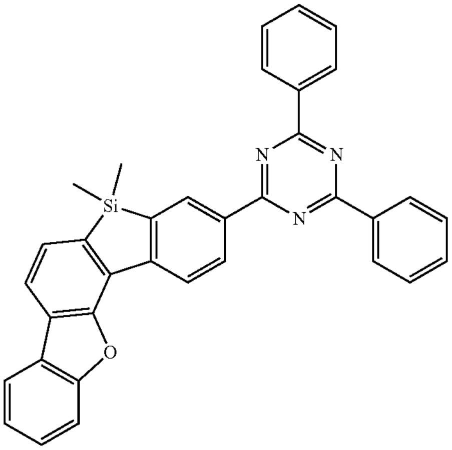
-continued
A-103
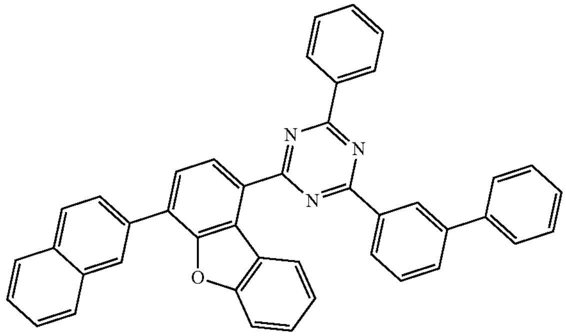
A-104
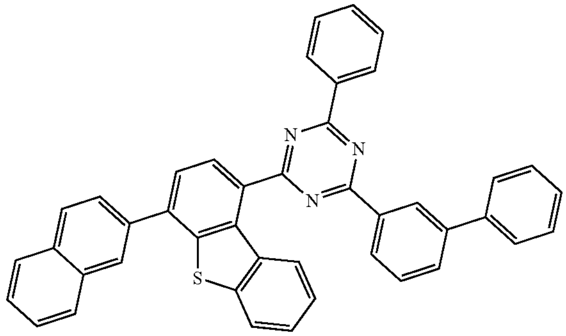
A-105
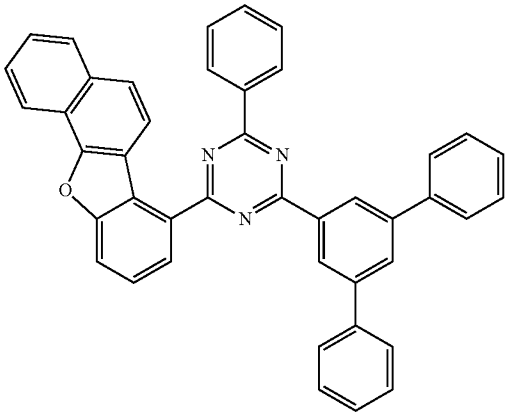
A-106
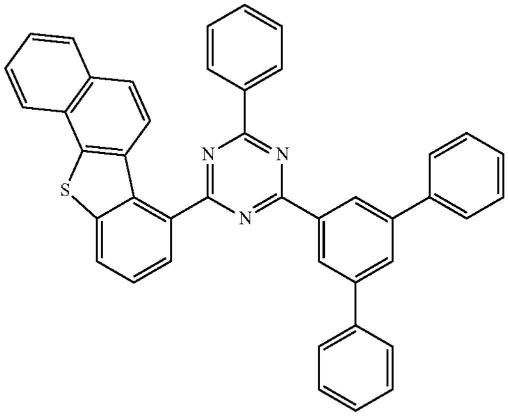

-continued

A-107

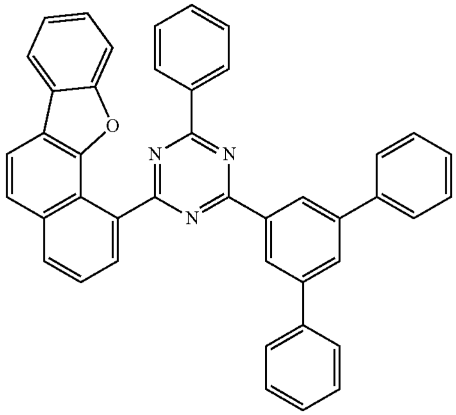

A-108

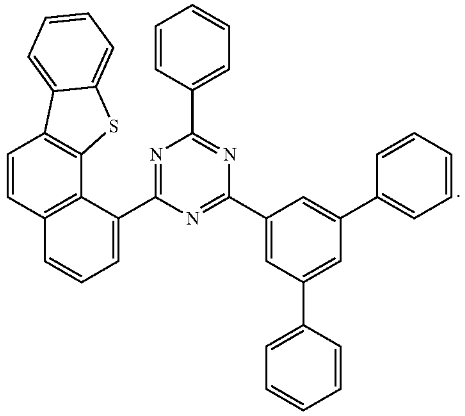

14. The composition for an organic optoelectronic device as claimed in claim 8, wherein:

the first compound is represented by Chemical Formula 1-2, and the second compound is represented by Chemical Formula 2A-3a, Chemical Formula 2C-1a, or Chemical Formula 2F-1a:

[Chemical Formula 1-2]

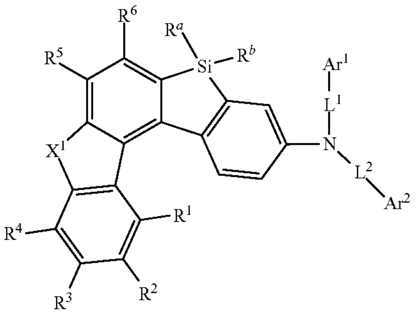

in Chemical Formula 1-2, $X^1$ is O or S, $Ar^1$ and $Ar^2$ are each independently a phenyl group that is unsubstituted or substituted with a C6 to C12 aryl group, a biphenyl group that is unsubstituted or substituted with a C6 to C12 aryl group, a naphthyl group that is unsubstituted or substituted with a C6 to C12 aryl group, a carbazolyl group that is unsubstituted or substituted with a C6 to C12 aryl group, a dibenzofuranyl group that is unsubstituted or substituted with a C6 to C12 aryl group, a dibenzothiophenyl group that is unsubstituted or substituted with a C6 to C12 aryl group, a dibenzosilolyl group that is unsubstituted or substituted with a C6 to C12 aryl group, a benzonaphthofuranyl group that is unsubstituted or substituted with a C6 to C12 aryl group, or a benzonaphthothiophenyl group that is unsubstituted or substituted with a C6 to C12 aryl group, $L^1$ and $L^2$ are each independently a single bond or a substituted or unsubstituted phenylene group, $R^1$ to $R^6$ are each independently hydrogen, deuterium, a substituted or unsubstituted C1 to C10 alkyl group, or a substituted or unsubstituted C6 to C12 aryl group, and $R^a$ and $R^b$ are each independently a substituted or unsubstituted C1 to C10 alkyl group or a substituted or unsubstituted C6 to C12 aryl group;

[Chemical Formula 2A-3a]

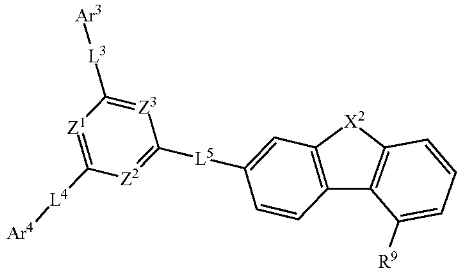

[Chemical Formula 2C-1a]

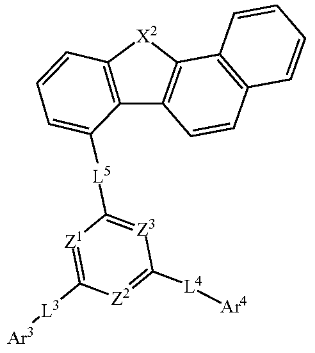

[Chemical Formula 2F-1a]

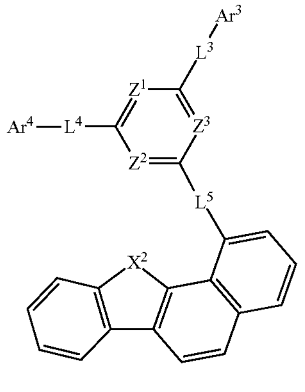

in Chemical Formula 2A-3a, Chemical Formula 2C-1a, and Chemical Formula 2F-1a, $X^2$ is O, S, $CR^dR^e$, or $SiR^fR^g$, $Z^1$ to $Z^3$ are each N, $R^d$, $R^e$, $R^f$, and $R^g$ are each independently a substituted or unsubstituted C1 to C10 alkyl group or a substituted or unsubstituted C6 to C12 aryl group, $R^9$ is hydrogen, deuterium, or a phenyl group, $L^3$ to $L^5$ are each independently a single bond or a substituted or unsubstituted phenylene group, and $Ar^3$ and $Ar^4$ are each independently a substituted or unsubstituted phenyl group, a substituted or unsubstituted biphenyl group, or a substituted or unsubstituted naphthyl group.

15. An organic optoelectronic device, comprising:

an anode and a cathode facing each other, and at least one organic layer between the anode and the cathode, wherein the at least one organic layer includes the compound for an organic optoelectronic device as claimed in claim 1.

16. The organic optoelectronic device as claimed in claim 15, wherein:

the at least one organic layer includes a light emitting layer, and the light emitting layer includes the compound.

17. A display device comprising the organic optoelectronic device as claimed in claim 15.

18. An organic optoelectronic device, comprising:

an anode and a cathode facing each other, and at least one organic layer between the anode and the cathode, wherein the at least one organic layer includes the composition for an organic optoelectronic device as claimed in claim 8.

19. The organic optoelectronic device as claimed in claim 18, wherein:

the at least one organic layer includes a light emitting layer, and the light emitting layer includes the composition.

20. A display device comprising the organic optoelectronic device as claimed in claim 18.

* * * * *